(12) United States Patent
Jain et al.

(10) Patent No.: US 9,248,117 B2
(45) Date of Patent: Feb. 2, 2016

(54) SUBSTITUTED N,N-DIHALOAMINES AS ANTIMICROBIALS

(75) Inventors: Rakesh K. Jain, Danville, CA (US); Timothy Shiau, Oakland, CA (US); Charles Francavilla, Fremont, CA (US); Eddy Low, Foster City, CA (US); Eric Douglas Turtle, Belmont, CA (US); Donogh John Roger O'Mahony, San Mateo, CA (US)

(73) Assignee: NOVABAY PHARMACEUTICALS, INC., Emeryville, CA (US)

( * ) Notice: Subject to any disclaimer, the term of this patent is extended or adjusted under 35 U.S.C. 154(b) by 0 days.

(21) Appl. No.: 13/276,145

(22) Filed: Oct. 18, 2011

(65) Prior Publication Data

US 2012/0129793 A1      May 24, 2012

Related U.S. Application Data

(60) Provisional application No. 61/394,697, filed on Oct. 19, 2010, provisional application No. 61/418,334, filed on Nov. 30, 2010.

(51) Int. Cl.
| | |
|---|---|
| *A61K 31/131* | (2006.01) |
| *C07C 211/02* | (2006.01) |
| *A61K 31/4166* | (2006.01) |
| *C07C 239/04* | (2006.01) |
| *C07C 317/28* | (2006.01) |
| *C07H 15/04* | (2006.01) |

(52) U.S. Cl.
CPC ............ *A61K 31/4166* (2013.01); *C07C 239/04* (2013.01); *C07C 317/28* (2013.01); *C07H 15/04* (2013.01)

(58) Field of Classification Search
CPC ............................ A61K 31/131; C07C 211/02
USPC ........................................ 514/740; 564/118
See application file for complete search history.

(56) References Cited

U.S. PATENT DOCUMENTS

| | | |
|---|---|---|
| 2010/0076089 A1 | 3/2010 | Wang et al. |
| 2010/0137349 A1 | 6/2010 | Jain et al. |
| 2010/0158818 A1 | 6/2010 | Jain et al. |

FOREIGN PATENT DOCUMENTS

| | | |
|---|---|---|
| EP | 0592876 | 4/1994 |
| WO | WO2005020896 | 3/2005 |
| WO | WO2008083347 | 7/2008 |
| WO | WO2010017405 | 2/2010 |
| WO | WO2010019723 | 2/2010 |
| WO | WO2010054009 | 5/2010 |
| WO | WO 2012/054821 | * 4/2012 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Low et al, N,N-Dichloroaminosulfonic acids as novel topical antimicrobial agents, Bioorg. Med. Chem. Lett., Jan. 1, 2009; 19(1):196-198.

* cited by examiner

*Primary Examiner* — Douglas M Willis
(74) *Attorney, Agent, or Firm* — Sam L. Nguyen; Hamilton, Desanctis & Cha, LLP

(57) ABSTRACT

The present application describes compounds of Formula I:

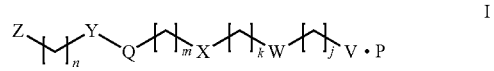

which are antimicrobial agents, including antibacterial, disinfectant, antifungal, germicidal and/or antiviral agents.

7 Claims, No Drawings

SUBSTITUTED N,N-DIHALOAMINES AS ANTIMICROBIALS

RELATED APPLICATION

This application claims the benefit of U.S. Provisional Application No. 61/394,697 filed Oct. 19, 2010 and U.S. Provisional Application No. 61/418,334 filed Nov. 30, 2010, which are incorporated herein by reference in their entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

Not applicable.

BRIEF DESCRIPTION OF THE SEVERAL VIEWS OF THE DRAWING(S)

Not applicable.

SEQUENCE LISTING

Not applicable.

SUMMARY OF THE INVENTION

This application describes compounds useful as anti-microbial agents, including as antibacterial, disinfectant, antifungal, germicidal or antiviral agents.

One aspect of the current disclosure relates to compounds of Formula I

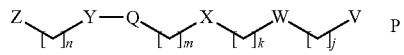

wherein
Z is

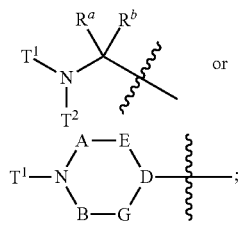

wherein
$T^1$ is —Cl or —Br;
$T^2$ is hydrogen, —Cl, —Br, alkyl, heteroalkyl, —SO$_2$R$^c$, —COR$^c$—, —C(=O)NHR$^c$, or —C(=O)OR$^c$;

A and B are each independently —CR$^a$R$^b$—, —(C=O)O—, —CH$_2$—, —SO$_2$— or absent;
G and E are each independently, —(C=O)—, —CR$^a$R$^b$—, —CH$_2$CH$_2$— or absent;
D is N, —N$^+$R$^a$—, or —CR$^a$—;
each R$^a$ and R$^b$ is independently hydrogen or optionally substituted alkyl;
R$^c$ is an alkyl, aryl, heteroalkyl or heteroaryl;
Y and W are each independently —O—, —SO$_2$—, —SO$_2$CH$_2$—, —SO$_2$NR$^5$—, —N$^+$(R$^1$R$^2$)—, —OC(=O)—, —NR$^5$C(=O)—, —NR$^5$C(=O)NR$^6$—, —NR$^5$C(=O)O—, —OC(=O)O—, —CF$_2$—, —CHF—, —CH(CF$_3$)— or absent;
Q is —CH—, —CH$_2$— or absent;
X is —(CHR$^4$—O)$_h$—, —(CH$_2$—CHR$^4$—O)$_h$—, —(CHOR$^3$)$_h$—, —(CH(CH$_2$OR$^3$))$_h$—, —(CH$_2$—CR$^4$(OR$^3$))$_h$—, or a combination thereof;
h is independently an integer from about 1 to about 1000;
V is hydrogen, acyl, alkyl, Z, —SO$_3$H, —O— or a single bond;
n is an integer from 1 to 3
m, k and j are each independently 0 or an integer from 1 to 3;
R$^1$ and R$^2$ are each independently selected from the group consisting of alkyl, aryl, heteroalkyl, and heteroaryl, each of which may be optionally substituted; or
R$^1$ and R$^2$ together with the nitrogen atom to which they are attached form a heterocycloalkyl group, each of which may be optionally substituted;
each R$^3$ is independently hydrogen, alkyl, acyl, aryl, heteroalkyl, heteroaryl, or heterocycloalkyl, each of which may be optionally substituted;
each R$^4$ is independently hydrogen or alkyl;
R$^5$ and R$^6$ are each independently hydrogen or alkyl;
and P is a counterion or absent;
with the provisos that (1) if Q is —CH— and V is —O— or a single bond, then V and Q are directly attached (i.e. bonded) to each other to form, together with the other groups to which they are attached, a cycloalkyl or a heterocycloalkyl, and (2) that compounds of Formula I do not include 2-(dichloroamino)-2-methylpropan-1-ol, 2-(chloroamino)-2-methylpropan-1-ol, 2-(dibromoamino)-2-methylpropan-1-ol, and 2-(bromoamino)-2-methylpropan-1-ol. In one variation of the above formula, h is an integer of 1 to 5, 1 to 10, 1 to 25, 1 to 50 or 1 to 100. In another variation, at least two of n, m, k and j are not 0.

In certain compounds of Formula I, Z is

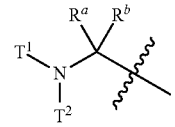

and $T^1$ is Cl.

In certain compounds of Formula I, Z is

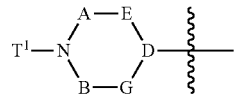

and $T^1$ is Cl.

In certain compounds of Formula I, R$^a$ and R$^b$ are alkyl. In certain of these compounds, R$^a$ and R$^b$ are both methyl. In certain compounds of Formula I, Y is —SO$_2$—. In other compounds of Formula I, Y is —SO$_2$CH$_2$—. In certain compounds of Formula I, X is —(CH$_2$CHR$^4$O)$_h$— wherein R$^4$ is hydrogen. In other compounds of Formula I, X is —(CHOR$^3$)$_h$— wherein R$^3$ is hydrogen. In other compounds of Formula I, X is a combination of —(CH$_2$CHR$^4$O)$_h$— wherein R$^4$ is hydrogen and —(CHOR$^3$)$_h$— wherein R$^3$ is hydrogen.

In certain compounds of Formula I, m is 0. In other compounds of Formula I, m is 1. In certain compounds of Formula I, j is 1. In certain compounds of Formula I, $T^2$ is Cl or H. In certain compounds of Formula I, each h is independently an integer from about 1 to about 100. In other compounds of Formula I, each h is an integer from about 1 to about 30.

In certain compounds of Formula I in which Q is —CH—, V is a single bond and V and Q are directly attached (i.e. bonded) to each other, X is a combination of —(CHR$^4$—O)$_h$— in which h is 1 and —(OCH$_2$CH$_2$)$_h$— in which h is an integer from about 3 to about 5. In these compounds, V, Q, and the groups to which they are attached, together may form a crown ether such as Alternatively, in certain compound of Formula I in which Q is —CH—, V is —O— and V and Q are directly attached (i.e. bonded) to each other, X is —(CHOH)$_h$— wherein h is an integer from about 3 to about 5. In these compounds, V, Q, and the groups to which they are attached, may form a group such as or a sugar.

Specific examples of such compounds are listed below.

Another aspect of the current disclosure relates to compounds of Formula IA

IA wherein

Z is wherein $T^1$ is —Cl or —Br;

$T^2$ is hydrogen, —Cl, —Br, alkyl, heteroalkyl, —SO$_2$R$^c$, —COR$^c$—, —C(═O)NHR$^c$, or —C(═O)OR$^c$;

A and B are each independently —CR$^a$R$^b$—, —(C═O)O—, —CH$_2$—, —SO$_2$— or absent;

G and E are each independently, —(C═O)—, —CR$^a$R$^b$—, —CH$_2$CH$_2$— or absent;

D is N, —N$^+$R$^a$—, or —CR$^a$—;

each R$^a$ and R$^b$ is independently hydrogen or optionally substituted alkyl;

R$^c$ is an alkyl, aryl, heteroalkyl or heteroaryl;

Y is —O—, —SO$_2$—, —SO$_2$CH$_2$—, —SO$_2$NR$^5$—, —N$^+$(R$^1$R$^2$)—, —OC(═O)—, —NR$^5$C(═O)—, —NR$^5$C(═O)NR$^6$—, —NR$^5$C(═O)O—, —OC(═O)O—, —CF$_2$—, —CHF—, —CH(CF$_3$)— or absent;

Q is —CH—, —CH$_2$— or absent;

X is —(CHR$^4$—O)$_h$—, —(CH$_2$—CHR$^4$—O)$_h$—, —(CHOR$^3$)$_h$—, —(CH(CH$_2$OR$^3$))$_h$—, —(CH$_2$—CR$^4$(OR$^3$))$_h$—, or a combination thereof;

h is independently an integer from about 1 to about 1000;

V is hydrogen, acyl, alkyl, Z, —SO$_3$H, —O— or a single bond;

n, m, and j are each independently 0 or an integer from 1 to 3;

R$^1$ and R$^2$ are each independently selected from the group consisting of alkyl, aryl, heteroalkyl, and heteroaryl, each of which may be optionally substituted; or R$^1$ and R$^2$ together with the nitrogen atom to which they are attached form a heterocycloalkyl group, each of which may be optionally substituted;

each R$^3$ is independently hydrogen, alkyl, acyl, aryl, heteroalkyl, heteroaryl, or heterocycloalkyl, each of which may be optionally substituted;

each R$^4$ is independently hydrogen or alkyl;

R$^5$ and R$^6$ are each independently hydrogen or alkyl;

and P is a counterion or absent;

with the proviso that compounds of Formula (IA) do not include 2-(dichloroamino)-2-methylpropan-1-ol, 2-(chloroamino)-2-methylpropan-1-ol, 2-(dibromoamino)-2-methylpropan-1-ol, and 2-(bromoamino)-2-methylpropan-1-ol. In one variation of the above formulae, h is an integer of 1 to 5, 1 to 10, 1 to 25, 1 to 50 or 1 to 100. In another variation, at least two of n, m, and j are not 0.

Other aspects of the current disclosure are described below.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more terminal dashes without losing their ordinary meaning. A wavy line drawn through a line in a structural formula indicates a point of attachment of a group. Unless chemically or structurally required, no directionality is indicated or implied by the way a chemical group is written. For instance, the group "—SO$_2$CH$_2$—" is equivalent to "—CH$_2$SO$_2$—" and may be connected in either direction.

Also, certain commonly used alternative chemical names may or may not be used. For example, a divalent group such as a divalent "alkyl" group, a divalent "aryl" group, etc., may also be referred to as an "alkylene" group or an "alkylenyl" group, an "arylene" group or an "arylenyl" group, respectively.

As utilized in accordance with the present disclosure, the following terms, unless otherwise indicated, shall be understood to have the following meanings:

"Alkyl" refers to any aliphatic hydrocarbon group, i.e. any linear, branched or cyclic nonaromatic hydrocarbon group or an isomer or combination thereof. As used herein, the term "alkyl" includes terms used in the art to describe saturated and unsaturated aliphatic hydrocarbon groups with one or more points of attachment, including alkenyl (an aliphatic group containing at least one carbon-carbon double bond), alkylene (a divalent aliphatic group), alkynyl (an aliphatic group containing at least one carbon-carbon triple bond), cycloalkyl (a cyclic aliphatic group), alkylcycloalkyl (a linear or branched aliphatic group attached to a cyclic aliphatic group), and the like. Alkyl groups include, but are not limited to, methyl; ethyl; propyls such as propan-1-yl, propan-2-yl (iso-propyl), cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; pentyls; hexyls; octyls; dodecyls; octadecyls; cyclopentyl, cyclohexyl, methylcyclohexyl, and the like. An alkyl group comprises from 1 to about 22 carbon atoms, e.g., from 1 to 22 carbon atoms, i.e. $C_{1-22}$alkyl, e.g. from 1 to 12 carbon atoms, or, e.g., from 1 to 6 carbon atoms, i.e. $C_{1-6}$alkyl.

"Acyl" refers to a group —C(=O)R, where R is hydrogen, alkyl, cycloalkyl, cycloheteroalkyl, aryl, arylalkyl, heteroalkyl, heteroaryl or heteroarylalkyl as defined herein, each of which may be optionally substituted, as defined herein. Representative examples include, but are not limited to formyl, acetyl, cylcohexylcarbonyl, cyclohexylmethylcarbonyl, benzoyl, benzyloxycarbonyl and the like.

"Acylamino" (or alternatively "acylamido") refers to a group —NR$^1$C(=O)R$^2$, where R$^1$ and R$^2$ are each independently hydrogen, alkyl, cycloalkyl, cycloheteroalkyl, aryl, arylalkyl, heteroalkyl, heteroaryl or heteroarylalkyl, as defined herein, each of which may be optionally substituted, as defined herein. Representative examples include, but are not limited to, formylamino, acetylamino (i.e., acetamido), cyclohexylcarbonylamino, cyclohexylmethyl-carbonylamino, benzoylamino (i.e., benzamido), benzylaxycarbonylamino and the like.

"Alkoxy" refers to a group —OR where R represents an alkyl or cycloalkyl group as defined herein, each of which may be optionally substituted, as defined herein. Representative examples include, but are not limited to, methoxy, ethoxy, propoxy, butoxy, cyclohexyloxy and the like.

"Aryl" refers to a group with one or more aromatic rings. It may be a single aromatic ring or multiple aromatic rings which are fused together, linked covalently, or linked via one or more such as a methylene or ethylene moiety. Aryls include, but are not limited to, those groups derived from acenaphthylene, anthracene, azulene, benzene, biphenyl, chrysene, cyclopentadienyl anion, diphenylmethyl, fluoranthene, fluorene, indane, indene, naphthalene, perylene, phenalene, phenanthrene, pyrene, triphenylene, and the like. An aryl group comprises from 5 to about 20 carbon atoms, e.g., from 6 to 20 carbon atoms, e.g. from 5 to 10 carbon atoms.

"Compounds" as used herein refers to any of the compounds encompassed by Formula I as disclosed herein. The compounds may be neutral, charged (e.g. cationic or anionic), or in a salt form. The compounds may be identified by structure and/or by name. If the chemical structure and chemical name conflict, the chemical structure will be determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, $^{18}$O, $^{18}$F, $^{31}$P, $^{32}$P, $^{35}$S and $^{36}$Cl. Compounds may exist in unsolvated forms as well as solvated forms, including hydrated forms. In general, the neutral, charged, protonated, salt, hydrated, solvated and N-oxide forms are within the scope of the present disclosure.

"Counterion" refers to a charged species which balances the charge on the rest of the molecule. Examples of cationic counterions include, but are not limited to, sodium, potassium, tetramethylammonium, and tetrabutylphosphonium. Examples of anionic counterions include, but are not limited to, acetate, phosphate, sulfonate, and citrate.

"Derivative" refers to salts, esters, amides, prodrugs, and tautomers of compounds described herein, including salts of those esters, amides, prodrugs, and tautomers. Derivatives include pharmaceutically acceptable derivatives, including pharmaceutically acceptable salts, esters and prodrugs.

"Effective amount" refers to the amount of a compound that, when administered to a subject, surface or area for treating or preventing a microbial infection or contamination, is sufficient to effect such treatment or prevention. The "effective amount" will vary depending on the compound, the severity of the condition causing the microbial infection and the age, weight, etc., of the subject to be treated.

"Electron-withdrawing" refers to one of more atoms or functional groups which are electronegative either through a resonance effect or an inductive effect. Examples of such atoms and functional groups include, but are not limited to —CO$_2$R$^O$, —CO—, —NO$_2$, —SO$_3$R$^O$, —PO$_3$R$^O$R$^{OO}$, cyano, halogen (F, Cl, Br, I), and haloalkyl (e.g. —CF$_3$), where R$^O$ and R$^{OO}$ are independently H, alkyl, aryl, heteroalkyl, or heteroaryl group, as defined herein, each of which may be optionally and independently substituted.

"Group" when used in a chemical context, refers to a chemical group, moiety or radical.

"Halide" refers to a halogen bearing a negative charge, including fluoride, chloride, bromide, and iodide.

"Halo" refers to a halogen, including fluoro, chloro, bromo, and iodo.

"Heteroalkyl" refers to an alkyl group in which one or more of the carbon atoms (and any associated hydrogen atoms) are each independently replaced with the same or different a heteroatomic group. Heteroatoms include, but are not limited to, N, P, O, S, etc. Heteroatomic groups include, but are not limited to, —NR$^O$—, —O—, —S—, —PH—, —P(O)$_2$—, —S(O)—, —S(O)$_2$—, and the like, where R$^O$ is defined above. The term "heteroalkyl" includes heterocycloalkyl (a cyclic heteroalkyl group), alkyl-heterocycloalkyl (a linear or branched aliphatic group attached to a cyclic heteroalkyl group), and the like. Heteroalkyl groups include, but are not limited to, —OCH$_3$, —CH$_2$OCH$_3$, —SCH$_3$, —CH$_2$SCH$_3$, —NR$^O$CH$_3$, —CH$_2$NR$^{OO}$CH$_3$, and the like, where R$^O$ and R$^{OO}$ are defined above. A heteroalkyl group comprises from 1 to about 22 carbon and hetero atoms, e.g., from 1 to 22 carbon and heteroatoms, e.g. from 1 to 12 carbon and hetero atoms, e.g., from 1 to 6 carbon and hetero atoms. A heterocycloalkyl group may also contain a charged heteroatom or group, e.g., a quaternized ammonium group such as —N$^+$(R)$_2$— wherein R is alkyl, e.g., methyl, ethyl, etc. Heterocycloalkyl groups include, but are not limited to, groups derived from epoxides, imidazolidine, morpholine, piperazine, piperidine, pyrazolidine, piperidine, pyrrolidine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidium, and the like. The heterocycloalkyl group comprises from 3 to about 10 carbon and hetero atoms in the ring.

"Heteroaryl" refers to an aryl group in which one or more of the carbon atoms (and any associated hydrogen atoms) are each independently replaced with the same or different heteroatomic groups, as defined above. Heteroaryl groups include, but are not limited to, groups derived from acridine, carbazole, carboline, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 atoms, e.g., from 5 to 20 atoms, e.g. from 5 to 10 atoms.

"Optionally" means that the subsequently defined event or circumstance may or may not occur, and that the description includes instances where the event or circumstance occurs and instances in which it does not. For example, an "optionally substituted aryl or heteroaryl" refers to an aryl or heteroaryl group, either of which may be substituted (as defined below) or not.

"Pharmaceutically acceptable" refers to that which is useful in preparing a pharmaceutical composition that is generally safe, non-toxic, and neither biologically nor otherwise undesirable, and includes that which is acceptable for veterinary or human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., *J. Pharma Sci*, 66(1), 1-19 (1977), and *Remington: The Science and Practice of Pharmacy*, R. Hendrickson, ed., 21st edition, Lippincott, Williams & Wilkins, Philadelphia, Pa., (2005), at p. 732, Table 38-5, both of which are hereby incorporated by reference herein.

"Pharmaceutically acceptable carrier" refers to a pharmaceutically acceptable diluent, adjuvant, excipient or vehicle and the like with which a compound is combined and/or administered.

"Pharmaceutical composition" as used herein comprises one or more compounds of Formula I and a pharmaceutically acceptable carrier.

"Prevent", "preventing" and "prevention" of a microbial infection refer to reducing the risk of a subject from developing a microbial infection, or reducing the frequency or severity of a microbial infection in a subject.

"Prodrug" and "prodrugs" refer to compounds that are rapidly transformed in vivo to yield a compound of the Formulae describe herein, for example by hydrolysis (chemical or enzymatic). By way of example but not limitation, one type of prodrug is esters, for example esters derived from pharmaceutically acceptable aliphatic carboxylic acids such as formates, acetates, propionates, butyrates, acrylates, ethylsuccinates, and the like. Further examples of prodrugs can be found in J. Rautio et al. *Prodrugs: design and clinical applications*, Nat. Rev. Drug Discov., 7, 255-270 (2008).

"Protecting group" refers to a group of atoms that when attached to a reactive functional group in a molecule masks, reduces or prevents reactivity of the functional group. Examples of protecting groups can be found in P. G. M. Wuts and T. W. Greene, *Greene's Protective Groups in Organic Synthesis* (4th Ed.), Wiley-Interscience, (2006), and Harrison et al., *Compendium of Synthetic Organic Methods*, Vols. 1-8 (John Wiley and Sons, 1971-1996). For example, representative amino protecting groups include, but are not limited to, formyl, acetyl, trifluoroacetyl, benzyl, benzyloxycarbonyl ("CBZ", "Cbz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Subject" refers to humans and wild or domestic animals including, without limitation, horses, cattle, swine, birds, dogs, cats, monotremes, and the like.

"Substituted" as in, for example, "substituted alkyl," refers to a group, for example an alkyl group, wherein one or more hydrogens (e.g., from 1 to 5, e.g., from 1 to 3) have been independently replaced with one or more substituents including, but not limited to, acylamino, alkoxy, alkyl, amino, amidino, aryl, carboxyl, carbamoyl, cyano, cycloalkyl, guanidino, halo, heteroalkyl, heteroaryl, heterocycloalkyl, hydroxyl, imidino, imino, nitro, oxamidino, oxo, methoxamidino, sulfonamido, thio, thioamido, an electron-withdrawing group, or a combination thereof.

"Treat", "treating" and "treatment" of a microbial infection or contamination refer to reducing the frequency or severity of symptoms of a microbial infection (including eliminating them), or avoiding or reducing the chances of the occurrence of a microbial infection, or killing or inhibiting the growth of bacteria, fungus or virus or associated biofilm.

The following abbreviations may also be used: APCI: atmospheric pressure chemical ionization; Boc$_2$O: di-tert-butyl dicarbonate; Cmpd: compound; DCM: dichloromethane, also known as methylene chloride; DIEA: diisopropylethylamine; DMF: N,N-dimethylformamide; EDT: ethanedithiol; ESI: electrospray ionization; EtOAc: ethyl acetate; EtOH: ethanol; h: hour; HPLC: high pressure liquid chromatography; LCMS: high pressure liquid chromatography with mass spectrometer detector; MeOH: methanol; m/z: mass to charge ratio; NMR: nuclear magnetic resonance; pos: positive; PTFE: polytetrafluoroethylene; RT or rt: room temperature; sat.: saturated; TFA: trifluoroacetic acid; TLC: thin layer chromatography. Other abbreviations commonly used in the art may also be used.

The present application includes the compounds in Tables 1 and 2, hereby identified by name, structure, and reference number. These and other compounds may be named or depicted with or without a particular counter ion (e.g., Na$^+$, Cl$^-$ etc.). It will nevertheless be understood that in those cases, the associated cation and any other salt form (e.g., the corresponding bromide, carbonate, hydroxide, etc.), as well as the particular salt named or depicted, may also be contemplated and are within the scope of this disclosure.

TABLE 1

| Name (Compound Number) | Structure |
|---|---|
| dichloro[1-({2-[2-(2-methoxyethoxy)ethoxy]ethane}sulfonyl)-2-methylpropan-2-yl]amine (38-01) | 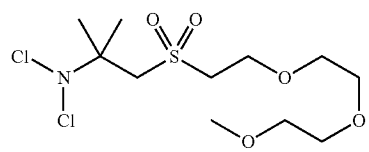 [SMILES: COCCOCCOCCS(=O)(=O)CC(C)(C)N(Cl)Cl] |
| chloro[1-({2-[2-(2-methoxyethoxy)ethoxy]ethane}sulfonyl)-2-methylpropan-2-yl]amine (38-02) | 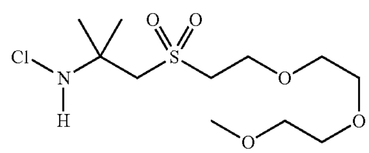 [SMILES: COCCOCCOCCS(=O)(=O)CC(C)(C)NCl] |
| 2-{2-[2-(2-{[2-(dichloroamino)-2-methylpropane]sulfonyl}ethoxy)ethoxy]ethoxy}ethan-1-ol (38-03) | 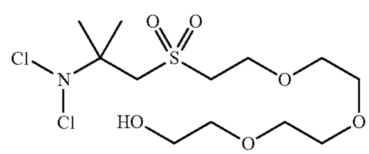 [SMILES: CC(C)(CS(=O)(=O)CCOCCOCCOCCO)N(Cl)Cl] |
| 2-{2-[2-(2-{[2-(chloroamino)-2-methylpropane]sulfonyl}ethoxy)ethoxy]ethoxy}ethan-1-ol (38-04) | 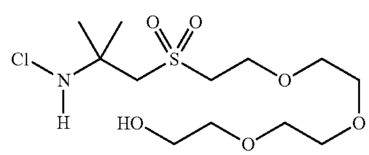 [SMILES: CC(C)(CS(=O)(=O)CCOCCOCCOCCO)NCl] |
| dichloro[4-({2-[2-(2-methoxyethoxy)ethoxy]ethane}sulfonyl)-2-methylbutan-2-yl]amine (38-05) | 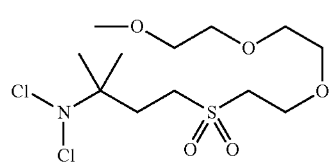 [SMILES: COCCOCCOCCS(=O)(=O)CCC(C)(C)N(Cl)Cl] |
| chloro[4-({2-[2-(2-methoxyethoxy)ethoxy]ethane}sulfonyl)-2-methylbutan-2-yl]amine (38-06) | 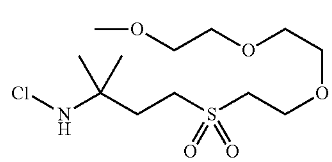 [SMILES: COCCOCCOCCS(=O)(=O)CCC(C)(C)NCl] |
| 2-{2-[2-(2-{[3-(dichloroamino)-3-methylbutane]sulfonyl}ethoxy)ethoxy]ethoxy}ethan-1-ol (38-07) | 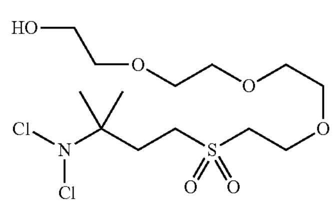 [SMILES: CC(C)(CCS(=O)(=O)CCOCCOCCOCCO)N(Cl)Cl] |

TABLE 1-continued

| Name (Compound Number) | Structure |
|---|---|
| 2-{2-[2-(2-{[3-(chloroamino)-3-methylbutane]sulfonyl}ethoxy)ethoxy]ethoxy}ethan-1-ol (38-08) | 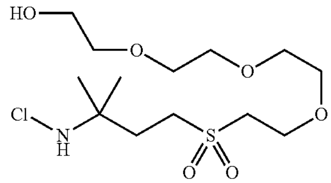 [SMILES: CC(C)(CCS(=O)(=O)CCOCCOCCOCCO)NCl] |
| dichloro[5-({2-[2-(2-methoxyethoxy)ethoxy]ethane}sulfonyl)-2-methylpentan-2-yl]amine (38-09) | 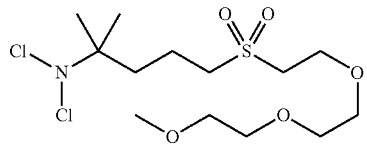 [SMILES: COCCOCCOCCS(=O)(=O)CCCC(C)(C)N(Cl)Cl] |
| chloro[5-({2-[2-(2-methoxyethoxy)ethoxy]ethane}sulfonyl)-2-methylpentan-2-yl]amine (38-10) | 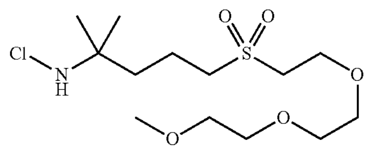 [SMILES: COCCOCCOCCS(=O)(=O)CCCC(C)(C)NCl] |
| 2-{2-[2-(2-{[4-(dichloroamino)-4-methylpentane]sulfonyl}ethoxy)ethoxy]ethoxy}ethan-1-ol (38-11) | 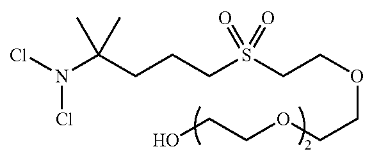 |
| 2-{2-[2-(2-{[4-(chloroamino)-4-methylpentane]sulfonyl}ethoxy)ethoxy]ethoxy}ethan-1-ol (38-12) | 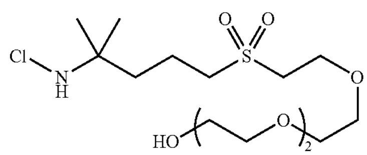 |
| 31-{[3-(dichloroamino)-3-methylbutane]sulfonyl}-2,5,8,11,14,17,20,23,26,29-decaoxahentriacontane (38-13) | 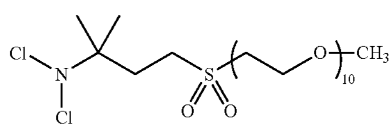 |
| 31-{[3-(chloroamino)-3-methylbutane]sulfonyl}-2,5,8,11,14,17,20,23,26,29-decaoxahentriacontane (38-14) | 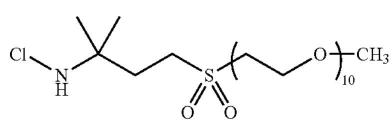 |
| 62{[3-(dichloroamino)-3-methylbutane]sulfonyl}-2,5,8,11,14,17,20,23,26,29,33,36,39,42,45,48,51,54,57,60-icosaoxadohexacontane (38-15) | 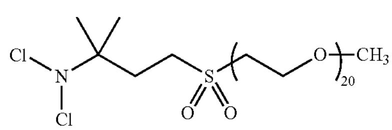 |
| 62-{[3-(chloroamino)-3-methylbutane]sulfonyl}-2,5,8,11,14,17,20,23,26,29,33,36,39,42,45,48,51,54,57,60-icosaoxadohexacontane (38-16) | 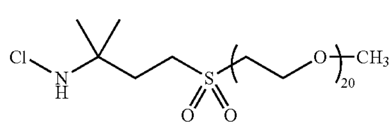 |
| 93-{[3-(dichloroamino)-3-methylbutane]sulfonyl}-2,5,8,11,14,17,20,23,27,30,33,36,39,42,45,48,51,54,57,60,64,67,70,73,76,79,82,85,88,91-triacontaoxatrinonacontane (38-17) | 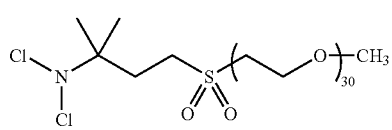 |
| 93-{[3-(chloroamino)-3-methylbutane]sulfonyl}-2,5,8,11,14,17,20,23,27,30,33,36,39,42,45,48,51,54,57,60,64,67,70,73,76,79,82,85,88,91-triacontaoxatrinonacontane (38-18) | 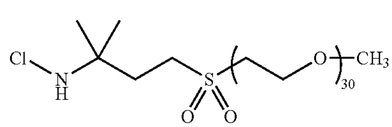 |

TABLE 1-continued

| Name (Compound Number) | Structure |
|---|---|
| 2-(2-(dichloroamino)-2-methylpropylsulfonyl)ethanol (38-19) | 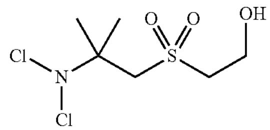 |
| 2-(2-(chloroamino)-2-methylpropylsulfonyl)ethanol (38-20) | 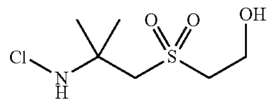 |
| 3-(2-(dichloroamino)-2-methylpropylsulfonyl)propane-1,2-diol (38-21) | 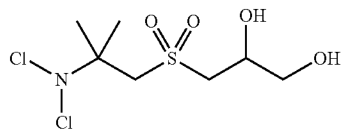 |
| 3-(2-(chloroamino)-2-methylpropylsulfonyl)propane-1,2-diol (38-22) | 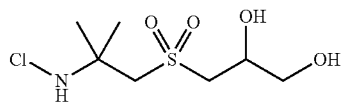 |
| 4-(2-(dichloroamino)-2-methylpropylsulfonyl)butane-1,2,3-triol (38-23) | 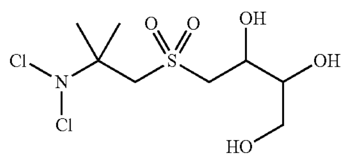 [SMILES: CC(C)(CS(=O)(=O)CC(O)C(O)CO)N(Cl)Cl] |
| 4-(2-(chloroamino)-2-methylpropylsulfonyl)butane-1,2,3-triol (38-24) | 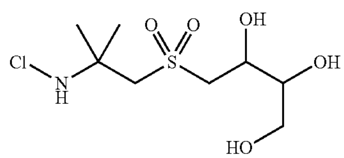 [SMILES: CC(C)(CS(=O)(=O)CC(O)C(O)CO)NCl] |
| 2-(3-(dichloroamino)-3-methylbutylsulfonyl)ethanol (38-25) | 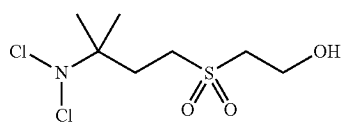 |
| 2-(3-(chloroamino)-3-methylbutylsulfonyl)ethanol (38-26) | 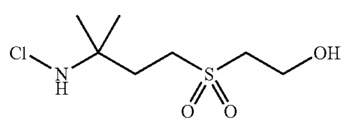 |
| 3-(2-(dichloroamino)-2-methylpropylsulfonyl)propane-1,2-diol (38-27) | 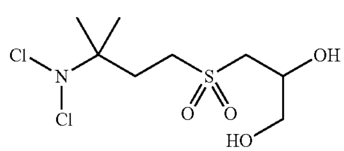 [SMILES: CC(C)(CCS(=O)(=O)CC(O)CO)N(Cl)Cl] |
| 3-(2-(chloroamino)-2-methylpropylsulfonyl)propane-1,2-diol (38-28) | 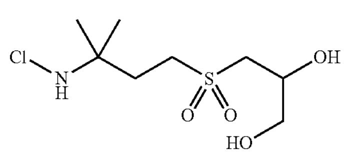 |
| 4-(3-(dichloroamino)-3-methylbutylsulfonyl)butane-1,2,3-triol (38-29) | 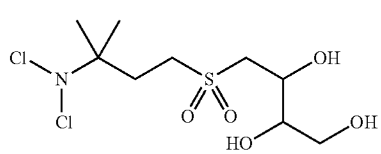 [SMILES: CC(C)(CCS(=O)(=O)CC(O)C(O)CO)N(Cl)Cl] |

TABLE 1-continued

| Name (Compound Number) | Structure |
| --- | --- |
| 4-(3-(chloroamino)-3-methylbutylsulfonyl)butane-1,2,3-triol (38-30) | 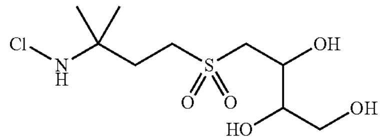 [SMILES: CC(C)(CCS(=O)(=O)CC(O)C(O)CO)NCl] |
| 2-(4-(dichloroamino)-4-methylpentylsulfonyl)ethanol (38-31) | 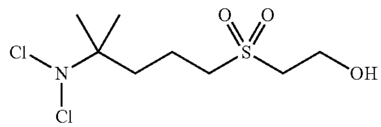 |
| 2-(4-(chloroamino)-4-methylpentylsulfonyl)ethanol (38-32) | 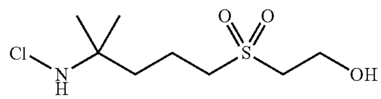 |
| 3-(4-(dichloroamino)-4-methylpentylsulfonyl)propane-1,2-diol (38-33) | 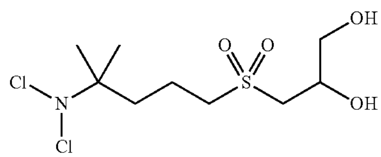 [SMILES: CC(C)(CCCS(=O)(=O)CC(O)CO)N(Cl)Cl] |
| 3-(4-(chloroamino)-4-methylpentylsulfonyl)propane-1,2-diol (38-34) | 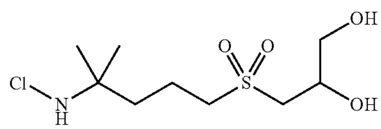 [SMILES: CC(C)(CCCS(=O)(=O)CC(O)CO)NCl] |
| 4-(4-(dichloroamino)-4-methylpentylsulfonyl)butane-1,2,3-triol (38-35) | 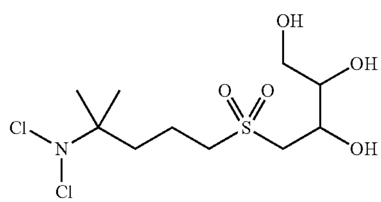 [SMILES: CC(C)(CCCS(=O)(=O)CC(O)C(O)CO)N(Cl)Cl] |
| 4-(4-(chloroamino)-4-methylpentylsulfonyl)butane-1,2,3-triol (38-36) | 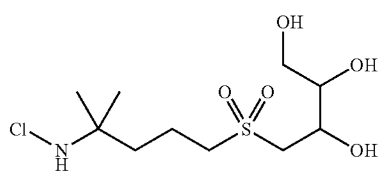 [SMILES: CC(C)(CCCS(=O)(=O)CC(O)C(O)CO)NCl] |
| 11-(4-(dichloroamino)-4-methylpentylsulfonyl)undecane-1,2,3,4,5,6,7,8,9,10-decaol (38-37) | 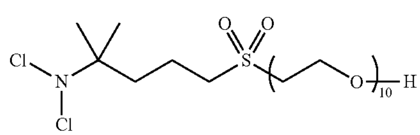 |
| 11-(4-(chloroamino)-4-methylpentylsulfonyl)undecane-1,2,3,4,5,6,7,8,9,10-decaol (38-38) | 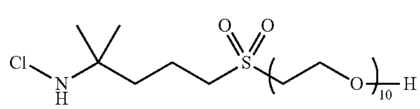 |
| 21-(4-(dichloroamino)-4-methylpentylsulfonyl)henicosan-1,2,3,4,5,6,7,8,9,10,11,12,13,14,15,16,17,18,19,20-icosaol (38-39) | 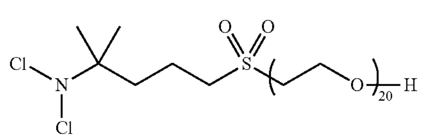 |
| 21-(4-(chloroamino)-4-methylpentylsulfonyl)henicosan-1,2,3,4,5,6,7,8,9,10,11,12,13,14,15,16,17,18,19,20-icosaol (38-40) | 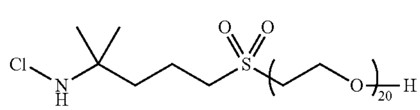 |

TABLE 1-continued

| Name (Compound Number) | Structure |
|---|---|
| 31-(4-(dichloroamino)-4-methylpentylsulfonyl)hentriacontane-1,2,3,4,5,6,7,8,9,10,11,12,13,14,15,16,17,18,19,20,21,22,23,24,25,26,27,28,29,30-triacontaol (38-41) | 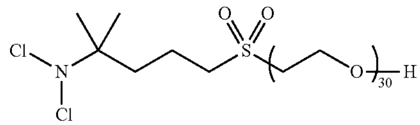 |
| 31-(4-(chloroamino)-4-methylpentylsulfonyl)hentriacontane-1,2,3,4,5,6,7,8,9,10,11,12,13,14,15,16,17,18,19,20,21,22,23,24,25,26,27,28,29,30-triacontaol (38-42) | 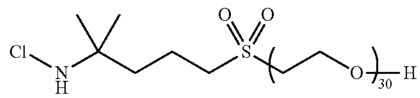 |
| 3-(dichloroamino)-N-(2-methoxyethyl)-N,N,3-trimethylbutan-1-aminium chloride (38-43) | 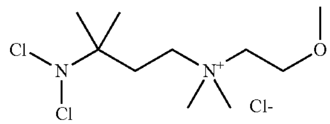 |
| 3-(chloroamino)-N-(2-methoxyethyl)-N,N,3-trimethylbutan-1-aminium chloride (38-44) | 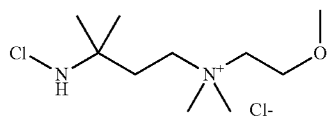 |
| 3-(dichloroamino)-N-(2-(2-(2-methoxyethoxy)ethoxy)ethyl)-N,N,3-trimethylbutan-1-aminium 4-methylbenzenesulfonate (38-45) | 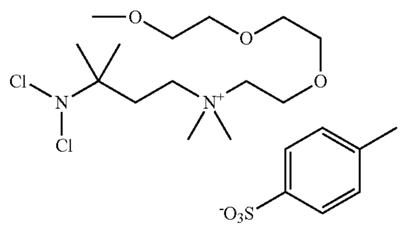 |
| 3-(chloroamino)-N-(2-(2-(2-methoxyethoxy)ethoxy)ethyl)-N,N,3-trimethylbutan-1-aminium 4-methylbenzenesulfonate (38-46) | 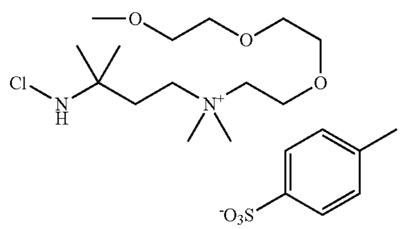 |
| 2-(3-(dichloroamino)-3-methylbutylsulfonyl)ethyl acetate (38-47) | 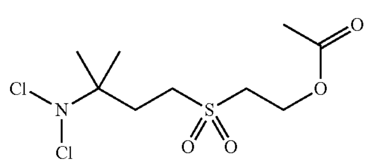 [SMILES: CC(=O)OCCS(=O)(=O)CCC(C)(C)N(Cl)Cl] |
| 2-(3-(chloroamino)-3-methylbutylsulfonyl)ethyl acetate (38-48) | 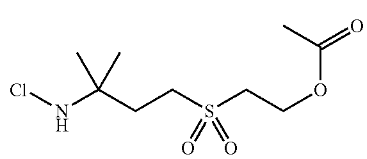 [SMILES: CC(=O)OCCS(=O)(=O)CCC(C)(C)NCl] |
| 3-(3-(dichloroamino)-3-methylbutylsulfonyl)-2-hydroxypropyl acetate (38-49) | 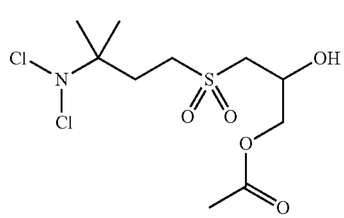 [SMILES: CC(=O)OCC(O)CS(=O)(=O)CCC(C)(C)N(Cl)Cl] |

TABLE 1-continued

| Name (Compound Number) | Structure |
| --- | --- |
| 3-(3-(chloroamino)-3-methylbutylsulfonyl)-2-hydroxypropyl acetate (38-50) | 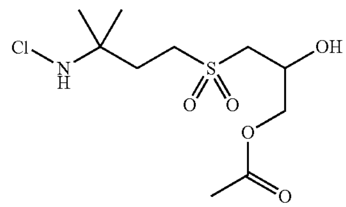 [SMILES: CC(=O)OCC(O)CS(=O)(=O)CCC(C)(C)NCl] |
| 3-(3-(dichloroamino)-3-methylbutylsulfonyl)propane-1,2-diyl diacetate (38-51) | 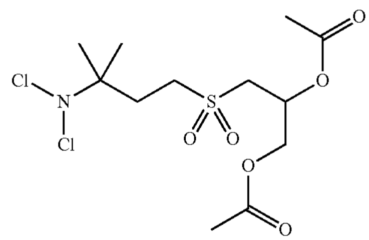 [SMILES: CC(=O)OCC(CS(=O)(=O)CCC(C)(C)N(Cl)Cl)OC(C)=O] |
| 3-(3-(chloroamino)-3-methylbutylsulfonyl)propane-1,2-diyl diacetate (38-52) | 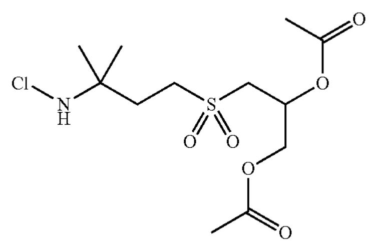 [SMILES: CC(=O)OCC(CS(=O)(=O)CCC(C)(C)NCl)OC(C)=O] |
| 3-(dichloroamino)-N-(2-hydroxyethyl)-N,N,3-trimethylbutan-1-aminium chloride (38-53) | 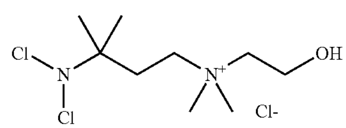 |
| 3-(dichloroamino)-N-(2-hydroxyethyl)-N,N,3-trimethylbutan-1-aminium chloride (38-54) | 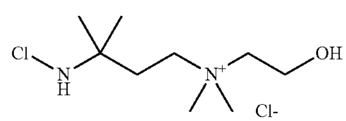 |
| 3-(dichloroamino)-N-(2,3-dihydroxypropyl)-N,N,3-trimethylbutan-1-aminium chloride (38-55) | 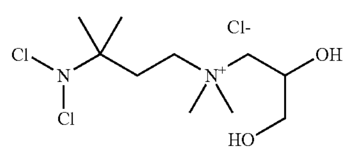 [SMILES: CC(C)(CC[N+](C)(C)CC(O)CO)N(Cl)Cl ; [Cl-]] |
| 3-(chloroamino)-N-(2,3-dihydroxypropyl)-N,N,3-trimethylbutan-1-aminium chloride (38-56) | 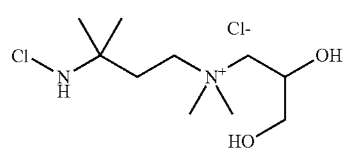 |
| 2-(2-(dichloroamino)-2-methylpropylsulfonyl)ethyl acetate (38-57) | 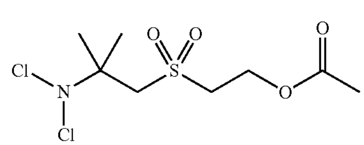 [SMILES: CC(=O)OCCS(=O)(=O)CC(C)(C)N(Cl)Cl] |
| 2-(2-(chloroamino)-2-methylpropylsulfonyl)ethyl acetate (38-58) | 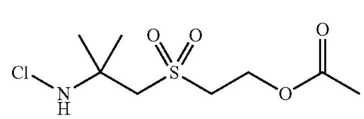 |

TABLE 1-continued

| Name (Compound Number) | Structure |
| --- | --- |
| 2-(2-(2-(dichloroamino)-2-methylpropylsulfonyl)ethoxy)ethyl acetate (38-59) | 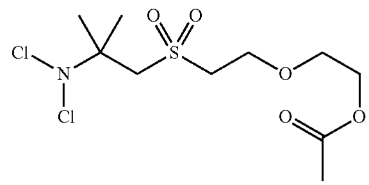 [SMILES: CC(=O)OCCOCCS(=O)(=O)CC(C)(C)N(Cl)Cl] |
| 2-(2-(2-(chloroamino)-2-methylpropylsulfonyl)ethoxy)ethyl acetate (38-60) | 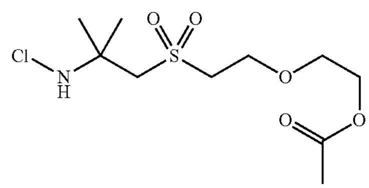 [SMILES: CC(=O)OCCOCCS(=O)(=O)CC(C)(C)NCl] |
| 2-(2-(2-(2-(dichloroamino)-2-methylpropylsulfonyl)ethoxy)ethoxy)ethyl acetate (38-61) | 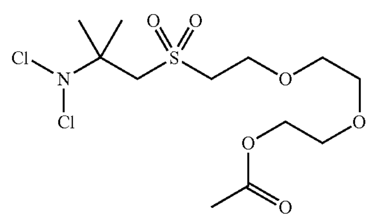 [SMILES: CC(=O)OCCOCCOCCS(=O)(=O)CC(C)(C)N(Cl)Cl] |
| 2-(2-(2-(2-(chloroamino)-2-methylpropylsulfonyl)ethoxy)ethoxy)ethyl acetate (38-62) | 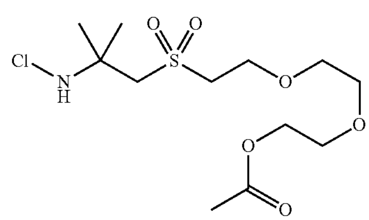 [SMILES: CC(=O)OCCOCCOCCS(=O)(=O)CC(C)(C)NCl] |
| 2-{2-[2-(2-{[2-(dichloroamino)-2-methylpropane]sulfonyl}ethoxy)ethoxy]ethoxy}ethyl acetate (38-63) | 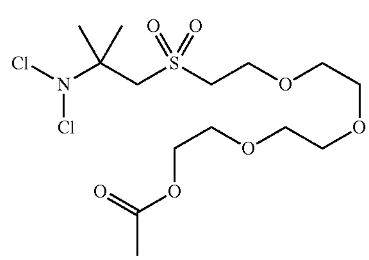 [SMILES: CC(=O)OCCOCCOCCOCCS(=O)(=O)CC(C)(C)N(Cl)Cl] |
| 2-{2-[2-(2-{[2-(chloroamino)-2-methylpropane]sulfonyl}ethoxy)ethoxy]ethoxy}ethyl acetate (38-64) | 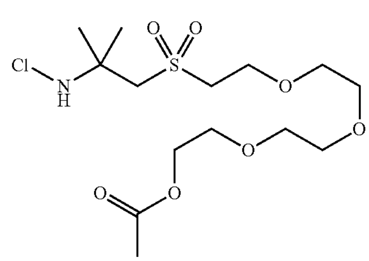 [SMILES: CC(=O)OCCOCCOCCOCCS(=O)(=O)CC(C)(C)NCl] |

TABLE 1-continued

| Name (Compound Number) | Structure |
| --- | --- |
| 1-((1,4,7,10,13,16-hexaoxacyclooctadecan-2-yl)methylsulfonyl)-N,N-dichloro-2-methylpropan-2-amine (38-65) | 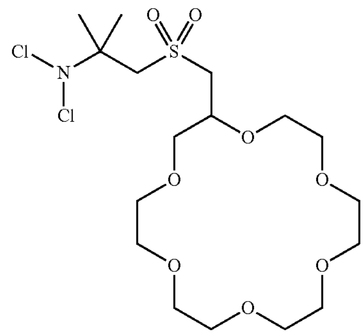 [SMILES: CC(C)(CS(=O)(=O)CC1COCCOCCOCCOCCOCCO1)N(Cl)Cl] |
| 1-((1,4,7,10,13,16-hexaoxacyclooctadecan-2-yl)methylsulfonyl)-N,N-chloro-2-methylpropan-2-amine (38-66) | 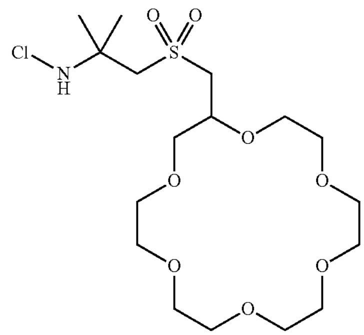 [SMILES: CC(C)(CS(=O)(=O)CC1COCCOCCOCCOCCOCCO1)NCl] |
| 4-((1,4,7,10,13,16-hexaoxacyclooctadecan-2-yl)methylsulfonyl)-N,N-dichloro-2-methylbutan-2-amine (38-67) | 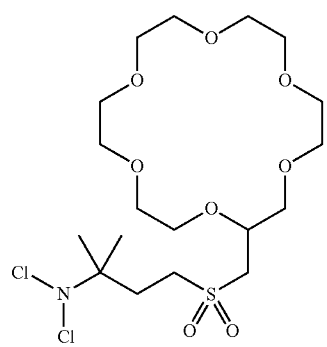 [SMILES: CC(C)(CCS(=O)(=O)CC1COCCOCCOCCOCCOCCO1)N(Cl)Cl] |
| 4-((1,4,7,10,13,16-hexaoxacyclooctadecan-2-yl)methylsulfonyl)-N,N-chloro-2-methylbutan-2-amine (38-68) | 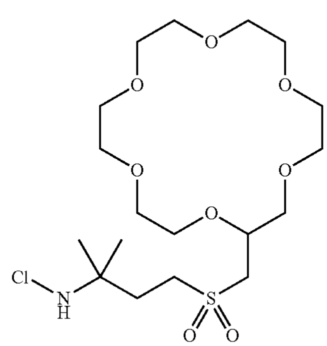 [SMILES: CC(C)(CCS(=O)(=O)CC1COCCOCCOCCOCCOCCO1)NCl] |
| 2-(2-(2-(dichloroamino)-2-methylpropylsulfonyl)ethoxy)ethanesulfonic acid (38-69) | 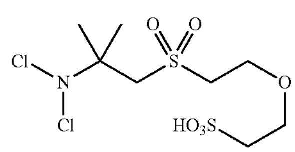 [SMILES: CC(C)(CS(=O)(=O)CCOCCS(=O)(=O)O)N(Cl)Cl] |

TABLE 1-continued

| Name (Compound Number) | Structure |
|---|---|
| 2-(2-(2-(chloroamino)-2-methylpropylsulfonyl)ethoxy)ethanesulfonic acid (38-70) | 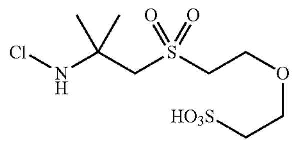 [SMILES: CC(C)(CS(=O)(=O)CCOCCS(=O)(=O)O)NCl] |
| 2-(2-(2-(2-(dichloroamino)-2-methylpropylsulfonyl)ethoxy)ethoxy)ethanesulfonic acid (38-71) | 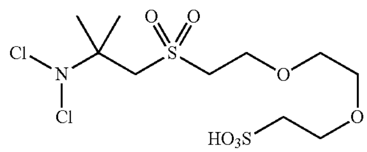 [SMILES: CC(C)(CS(=O)(=O)CCOCCOCCS(=O)(=O)O)N(Cl)Cl] |
| 2-(2-(2-(2-(chloroamino)-2-methylpropylsulfonyl)ethoxy)ethoxy)ethanesulfonic acid (38-72) | 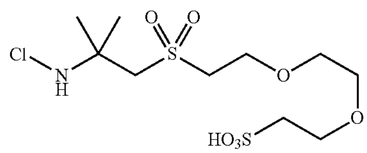 [SMILES: CC(C)(CS(=O)(=O)CCOCCOCCS(=O)(=O)O)NCl] |
| 2-(2-(2-(2-(2-(dichloroamino)-2-methylpropylsulfonyl)ethoxy)ethoxy)ethoxy)ethanesulfonic acid (38-73) | 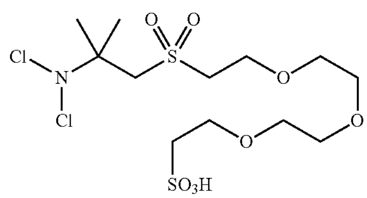 [SMILES: CC(C)(CS(=O)(=O)CCOCCOCCOCCS(=O)(=O)O)N(Cl)Cl] |
| 2-(2-(2-(2-(2-(chloroamino)-2-methylpropylsulfonyl)ethoxy)ethoxy)ethoxy)ethanesulfonic acid (38-74) | 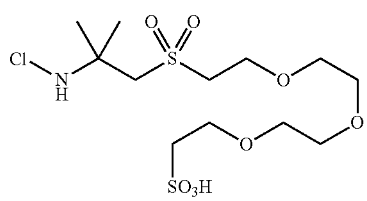 [SMILES: CC(C)(CS(=O)(=O)CCOCCOCCOCCS(=O)(=O)O)NCl] |
| 4-((1,4,7,10-tetraoxacyclododecan-2-yl)methylsulfonyl)-N,N-dichloro-2-methylbutan-2-amine (38-75) | 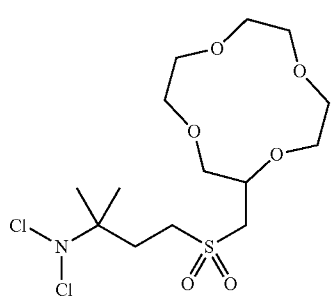 [SMILES: CC(C)(CCS(=O)(=O)CC1COCCOCCOCCO1)N(Cl)Cl] |
| 4-((1,4,7,10-tetraoxacyclododecan-2-yl)methylsulfonyl)-N,N-chloro-2-methylbutan-2-amine (38-76) | 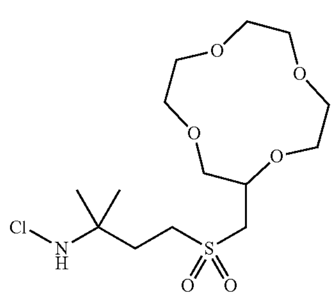 [SMILES: CC(C)(CCS(=O)(=O)CC1COCCOCCOCCO1)NCl] |

TABLE 1-continued

| Name (Compound Number) | Structure |
|---|---|
| 4-((1,4,7,10,13-pentaoxacyclopentadecan-2-yl)methylsulfonyl)-N,N-dichloro-2-methylbutan-2-amine (38-77) | 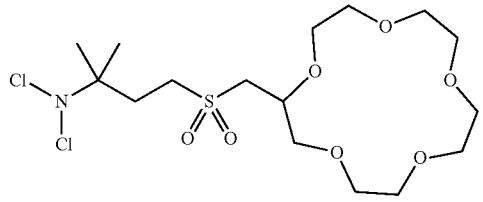 [SMILES: CC(C)(CCS(=O)(=O)CC1COCCOCCOCCOCCO1)N(Cl)Cl] |
| 4-((1,4,7,10,13-pentaoxacyclopentadecan-2-yl)methylsulfonyl)-N,N-chloro-2-methylbutan-2-amine (38-78) | 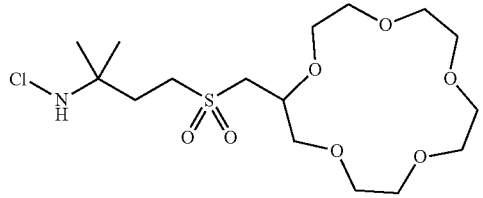 [SMILES: CC(C)(CCS(=O)(=O)CC1COCCOCCOCCOCCO1)NCl] |
| 2-(2-(2-(2-(3-(dichloroamino)-3-methylbutylsulfonyl)ethoxy)ethoxy)ethoxy)ethanesulfonic acid (38-79) | 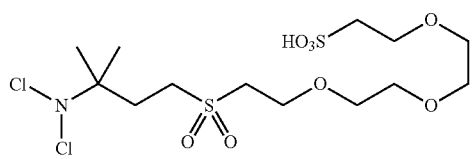 [SMILES: CC(C)(CCS(=O)(=O)CCOCCOCCOCCS(=O)(=O)O)N(Cl)Cl] |
| 2-(2-(2-(2-(3-(chloroamino)-3-methylbutylsulfonyl)ethoxy)ethoxy)ethoxy)ethanesulfonic acid (38-80) | 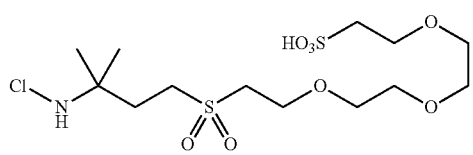 [SMILES: CC(C)(CCS(=O)(=O)CCOCCOCCOCCS(=O)(=O)O)NCl] |
| 2-(2-(2-(3-(dichloroamino)-3-methylbutylsulfonyl)ethoxy)ethoxy)ethanesulfonic acid (38-81) | 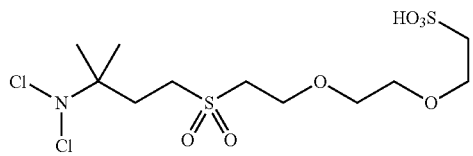 [SMILES: CC(C)(CCS(=O)(=O)CCOCCOCCS(=O)(=O)O)N(Cl)Cl] |
| 2-(2-(2-(3-(chloroamino)-3-methylbutylsulfonyl)ethoxy)ethoxy)ethanesulfonic acid (38-82) | 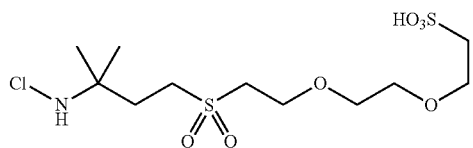 [SMILES: CC(C)(CCS(=O)(=O)CCOCCOCCS(=O)(=O)O)NCl] |
| 2-(2-(3-(dichloroamino)-3-methylbutylsulfonyl)ethoxy)ethanesulfonic acid (38-83) | 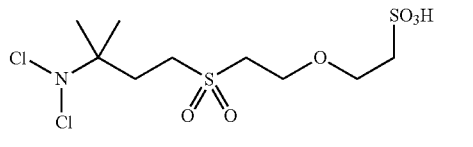 [SMILES: CC(C)(CCS(=O)(=O)CCOCCS(=O)(=O)O)N(Cl)Cl] |
| 2-(2-(3-(chloroamino)-3-methylbutylsulfonyl)ethoxy)ethanesulfonic acid (38-84) | 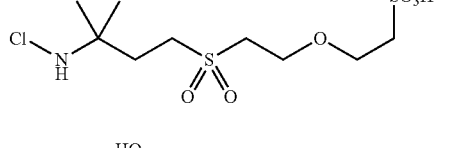 |
| 2-(2-(2-(3-(dichloroamino)-3-methylbutylsulfonyl)ethoxy)ethoxy)ethanol (38-85) | 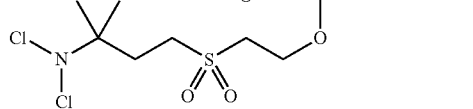 |

TABLE 1-continued

| Name (Compound Number) | Structure |
| --- | --- |
| 2-(2-(2-(3-(dichloroamino)-3-methylbutylsulfonyl)ethoxy)ethoxy)ethanol (38-86) | 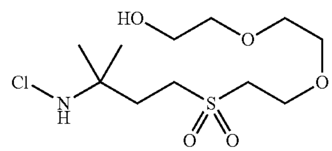 [SMILES: CC(C)(CCS(=O)(=O)CCOCCOCCO)NCl] |
| 2-(2-(2-(3-(dichloroamino)-3-methylbutylsulfonyl)ethoxy)ethoxy)ethyl acetate (38-87) | 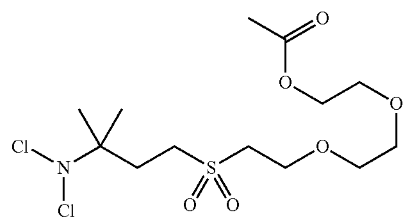 [SMILES: CC(=O)OCCOCCOCCS(=O)(=O)CCC(C)(C)N(Cl)Cl] |
| 2-(2-(2-(3-(chloroamino)-3-methylbutylsulfonyl)ethoxy)ethoxy)ethyl acetate (38-88) | 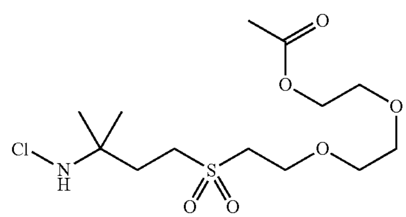 [SMILES: CC(=O)OCCOCCOCCS(=O)(=O)CCC(C)(C)NCl] |
| dichloro[4-({2-[2-(2-ethoxyethoxy)ethoxy]ethane}sulfonyl)-2-methylbutan-2-yl]amine (38-89) | 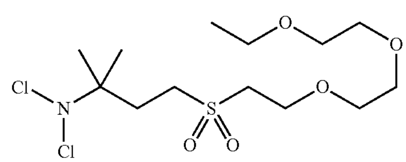 [SMILES: CCOCCOCCOCCS(=O)(=O)CCC(C)(C)N(Cl)Cl] |
| chloro[4-({2-[2-(2-ethoxyethoxy)ethoxy]ethane}sulfonyl)-2-methylbutan-2-yl]amine (38-90) | 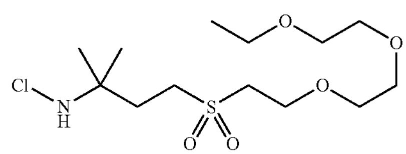 [SMILES: CCOCCOCCOCCS(=O)(=O)CCC(C)(C)NCl] |
| {4-[(2-{2-[2-(tert-butoxy)ethoxy]ethoxy}ethane)sulfonyl]-2-methylbutan-2-yl}dichloroamine (38-91) | 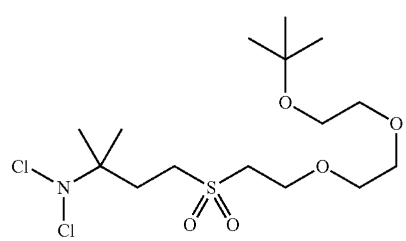 [SMILES: CC(C)(C)OCCOCCOCCS(=O)(=O)CCC(C)(C)N(Cl)Cl] |
| {4-[(2-{2-[2-(tert-butoxy)ethoxy]ethoxy}ethane)sulfonyl]-2-methylbutan-2-yl}dichloroamine (38-92) | 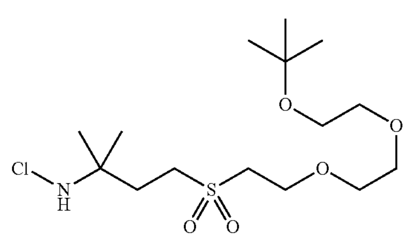 [SMILES: CC(C)(CCS(=O)(=O)CCOCCOCCOC(C)(C)C)NCl] |
| 4-(3-(dichloroamino)-3-methylbutylsulfonyl)butane-1,3-diol (38-93) | 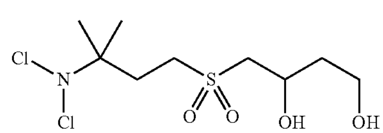 [SMILES: CC(C)(CCS(=O)(=O)CC(O)CCO)N(Cl)Cl] |

TABLE 1-continued

| Name (Compound Number) | Structure |
|---|---|
| 4-(3-(chloroamino)-3-methylbutylsulfonyl)butane-1,3-diol (38-94) | 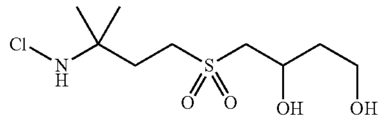 [SMILES: CC(C)(CCS(=O)(=O)CC(O)CCO)NCl] |
| 6-(3-(dichloroamino)-3-methylbutylsulfonyl)hexane-1,3,5-triol (38-95) | 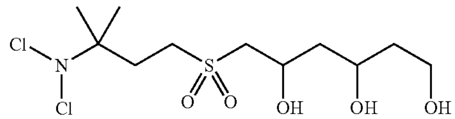 [SMILES: CC(C)(CCS(=O)(=O)CC(O)CC(O)CCO)N(Cl)Cl] |
| 6-(3-(chloroamino)-3-methylbutylsulfonyl)hexane-1,3,5-triol (38-96) | 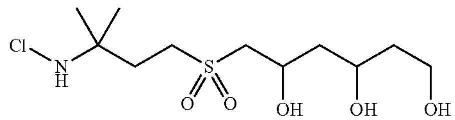 [SMILES: CC(C)(CCS(=O)(=O)CC(O)CC(O)CCO)NCl] |
| 6-(3-(dichloroamino)-3-methylbutylsulfonyl)hexane-1,2,3,5-tetraol (38-97) | 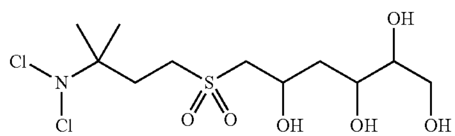 [SMILES: CC(C)(CCS(=O)(=O)CC(O)CC(O)C(O)CO)N(Cl)Cl] |
| 6-(3-(chloroamino)-3-methylbutylsulfonyl)hexane-1,2,3,5-tetraol (38-98) | 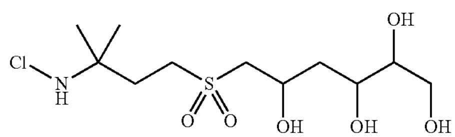 [SMILES: CC(C)(CCS(=O)(=O)CC(O)CC(O)C(O)CO)NCl] |
| 1-(3-(dichloroamino)-3-methylbutylsulfonyl)-3-(2-hydroxyethoxy)propan-2-ol (38-99) | 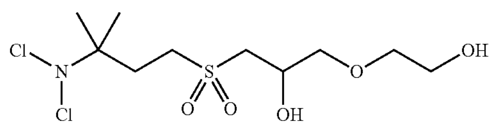 [SMILES: CC(C)(CCS(=O)(=O)CC(O)COCCO)N(Cl)Cl] |
| 1-(3-(chloroamino)-3-methylbutylsulfonyl)-3-(2-hydroxyethoxy)propan-2-ol (38-100) | 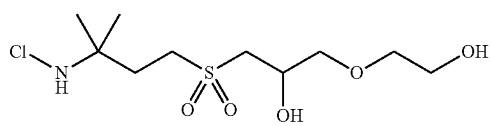 [SMILES: CC(C)(CCS(=O)(=O)CC(O)COCCO)NCl] |
| N,N-dichloro-13-methyl-2,5,8,11-tetraoxatetradecan-13-amine (38-101) | 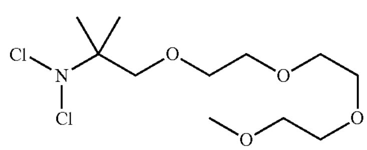 [SMILES: COCCOCCOCCOCC(C)(C)N(Cl)Cl] |
| N-chloro-13-methyl-2,5,8,11-tetraoxatetradecan-13-amine (38-102) | 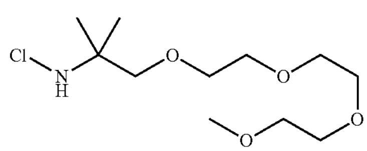 [SMILES: COCCOCCOCCOCC(C)(C)NCl] |
| N,N-dichloro-16-methyl-2,5,8,11,14-pentaoxaheptadecan-16-amine (38-103) | 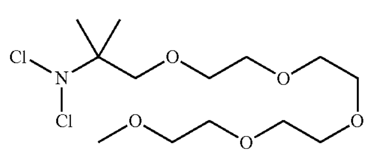 [SMILES: COCCOCCOCCOCCOCC(C)(C)N(Cl)Cl] |
| N-chloro-16-methyl-2,5,8,11,14-pentaoxaheptadecan-16-amine (38-104) | 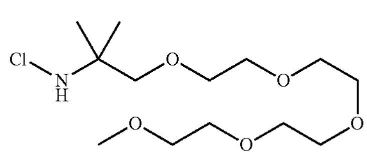 [SMILES: COCCOCCOCCOCCOCC(C)(C)NCl] |

TABLE 1-continued

| Name (Compound Number) | Structure |
|---|---|
| 8-(dichloroamino)-8-methylnonane-1,2,3,4,5,6-hexaol (38-105) | 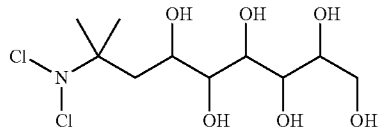 [SMILES: CC(C)(CC(O)C(O)C(O)C(O)C(O)CO)N(Cl)Cl] |
| 8-(chloroamino)-8-methylnonane-1,2,3,4,5,6-hexaol (38-106) | 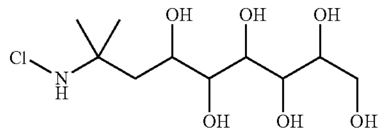 [SMILES: CC(C)(CC(O)C(O)C(O)C(O)C(O)CO)NCl] |
| 8-(dichloroamino)-8-methylnonane-1,2,3,4,5-pentaol (38-107) | 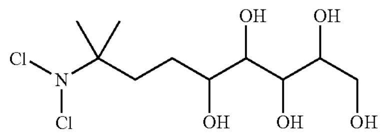 [SMILES: CC(C)(CCC(O)C(O)C(O)C(O)CO)N(Cl)Cl] |
| 8-(chloroamino)-8-methylnonane-1,2,3,4,5-pentaol (38-108) | 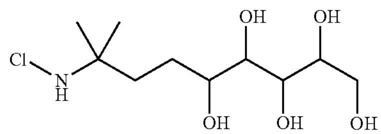 [SMILES: CC(C)(CCC(O)C(O)C(O)C(O)CO)NCl] |
| 1,6-bis(3-(dichloroamino)-3-methylbutylsulfonyl)hexane-2,3,4,5-tetraol (38-109) | 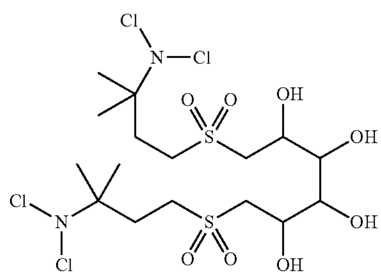 [SMILES: CC(C)(CCS(=O)(=O)CC(O)C(O)C(O)C(O)CS(=O)(=O)CCC(C)(C)N(Cl)Cl)N(Cl)Cl] |
| 1,6-bis(3-(chloroamino)-3-methylbutylsulfonyl)hexane-2,3,4,5-tetraol (38-110) | 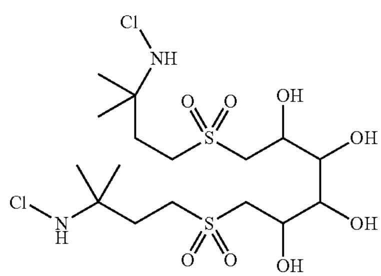 [SMILES: CC(C)(CCS(=O)(=O)CC(O)C(O)C(O)C(O)CS(=O)(=O)CCC(C)(C)NCl)NCl] |
| 299{[3-(dichloroamino)-3-methylbutane]sulfonyl}-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156,159,162,165,168,171,174,177,180,183,186,189,192,195,198,201,204,207,210,213,216,219,222,225,228,231,234,237,240,243,246,249,252,255,258,261,264,267,270,273,276,279,282,285,288,291,294,297-nonanonacontaoxa299n-1-ol (38-111) | 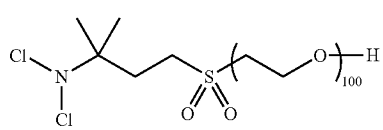 |
| 299-{[3-(chloroamino)-3-methylbutane]sulfonyl}-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156,159,162,165,168,171,174,177,180,183,186,189,192,195,198,201,204,207,210,213,216,219,222,225,228,231,234,237,240,243,246,249,252,255,258,261,264,267,270,273,276,279,282,285,288,291,294,297-nonanonacontaoxa299n-1-ol (38-112) | 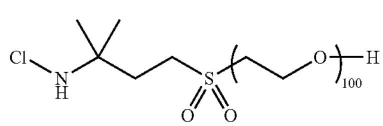 |

TABLE 1-continued

| Name (Compound Number) | Structure |
|---|---|
| 301-{[3-(dichloroamino)-3-methylbutane]sulfonyl}-2,5,8,11,14,17,20,23,26,29,32,35,38,41,44,47,50, 53,56,59,62,65,68,71,74,77,80,83,86,89,92,95, 98,101,104,107,110,113,116,119,122,125,128, 131,134,137,140,143,146,149,152,155,158, 161,164,167,170,173,176,179,182,185,188,191, 194,197,200,203,206,209,212,215,218,221,224, 227,230,233,236,239,242,245,248,251,254,257, 260,263,266,269,272,275,278,281,284,287, 290,293,296,299-100oxa301ne (38-113) | 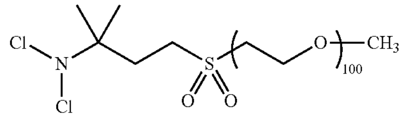 |
| 301-{[3-(chloroamino)-3-methylbutane]sulfonyl}-2,5,8,11,14,17,20,23,26,29,32,35,38,41,44,47,50, 53,56,59,62,65,68,71,74,77,80,83,86,89,92,95, 98,101,104,107,110,113,116,119,122,125,128, 131,134,137,140,143,146,149,152,155,158, 161,164,167,170,173,176,179,182,185,188,191, 194,197,200,203,206,209,212,215,218,221,224, 227,230,233,236,239,242,245,248,251,254,257, 260,263,266,269,272,275,278,281,284,287, 290,293,296,299-100oxa301ne (38-114) | 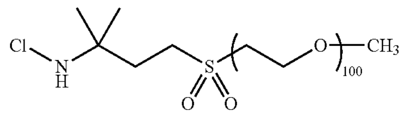 |
| 299-{[3-(dibromoamino)-3-methylbutane]sulfonyl}-3,6,9,12,15,18,21,24,27,30,33,36,39,42,45,48,51, 54,57,60,63,66,69,72,75,78,81,84,87,90,93,96, 99,102,105,108,111,114,117,120,123,126,129, 132,135,138,141,144,147,150,153,156,159, 162,165,168,171,174,177,180,183,186,189,192, 195,198,201,204,207,210,213,216,219,222,225, 228,231,234,237,240,243,246,249,252,255,258, 261,264,267,270,273,276,279,282,285,288, 291,294,297-nonanonacontaoxa299n-1-ol (38-115) | 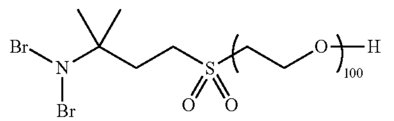 |
| 299-{[3-(bromoamino)-3-methylbutane]sulfonyl}-3,6,9,12,15,18,21,24,27,30,33,36,39,42,45,48,51, 54,57,60,63,66,69,72,75,78,81,84,87,90,93,96, 99,102,105,108,111,114,117,120,123,126,129, 132,135,138,141,144,147,150,153,156,159, 162,165,168,171,174,177,180,183,186,189,192, 195,198,201,204,207,210,213,216,219,222,225, 228,231,234,237,240,243,246,249,252,255,258, 261,264,267,270,273,276,279,282,285,288, 291,294,297-nonanonacontaoxa299n-1-ol (38-116) | 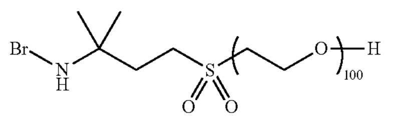 |
| 301-{[3-(dibromoamino)-3-methylbutane]sulfonyl}-2,5,8,11,14,17,20,23,26,29,32,35,38,41,44,47,50, 53,56,59,62,65,68,71,74,77,80,83,86,89,92,95, 98,101,104,107,110,113,116,119,122,125,128, 131,134,137,140,143,146,149,152,155,158, 161,164,167,170,173,176,179,182,185,188,191, 194,197,200,203,206,209,212,215,218,221,224, 227,230,233,236,239,242,245,248,251,254,257, 260,263,266,269,272,275,278,281,284,287, 290,293,296,299-100oxa301ne (38-117) | 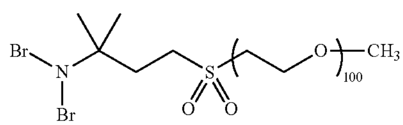 |
| 301-{[3-(bromoamino)-3-methylbutane]sulfonyl}-2,5,8,11,14,17,20,23,26,29,32,35,38,41,44,47,50, 53,56,59,62,65,68,71,74,77,80,83,86,89,92,95, 98,101,104,107,110,113,116,119,122,125,128, 131,134,137,140,143,146,149,152,155,158, 161,164,167,170,173,176,179,182,185,188,191, 194,197,200,203,206,209,212,215,218,221,224, 227,230,233,236,239,242,245,248,251,254,257, 260,263,266,269,272,275,278,281,284,287,290, 293,296,299-100oxa301ne (38-118) | 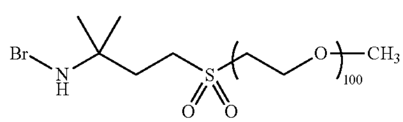 |
| dichloro({4-[(2-{2-[2-(2-{[3-(dichloroamino)-3-methylbutane]sulfonyl}ethoxy)ethoxy]ethoxy} ethane)sulfonyl]-2-methylbutan-2-yl}amine (38-119) | 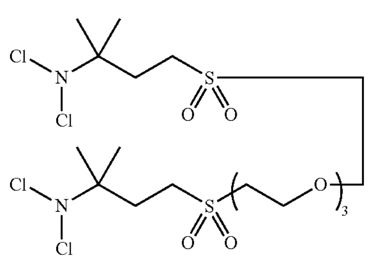 |

TABLE 1-continued

| Name (Compound Number) | Structure |
|---|---|
| chloro({4-[(2-{2-[2-(2-{[3-(chloroamino)-3-methylbutane]sulfonyl}ethoxy)ethoxy]ethoxy}ethane)sulfonyl]-2-methylbutan-2-yl}amine (38-120) | 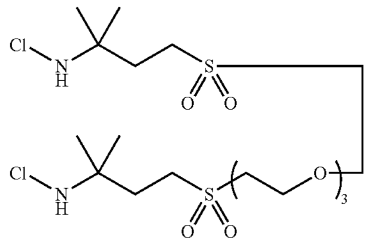 |
| dichloro[4-(32-{[3-(dichloroamino)-3-methylbutane]sulfonyl}-3,6,9,12,15,18,21,24,27,30-decaoxadotriacontane-1-sulfonyl)-2-methylbutan-2-yl]amine (38-121) | 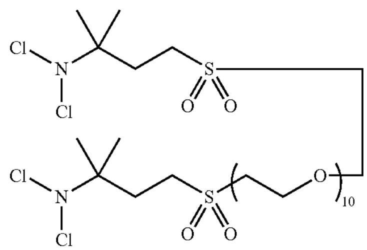 |
| chloro[4-(32-{[3-(chloroamino)-3-methylbutane]sulfonyl}-3,6,9,12,15,18,21,24,27,30-decaoxadotriacontane-1-sulfonyl)-2-methylbutan-2-yl]amine (38-122) | 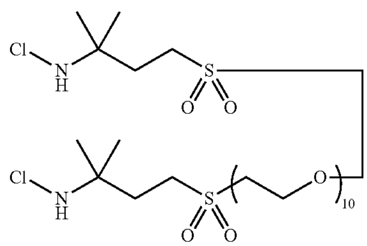 |
| dichloro[4-(302-{[3-(dichloroamino)-3-methylbutane]sulfonyl}-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156,159,162,165,168,171,174,177,180,183,186,189,192,195,198,201,204,207,210,213,216,219,222,225,228,231,234,237,240,243,246,249,252,255,258,261,264,267,270,273,276,279,282,285,288,291,294,297,300-100oxa302ne-1-sulfonyl)-2-methylbutan-2-yl]amine (38-123) | 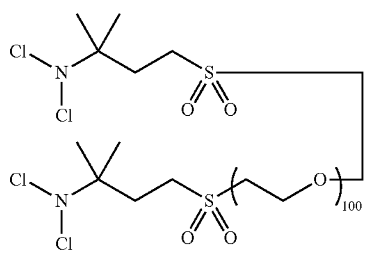 |
| chloro[4-(302-{[3-(chloroamino)-3-methylbutane]sulfonyl}-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156,159,162,165,168,171,174,177,180,183,186,189,192,195,198,201,204,207,210,213,216,219,222,225,228,231,234,237,240,243,246,249,252,255,258,261,264,267,270,273,276,279,282,285,288,291,294,297,300-100oxa302ne-1-sulfonyl)-2-methylbutan-2-yl]amine (38-124) | 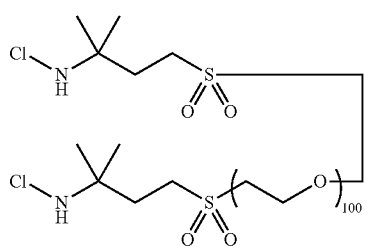 |
| dibromo({4-[(2-{2-[2-(2-{[3-(dibromoamino)-3-methylbutane]sulfonyl}ethoxy)ethoxy]ethoxy}ethane)sufonyl]-2-methylbutan-2-yl})amine (38-125) | |

TABLE 1-continued

| Name (Compound Number) | Structure |
| --- | --- |
| bromo({4-[(2-{2-[2-(2-{[3-(bromoamino)-3-methylbutane]sulfonyl}ethoxy)ethoxy]ethoxy}ethane)sufonyl]-2-methylbutan-2-yl})amine (38-126) | |
| dibromo[4-(32-{[3-(dibromoamino)-3-methylbutane]sulfonyl}-3,6,9,12,15,18,21,24,27,30-decaoxadotriacontane-1-sulfonyl)-2-methylbutan-2-yl]amine (38-127) | 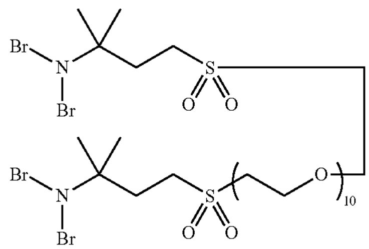 |
| bromo[4-(32-{[3-(bromoamino)-3-methylbutane]sulfonyl}-3,6,9,12,15,18,21,24,27,30-decaoxadotriacontane-1-sulfonyl)-2-methylbutan-2-yl]amine (38-128) | 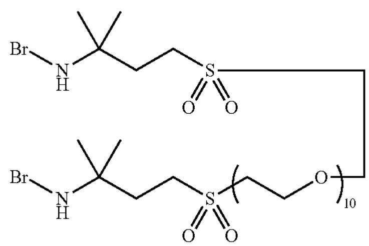 |
| dibromo[4-(302-{[3-(dibromoamino)-3-methylbutane]sulfonyl}-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156,159,162,165,168,171,174,177,180,183,186,189,192,195,198,201,204,207,210,213,216,219,222,225,228,231,234,237,240,243,246,249,252,255,258,261,264,267,270,273,276,279,282,285,288,291,294,297,300-100oxa302ne-1-sulfonyl)-2-methylbutan-2-yl]amine (38-129) | 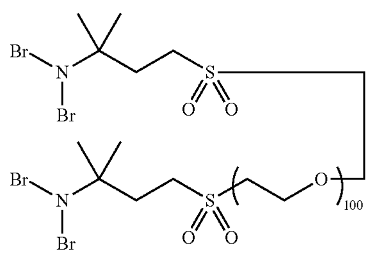 |
| bromo[4-(302{[3-(bromoamino)-3-methylbutane]sulfonyl}-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156,159,162,165,168,171,174,177,180,183,186,189,192,195,198,201,204,207,210,213,216,219,222,225,228,231,234,237,240,243,246,249,252,255,258,261,264,267,270,273,276,279,282,285,288,291,294,297,300-100oxa302ne-1-sulfonyl)-2-methylbutan-2-yl]amine (38-130) | 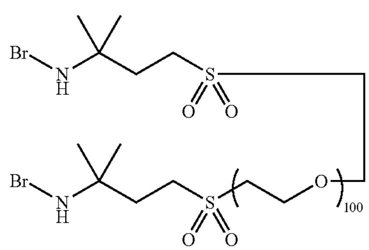 |
| 136-{[3-(dichloroamino)-3-methylbutane]sulfonyl}-2,5,8,11,14,17,20,23,26,29,32,35,38,41,44,47,50,53,56,59,62,65,68,71,74,77,80,83,86,89,92,95,98,101,104,107,110,113,116,119,122,125,128,131,134-pentatetracontaoxa136ne (38-131) | 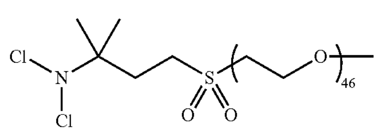 |
| 136-{[3-(chloroamino)-3-methylbutane]sulfonyl}-2,5,8,11,14,17,20,23,26,29,32,35,38,41,44,47,50,53,56,59,62,65,68,71,74,77,80,83,86,89,92,95,98,101,104,107,110,113,116,119,122,125,128,131,134-pentatetracontaoxa136ne (38-132) | 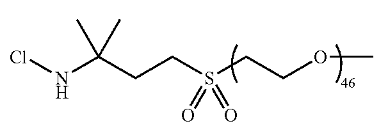 |

TABLE 1-continued

| Name (Compound Number) | Structure |
| --- | --- |
| N-(2-butoxyethyl)-3-(dichloroamino)-N,N,3-trimethylbutan-1-aminium chloride (38-133) | 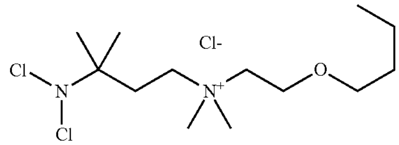 [SMILES: CCCCOCC[N+](C)(C)CCC(C)(C)N(Cl)Cl ; [Cl-]] |
| N-(2-butoxyethyl)-3-(chloroamino)-N,N,3-trimethylbutan-1-aminium chloride (38-134) | 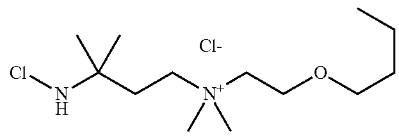 [SMILES: CCCCOCC[N+](C)(C)CCC(C)(C)NCl ; [Cl-]] |
| 3-(dichloroamino)-N-(2-(hexyloxy)ethyl)-N,N,3-trimethylbutan-1-aminium 4-methylbenzenesulfonate (38-135) | 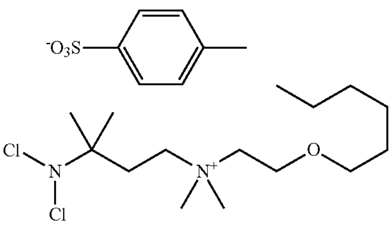 |
| 3-(chloroamino)-N-(2-(hexyloxy)ethyl)-N,N,3-trimethylbutan-1-aminium 4-methylbenzenesulfonate (38-136) | 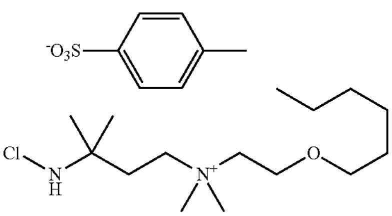 |
| 3-(dichloroamino)-N-(3-methoxypropyl)-N,N,3-trimethylbutan-1-aminium chloride (38-137) | 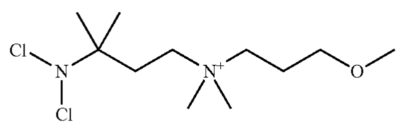 [SMILES: COCCC[N+](C)(C)CCC(C)(C)N(Cl)Cl] |
| 3-(chloroamino)-N-(3-methoxypropyl)-N,N,3-trimethylbutan-1-aminium chloride (38-138) | 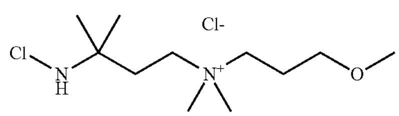 |
| 1-(3-(dichloroamino)-3-methylbutylsulfonyl)-3-(2-(2-methoxyethoxy)ethoxy)propan-2-ol (38-139) | 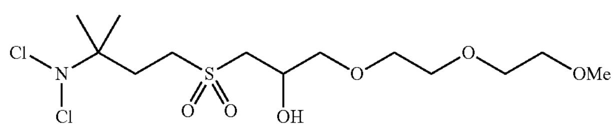 [SMILES: COCCOCCOCC(O)CS(=O)(=O)CCC(C)(C)N(Cl)Cl] |
| 1-(3-(chloroamino)-3-methylbutylsulfonyl)-3-(2-(2-methoxyethoxy)ethoxy)propan-2-ol (38-140) | 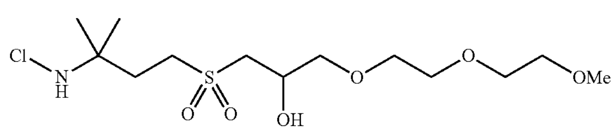 [SMILES: COCCOCCOCC(O)CS(=O)(=O)CCC(C)(C)NCl] |
| 2-((3-(dichloroamino)-3-methylbutylsulfonyl)methyl)-6-methoxytetrahydro-2H-pyran-3,4,5-triol (38-141) | 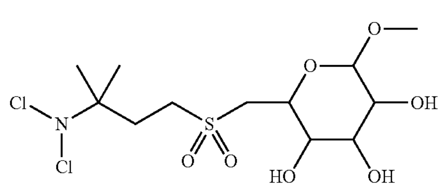 [SMILES: COC1OC(CS(=O)(=O)CCC(C)(C)N(Cl)Cl)C(O)C(O)C1O] |

TABLE 1-continued

| Name (Compound Number) | Structure |
|---|---|
| 2-((3-(chloroamino)-3-methylbutylsulfonyl)methyl)-6-methoxytetrahydro-2H-pyran-3,4,5-triol (38-142) | 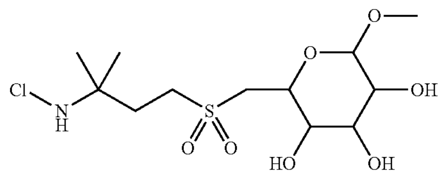 [SMILES: COC1OC(CS(=O)(=O)CCC(C)(C)NCl)C(O)C(O)C1O] |
| 2-((3-(dichloroamino)-3-methylbutylsulfonyl)methyl)-6-(hydroxymethyl)tetrahydro-2H-pyran-3,4,5-triol (38-143) | 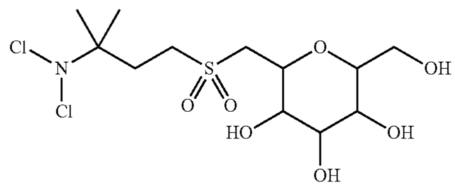 [SMILES: CC(C)(CCS(=O)(=O)CC1OC(CO)C(O)C(O)C1O)N(Cl)Cl] |
| 2-((3-(chloroamino)-3-methylbutylsulfonyl)methyl)-6-(hydroxymethyl)tetrahydro-2H-pyran-3,4,5-triol (38-144) | 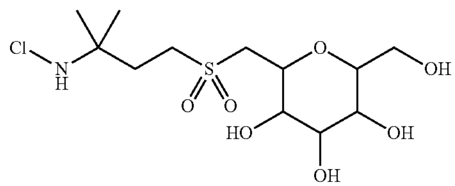 [SMILES: CC(C)(CCS(=O)(=O)CC1OC(CO)C(O)C(O)C1O)NCl] |
| 3-(3-(dichloroamino)-3-methylbutylsulfonyl)butane-1,2,4-triol (38-145) | 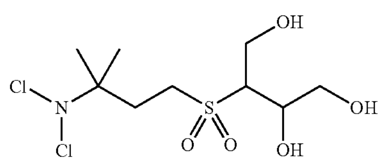 [SMILES: CC(C)(CCS(=O)(=O)C(CO)C(O)CO)N(Cl)Cl] |
| 3-(3-(chloroamino)-3-methylbutylsulfonyl)butane-1,2,4-triol (38-146) | 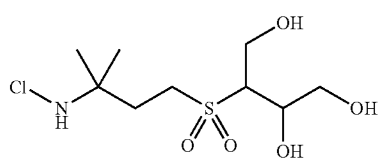 [SMILES: CC(C)(CCS(=O)(=O)C(CO)C(O)CO)NCl] |
| 13-{[3-(dichloroamino)-3-methylbutane]sulfonyl}-2,5,8,11-tetraoxatridecane (38-147) | 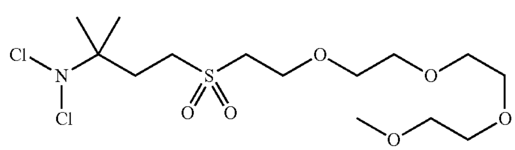 [SMILES: COCCOCCOCCOCCS(=O)(=O)CCC(C)(C)N(Cl)Cl] |
| 13-{[3-(chloroamino)-3-methylbutane]sulfonyl}-2,5,8,11-tetraoxatridecane (38-148) | 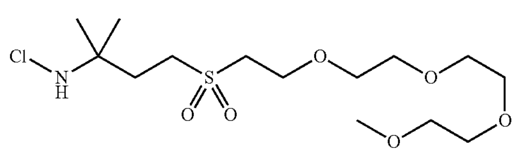 [SMILES: COCCOCCOCCOCCS(=O)(=O)CCC(C)(C)NCl] |
| 3-(dichloroamino)-N-(3-hydroxypropyl)-N,3-dimethylbutane-1-sulfonamide (38-149) | 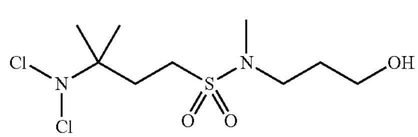 [SMILES: CN(CCCO)S(=O)(=O)CCC(C)(C)N(Cl)Cl] |
| 3-(chloroamino)-N-(3-hydroxypropyl)-N,3-dimethylbutane-1-sulfonamide (38-150) | 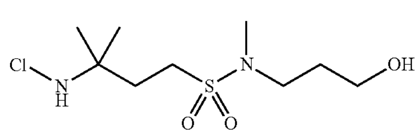 [SMILES: CN(CCCO)S(=O)(=O)CCC(C)(C)NCl] |
| 3-(dichloroamino)-N-(3-hydroxypropyl)-N,N,3-trimethylbutan-1-aminium (38-151) | 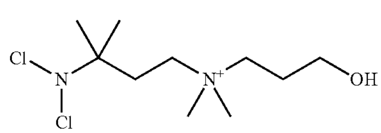 |

TABLE 1-continued

| Name (Compound Number) | Structure |
|---|---|
| 3-(chloroamino)-N-(3-hydroxypropyl)-N,N,3-trimethylbutan-1-aminium (38-152) | 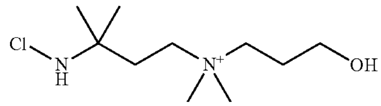 |
| 4-(dichloroamino)-N-(2-methoxyethyl)-4-methylpentanamide (38-153) | 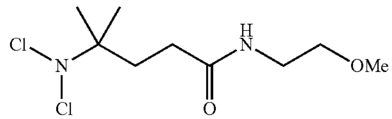 |
| 4-(chloroamino)-N-(2-methoxyethyl)-4-methylpentanamide (38-154) | 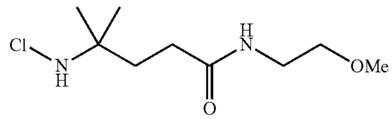 |
| 4-(dichloroamino)-N-(2-methoxyethyl)-N,4-dimethylpentanamide (38-155) | 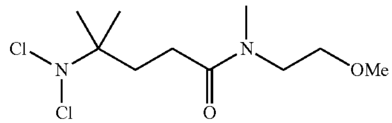 [SMILES: COCCN(C)C(=O)CCC(C)(C)N(Cl)Cl] |
| 4-(chloroamino)-N-(2-methoxyethyl)-N,4-dimethylpentanamide (38-156) | 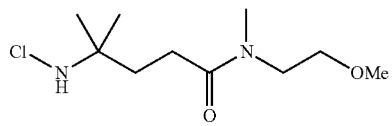 |
| N-(3-(dichloroamino)-3-methylbutyl)-3-methoxypropanamide (38-157) | 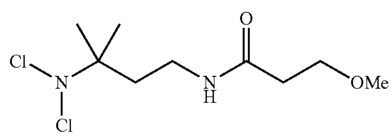 |
| N-(3-(chloroamino)-3-methylbutyl)-3-methoxypropanamide (38-158) | 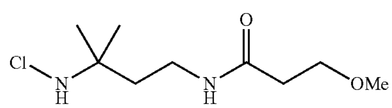 |
| 16-(dichloroamino)-N-(2-(dichloroamino)-2-methylpropyl)-N,N,13,16-tetramethyl-12-oxo-3,6,9-trioxa-13-azaheptadecan-1-aminium chloride (38-159) | 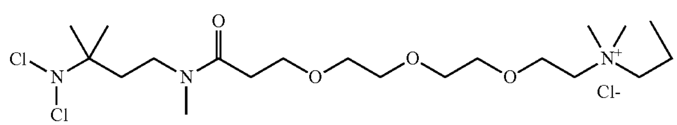 [SMILES: CCC[N+](C)(C)CCOCCOCCOCCC(=O)N(C)CCC(C)(C)N(Cl)Cl ; [Cl-]] |
| 16-(chloroamino)-N-(2-(chloroamino)-2-methylpropyl)-N,N,13,16-tetramethyl-12-oxo-3,6,9-trioxa-13-azaheptadecan-1-aminium chloride (38-160) | 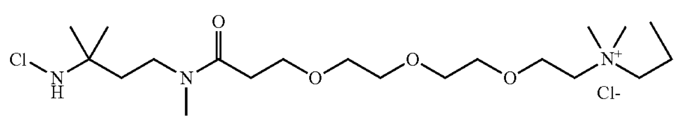 [SMILES: CCC[N+](C)(C)CCOCCOCCOCCC(=O)N(C)CCC(C)(C)NCl ; [Cl-]] |
| 2-hydroxyethyl 3-(dichloroamino)-3-methylbutylcarbamate (38-161) | 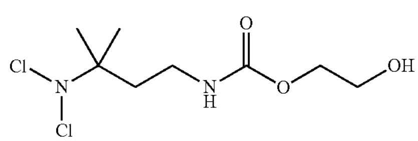 |
| 2-hydroxyethyl 3-(chloroamino)-3-methylbutylcarbamate (38-162) | 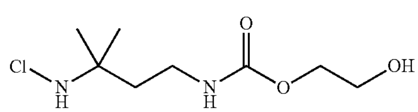 |
| 3-(dichloroamino)-3-methylbutyl 2-hydroxyethylcarbamate (38-163) | 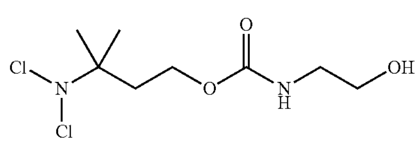 |

TABLE 1-continued

| Name (Compound Number) | Structure |
|---|---|
| 3-(chloroamino)-3-methylbutyl 2-hydroxyethylcarbamate (38-164) | Cl-NH-C(CH₃)₂-CH₂CH₂-O-C(=O)-NH-CH₂CH₂-OH |
| N,N-dichloro-5-fluoro-7-(2-methoxyethoxy)-2-methylheptan-2-amine (38-165) | Cl₂N-C(CH₃)₂-CH₂CH₂-CHF-CH₂CH₂-O-CH₂CH₂-OMe |
| N-chloro-5-fluoro-7-(2-methoxyethoxy)-2-methylheptan-2-amine (38-166) | Cl-NH-C(CH₃)₂-CH₂CH₂-CHF-CH₂CH₂-O-CH₂CH₂-OMe |
| N,N-dichloro-5,5-difluoro-7-(2-methoxyethoxy)-2-methylheptan-2-amine (38-167) | Cl₂N-C(CH₃)₂-CH₂CH₂-CF₂-CH₂CH₂-O-CH₂CH₂-OMe |
| N-chloro-5,5-difluoro-7-(2-methoxyethoxy)-2-methylheptan-2-amine (38-168) | Cl-NH-C(CH₃)₂-CH₂CH₂-CF₂-CH₂CH₂-O-CH₂CH₂-OMe |
| N,N-dichloro-7-(2-methoxyethoxy)-2-methyl-5-(trifluoromethyl)heptan-2-amine (38-169) | Cl₂N-C(CH₃)₂-CH₂CH₂-CH(CF₃)-CH₂CH₂-O-CH₂CH₂-OMe |
| N-chloro-7-(2-methoxyethoxy)-2-methyl-5-(trifluoromethyl)heptan-2-amine (38-170) | Cl-NH-C(CH₃)₂-CH₂CH₂-CH(CF₃)-CH₂CH₂-O-CH₂CH₂-OMe |
| 3-(dichloroamino)-3-methylbutan-1-ol (38-171) | Cl₂N-C(CH₃)₂-CH₂CH₂-OH |
| 3-(chloroamino)-3-methylbutan-1-ol (38-172) | Cl-NH-C(CH₃)₂-CH₂CH₂-OH |
| 4-(dichloroamino)-4-methylpentan-1-ol (38-173) | Cl₂N-C(CH₃)₂-CH₂CH₂CH₂-OH |
| 4-(chloroamino)-4-methylpentan-1-ol (38-174) | Cl-NH-C(CH₃)₂-CH₂CH₂CH₂-OH |

TABLE 2

| Name (Compound No.) | Structure |
| --- | --- |
| 1-chloro-3-(2-methoxyethyl)-2,2,5,5-tetramethylimidazolidin-4-one (39-01) | 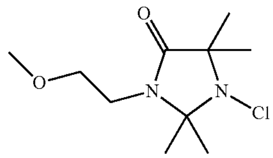 |
| 1-chloro-3-(2-hydroxyethyl)-2,2,5,5-tetramethylimidazolidin-4-one (39-02) | 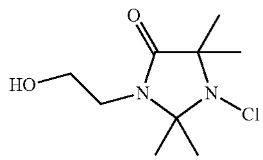 |
| 1-chloro-3-(2-(2-hydroxyethoxy)ethyl)-2,2,5,5-tetramethylimidazolidin-4-one (39-03) | 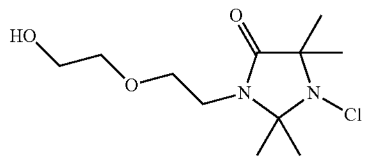 [SMILES: CC1(C)C(=O)N(CCOCCO)C(C)(C)N1Cl] |
| 1-chloro-3-(2-(2-(2-methoxyethoxy)ethoxy)ethyl)-2,2,5,5-tetramethylimidazolidin-4-one (39-04) | 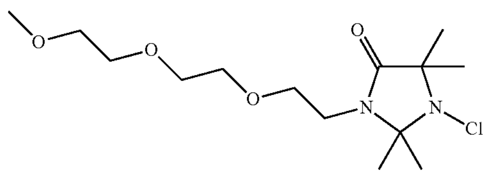 [SMILES: COCCOCCOCCN1C(=O)C(C)(C)N(Cl)C1(C)C] |
| 1-bromo-3-(2-(2-(2-methoxyethoxy)ethoxy)ethyl)-2,2,5,5-tetramethylimidazolidin-4-one (39-05) | 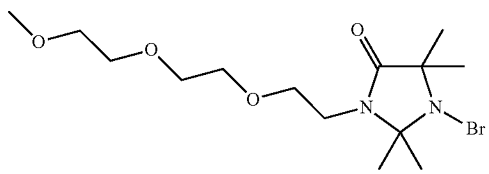 [SMILES: COCCOCCOCCN1C(=O)C(C)(C)N(Br)C1(C)C] |
| 1-chloro-3-(2-(2-(2-hydroxyethoxy)ethoxy)ethyl)-2,2,5,5-tetramethylimidazolidin-4-one (39-06) | 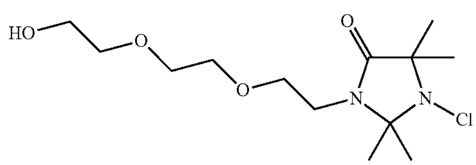 [SMILES: CC1(C)C(=O)N(CCOCCOCCO)C(C)(C)N1Cl] |
| 1-bromo-3-(2-(2-(2-hydroxyethoxy)ethoxy)ethyl)-2,2,5,5-tetramethylimidazolidin-4-one (39-07) | 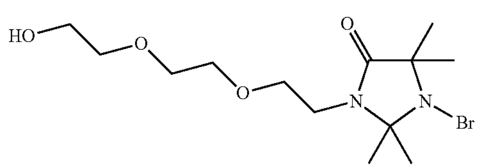 [SMILES: CC1(C)C(=O)N(CCOCCOCCO)C(C)(C)N1Br] |
| 1-chloro-3-(2-(2-(2-ethoxyethoxy)ethoxy)ethyl)-2,2,5,5-tetramethylimidazolidin-4-one (39-08) | 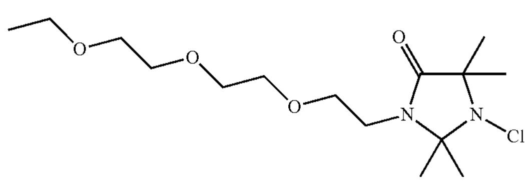 [SMILES: CCOCCOCCOCCN1C(=O)C(C)(C)N(Cl)C1(C)C] |
| 1-bromo-3-(2-(2-(2-ethoxyethoxy)ethoxy)ethyl)-2,2,5,5-tetramethylimidazolidin-4-one (39-09) | 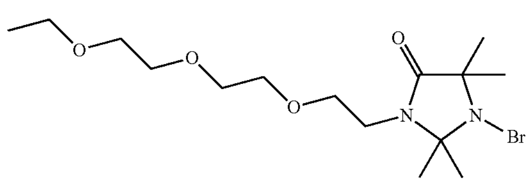 [SMILES: CCOCCOCCOCCN1C(=O)C(C)(C)N(Br)C1(C)C] |

TABLE 2-continued

| Name (Compound No.) | Structure |
| --- | --- |
| 2-(2-(2-(3-chloro-2,2,4,4-tetramethyl-5-oxoimidazolidin-1-yl)ethoxy)ethoxy)ethyl acetate (39-10) | 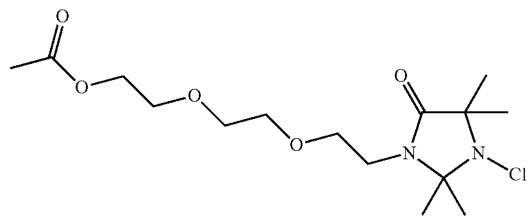 [SMILES: CC(=O)OCCOCCOCCN1C(=O)C(C)(C)N(Cl)C1(C)C] |
| 3-(2-(2-(2-tert-butoxyethoxy)ethoxy)ethyl-1-chloro-2,2,5,5-tetramethylimidazolidin-4-one (39-11) | 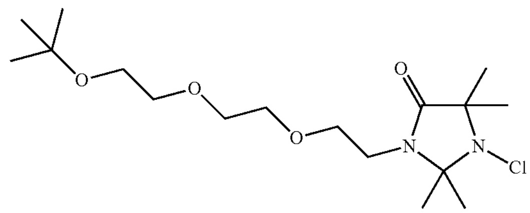 [SMILES: CC(C)(C)OCCOCCOCCN1C(=O)C(C)(C)N(Cl)C1(C)C] |
| 1-chloro-2,2,5,5-tetramethyl-3-(2,5,8,11-tetraoxatridecan-13-yl)imidazolidin-4-one (39-12) | 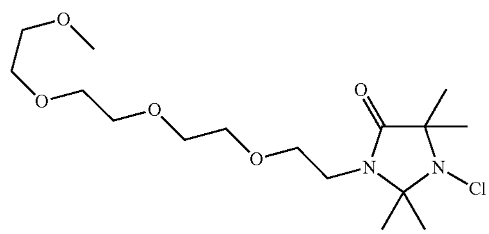 [SMILES: COCCOCCOCCOCCN1C(=O)C(C)(C)N(Cl)C1(C)C] |
| 1-bromo-2,2,5,5-tetramethyl-3-(2,5,8,11-tetraoxatridecan-13-yl)imidazolidin-4-one (39-13) | 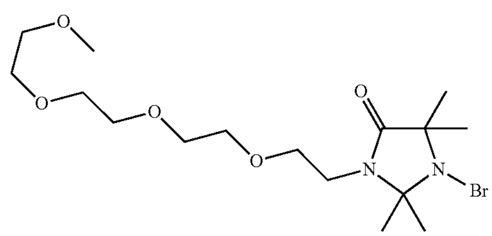 [SMILES: COCCOCCOCCOCCN1C(=O)C(C)(C)N(Br)C1(C)C] |
| 1-chloro-3-(2-(2-(2-(2-hydroxyethoxy)ethoxy)ethoxy)ethyl)-2,2,5,5-tetramethylimidazolidin-4-one (39-14) | 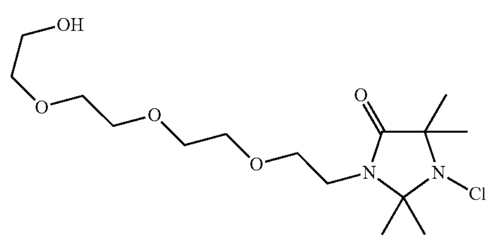 [SMILES: CC1(C)C(=O)N(CCOCCOCCOCCO)C(C)(C)N1Cl] |
| 1-bromo-3-(2-(2-(2-(2-hydroxyethoxy)ethoxy)ethoxy)ethyl-2,2,5,5-tetramethylimidazolidin-4-one (39-15) | 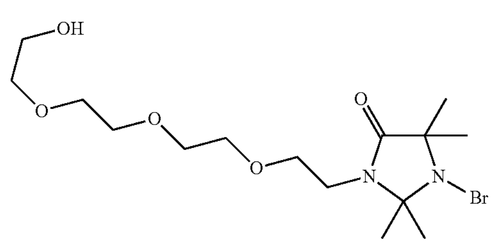 [SMILES: CC1(C)C(=O)N(CCOCCOCCOCCO)C(C)(C)N1Br] |

TABLE 2-continued

| Name (Compound No.) | Structure |
|---|---|
| 1-chloro-3-(2,5,8,11,14-pentaoxahexadecan-16-yl)-2,2,5,5-tetramethylimidazolidin-4-one (39-16) | 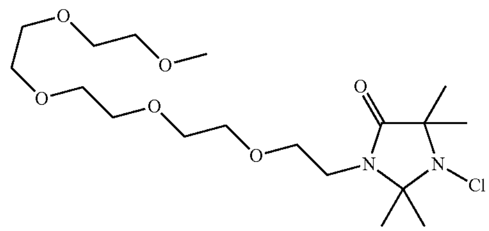 [SMILES: COCCOCCOCCOCCOCCN1C(=O)C(C)(C)N(Cl)C1(C)C] |
| 1-bromo-3-(2,5,8,11,14-pentaoxahexadecan-16-yl)-2,2,5,5-tetramethylimidazolidin-4-one (39-17) | 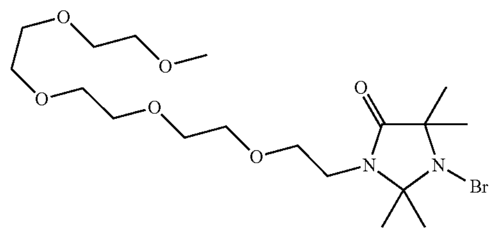 [SMILES: COCCOCCOCCOCCOCCN1C(=O)C(C)(C)N(Br)C1(C)C] |
| 1-chloro-2,2,5,5-tetramethyl-3-(2,5,8,11,14,17-hexaoxanonadecan-19-yl)imidazolidin-4-one (39-18) | 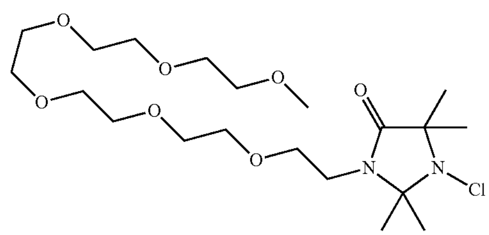 [SMILES: COCCOCCOCCOCCOCCOCCN1C(=O)C(C)(C)N(Cl)C1(C)C] |
| 1-bromo-2,2,5,5-tetramethyl-3-(2,5,8,11,17-hexaoxanonadecan-19-yl)imidazolidin-4-one (39-19) | 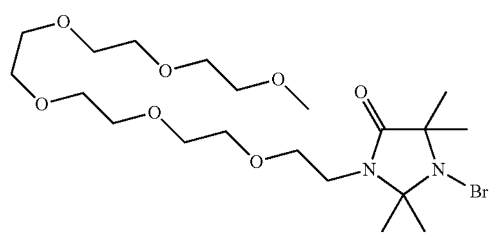 [SMILES: COCCOCCOCCOCCOCCOCCN1C(=O)C(C)(C)N(Br)C1(C)C] |
| 1-bromo-3-(2,5,8,11,14,17,20,23,26,29-decaoxahentriacontan-31-yl)-2,2,5,5-tetramethylimidazolidin-4-one (39-20) | 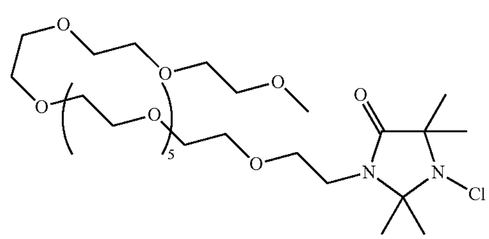 |
| 1-bromo-3-(2,5,8,11,14,17,20,23,26,29-decaoxahentriacontan-31-yl)-2,2,5,5-tetramethylimidazolidin-4-one (39-21) | 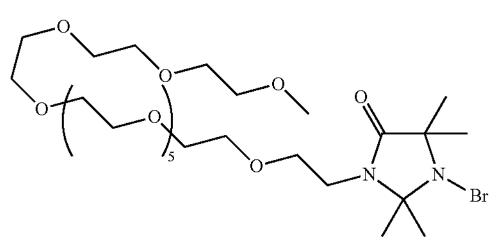 |

TABLE 2-continued

| Name (Compound No.) | Structure |
|---|---|
| 11-chloro-3-(2,5,8,11,14,17,20,23,26,29,32,35,38,41,44,47,50,53,56,59-icosaoxahenhexacontan-61-yl)-2,2,5,5-tetramethylimidazolidin-4-one (39-22) | 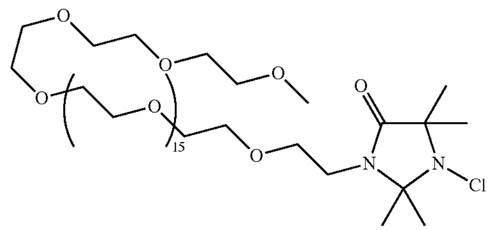 |
| 1-bromo-3-(2,5,8,11,14,17,20,23,26,29,32,35,38,41,44,47,50,53,56,59-icosaoxahenhexacontan-61-yl)-2,2,5,5-tetramethylimidazolidin-4-one (39-23) | 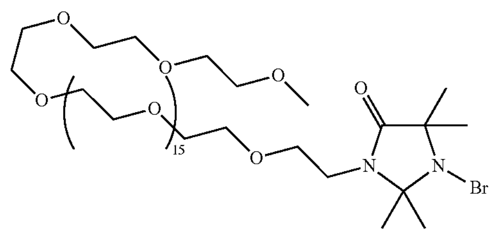 |
| 1-chloro-3-(2,5,8,11,14,17,20,23,26,29,32,35,38,41,44,47,50,53,56,59,62,65,68,71,74,77,80,83,86,89-triacontaoxahennonacontan-91-yl)-2,2,5,5-tetramethylimidazolidin-4-one (39-24) | 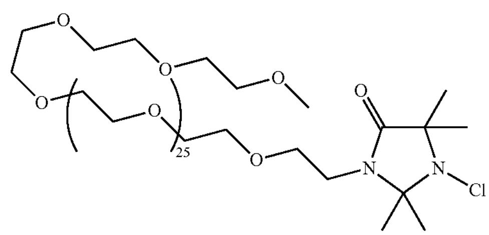 |
| 1-bromo-3-(2,5,8,11,14,17,20,23,26,29,32,35,38,41,44,47,50,53,56,59,62,65,68,71,74,77,80,83,86,89-triacontaoxahennonacontan-91-yl)-2,2,5,5-tetramethylimidazolidin-4-one (39-25) | 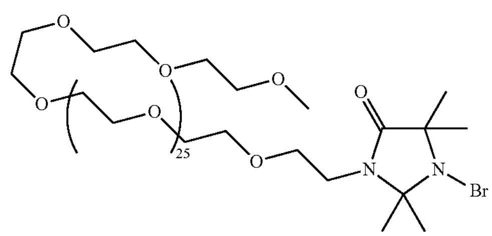 |
| 1-chloro-3-[2-({2-[2-(2-methoxyethoxy)ethoxy]ethane}sulfonyl)ethyl]-2,2,5,5-tetramethylimidazolidin-4-one (39-26) | 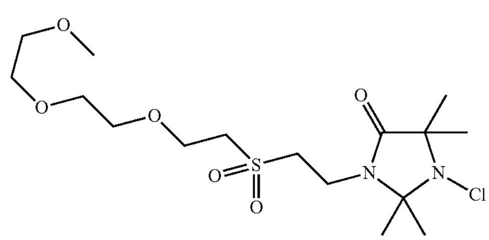 [SMILES: COCCOCCOCCS(=O)(=O)CCN1C(=O)C(C)(C)N(Cl)C1(C)C] |
| 1-chloro-3-(2,3-dihydroxypropyl)-2,2,5,5-tetramethylimidazolidin-4-one (39-27) | 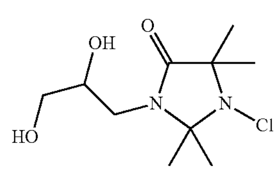 [SMILES: CC1(C)C(=O)N(CC(O)CO)C(C)(C)N1Cl] |
| 1-chloro-2,2,5,5-tetramethyl-3-(2,3,4-trihydroxybutyl)imidazaolidin-4-one (39-28) | 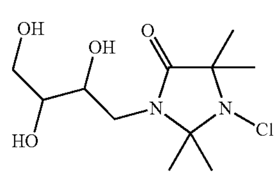 [SMILES: CC1(C)C(=O)N(CC(O)C(O)CO)C(C)(C)N1Cl] |

TABLE 2-continued

| Name (Compound No.) | Structure |
|---|---|
| 1-chloro-2,2,5,5,-tetramethyl-3-(2,3,4,5-tetrahydroxypentyl)imidazolidin-4-one (39-29) | 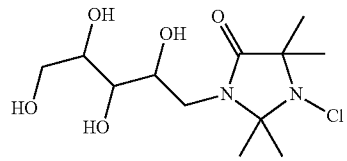 [SMILES: CC1(C)C(=O)N(CC(O)C(O)C(O)CO)C(C)(C)N1Cl] |
| 3,3'-(2,2'-(ethane-1,2-diylbis(oxy))bis(ethane-2,1-diyl))bis(1-chloro-2,2,5,5-tetramethylimidazolidin-4-one) (39-30) | 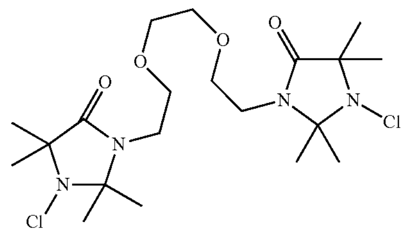 [SMILES: CC1(C)C(=O)N(CCOCCOCCN2C(=O)C(C)(C)N(Cl)C2(C)C)C(C)(C)N1Cl] |
| 3,3'-(2,2'-(ethane-1,2-diylbis(oxy))bis(ethane-2,1-diyl))bis(1-bromo-2,2,5,5-tetramethylimidazolidin-4-one) (39-31) | 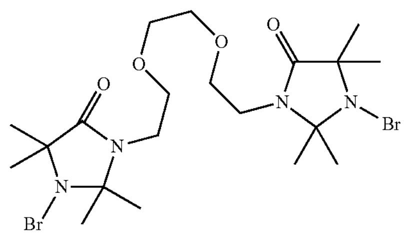 [SMILES: CC1(C)C(=O)N(CCOCCOCCN2C(=O)C(C)(C)N(Br)C2(C)C)C(C)(C)N1Br] |
| 3,3'-(2,2'-(2,2'-oxybis(ethane-2,1-diyl)bis(oxy))bis(ethane-2,1-diyl))bis(1-chloro-2,2,5,5-tetramethylimidazolidin-4-one) (39-32) | 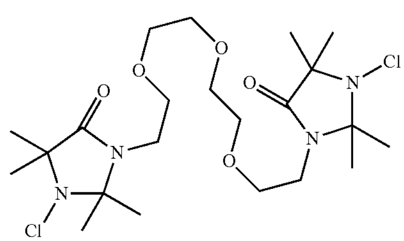 |
| 3,3'-(2,2'-(2,2'-oxybis(ethane-2,1-diyl)bis(oxy))bis(ethane-2,1-diyl))bis(1-bromo-2,2,5,5-tetramethylimidazolidin-4-one) (39-33) | 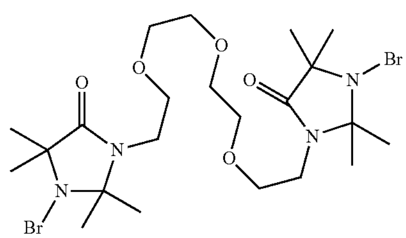 |
| 1-chloro-3-[14-(3-chloro-2,2,4,4-tetramethyl-5-oxoimidazolidin-1-yl)-3,6,9,12-tetraoxatetradecan-1-yl]-2,2,5,5-tetramethylimidazolidin-4-one (39-34) | 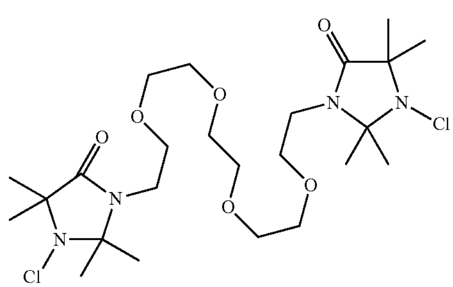 [SMILES: CC1(C)C(=O)N(CCOCCOCCOCCOCCN2C(=O)C(C)(C)N(Cl)C2(C)C)C(C)(C)N1Cl] |

TABLE 2-continued

| Name (Compound No.) | Structure |
|---|---|
| 1-bromo-3-[14-(3-chloro-2,2,4,4-tetramethyl-5-oxoimidazolidin-1-yl)-3,6,9,12-tetraoxatetradecan-1-yl]-2,2,5,5-tetramethylimidazolidin-4-one (39-35) | 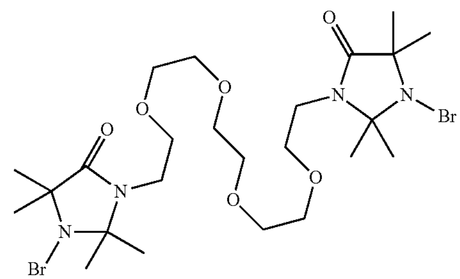 [SMILES: CC1(C)C(=O)N(CCOCCOCCOCCOCCN2C(=O)C(C)(C)N(Br)C2(C)C)C(C)(C)N1Br] |
| 1-chloro-3-[17-(3-chloro-2,2,4,4-tetramethyl-5-oxoimidazolidin-1-yl)-3,6,9,12,15-pentaoxaheptadecan-1-yl]-2,2,5,5-tetramethylimidazolidin-4-one (39-36) | 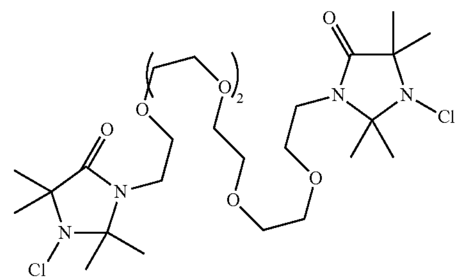 |
| 1-bromo-3-[17-(3-chloro-2,2,4,4-tetramethyl-5-oxoimidazolidin-1-yl)-3,6,9,12,15-pentaoxaheptadecan-1-yl]-2,2,5,5-tetramethylimidazolidin-4-one (39-37) | 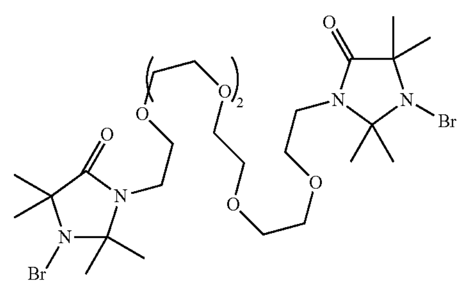 |
| 1-chloro-3-[21-(3-chloro-2,2,4,4-tetramethyl-5-oxoimidazolidin-1-yl)-3,6,9,12,15,19-hexaoxahenicosan-1-yl]-2,2,5,5-tetramethylimidazolidin-4-one (39-38) | 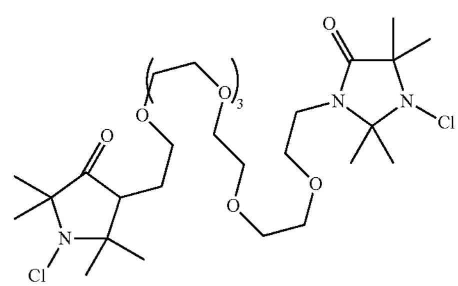 |
| 1-bromo-3-[21-(3-chloro-2,2,4,4-tetramethyl-5-oxoimidazolidin-1-yl)-3,6,9,12,15,19-hexaoxahenicosan-1-y]-2,2,5,5-tetramethylimidazolidin-4-one (39-39) | 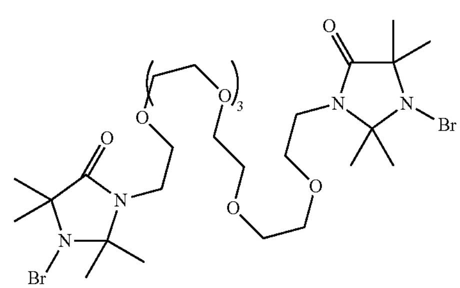 |

TABLE 2-continued

| Name (Compound No.) | Structure |
| --- | --- |
| 1-chloro-3-[23-(3-chloro-2,2,4-tetramethyl-5-oxoimidazolidin-1-yl)-3,6,9,12,15,18,21-heptaoxatricosan-1-yl]-2,2,5,5-tetramethylimidazolidin-4-one (39-40) | |
| 1-bromo-3-[23-(3-chloro-2,2,4-tetramethyl-5-oxoimidazolidin-1-yl)-3,6,9,12,15,18,21-heptaoxatricosan-1-yl]-2,2,5,5-tetramethylimidazolidin-4-one (39-41) | |
| 2-(2-(2-(3-chloro-2,2,4-tetramethyl-5-oxoimidazolidin-1-yl)ethoxy)ethoxy)ethanesulfonic acid (39-42) | |
| 2-(2-(2-(3-chloro-2,2,4-tetramethyl-5-oxoimidazolidin-1-yl)ethoxy)ethoxy)ethanesulfonic acid (39-43) | |
| 2-(2-(2-(2-(3-chloro-2,2,4-tetramethyl-5-oxoimidazolidin-1-yl)ethoxy)ethoxy)ethanesulfonic acid (39-44) | |
| 2-(2-(2-(2-(3-chloro-2,2,4-tetramethyl-5-oxoimidazolidin-1-yl)ethoxy)ethoxy)ethanesulfonic acid (39-45) | |
| 14-(3-chloro-2,2,4,4-tetramethyl-5-oxoimidazolidin-1-yl)-3,6,9,12-tetraoxatetradecane-1-sulfonic acid (39-46) | |
| 14-(3-chloro-2,2,4,4-tetramethyl-5-oxoimidazolidin-1-yl)-3,6,9,12-tetraoxatetradecane-1-sulfonic acid (39-47) | |

TABLE 2-continued

| Name (Compound No.) | Structure |
|---|---|
| 17-(3-chloro-2,2,4,4-tetramethyl-5-oxoimidazolidin-1-yl)-3,6,9,12,15-pentaoxaheptadecane-1-sulfonic acid (39-48) | 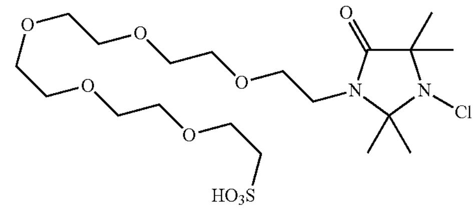 [SMILES: CC1(C)C(=O)N(CCOCCOCCOCCOCCOCCS(=O)(=O)O)C(C)(C)N1Cl] |
| 17-(3-chloro-2,2,4,4-tetramethyl-5-oxoimidazolidin-1-yl)-3,6,9,12,15-pentaoxaheptadecane-1-sulfonic acid (39-49) | 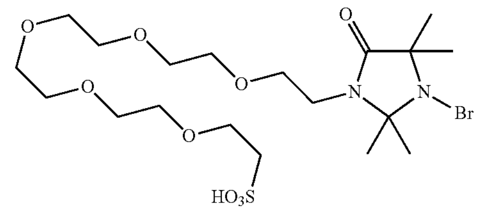 [SMILES: CC1(C)C(=O)N(CCOCCOCCOCCOCCOCCS(=O)(=O)O)C(C)(C)N1Br] |
| 1-chloro-4-(2-(2-(2-methoxyethoxy)ethoxy)ethoxy)-2,2,6,6-tetramethylpiperidine (39-50) | 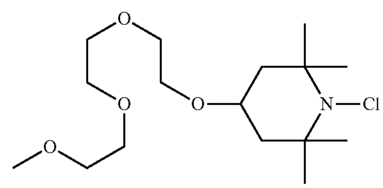 [SMILES: COCCOCCOCCOC1CC(C)(C)N(Cl)C(C)(C)C1] |
| 1-bromo-4-(2-(2-(2-methoxyethoxy)ethoxy)ethoxy)-2,2,6,6-tetramethylpiperidine (39-51) | 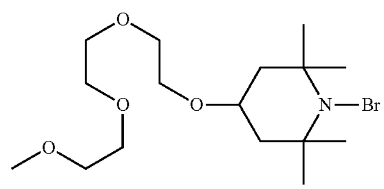 [SMILES: COCCOCCOCCOC1CC(C)(C)N(Br)C(C)(C)C1] |
| 1-chloro-4-(2-(2-(2-methoxyethoxy)ethoxy)ethylsulfonyl)-2,2,6,6-tetramethylpiperidine (39-52) | 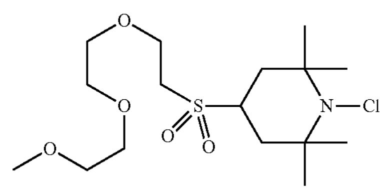 [SMILES: COCCOCCOCCS(=O)(=O)C1CC(C)(C)N(Cl)C(C)(C)C1] |
| 1-bromo-4-(2-(2-(2-methoxyethoxy)ethoxy)ethylsulfonyl)-2,2,6,6-tetramethylpiperidine (39-53) | 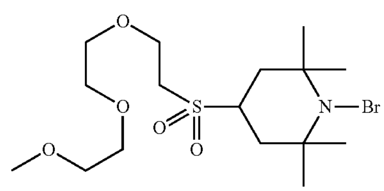 [SMILES: COCCOCCOCCS(=O)(=O)C1CC(C)(C)N(Br)C(C)(C)C1] |
| 4-(2,5,8,11-tetraoxatridecan-13-yloxy)-1-chloro-2,2,6,6-tetramethylpiperidine (39-54) | 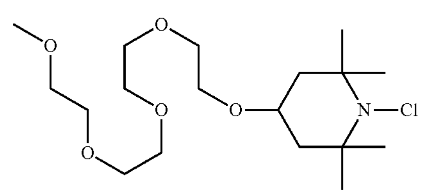 [SMILES: COCCOCCOCCOCCOC1CC(C)(C)N(Cl)C(C)(C)C1] |
| 4-(2,5,8,11-tetraoxatridecan-13-yloxy)-1-bromo-2,2,6,6-tetramethylpiperidine (39-55) | 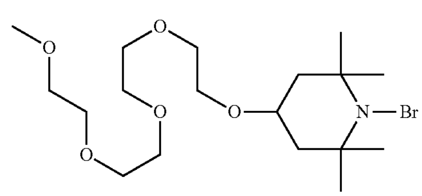 [SMILES: COCCOCCOCCOCCOC1CC(C)(C)N(Br)C(C)(C)C1] |

TABLE 2-continued

| Name (Compound No.) | Structure |
|---|---|
| 2-(2-(2-(2-(1-chloro-2,2,6,6-tetramethylpiperidin-4-yloxy)ethoxy)ethoxy)ethoxy)ethanesulfonic acid (39-56) | 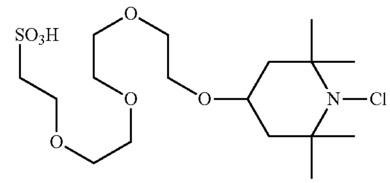 [SMILES: CC1(C)CC(OCCOCCOCCOCCS(=O)(=O)O)CC(C)(C)N1Cl] |
| 2-(2-(2-(2-(1-bromo-2,2,6,6-tetramethylpiperidin-4-yloxy)ethoxy)ethoxy)ethoxy)ethanesulfonic acid (39-57) | 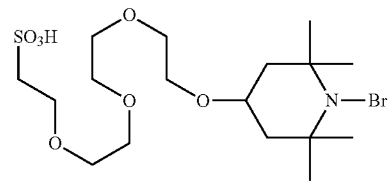 [SMILES: CC1(C)CC(OCCOCCOCCOCCS(=O)(=O)O)CC(C)(C)N1Br] |
| 2-(2-(2-(1-chloro-2,2,6,6-tetramethylpiperidin-4-yloxy)ethoxy)ethoxy)ethanol (39-58) | 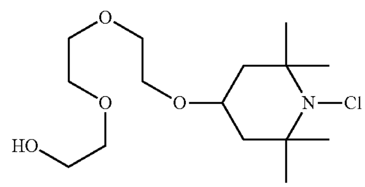 [SMILES: CC1(C)CC(OCCOCCOCCO)CC(C)(C)N1Cl] |
| 2-(2-(2-(1-bromo-2,2,6,6-tetramethylpiperidin-4-yloxy)ethoxy)ethoxy)ethanol (39-59) | 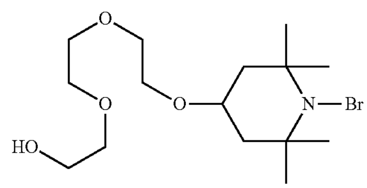 [SMILES: CC1(C)CC(OCCOCCOCCO)CC(C)(C)N1Br] |
| 2-(2-(2-(1-chloro-2,2,6,6-tetramethylpiperidin-4-yloxy)ethoxy)ethoxy)ethanesulfonic acid (39-60) | 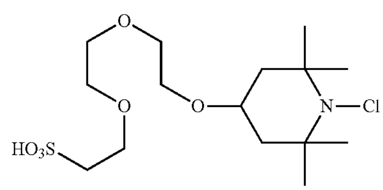 [SMILES: CC1(C)CC(OCCOCCOCCS(=O)(=O)O)CC(C)(C)N1Cl] |
| 2-(2-(2-(1-bromo-2,2,6,6-tetramethylpiperidin-4-yloxy)ethoxy)ethoxy)ethanesulfonic acid (39-61) | 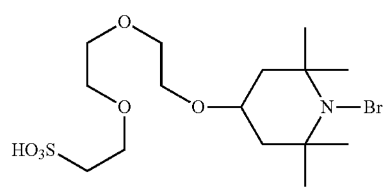 [SMILES: CC1(C)CC(OCCOCCOCCS(=O)(=O)O)CC(C)(C)N1Br] |
| 2-(2-(2-(1-chloro-2,2,6,6-tetramethylpiperidin-4-ylsulfonyl)ethoxy)ethoxy)ethanol (39-62) | 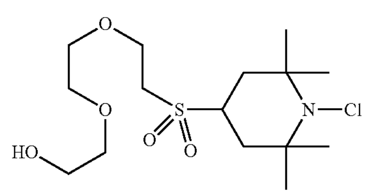 [SMILES: CC1(C)CC(S(=O)(=O)CCOCCOCCO)CC(C)(C)N1Cl] |
| 2-(2-(2-(1-bromo-2,2,6,6-tetramethylpiperidin-4-ylsulfonyl)ethoxy)ethoxy)ethanol (39-63) | 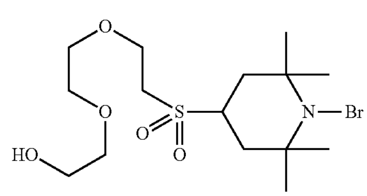 [SMILES: CC1(C)CC(S(=O)(=O)CCOCCOCCO)CC(C)(C)N1Br] |

TABLE 2-continued

| Name (Compound No.) | Structure |
|---|---|
| 3-chloro-4-((2-hydroxyethylsulfonyl)methyl)-4-methyloxazolidin-2-one (39-64) | 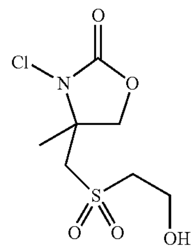 |
| 3-chloro-4-((2,3-dihydroxypropylsulfonyl)methyl)-4-methyloxazolidin-2-one (39-65) | 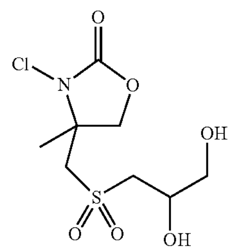 [SMILES: CC1(CS(=O)(=O)CC(O)CO)COC(=O)N1Cl] |
| 3-chloro-4-methyl-4-((2,3,4-trihydroxybutylsulfonyl)methyl)oxazolidin-2-one (39-66) | 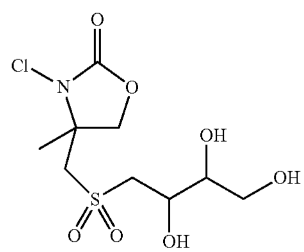 [SMILES: CC1(CS(=O)(=O)CC(O)C(O)CO)COC(=O)N1Cl] |
| 3-chloro-4-[({2-[2-(2-hydroxyethoxy)ethoxy]ethane}sulfonyl)methyl]-4-methyl-1,3-oxazolidin-2-one (39-67) | 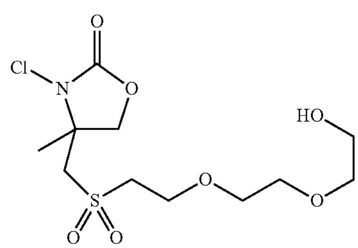 [SMILES: CC1(CS(=O)(=O)CCOCCOCCO)COC(=O)N1Cl] |
| 3-chloro-4-[({2-[2-(2-methoxyethoxy)ethoxy]ethane}sulfonyl)methyl]-4-methyl-1,3-oxazolidin-2-one (39-68) | 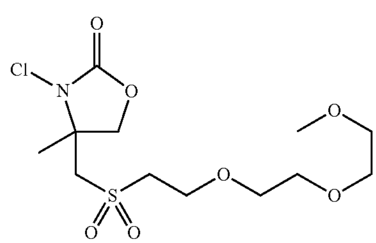 [SMILES: COCCOCCOCCS(=O)(=O)CC1(C)COC(=O)N1Cl] |
| 3-chloro-4-methyl-4-[(2,5,8,11-tetraoxatridecane-13-sulfonyl)methyl]-1,3-oxazolidin-2-one (39-69) | 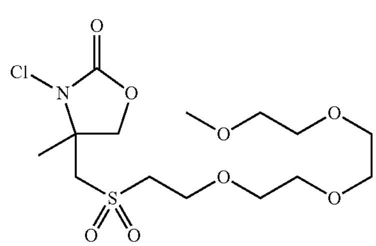 [SMILES: COCCOCCOCCOCCS(=O)(=O)CC1(C)COC(=O)N1Cl] |

TABLE 2-continued

| Name (Compound No.) | Structure |
|---|---|
| 3-chloro-4-{[(2-{2-[2-(2-hydroxyethoxy)ethoxy]ethoxy}ethane)sulfonyl]methyl}-4-methyl-1,3-oxazolidin-2-one (39-70) | 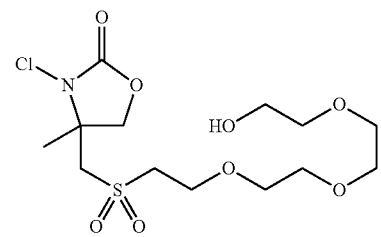 [SMILES: CC1(CS(=O)(=O)CCOCCOCCOCCO)COC(=O)N1Cl] |
| 2-{2-[2-(2-{[(3-chloro-4-methyl-2-oxo-1,3-oxazolidin-4-yl)methane]sulfonyl}ethoxy)ethoxy]ethoxy}ethane-1-sulfonic acid (39-71) | 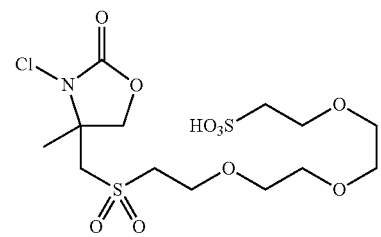 [SMILES: CC1(CS(=O)(=O)CCOCCOCCOCCS(=O)(=O)O)COC(=O)N1Cl] |
| 3-chloro-4-{[(2-{2-[2-(2-{[(3-chloro-4-methyl-2-oxo-1,3-oxazolidin-4-yl)methane]sulfonyl}ethoxy)ethoxy]ethoxy}ethane)sulfonyl]methyl}-4-methyl-1,3-oxazolidin-2-one (39-72) | 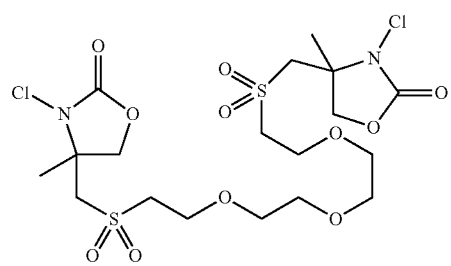 [SMILES: CC1(CS(=O)(=O)CCOCCOCCOCCS(=O)(=O)CC2(C)COC(=O)N2Cl)COC(=O)N1Cl] |
| 3-chloro-4-((2-(2-hydroxyethoxy)ethoxy)methyl)-4-methyloxazolidin-2-one (39-73) | 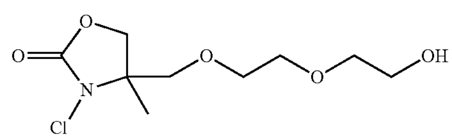 [SMILES: CC1(COCCOCCO)COC(=O)N1Cl] |
| 4-chloro-1-(2-hydroxyethyl)-3,3-dimethylpiperazine-2,5-dione (39-74) | 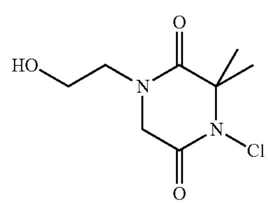 |
| 4-chloro-1-(2-(2-(2-methoxyethoxy)ethoxy)ethyl)-3,3-dimethylpiperazine-2,5-dione (39-75) | 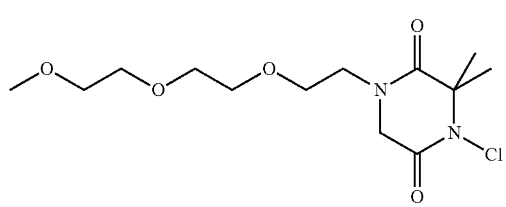 |
| 4-chloro-1-(2,3-dihydroxypropyl)-3,3-dimethylpiperazine-2,5-dione (39-76) | 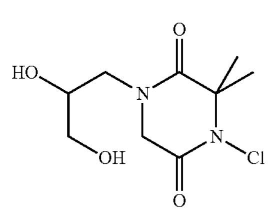 [SMILES: CC1(C)C(=O)N(CC(O)CO)CC(=O)N1Cl] |

TABLE 2-continued

| Name (Compound No.) | Structure |
|---|---|
| 4-chloro-1,3-dimethyl-1-(2,3,4-trihydroxybutyl)piperazine-2,5-dione (39-77) | 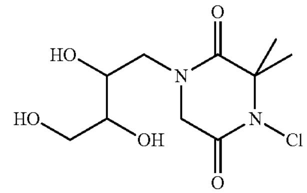 [SMILES: CC1(C)C(=O)N(CC(O)C(O)CO)CC(=O)N1Cl] |
| 1-chloro-3-(2-(2-(2-methoxyethoxy)ethoxy)ethyl)-5,5-dimethylpiperazine-2,4-dione (39-78) | 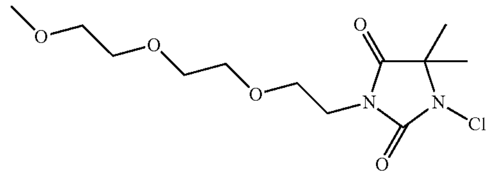 [SMILES: COCCOCCOCCN1C(=O)N(Cl)C(C)(C)C1=O] |
| 1-chloro-3-(2-((2-(2-(2-methoxyethoxy)ethoxy)ethyl)sulfonyl)ethyl)-5,5-dimethylimidazolidine-2,4-dione (39-79) | 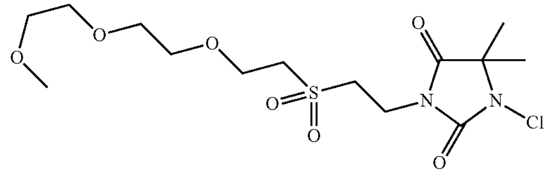 [SMILES: COCCOCCOCCS(=O)(=O)CCN1C(=O)N(Cl)C(C)(C)C1=O] |
| 3-chloro-1-(2-((2-(2-(2-hydroxyethoxy)ethoxy)ethyl)sulfonyl)ethyl)-4,4-dimethylimidazolidin-2-one (39-80) | 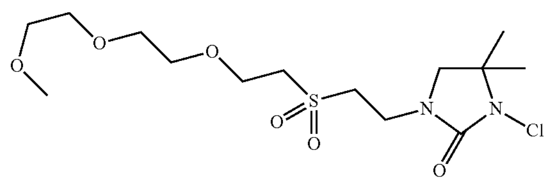 [SMILES: COCCOCCOCCS(=O)(=O)CCN1CC(C)(C)N(Cl)C1=O] |
| 4-chloro-1-(2-hydroxyethyl)-3,3,5,5-tetramethylpiperazin-2-one (39-81) | 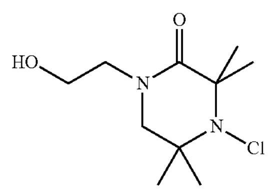 |
| 4-chloro-1-(2-(2-(2-methoxyethoxy)ethoxy)ethyl)-3,3,5,5-tetramethylpiperazin-2-one (39-82) | 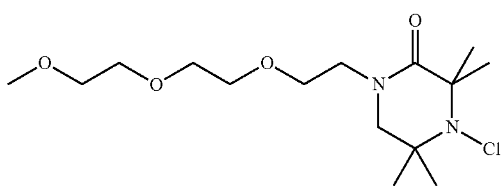 |
| 4-chloro-1-(2,3-dihydroxypropyl)-3,3,5,5-tetramethylpiperazin-2-one (39-83) | 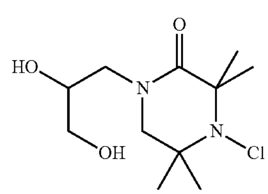 [SMILES: CC1(C)CN(CC(O)CO)C(=O)C(C)(C)N1Cl] |
| 4-chloro-3,3,5,5-tetramethyl-1-(2,3,4-trihydroxybutyl)piperazin-2-one (39-84) | 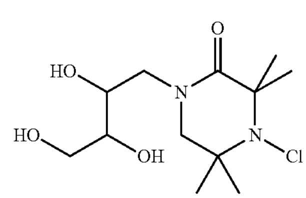 [SMILES: CC1(C)CN(CC(O)C(O)CO)C(=O)C(C)(C)N1Cl] |

TABLE 2-continued

| Name (Compound No.) | Structure |
|---|---|
| 2-(3-chloro-4,4-dimethyl-2-oxoimidazolidin-1-yl)-N-(2-(2-(2-methoxyethoxy)ethoxy)ethyl)-N,N-dimethylethanaminium 4-methylbenzenesulfonate (39-85) | 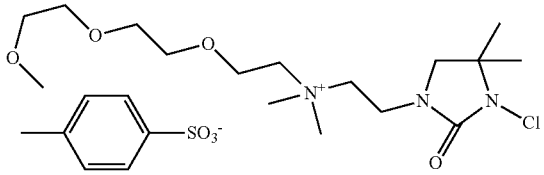 |
| 1-chloro-N,N,2,2,6,6-hexamethyl-N-(2,5,8,11-tetraoxatridecan-13-yl)piperidin-4-aminium 4-methylbenzenesulfonate (39-86) | 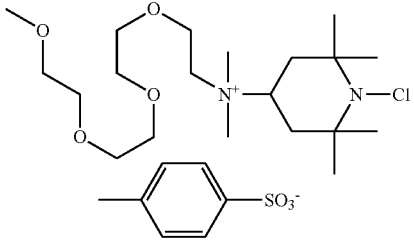 |
| 1-bromo-N,N,2,2,6,6-hexamethyl-N-(2,5,8,11-tetraoxatridecan-13-yl)piperidin-4-aminium 4-methylbenzenesulfonate (39-87) | 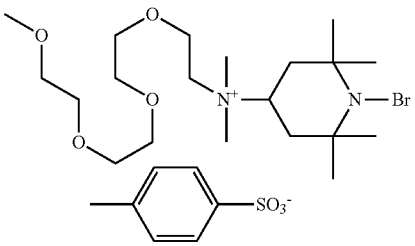 |
| 1-chloro-N,N,2,2,6,6-hexamethyl-N-(2-(2-(2-(2-sulfoethoxy)ethoxy)ethoxy)ethyl)piperidin-4-aminium 4-methylbenzenesulfonate (39-88) | 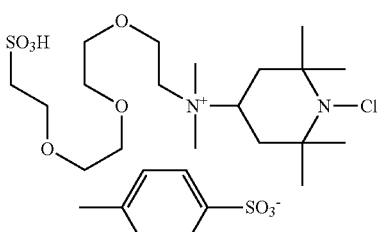 |
| 1-bromo-N,N,2,2,6,6-hexamethyl-N-(2-(2-(2-(2-sulfoethoxy)ethoxy)ethoxy)ethyl)piperidin-4-aminium 4-methylbenzenesulfonate (39-89) | 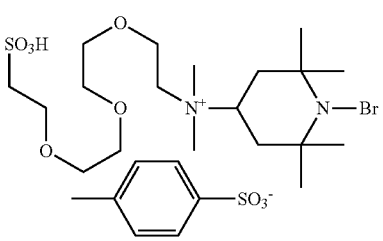 |
| 1-chloro-N-(2-(2-(2-hydroxyethoxy)ethoxy)ethyl)-N,N,2,2,6,6-hexamethylpiperidin-4-aminium 4-methylbenzenesulfonate (39-90) | 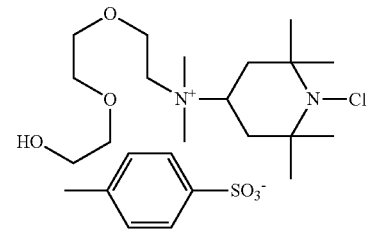 |

TABLE 2-continued

| Name (Compound No.) | Structure |
|---|---|
| 1-bromo-N-(2-(2-(2-hydroxyethoxy)ethoxy)ethyl)-N,N,2,2,6,6-hexamethylpiperidin-4-aminium 4-methylbezenesulfonate (39-91) | 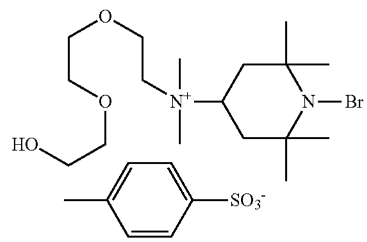 |
| 1-chloro-N,N,2,2,6,6-hexamethyl-N-(2-(2-(2-sulfoethoxy)ethoxy)ethyl)piperidin-4-aminium 4-methylbenzenesulfonate (39-92) | 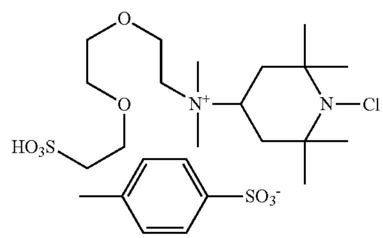 |
| 1-bromo-N,N,2,2,6,6-hexamethyl-N-(2-(2-(2-sulfoethoxy)ethoxy)ethyl)piperidin-4-aminium 4-methylbenzenesulfonate (39-93) | 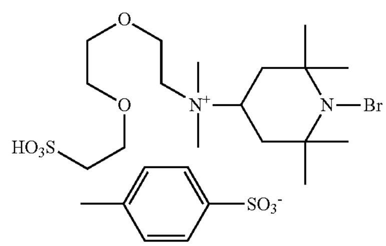 |
| 1-chloro-2,2,5,5-tetramethyl-3-(2,5,8,11,14,17,20,23,26,29,32,35,38,41,44,47,50,53,56,59,62,65,68,71,74,77,80,83,86,89,92,95,98,101,104,107,110,113,116-nonatriacontaoxaoctadecahextan-118-yl)imidazolidin-4-one (39-94) | 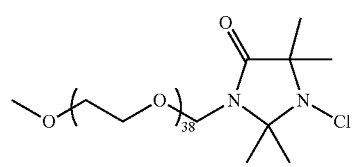 |
| 2-bromo-5-{2-[2-(2-methoxyethoxy)ethoxy]ethyl}-3,3-dimethyl-1$\lambda^6$,2,5-thiazolidine-1,1-dione (39-95) | 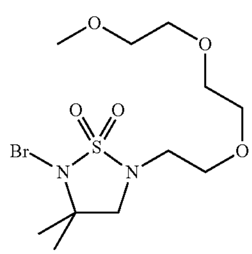 [SMILES: COCCOCCOCCN1CC(C)(C)N(Br)S1(=O)=O] |
| 1-chloro-3-(2-(2-hydroxyethylsulfonyl)ethyl)-2,2,5,5-tetramethylimidazolidin-4-one (39-96) | 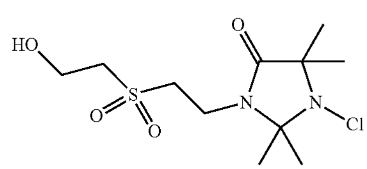 [SMILES: CC1(C)C(=O)N(CCS(=O)(=O)CCO)C(C)(C)N1Cl] |
| 2-chloro-5-{2-[2-(2-methoxyethoxy)ethoxy]ethyl}-3,3-dimethyl-1$\lambda^6$,2,5-thiadiazolidine-1,1-dione (39-97) | 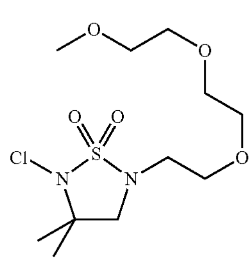 [SMILES: COCCOCCOCCN1CC(C)(C)N(Cl)S1(=O)=O] |

TABLE 2-continued

| Name (Compound No.) | Structure |
| --- | --- |
| 3-(3-(2-(2-tert-butoxyethoxy)ethoxy)propyl)-1-chloro-2,2,5,5-tetramethylimidazolidin-4-one (39-98) | 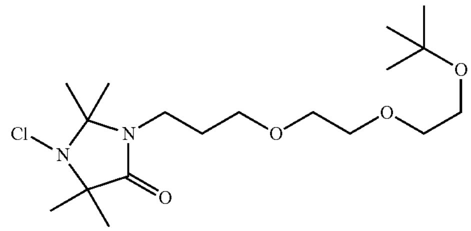 [SMILES: CC(C)(C)OCCOCCOCCCN1C(=O)C(C)(C)N(Cl)C1(C)C] |
| 1-bromo-3-(3-(2-(2-tert-butoxyethoxy)ethoxy)propyl)-2,2,5,5-tetramethylimidazolidin-4-one (39-99) | 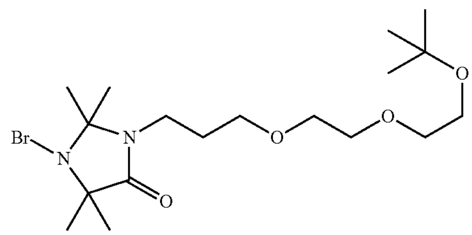 [SMILES: CC(C)(C)OCCOCCOCCCN1C(=O)C(C)(C)N(Br)C1(C)C] |
| 1-chloro-3-(2-(2-methoxyethoxy)ethyl)-2,2,5,5-tetramethylimidazolidin-4-one (39-100) | 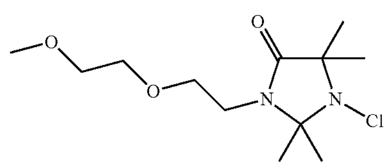 [SMILES: COCCOCCN1C(=O)C(C)(C)N(Cl)C1(C)C] |
| 1-bromo-3-(2-(2-methoxyethoxy)ethyl)-2,2,5,5-tetramethylimidazolidin-4-one (39-101) | 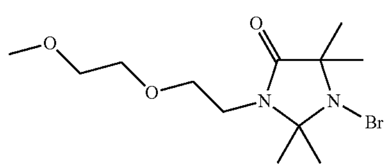 [SMILES: COCCOCCN1C(=O)C(C)(C)N(Br)C1(C)C] |
| 4-chloro-1-(2-(2-(2-hydroxyethoxy)ethoxy)ethyl)-3,3-dimethylpiperazine-2,5-dione (39-102) | 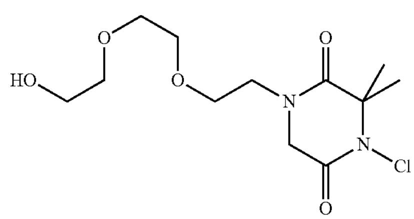 [SMILES: CC1(C)C(=O)N(CCOCCOCCO)CC(=O)N1Cl] |
| 4-bromo-1-(2-(2-(2-methoxyethoxy)ethoxy)ethyl)-3,3-dimethylpiperazine-2,5-dione (39-103) | 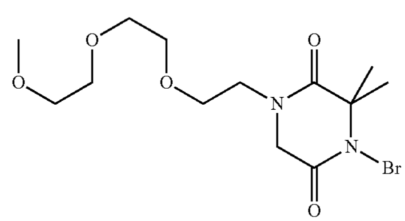 [SMILES: COCCOCCOCCN1CC(=O)N(Br)C(C)(C)C1=O] |
| 4-chloro-1-(2-(2-(2-methoxyethoxy)ethoxy)ethyl)-3,3,5,5-tetramethylpiperazine-2,6-dione (39-104) | 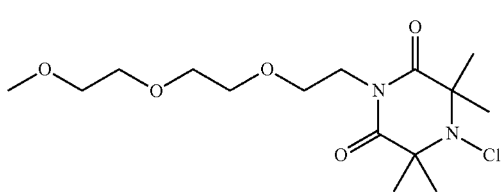 [SMILES: COCCOCCOCCN1C(=O)C(C)(C)N(Cl)C(C)(C)C1=O] |

TABLE 2-continued

| Name (Compound No.) | Structure |
|---|---|
| 4-bromo-1-(2-(2-(2-methoxyethoxy)ethoxy)ethyl)-3,3,5,5-tetramethylpiperazine-2,6-dione (39-105) | 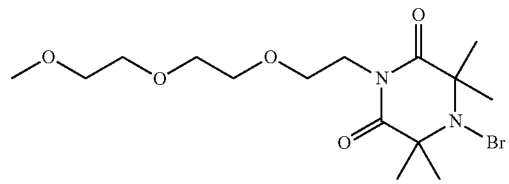 [SMILES: COCCOCCOCCN1C(=O)C(C)(C)N(Br)C(C)(C)C1=O] |
| 4-chloro-1-(2-(2-(2-methoxyethoxy)ethoxy)ethyl)-1,3,3,5,5-pentamethylpiperazin-1-ium chloride (39-106) | 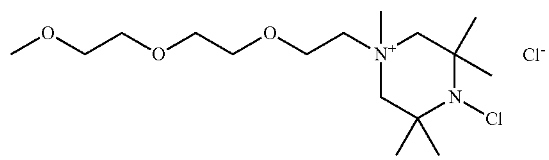 [SMILES: COCCOCCOCC[N+]1(C)CC(C)(C)N(Cl)C(C)(C)C1 ; [Cl-]] |
| 4-bromo-1-(2-(2-(2-methoxyethoxy)ethoxy)ethyl)-1,3,3,5,5-pentamethylpiperazin-1-ium bromide (39-107) | 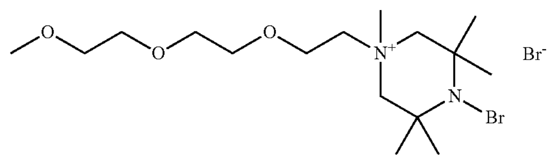 [SMILES: COCCOCCOCC[N+]1(C)CC(C)(C)N(Br)C(C)(C)C1 ; [Br-]] |
| 4-chloro-1-(2-hydroxyethyl)-3,3,5,5-tetramethylpiperazin-2-one (39-108) | 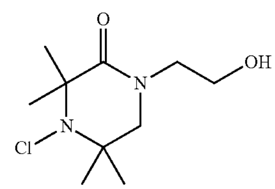 |
| 4-bromo-1-(2-hydroxyethyl)-3,3,5,5-tetramethylpiperazin-2-one (39-109) | 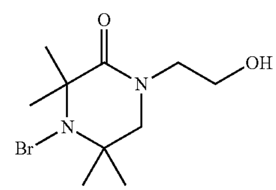 |
| 2-(3-chloro-4,4-dimethyl-2-oxoimidazolidin-1-yl)-N-(2-(2-(2-methoxyethoxy)ethoxy)ethyl)-N,N-dimethylethanaminium 4-methylbenzenesulfonate (39-110) | 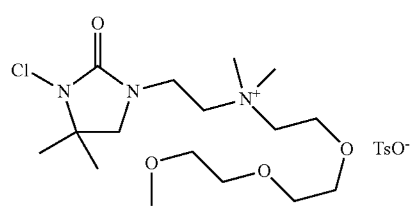 |
| 2-(3-bromo-4,4-dimethyl-2-oxoimidazolidin-1-yl)-N-(2-(2-(2-methoxyethoxy)ethoxy)ethyl)-N,N-dimethylethanaminium 4-methylbenzenesulfonate (39-111) | 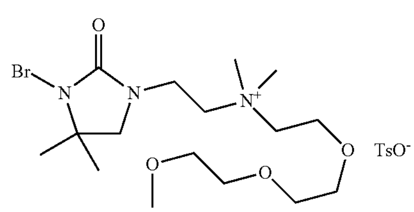 |
| 1-chloro-3-(2-(2-methoxyethoxy)ethyl)-2,2,5,5-tetramethylimidazolidin-4-one (39-112) | 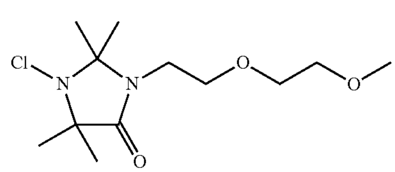 [SMILES: COCCOCCN1C(=O)C(C)(C)N(Cl)C1(C)C] |

TABLE 2-continued

| Name (Compound No.) | Structure |
|---|---|
| 1-bromo-3-(2-(2-methoxyethoxy)ethyl)-2,2,5,5-tetramethylimidazolidin-4-one (39-113) | 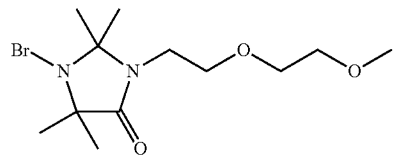 |
| 1-chloro-3-(3-(2-(2-methoxyethoxy)ethoxy)propyl)-2,2,5,5-tetramethylimidazolidin-4-one (39-114) | 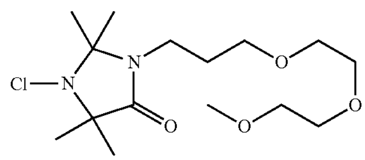 [SMILES: COCCOCCOCCCN1C(=O)C(C)(C)N(Cl)C1(C)C] |
| 1-bromo-3-(3-(2-(2-methoxyethoxy)ethoxy)propyl)-2,2,5,5-tetramethylimidazolidin-4-one (39-115) | 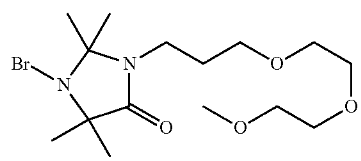 [SMILES: COCCOCCOCCCN1C(=O)C(C)(C)N(Br)C1(C)C] |
| 1-chloro-2,2,5,5-tetramethyl-3-(2,5,8,11,14,17,20,23,26,29,32,35,38,41-tetradecaoxatritetracontan-43-yl)imidazolidin-4-one (39-116) | 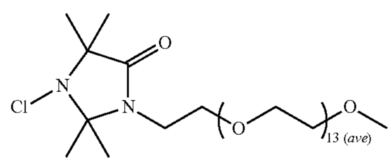 |
| 1-bromo-2,2,5,5-tetramethyl-3-(2,5,8,11,14,17,20,23,26,29,32,35,38,41-tetradecaoxatritetracontan-43-yl)imidazolidin-4-one (39-117) | 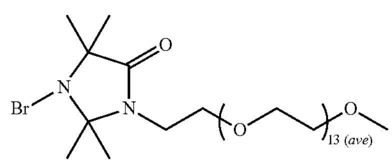 |
| 1-chloro-2,2,5,5-tetramethyl-3-(2,5,8,11,14,17,20,23,26,29,32,35,38,41,44,47,50,53,56,59,62,65,68,71,74,77,80,83,86,89,92,95,98,101,104,107,110,113,116-nonatriacontaoxaoctadecahectan-118-yl)imidazolidin-4-one (39-118) | 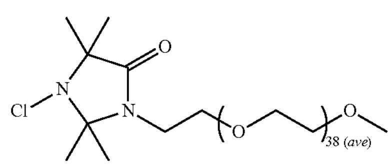 |
| 1-bromo-2,2,5,5-tetramethyl-3-(2,5,8,11,14,17,20,23,26,29,32,35,38,41,44,47,50,53,56,59,62,65,68,71,74,77,80,83,86,89,92,95,98,101,104,107,110,113,116-nonatriacontaoxaoctadecahectan-118-yl)imidazolidin-4-one (39-119) | 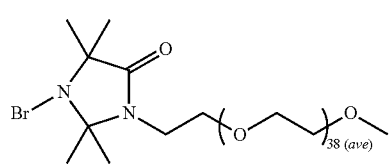 |
| 1-chloro-3-(2-hydroxyethyl)imidazolidin-2-one (39-120) | 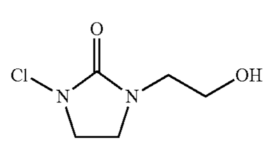 |
| 1-bromo-3-(2-hydroxyethyl)imidazolidin-2-one (39-121) | 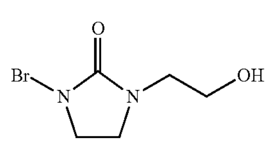 |

TABLE 2-continued

| Name (Compound No.) | Structure |
| --- | --- |
| 3-chloro-5-(hydroxymethyl)-4,4-dimethyloxazolidin-2-one (39-122) | 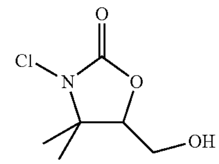 |
| 3-chloro-6-(2-hydroxyethyl)-4,4-dimethyl-1,3-oxazinan-2-one (39-123) | 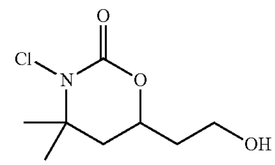 |
| 3-chloro-4-(hydroxymethyl)-1,4-dimethylimidazolidin-2-one (39-124) | 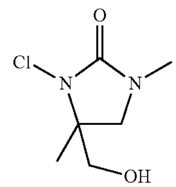 |
| 1-chloro-3-(4-hydroxybutyl)-2,2,5,5-tetramethylimidazolidin-4-one (39-125) | 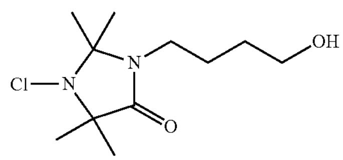 [SMILES: CC1(C)C(=O)N(CCCCO)C(C)(C)N1Cl] |
| 3-(((1,4,7,10,13,16-hexaoxacyclooctadecan-2-yl)methylsulfonyl)methyl)-1-chloro-2,2,5,5-tetramethylimidazolidin-4-one (39-126) | 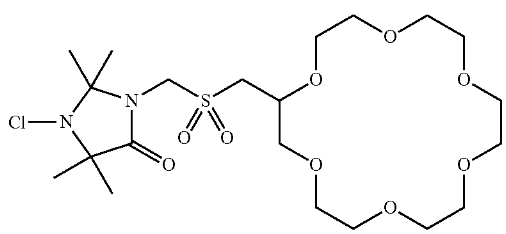 [SMILES: CC1(C)C(=O)N(CS(=O)(=O)CC2COCCOCCOCCOCCOCCO2)C(C)(C)N1Cl] |
| 3-chloro-4,4-dimethyl-1-(2-(((2S,3S,4S,5R,6R)-3,4,5-trihydroxy-6-methoxytetrahydro-2H-pyran-2-yl)methylsulfonyl)ethyl)imidazolidin-2-one (39-127) | 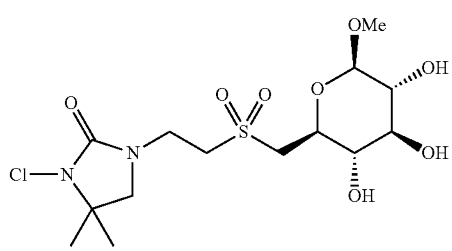 [SMILES: CO[C@@H]1O[C@H](CS(=O)(=O)CCN2CC(C)(C)N(Cl)C2=O)[C@@H](O)[C@H](O)[C@H]1O] |
| 3-chloro-4-((2,3-dihydroxy-5-(2-methoxyethoxy)pentylsulfonyl)methyl)-4-methyloxazolidin-2-one (39-128) | 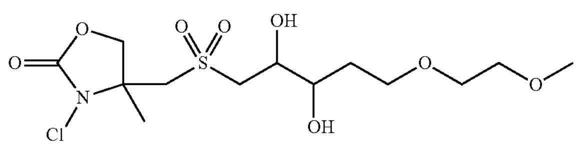 [SMILES: COCCOCCC(O)C(O)CS(=O)(=O)CC1(C)COC(=O)N1Cl] |
| 1-chloro-3-(6,12-dimethyl-2,5,8,11,14-pentaoxahexadecan-16-yl)-5,5-dimethylimidazolidine-2,4-dione (39-129) | 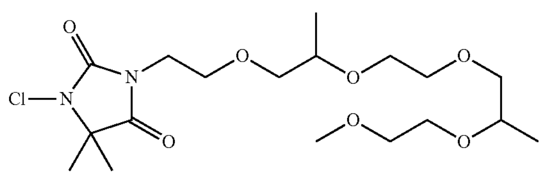 [SMILES: COCCOC(C)COCCOC(C)COCCN1C(=O)N(Cl)C(C)(C)C1=O] |

TABLE 2-continued

| Name (Compound No.) | Structure |
|---|---|
| 1-chloro-2,2,5,5-tetramethyl-3-(2-(((2S,3S,4S,5R,6R)-3,4,5-trihydroxy-6-methoxytetrahydro-2H-pyran-2-yl)methylsulfonyl)ethyl)imidazolidin-4-one (39-130) | 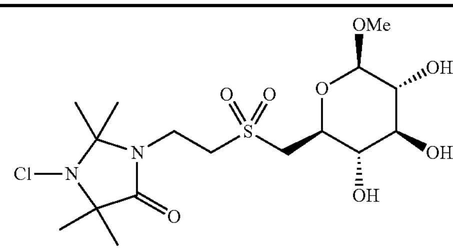 |
| 1-chloro-3-(6,12-dimethyl-2,5,8,11,14-pentaoxahexadecan-16-yl)-2,2,5,5-tetramethylimidazolidin-4-one (39-131) | 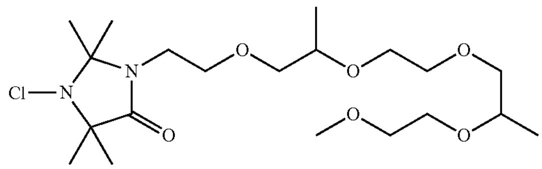 [SMILES: COCCOC(C)COCCOC(C)COCCN1C(=O)C(C)(C)N(Cl)C1(C)C] |
| 1-chloro-2,2,5,5-tetramethyl-3-(2,5,8,11,14,17,20,23,26,29,32,35,38,41-tetradecaoxatritetracontan-43-yl)imidazolidin-4-one (39-132) | 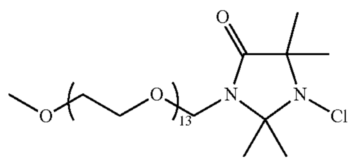 |
| 1-chloro-3-(4-hydroxybutyl)-2,2,5,5-tetramethylimidazolidin-4-one (39-133) | 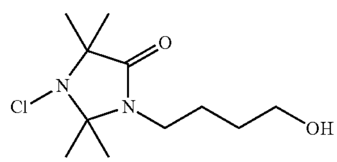 [SMILES: CC1(C)C(=O)N(CCCCO)C(C)(C)N1Cl] |

Compounds described herein may contain one or more polyethylene glycol (PEG) groups (polymers of ethylene oxide). The size of the PEG groups can be characterized by molecular formula, the number of monomer units, or by average molecular weight. It is well known in the art that PEG is available in a wide range of lengths or average molecular weights, and that PEG characterized by average molecular weight will have some distribution in the exact number of monomers in each polymer. Suitable PEG groups are available from Sigma-Aldrich Corporation and other chemical suppliers. In general, and without limiting the scope of this disclosure, compounds described herein may have from about 1 to about 1000 monomers, or PEG groups with average molecular weights from about 44 to about 44,000. For example, compound 38-1 contains 2 ethylene oxide groups (in this compound, X is —(OCH$_2$CH$_2$)$_h$— wherein h is 3, and V is methyl). By way of further example, compound 38-125 has a PEG group with an average molecular weight of about 2000 (an average of about 43 monomers). By way of further example, compound 38-113 has 100 ethylene oxide groups. By way of further example, compound 39-4 contains 2 ethylene oxide groups (in this compound, X is —(OCH$_2$CH$_2$)$_h$— wherein h is 2, and V is methyl). By way of further example, compound 39-24 has a PEG group with an average molecular weight of about 1276 (an average of about 29 monomers). By way of further example, compound 39-23 has 19 ethylene oxide groups.

Certain compounds described herein may contain more than one polyol group. For example, compound 38-97 may be described as containing four polyol groups, two two-carbon groups and two one-carbon groups, and terminates in a hydrogen (i.e., following the description of Formula I, X is —CH$_2$CHOH—, —CH$_2$CHOH—, —CHOH—, and —CHOH—; and V is H). By way of further example, compound 39-29 may be described as containing three polyol groups, three one-carbon groups, and terminates in a hydrogen (i.e., following the description of Formula I, X is (CHOR$^3$)$_h$ where R$^3$ is H and h is 3; and V is H).

Furthermore, certain compounds described herein may be described as copolymers or block copolymers. That is, in compounds of Formula I wherein X is a combination of the groups described, X may be described as a copolymer or block copolymer of those substitutents. For example, in certain compounds, X may be block copolymer of a first block of —(CH$_2$CH$_2$O)$_h$— and a second block of —(CHOR$^3$)$_h$— wherein R$^3$ is hydrogen, alkyl, acyl, aryl, heteroalkyl, or heteroaryl, each of which may be optionally substituted, and h in each instance is from about 1 to about 1000. As an illustrative and nonlimiting example, compounds 38-141 and 38-142 describe compounds wherein X is three groups of —CHOH— (that is, (CHOR$^3$)$_h$ wherein R$^3$ is H and h is 3) and one group of CHOCH$_3$ (that is, (CHOR$^3$)$_h$ wherein R$^3$ is CH$_3$ and h is 1). By way of further example, compound 39-127 describes a compound wherein X is three groups of —CHOH— (that is, (CHOR$^3$)$_h$ wherein R$^3$ is H and h is 3) and one group of CHOCH$_3$ (that is, (CHOR$^3$)$_h$ wherein R$^3$ is CH$_3$ and h is 1).

Salts of the compounds of the present application may be prepared by reacting the free acid or base moieties of these compounds, where present, with a stoichiometric or greater amount of the appropriate base or acid in water or in an organic solvent, or in a mixture of the two; generally, e.g., non-aqueous media like ether, ethyl acetate, ethanol, isopropanol. The salts of the present application may also be prepared by ion exchange.

Compounds of Formula I may be formulated as solids, liquids, gels, aerosols, and other forms. For example, solid formulations may consist primarily of a compound of Formula I as a salt. Compositions comprising one or more compounds of Formula I and one or more other substances (e.g. excipients) may be formed, and may take the form of aerosols, creams, emulsions, gels, lotions, ointments, pastes, powders, solutions, suspensions, and other forms suitable for their intended use or application.

Compositions may also include multiple (e.g. two or more) compounds of Formula I. The compositions may also comprise other active ingredients, such as HOCl, OCl$^-$, and other antimicrobial agents.

Compositions or formulations may include a pharmaceutically acceptable carrier, as defined above. By way of example, the compositions of the present application may include the following pharmaceutically acceptable carriers: sodium chloride to attain isotonicity, buffers, stabilizers, solvents, flavoring agents (in case of oral or nasopharyngeal administration or the food industry), preserving agents, diluents, extenders and other auxiliary substances or excipients. Examples of pharmaceutically acceptable carriers and excipients that may be used are described in *Remington: The Science and Practice of Pharmacy*, R. Hendrickson, ed., 21st edition, Lippincott, Williams & Wilkins, Philadelphia, Pa., (2005) at pages 317-318, which are hereby incorporated by reference in their entireties. In general, water, saline, oils, alcohols (e.g. 2-propanol, 1-butanol, etc.), polyols (e.g. 1,2-propanediol, 2,3-butanediol, etc.), and glycols (e.g. propylene glycol, polyethylene glycols, etc.) may be suitable carriers for solutions. In one aspect solutions contain the active ingredient in a water soluble or aqueous medium soluble form, e.g. as a salt, together with suitable stabilizing agents, and if necessary, buffer substances.

For example, compounds of Formula I may be formulated with cyclodextrin or cyclodextrin derivatives, including cyclodextrin sulfobutyl ether (Capisol®, Cydex Pharmaceuticals, Inc., Overland Park, Kans., USA). These and other carriers may be used to improve or otherwise modulate the solubility, penetration, uptake, and other properties of compositions comprising the compounds described herein.

Aerosols can range from colloidal dispersions to formulations designed for pressurized delivery. Modes of operation include liquefied-gas systems, compressed-gas systems, and barrier-type systems.

Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Emulsions are two-phase systems prepared by combining two immiscible liquids, in which small globules of one liquid are dispersed uniformly throughout the other liquid. Emulsions may be designated as oil-in-water or water-in-oil type emulsions. Certain emulsions may not be classified as such because they are described by another category, such as a lotion, cream, and the like.

Gels are semisolid, suspension-type systems. Single-phase gels contain organic macromolecules distributed substantially uniformly throughout the carrier liquid, which is typically aqueous, but also, e.g., contain an alcohol such as ethanol or isopropanol and, optionally, an oil. Exemplary gelling agents include crosslinked acrylic acid polymers such as the "carbomer" family of polymers, e.g., carboxypolyalkylenes that may be obtained commercially under the Carbopol® trademark. Also useful are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations generally applied to the skin surface so as to avoid high friction, and are typically liquid or semiliquid preparations in which solid particles, including the active agent, are present in a water or alcohol base. Lotions are usually suspensions of solids, and, e.g., comprise a liquid oily emulsion of the oil-in-water type. Lotions can be used to large body areas, because of the ease of applying a generally fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Ointments are semi-solid preparations that are typically based on petrolatum or other petroleum derivatives. The specific ointment base to be used is one that will provide for optimum active ingredient delivery, and other desired characteristics, e.g., emolliency. As with other carriers or vehicles, an ointment base should be inert, stable, nonirritating and nonsensitizing. Ointment bases may be grouped in four classes: oleaginous bases, emulsifiable bases, emulsion bases and water-soluble bases. Oleaginous ointment bases include, e.g., vegetable oils, fats obtained from animals, and semisolid hydrocarbons obtained from petroleum. Emulsifiable ointment bases, also known as absorbent ointment bases, contain little or no water and include, e.g., hydroxystearin sulfate, anhydrous lanolin and hydrophilic petrolatum. Emulsion ointment bases are either water-in-oil (W/O) emulsions or oil-in-water (O/W) emulsions, and include, e.g., cetyl alcohol, glyceryl monostearate, lanolin and stearic acid. For example, water-soluble ointment bases are prepared from polyethylene glycols of varying molecular weight.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Suspensions may be defined as a coarse dispersion containing finely divided insoluble material suspended in a liquid medium. Formulations may also be prepared with liposomes, micelles and microspheres.

Various additives may also be included in formulations, e.g. to solubilize the active ingredients. Other optional additives include opacifiers, antioxidants, fragrances, colorants, gelling agents, thickening agents, stabilizers, surfactants and the like.

These and other compositions or formulations suitable for carrying and delivering compounds of Formula I (which include compounds of Formula IA) are described in Chapters 22, 39, 43, 45, 50 and 55 of *Remington*, above, which are hereby incorporated by reference in their entireties.

The concentration of compounds of Formula I (which include compounds of Formula IA) or their salts in compositions, formulations, and dosage forms may be up to the saturation concentration of those compounds (or salts), e.g., up to about 1 M (molar), up to about 500 mM (millimolar), or up to about 150 mM. For example, compositions of the present application can comprise a concentration of a compound of Formula I (or its salt) ranging from about 0.001 mM to about 1 M, from about 0.01 mM to about 500 mM, from about 0.05 mM to about 150 mM, from about 0.1 mM to about 10 mM, and about 0.5 mM to about 2 mM.

In a further aspect, compositions of the present application comprise isotonic or physiologically balanced solutions of compounds of Formula I or their salts.

The compounds of Formula I, or their salts, are useful in methods of preventing or treating microbial (e.g. bacterial, viral, or fungal) infection or contamination. Compounds described herein may also be administered to prevent or treat a disease, disorder, ailment, or other pathology caused by bacteria, fungus, virus, or associated biofilm. The compounds or salts described herein may also be used for the preparation of a medicine for the prevention or treatment of microbial infection, contamination or activity in a subject. Such methods comprise administering or applying an effective amount of the compound or salt thereof in or near the area of interest, e.g. in or near a tissue or organ, to a surface of a medical device, within a storage container, and so on.

Compositions described herein have antimicrobial activity against a broad range of microorganisms. Tables 3 and 4 show activity of selected compounds against *Escherichia coli*, *Staphylococcus aureus*, and *Candida albicans*. These compounds may be effective against other organisms including *Haemophilus influenzae*, *Enterococcus faecium*, *Enterococcus faecalis*, *Listeria monocytogenes*, methicillin-resistant *S. aureus* (MRSA), *Staphylococcus epidermidis*, *Streptococcus pneumoniae*, *Pseudomonas aeruginosa*, *Proteus mirabilis*, *Klebsiella pneumoniae*, *Lactobacillus* spp., *Acinetobacter junii*, yeast, (e.g. *Candida albicans*), vancomycin-resistant *Enterococcus* spp., molds, and spores, including spores of anthrax and cysts of *Acanthamoeba* spp.

TABLE 3

| | MBC/MFC (ug/mL) | | | | | | $CT_{50}$ (mM) L929 |
|---|---|---|---|---|---|---|---|
| | *E. coli* 25922 | | *S. aureus* 29213 | | *C. albicans* 10231 | | cells |
| Compound | pH 4 acetate | pH 7 phosphate | pH 4 acetate | pH 7 phosphate | pH 4 acetate | pH 7 phosphate | pH 7 phosphate |
| 38-01 | 2 | 256 | 2 | 256 | 32 | >512 | 0.06 |
| 38-25 | 0.5 | 8 | 1 | 16 | 16 | 512 | * |
| 38-27 | 2 | 16 | 2 | 4 | >256 | >1024 | 0.13 |
| 38-29 | 2 | 128 | 1 | 32 | 256 | >1024 | * |
| 38-43 | 2 | 1024 | 1 | 512 | 32 | >2048 | 1.2 |
| 38-45 | 4 | 1024 | 4 | 1024 | 64 | >2048 | 3.2 |
| 38-49 | 2 | 64 | 4 | 32 | 16 | >512 | * |
| 38-51 | 1 | 128 | 2 | 128 | 16 | 128 | * |
| 38-81 | 2 | 32 | 4 | 256 | 128 | >2048 | 2.13 |
| 38-83 | 2 | 128 | 1 | 256 | 128 | >1024 | 1.74 |
| 38-85 | 4 | 64 | 4 | 64 | 32 | >1024 | 0.04 |
| 38-87 | 4 | 128 | 4 | 128 | 32 | 512 | * |
| 38-89 | 8 | 256 | 8 | 128 | 4 | 512 | 0.06 |
| 38-91 | 8 | >256 | 4 | 128 | 16 | 128 | * |
| 38-133 | 8 | 128 | 8 | 128 | 64 | 1024 | 0.26 |
| 38-135 | 8 | 256 | 2 | 512 | 32 | >1024 | 0.08 |
| 38-137 | 8 | 512 | 4 | >1024 | 32 | >1024 | 1.62 |
| 38-141 | 8 | 512 | 8 | 256 | 16 | >1024 | * |
| 38-145 | 2 | 64 | 2 | 16 | 64 | 1024 | * |
| 38-147 | 8 | 256 | 8 | 128 | >256 | 2048 | 0.039 |
| 38-151 | 4 | 1024 | 4 | >2048 | 64 | >1024 | 0.12 |

* Not tested

TABLE 4

| | MBC/MFC (ug/mL) | | | | | | $CT_{50}$ (mM) L929 |
|---|---|---|---|---|---|---|---|
| | *E. coli* 25922 | | *S. aureus* 29213 | | *C. albicans* 10231 | | cells |
| Compound | pH 4 acetate | pH 7 phosphate | pH 4 acetate | pH 7 phosphate | pH 4 acetate | pH 7 phosphate | pH 7 phosphate |
| 39-01 | 2 | 128 | 2 | 128 | 8 | 256 | 0.08 |
| 39-04 | 2 | 256 | 2 | 256 | 16 | 1024 | 0.14 |
| 39-12 | 8 | 256 | 8 | 256 | 16 | >1024 | 0.18 |
| 39-27 | 4 | 512 | 4 | 1024 | 16 | >2048 | 0.14 |
| 39-94 | 32 | 2048 | 8 | 4096 | 256 | >2048 | 11.3 |
| 39-106 | 16 | 256 | 32 | >512 | 64 | >512 | 0.24 |
| 39-108 | 1 | 32 | 2 | 128 | 8 | 64 | 0.1 |
| 39-110 | 128 | 1024 | 128 | 2048 | 256 | >2048 | 3.9 |
| 39-112 | 4 | 128 | 8 | 128 | 8 | 1024 | 0.16 |

TABLE 4-continued

| | MBC/MFC (ug/mL) | | | | | | CT$_{50}$ (mM) L929 |
| --- | --- | --- | --- | --- | --- | --- | --- |
| | E. coli 25922 | | S. aureus 29213 | | C. albicans 10231 | | cells |
| Compound | pH 4 acetate | pH 7 phosphate | pH 4 acetate | pH 7 phosphate | pH 4 acetate | pH 7 phosphate | pH 7 phosphate |
| 39-114 | 8 | 256 | 4 | 256 | 8 | >1024 | 0.24 |
| 39-116 | 16 | 512 | 16 | 1024 | 128 | >2048 | 4.1 |
| 39-118 | 32 | 2048 | 8 | 4096 | 256 | >2048 | 11.3 |
| 39-122 | 2 | 2 | 4 | 4 | >512 | 1024 | 0.14 |
| 39-124 | 16 | 8 | 16 | 32 | 8 | >1024 | 0.33 |
| 39-125 | 2 | 32 | 2 | 256 | 128 | >1024 | 2.21 |
| 39-132 | 16 | 512 | 16 | 1024 | 128 | >2048 | 4.1 |

Compositions of the present application are useful in a wide range or applications in which antimicrobial properties are desirable. Such applications include, without limitation, treatment or reduction of pathogens on or in the skin, nails, hair, or mucous membranes, wounds, surgical sites, and so forth. Applications and areas of interest include wounds, burns, ulcers, inflammation or lesions of the skin, the eyes, ears, nasal passages, sinus, bronchopulmonary system, vagina, rectum and other mucous membranes or related tissues.

While N-halogenated compounds of Formula I may have inherent antimicrobial activity, the corresponding N-protonated (i.e. non-halogenated) analogs may also have antimicrobial activity, or may be activated to an antimicrobial (or increased antimicrobial) state by a source of halogen. For example, it is well known that hypochlorite and/or hypochlorous acid is generated by neutrophils, eosinophils, mononuclear phagocytes, and B lymphocytes [see, e.g., L. Wang et al., *J. Burns Wounds*, 6, 65-79 (2007) and M. Nagl et al., *Antimicrob. Agents Chemother.* 44(9) 2507-13 (2000)]. Certain organic chloramines, including N-chlorotaurine, have been detected in the supernatants of stimulated granulocytes, and are thought to prolong the oxidative capacity of these cells during oxidative burst and to protect cells from damage by HOCl/OCl$^-$. In a similar fashion to taurine, N-protonated compounds of Formula I in or near these cells may be chlorinated during oxidative burst, and may serve a similar microbicidal and/or protective effect. Thus, compounds of Formula I may be used in methods to generate antimicrobial activity in situ, to prolong or otherwise modulate the oxidative capacity of cells during oxidative burst, or to decrease associated cyctotoxicity.

The compounds described herein may also be useful in a method to decontaminate, disinfect, or clean surfaces of materials, devices, or equipment, the method comprising contacting the material, device, or equipment with a solution comprising a compound or salt thereof. For example, a solution comprising a compound of Formula I can be applied by spray or an applicator such as a cotton ball or cloth to the medical device, or the medical device can be immersed in said solution. Applications include the elimination or reduction of pathogens (e.g. bacteria, virus, fungus, microbe, etc.) on or in medical (including surgical, dental, optical, and other) devices, equipment and instruments, (e.g. breathing tubes, catheters, contact lenses, dental implants and equipment, equipment used for organ preservation, hearing aids, prostheses, stents, etc.), devices, food (e.g., meats, fish, fruits, vegetables, nuts, etc.) and food contact surfaces (e.g. cutting tools, cutting surfaces, storage rooms or containers, etc.) including the elimination or reduction of bacterial biofilms, and agricultural uses including protection of seed stocks.

By way of example, compounds and compositions of the present application may be used for the eradication of bacteria (including bacteria in a biofilm), such as, but not limited to, bacterial and biofilms in or on medical devices, e.g. in the lumen of a catheter (e.g. urinary, central venous, hemodialysis catheters and the like), stent, breathing tube, etc. Such methods may include the destruction of the corresponding biofilm matrix to clear the bacterial load from the medical device, such as improving or maintaining patency in the lumen of a catheter, stent, or breathing tube. Biofilms are a group of microorganisms attached to a substrate and are often associated with the excretion of extraculullar polymeric substance [R. M. Donlan et al., *Clin. Microbiol. Rev.*, 4, 167-193 (2002)]. The demonstrated resistance of biofilms to antimicrobials has caused problems in human health and has had a significant impact on the success of medical implants, e.g., catheters [J. W. Costerton et al., *Science*, 284(5418), 1318-22 (1999)]. Once catheters are colonized, biofilms will develop on the outer and inner surfaces and cause infections. Reduction of the bacterial load by prevention of the formation of biofilm [J. F. Williams and S. D. Worley, *J. Endourology*, 14(5), 395-400 (2000); K. Lewis and A. M. Klibanov, *Trends in Biotech.*, 23, 7, 343-348 (2005)], destruction of an existing biofilm [P. Wood et al., *Appl. Env. Microb.* 62(7), 2598-2602 (1996)] and killing bacteria in biofilm [P. Gilbert and A. J. McBain, *Am. J. Infect. Control*, 29, 252-255 (2001)] are strategies towards lowering microbial load and reducing biofilm-related infection from any catheters and shunts, such as but not limited to, urinary and central venous catheters, implanted artificial joints, implanted artificial hearts, gastric feeding tubes, and colostomy tubes.

Compounds described herein may be used to treat, eradicate, or prevent the formation of biofilm formed by a variety of bacteria and fungi, including, but not limited to, gram-positive cocci, gram-negative rods, *P. aeruginosa*, *C. albicans*, *S. aureus*, *B. cepacia*, *E. coli*, *S. epidermidis*, *A. hydrophila*, *H. influenzae*, *S. liquifaciens*, *P. mirabilis*, *K. pneumoniae*, and *P. vulgaris*. A discussion of these, and examples of other, biofilm-forming species may be found in, e.g., S. Kjelleberg, and S. Molin, *Curr Opin Microbiol.*, June, 5(3):254-8 (2002); J. W. Consterton et al., *Science*, 284, May 21, 1318-11 (1999); and D. J. Stickler et al., *Methods in Enzymology*, 310: 494-501 (1999).

In another application of decontaminating, disinfecting, or cleaning medical devices, a solution of a compound of the present application may be used to decontaminate, disinfect, or clean contact lenses. Disinfection of contact lenses is important in the prevention of infections of the eye caused by micro-organisms. Microbes are primarily introduced to the eye by handling of the lens. For example, introduction of *E. coli* may lead to infections of various eye structures, such as microbial keratitis. Fungal pathogens, such as *Fusarium* spp., can also infect the eye when transferred from a colonized contact lens. See, e.g., J. K. Suchecki et al., *Ophthalmol. Clin. North Am.*, 16(3), 471-84 (2003). In one embodiment, a method provides for immersing a contact lens in an aqueous solution of a compound of Formula I for a sufficient period of time so as to kill or otherwise inactivate substantially all of bacteria, viruses or other microbes present thereon. For example, contact lenses can be left overnight in an aqueous solution of a compound of Formula I. Such solutions may also contain additional preservatives and disinfecting agents as well as cleaning and other agents. These solutions may be used to store contact lenses (e.g., in packaging, between uses, in carrying cases, etc.), to condition lenses, to wet or re-wet lenses before insertion into the eye, or to clean and rinse lenses.

The starting materials and reagents employed in preparing the compounds described herein are either available from commercial suppliers such as Sigma-Aldrich Corporation (Milwaukee, Wis., USA), TCI America (Portland, Oreg., USA), Matrix Scientific (Columbia, S.C., USA), VWR International (Pasadena, Calif., USA), Fisher Scientific (Chicago, Ill., USA), Alfa Aesar (Ward Hill, Mass., USA), Advanced ChemTech (Louisville, Ky., USA), Chem-Impex International Inc. (Wood Dale, Ill., USA), and Advanced Asymmetrics (Millstadt, Ill., USA) or are prepared by methods known in the art following procedures available in the literature and references such as *Protective Groups in Organic Synthesis* (John Wiley & Sons, 3$^{rd}$ Edition), *Protective Groups (Foundation of Organic Chemistry)* (Thieme & Sons Inc.), *Fieser and Fieser's Reagents for Organic Synthesis*, Volumes 1-15 (John Wiley and Sons, 1991), *Rodd's Chemistry of Carbon Compounds*, Volumes 1-15 and Supplemental Materials (Elsevier Science Publishers, 1989), *Organic Reactions*, Volume 1-40 (John Wiley & Sons, 1991), *March's Advanced Organic Chemistry*, (Wiley-Interscience, 6$^{th}$ Edition, 2007), M. C. Pirrung, *The Synthetic Organic Chemist's Companion* (John Wiley & Sons, Inc., 2007), and R. C. Larock *Comprehensive Organic Transformation: A Guide to Functional Group Preparations* (John Wiley & Sons, Inc. 1999).

Various chlorine sources may be used to produce the N-chlorinated compounds, e.g., chlorine itself (i.e., $Cl_2$ gas), certain N-chloroarylsulfonamide salts, wherein the aryl group contains from about 6 to about 15 carbon atoms with 1 or 2 aromatic rings, or 6 to 10 or 6 to 8 carbon atoms and one aromatic ring, such as N-chlorobenzene-sulfonamide or N-chloro-4-alkylbenzenesulfonamide, wherein the alkyl group is an alkyl from about 1 to about 4 carbons, such as methyl or ethyl. The N-chlorobenzene-sulfonamides or N-chloro-4-alkylbenzenesulfonamides are often used in the form of their salts, e.g., alkali salts, e.g., sodium or potassium salts. Frequently used reagents include N-chlorobenzene-sulfonamide and N-chloro-4-methyl-benzenesulfonamide in the form of their sodium salts, because they are readily commercially available. Other non-limiting chlorinating agents include HOCl and N-chlorosuccinimide. Other chlorinated agents are listed in the schemes below. Similarly, the halogenation reaction may be accomplished using the corresponding reagents as disclosed herein that provide a source of bromine, as in known in the art. Examples of such bromination reagents include $Br_2$, N-bromoarylsulfonamide salts, HOBr and N-bromosuccinimide, and the like.

Compounds of Formula I (which includes compounds of Formula IA) may be prepared according to the following exemplary generalized schemes in addition to other standard manipulations known in the art. These schemes are illustrative and are not limiting. Compound numbers shown in the schemes do not necessarily correlate to compound numbers used in Table 1 or the Examples.

Scheme 1

Certain compounds of Formula I may be prepared according to the following exemplary generalized scheme, wherein Y is —$SO_2$—, wherein LG is a leaving group, such as bromo, iodo, methanesulfonate, 4-methylbenzenesulfonate or trifluoromethanesulfonate, wherein Cbz-NH— is benzyl carbamate.

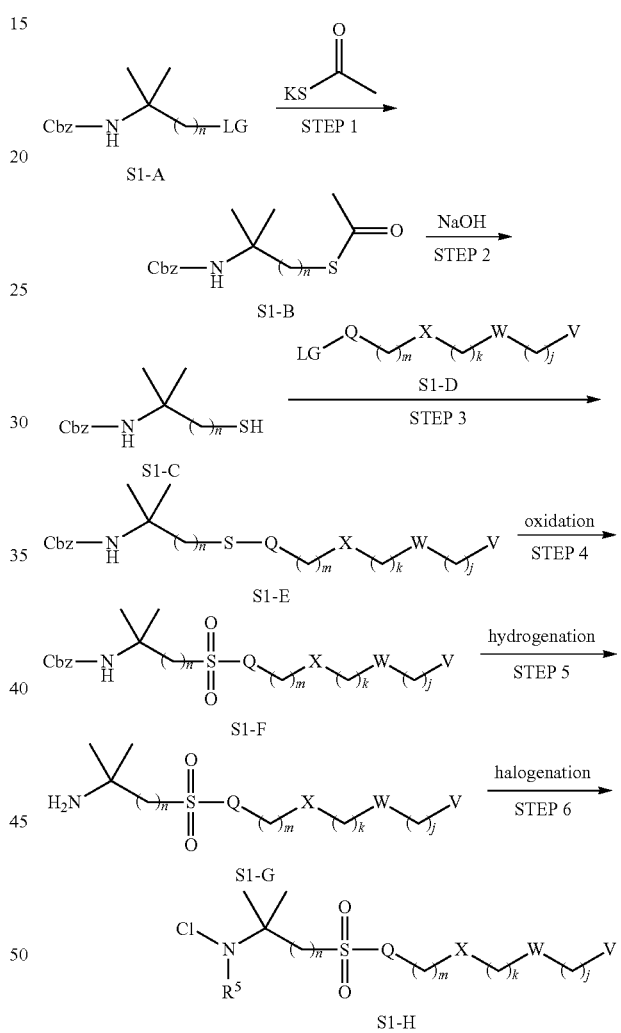

STEP 1: Intermediate compound S1-B can be generated by reaction of compound S1-A with potassium thioacetate in a suitable solvent such as N,N-dimethylformamide, and the like. This reaction is typically carried out at temperature ranging from 0° C. to 100° C. for about 8 to about 24 hours.

STEP 2: The thiol S1-C can be obtained by treating S1-B with aqueous sodium hydroxide in a water miscible solvent, such as methanol or ethanol. The reaction is typically carried out at temperature ranging from 0° C. to 100° C. for about 30 minutes to about 8 hours.

STEP 3: Thioether S1-E can be generated by alkylation of thiol S1-C with compound S1-D. The reaction is typically carried out in a suitable solvent such as N,N-dimethylformamide, and the like, and a suitable base, such as cesium carbonate or sodium carbonate. The reaction is conducted at a temperature ranging from ambient temperature to 100° C. for 1 to 24 hours.

STEP 4: Sulfonyl S1-F can be obtained by oxidation of thioether S1-E. The oxidation is typically conducted using 3-chloroperoxybenzoic acid in an inert solvent such as dichloromethane. The reaction is conducted at a temperature ranging from 0° C. to ambient temperature for 1 to 24 hours.

STEP 5: Amine S1-G can be generated from sulfonyl S1-F by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 6: Wherein T=Cl: Chloroamine S1-H can be generated by treating S1-G with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S1-H can be generated from amine S1-G by treatment with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 2

Certain compounds of Formula I may be prepared according to the following exemplary generalized scheme, wherein Y is —$N^+(R^1R^2)$—, wherein LG is a leaving group, such as bromo, iodo, methanesulfonate, 4-methylbenzenesulfonate or trifluoromethanesulfonate, wherein Cbz-NH— is benzyl carbamate.

typically carried out with or without a solvent. A suitable solvent, such as dichloromethane or methanol, may be used. The reaction is conducted at a temperature ranging from ambient temperature to 100° C. for 1 to 24 hours.

STEP 2: Amine S2-D can be generated from ammonium salt S2-C by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 3: Wherein T=Cl: Chloroamine S2-E can be generated from S2-D by treating S2-D with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S2-E can be generated from amine S2-D by treating S2-D with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 3

Certain compounds of Formula I may be prepared according to the following exemplary generalized scheme, wherein Y is —$SO_2$—, wherein $R^5$ is either hydrogen or chloro, wherein X is —$(CHOR^3)_n$—, wherein $R^3$=hydrogen, wherein m=1, wherein v is an integer from 1 to 199, wherein Cbz-NH— is benzyl carbamate.

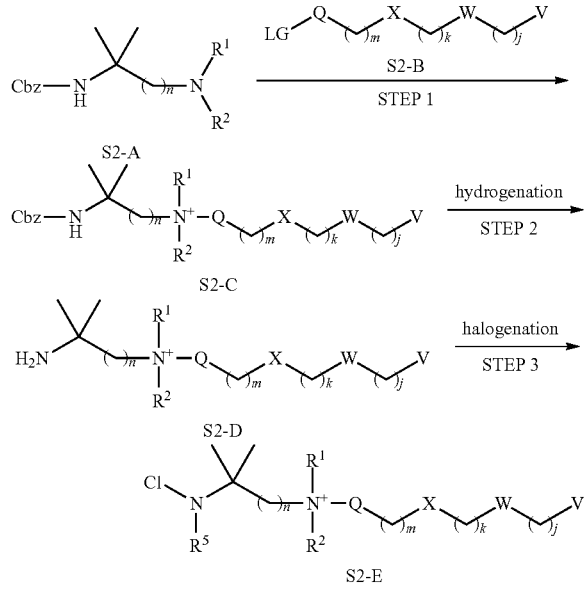

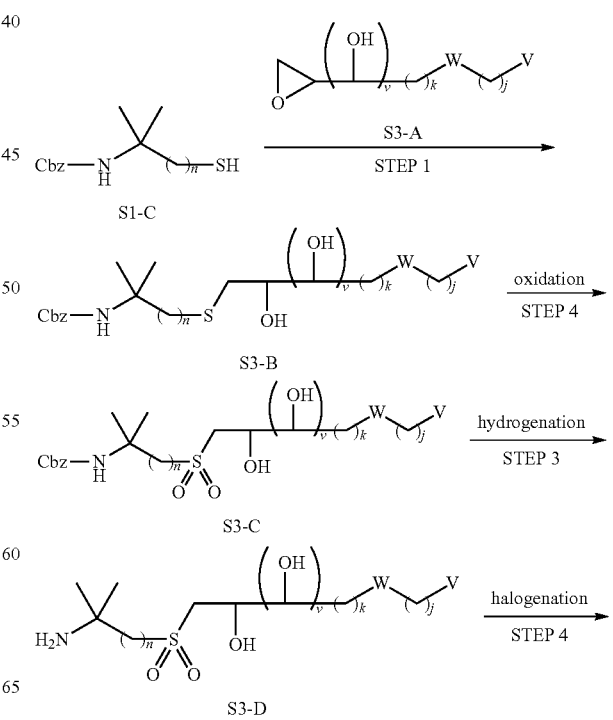

STEP 1: Ammonium salt S2-C can be generated by alkylation of amine S2-A with compound S2-B. The reaction is

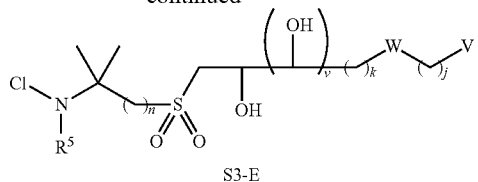

STEP 1: Thioether S3-B can be generated by alkylation of thiol S1-C (from Scheme 1) with epoxide S3-A. The reaction is typically carried out in a suitable solvent, such as N,N-dimethylformamide, with a base, such as cesium carbonate or sodium carbonate. The reaction is conducted at a temperature ranging from ambient temperature to 100° C. for 1 to 24 hours.

STEP 2: Sulfonyl S3-C can be obtained by oxidation of thioether S3-B. The oxidation is typically conducted using 3-chloroperoxybenzoic acid in an inert solvent such as dichloromethane. The reaction is conducted at a temperature ranging from 0° C. to ambient temperature for 1 to 24 hours.

STEP 3: Amine S3-D can be generated from polyol S3-C by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 4: Wherein T=Cl: Chloroamine S3-E can be generated by treating amine S3-D with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S3-E can be generated by treating amine S3-D with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 4

Certain compounds of Formula I may be prepared according to the following exemplary generalized scheme, wherein Y is —$SO_2$—, wherein X is —$(CHOR^3)_n$—, wherein m=1, wherein v is an integer from 1 to 999, wherein LG is a leaving group, such as bromo, iodo, methanesulfonate, 4-methylbenzenesulfonate or trifluoromethanesulfonate, wherein Cbz-NH— is benzyl carbamate.

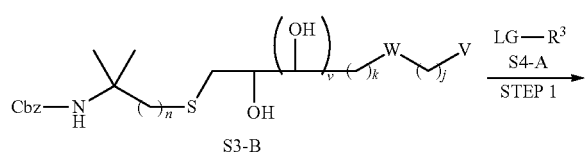

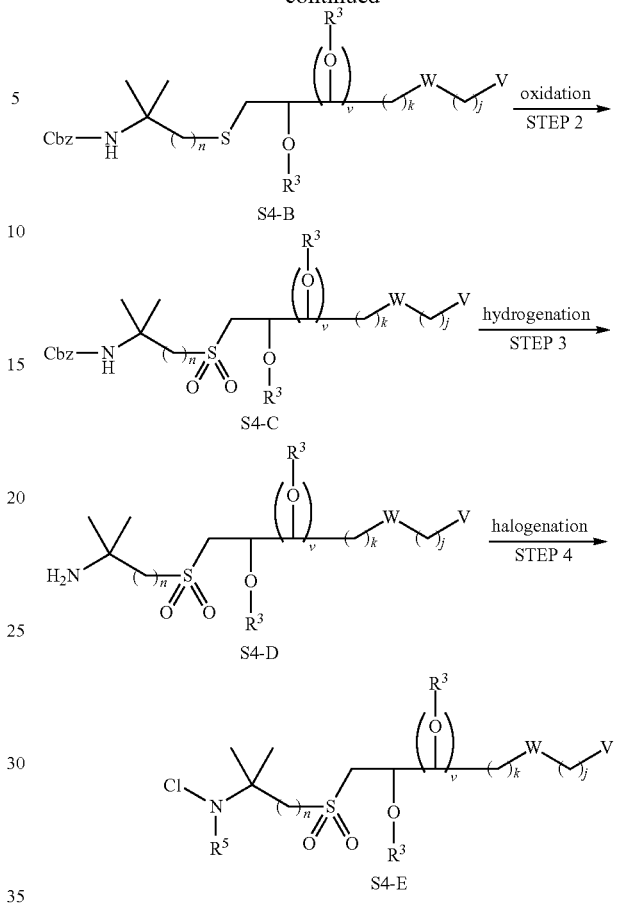

STEP 1: Polyalkylated-ether S4-B can be generated by alkylation of polyol S3-B (from Scheme 3) with alkylating compound S4-A. The reaction is typically carried out in a suitable solvent, such as N,N-dimethylformamide or tetrahydrofuran, with a base, such as lithium hydride or sodium hydride. The reaction is conducted at a temperature ranging from ambient temperature to 100° C. for 1 to 24 hours.

STEP 2: Sulfonyl S4-C can be obtained by oxidation of thioether S4-B. The oxidation is typically conducted using 3-chloroperoxybenzoic acid in an inert solvent such as dichloromethane. The reaction is conducted at a temperature ranging from 0° C. to ambient temperature for 1 to 24 hours.

STEP 3: Amine S4-D can be generated from sulfonyl S4-C by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 4: Wherein T=Cl: Chloroamine S4-E can be generated from amine S4-D by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S4-E can be generated from amine S4-D by treating S4-D with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 5

Certain compounds of Formula I may be prepared according to the following exemplary generalized scheme, wherein Y is —OC(=O)$NR^{10}$—, wherein LG is a leaving group, such as bromo, iodo, methanesulfonate, 4-methylbenzenesulfonate or trifluoromethanesulfonate, wherein Cbz-NH— is benzyl carbamate.

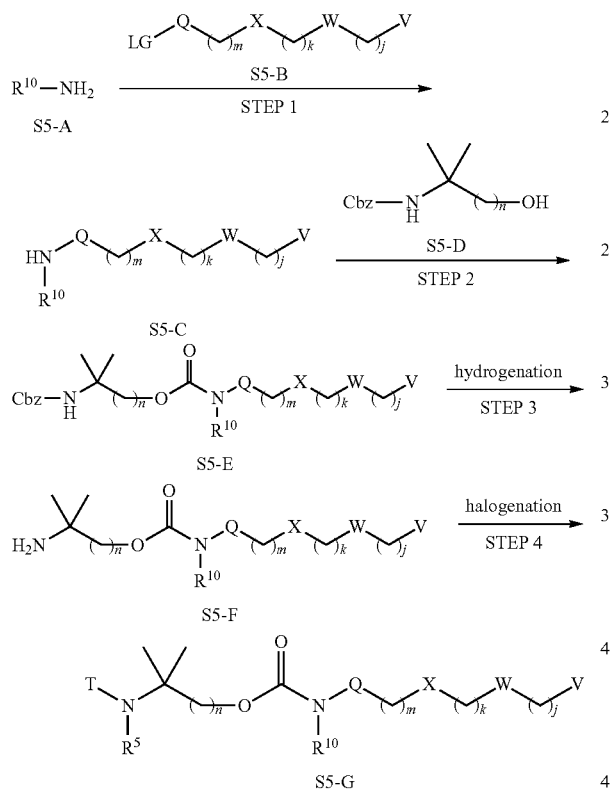

STEP 1: Amine S5-C can be generated by treating S5-A with S5-B in an inert solvent, such as dichloromethane, tetrahydrofuran or N,N-dimethylformamide, at 0° C. to ambient temperature for 1 to 24 hours.

STEP 2: Carbamate S5-E can be generated from alcohol S5-D and amine S5-C by treating amine S5-C with either 1,1'-carbonyldiimidazole, phosgene or triphosgene in an inert solvent, such as dichloromethane or N,N-dimethylformamide, at 0° C. to ambient temperature for 1 to 24 hours, followed by treatment with S5-D at 0° C. to ambient temperature for an additional 1 to 24 hours.

STEP 3: Amine S5-F can be generated from carbamate S5-E by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 4: Wherein T=Cl: Chloroamine S5-G can be generated by treating amine S5-F with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S5-G can be generated by treating amine S5-F with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 6

Certain compounds of Formula I may be prepared according to the following exemplary generalized scheme, wherein Y is —$NR^9$C(=O)$NR^{10}$—, wherein Cbz-NH— is benzyl carbamate.

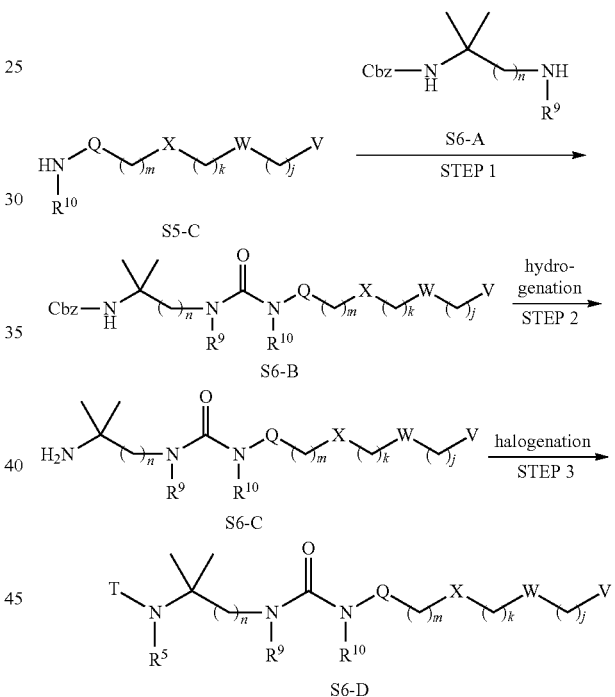

STEP 1: N,N-substituted urea S6-B can be generated from amine S5-C (from Scheme 5) and amine S6-A by treating amine S5-C with either 1,1'-carbonyldiimidazole, phosgene or triphosgene in an inert solvent, such as dichloromethane or N,N-dimethylformamide, at 0° C. to ambient temperature for 1 to 24 hours, followed by treatment with S6-A at 0° C. to ambient temperature for an additional 1 to 24 hours.

STEP 2: Amine S6-C can be generated from carbamate-protected S6-B by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 3: Wherein T=Cl: Chloroamine S6-D can be generated from amine S6-C by treatment with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S6-D can be generated from amine S6-C by treatment with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 7

Certain compounds of Formula I may be prepared according to the following exemplary generalized scheme, wherein Y is —OC(=O)O—, wherein Cbz-NH— is benzyl carbamate.

formamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S7-D can be generated by treating amine S7-C with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 8

Certain compounds of Formula I may be prepared according to the following exemplary generalized scheme, wherein Y is —NR$^9$C(=O)O—, wherein LG is a leaving group, such as bromo, iodo, methanesulfonate, 4-methylbenzenesulfonate or trifluoromethanesulfonate, wherein Cbz-NH— is benzyl carbamate.

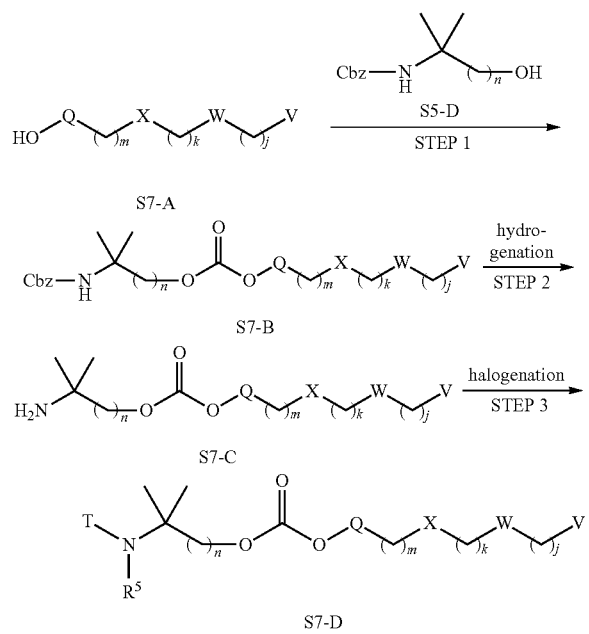

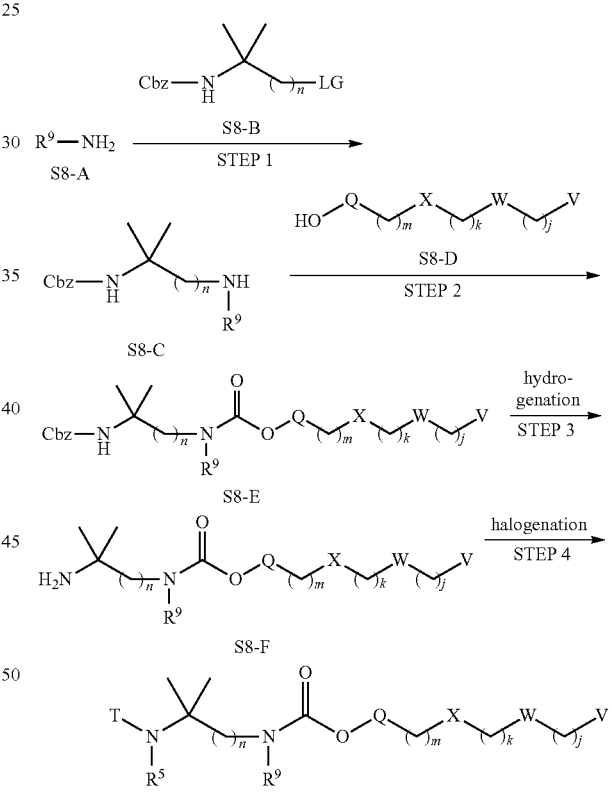

STEP 1: Carbonate S7-B can be generated from alcohol S5-D and alcohol S7-A by treating alcohol S7-A with either 1,1'-carbonyldiimidazole, phosgene or triphosgene in an inert solvent, such as dichloromethane or N,N-dimethylformamide, at 0° C. to ambient temperature for 1 to 24 hours, followed by treatment with S5-D at 0° C. to ambient temperature for an additional 1 to 24 hours.

STEP 2: Amine S7-C can be generated from carbamate S7-B by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 3: Wherein T=Cl: Chloroamine S7-D can be generated by treating amine S7-C with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethyl- STEP 1: Amine S8-C can be generated by treating S8-A with S8-B in an inert solvent, such as dichloromethane, tetrahydrofuran or N,N-dimethylformamide, at 0° C. to ambient temperature for 1 to 24 hours.

STEP 2: Carbamate S8-E can be generated from alcohol S8-D and amine S8-C by treating amine S8-C with either 1,1'-carbonyldiimidazole, phosgene or triphosgene in an inert solvent, such as dichloromethane or N,N-dimethylformamide, at 0° C. to ambient temperature for 1 to 24 hours, followed by treatment with alcohol S8-D at 0° C. to ambient temperature for an additional 1 to 24 hours.

STEP 3: Amine S8-F can be generated from carbamate S8-E by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 4: Wherein T=Cl: Chloroamine S8-G can be generated by treating amine S8-F with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, one equivalent of chlorinating agent is used. In the case of $R^5$=Cl, 2 to 4 equivalents of chlorinating agent is used. Wherein T=Br: Bromoamine S8-G can be generated by treating amine S8-F with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, one equivalent of brominating agent is used. In the case of $R^5$=Br, 2 to 4 equivalents of brominating agent is used.

Scheme 9

Certain compounds of Formula I may be prepared according to the following exemplary generalized scheme, wherein LG is a leaving group such as bromo, iodo, methanesulfonate, 4-methylbenzenesulfonate or trifluoromethanesulfonate, wherein V=LG, wherein Y and W are —SO$_2$—, wherein Cbz-NH— is benzyl carbamate.

STEP 1: Thioether S9-B can be generated by alkylation of thiol S1-C (from scheme 1) with compound S9-A. The reaction is typically carried out in a suitable solvent such as N,N-dimethylformamide, and the like, and a suitable base, such as cesium carbonate or sodium carbonate. The reaction is conducted at a temperature ranging from ambient temperature to 100° C. for 1 to 24 hours.

STEP 4: Sulfonyl S9-C can be obtained by oxidation of thioether S9-B. The oxidation is typically conducted using 3-chloroperoxybenzoic acid in an inert solvent such as dichloromethane. The reaction is conducted at a temperature ranging from 0° C. to ambient temperature for 1 to 24 hours.

STEP 5: Amine S9-D can be generated from sulfonyl S9-C by hydrogenation with a suitable catalyst, such as palladium on carbon, in a polar solvent, such as methanol or ethanol. The reaction is typically conducted at ambient temperature for 1 to 24 hours, under hydrogen gas at 1 to 20 atmospheres of pressure.

STEP 6: Wherein T=Cl: Chloroamine S9-E can be generated by treating S9-D with a chlorinating agent such as tert-butyl hypochlorite, trichloroisocyanuric acid, sodium hypochlorite, N-chlorosuccinimide, N-chlorohydantoins and chlorine gas in a polar solvent such as water, N,N-dimethylformamide, methylene chloride, and the like. The reaction is typically carried out at −20° C. to ambient temperature for about 30 minutes to about 24 hours. In the case of $R^5$=H, 2 equivalents of chlorinating agent is used. In the case of $R^5$=Cl, 4 to 8 equivalents of chlorinating agent is used. Wherein T=Br: Bromoamine S9-E can be generated from amine S9-D by treatment with a brominating agent, such as bromine, and a base, such as sodium hydroxide, in a suitable solvent, such as water. The reaction is typically carried out at −20° C. to ambient temperature for about 30 minutes to about 24 hours. In the case of $R^5$=H, 2 equivalents of brominating agent is used. In the case of $R^5$=Br, 4 to 8 equivalents of brominating agent is used.

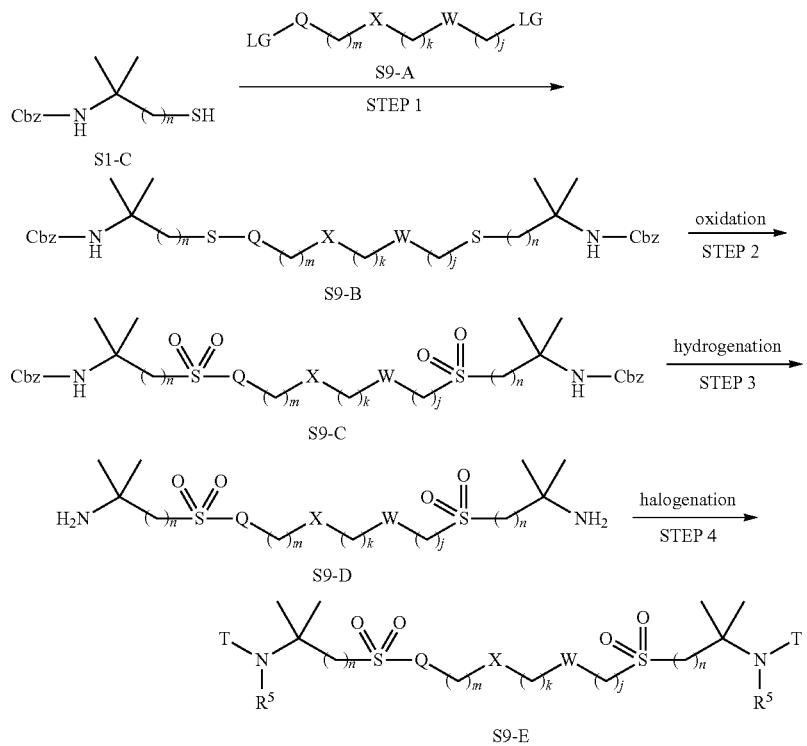

Scheme 10

Certain compounds of Formula I may be prepared according to the following exemplary generalized scheme, wherein D is nitrogen, wherein Z is 2,2,5,5-tetramethylimidazolidin-4-one, wherein LG is a leaving group, such as bromo, iodo, methanesulfonate, 4-methylbenzenesulfonate or trifluoromethanesulfonate.

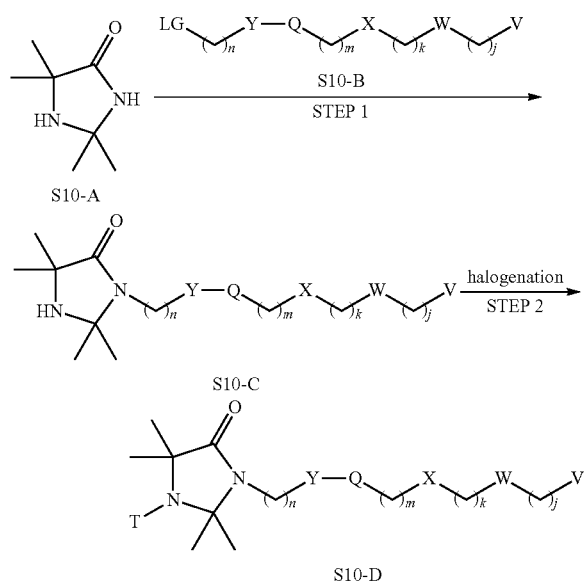

STEP 1: Imidazolidinone S10-C can be generated by alkylation of amide S1-A with compound S10-B. The reaction is typically carried out with a solvent such as N,N-dimethylformamide, tetrahydrofuran, and the like, with a base, such as sodium hydride, potassium hydride, lithium bis(trimethylsilyl)amide, or the like, at a temperature ranging from 0° C. to 80° C. for 1 to 24 hours.

STEP 2: Wherein T=Cl: Chloroamine S10-D can be generated from amine 510-C treatment with a chlorinating agent such as tert-butyl hypochlorite, chloramine-T, trichloroisocyanuric acid, sodium hypochlorite, N-chlorosuccinimide, N-chlorohydantoins or chlorine gas in a polar solvent such as water, N,N-dimethylformamide, methylene chloride, methanol, ethanol, or the like. The reaction is typically carried out at −20° C. to ambient temperature for about 30 minutes to about 24 hours. Wherein T=Br: Bromoamine S10-D can be generated from amine S10-C by treatment with a brominating agent, such as bromine, and a base, such as sodium hydroxide, in a suitable solvent, such as water. The reaction is typically carried out at −20° C. to ambient temperature for about 30 minutes to about 24 hours.

Scheme 11

Certain compounds of Formula I may be prepared according to the following exemplary generalized scheme, wherein D is nitrogen, wherein LG is a leaving group, such as bromo, iodo, methanesulfonate, 4-methylbenzenesulfonate or trifluoromethanesulfonate.

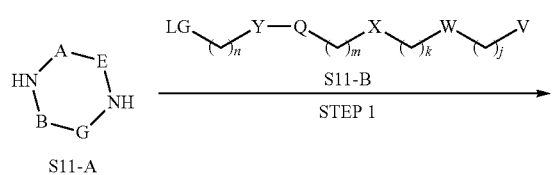

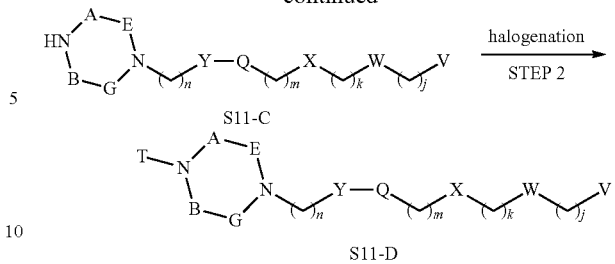

STEP 1: Compound S11-C can be generated by alkylation of S11-A with S11-B. The reaction is typically carried out with a solvent such as N,N-dimethylformamide, tetrahydrofuran, and the like, with a base, such as sodium hydride, potassium hydride, lithium bis(trimethylsilyl)amide, or the like, at a temperature ranging from 0° C. to 80° C. for 1 to 24 hours.

STEP 2: Wherein T=Cl: Chloroamine S11-D can be generated from amine S11-C treatment with a chlorinating agent such as tert-butyl hypochlorite, chloramine-T, trichloroisocyanuric acid, sodium hypochlorite, N-chlorosuccinimide or N-chlorohydantoins and chlorine gas in a polar solvent such as water, N,N-dimethylformamide, methylene chloride, methanol, ethanol, or the like. The reaction is typically carried out at −20° C. to ambient temperature for about 30 minutes to about 24 hours. Wherein T=Br: Bromoamine S11-D can be generated from amine S11-C by treatment with a brominating agent, such as bromine, and a base, such as sodium hydroxide, in a suitable solvent, such as water. The reaction is typically carried out at −20° C. to ambient temperature for about 30 minutes to about 24 hours.

Scheme 12

Certain compounds of Formula I may be prepared according to the following exemplary generalized scheme, wherein D is nitrogen, wherein LG is a alkylsulfonate, 4-alkylsulfonate, or a halide.

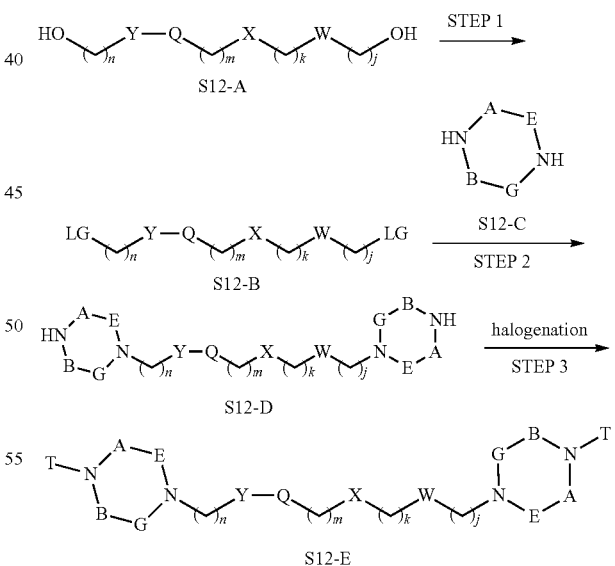

STEP 1: Compound S12-B can be generated by treating S12-A with ether methanesulfonyl chloride or p-toluenesulfonyl chloride with a base, such a triethylamine or pyridine, in a suitable solvent, such as dichloromethane, tetrahydrofuran, pyridine, 1,2-dichlorethane, or the like at a temperature ranging from 0° C. to 80° C. for 30 minutes to 8 hours.

STEP 2: Dimer S12-D can be generated by alkylation of S12-C with compound S12-B. The reaction is typically carried out with a solvent such as N,N-dimethylformamide, tetrahydrofuran, and the like, with a base, such as sodium hydride, potassium hydride, lithium bis(trimethylsilyl) amide, or the like, at a temperature ranging from 0° C. to 80° C. for 1 to 24 hours.

STEP 3: Wherein T=Cl: Chloroamine S12-E can be generated from compound S12-D treatment with a chlorinating agent such as tert-butyl hypochlorite, chloramine-T, trichloroisocyanuric acid, sodium hypochlorite, N-chlorosuccinimide, N-chlorohydantoins and chlorine gas in a polar solvent such as water, N,N-dimethylformamide, methylene chloride, methanol, ethanol, or the like. The reaction is typically carried out at −20° C. to ambient temperature for about 30 minutes to about 24 hours. Wherein T=Br: Bromoamine S12-E can be generated from amine S12-D by treatment with a brominating agent, such as bromine, and a base, such as sodium hydroxide, in a suitable solvent, such as water. The reaction is typically carried out at −20° C. to ambient temperature for about 30 minutes to about 24 hours.

Synthetic routes to specific individual compounds of Formula I are provided below (see Examples).

EXAMPLES

The following examples are offered by way of illustration and not by way of limitation.

Example 1

N,N-Dichloro-2-methyl-4-(2-(2-(2-methoxyethoxy) ethoxy)ethylsulfonyl)butan-2-amine (Compound 38-05)

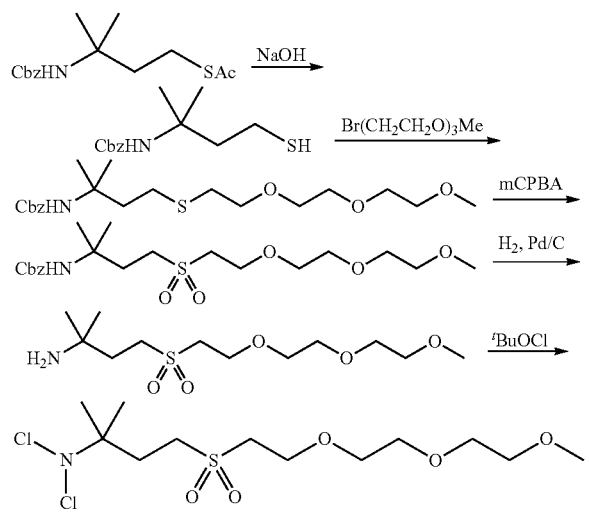

Benzyl 4-mercapto-2-methylbutan-2-ylcarbamate

To a solution of S-3-(benzyloxycarbonylamino)-3-methylbutyl ethanethioate (1.52 g, 5.14 mmol, prepared as described in WO 2008/083347) in methanol (25 ml) was added 5.0 M NaOH in $H_2O$ (3.3 ml, 16.5 mmol). The solution was stirred for 1 hour, concentrated in vacuo, and the residue suspended in 100 ml 1M $H_3PO_4$, extracted with 5×50 ml ethyl acetate, the organic layers combined and washed once with 100 ml saturated NaCl, dried on $MgSO_4$, and concentrated in vacuo. The reaction product was used in the next step without further purification.

Benzyl 14-methyl-2,5,8-trioxa-11-thiapentadecan-14-ylcarbamate

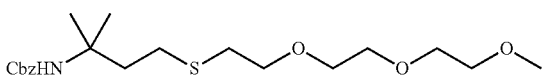 [SMILES: COCCOCCOCCSCCC(C)(C)NC(=O)OCc1ccccc1]

To a solution of benzyl 4-mercapto-2-methylbutan-2-ylcarbamate (2.05 g, 8.1 mmol) in N,N-dimethylformamide (10 ml) was added cesium carbonate (2.27 g, 6.97 mmol) and 2-(2-(2-methoxyethoxy)ethoxy)ethyl 4-methylbenzenesulfonate (2.32 g, 7.29 mmol). The solution was heated to 60° C. for 2 hour, then 70° C. for 16 hour, cooled to room temperature, concentrated in vacuo, and the residue dissolved in 50 ml 5% $NaHSO_4$, extracted with 3×50 ml ethyl acetate, dried on $MgSO_4$, and concentrated in vacuo. The residue was purified by flash chromatography (10% to 60% ethyl acetate in hexanes) to give the title compound as a clear oil (1.24 g, 3.10 mmol, 60%). $^1H$ NMR (400 MHz, $CDCl_3$) δ 1.32 (s, 6H), 1.99 (m, 2H), 2.53 (m, 2H), 2.73 (m, 2H), 3.39 (s, 3H), 3.5-3.7 (m, 10H), 4.8 (s, 1H), 5.05 (s, 2H), 7.3-7.4 (m, 5H). LRMS (ESI/APCI) m/z 422 $[M+Na]^+$.

Benzyl 2-methyl-4-(2-(2-(2-methoxyethoxy)ethoxy) ethylsulfonyl)butan-2-ylcarbamate

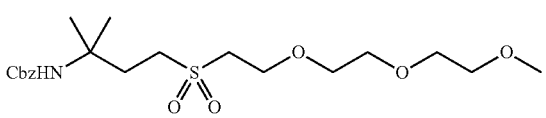 [SMILES: COCCOCCOCCS(=O)(=O)CCC(C)(C)NC(=O)OCc1ccccc1]

A solution of benzyl 14-methyl-2,5,8-trioxa-11-thiapentadecan-14-ylcarbamate (1.24 g, 3.10 mmol) in dichloromethane (30 ml) was cooled to 0° C. 3-Chloroperbenzoic acid (77%, 2.18 g, 9.72 mmol) was added portion-wise, and the solution stirred for 2 hour. The solution was diluted with 500 ml ethyl acetate, washed with 3×100 ml saturated $NaHCO_3$, 1×100 ml saturated NaCl, dried on $MgSO_4$, and concentrated in vacuo. The residue was purified by flash chromatography (10% to 80% ethyl acetate in hexanes) to afford the title compound as a clear oil (790 mg, 1.83 mmol, 59%). $^1H$ NMR (400 MHz, $CDCl_3$) δ 1.35 (s, 6H), 2.21 (m, 2H), 3.19 (m, 2H), 3.37 (s, 3H), 3.5-3.7 (m, 8H), 3.90 (m, 2H), 5.06 (m, 3H), 7.2-7.4 (m, 5H); LRMS (ESI/APCI) m/z 432 $[M+H]^+$, 454 $[M+Na]^+$.

2-Methyl-4-(2-(2-(2-methoxyethoxy)ethoxy)ethyl-sulfonyl)butan-2-amine

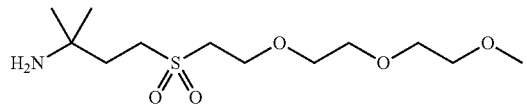 [SMILES: COCCOCCOCCS(=O)(=O)CCC(C)(C)N]

Benzyl 2-methyl-4-(2-(2-(2-methoxyethoxy)ethoxy)ethylsulfonyl)butan-2-ylcarbamate (790 mg, 1.83 mmol) was dissolved in methanol (15 ml) and was purged with nitrogen. Palladium on carbon (10%, 40 mg) was added, and the suspension was put under a blanket of hydrogen (1.3 atmospheres). The suspension was stirred for 1.5 hours, filtered through a 0.45 um PTFE filter, and the solution concentrated in vacuo. The material was used without further purification. $^1$H NMR (400 MHz, CDCl$_3$) δ 1.19 (s, 6H), 1.91 (m, 2H), 2.14 (s, 2H), 3.2-3.3 (m, 4H), 3.38 (s, 3H), 3.5-3.7 (m, 8H), 3.92 (m, 2H); LRMS (ESI/APCI) m/z 298 [M+H]$^+$.

N,N-Dichloro-2-methyl-4-(2-(2-(2-methoxyethoxy)ethoxy)ethylsulfonyl)butan-2-amine

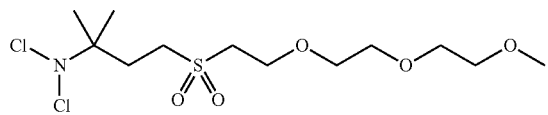 [SMILES: COCCOCCOCCS(=O)(=O)CCC(C)(C)N(Cl)Cl]

A solution of 2-methyl-4-(2-(2-(2-methoxyethoxy)ethoxy)ethylsulfonyl)butan-2-amine (1.83 mmol) in methanol (6 ml) was cooled to 0° C. tert-Butylhypochlorite (600 μl, 5.0 mmol) was added drop-wise over 10 minutes, and the solution stirred for 1 hour. The solution was concentrated in vacuo and the residue purified by preparatory HPLC (H$_2$O/acetonitrile) to afford the title compound as a clear oil (638.3 mg, 1.743 mmol, 95% over two steps). $^1$H NMR (400 MHz, CDCl$_3$) δ 1.41 (s, 6H), 2.20 (m, 2H), 3.17-3.21 (m, 4H), 3.37 (s, 3H), 3.5-3.7 (m, 8H), 3.90 (m, 2H). $^{13}$C NMR (100 MHz, CDCl$_3$) δ 23.5, 31.6, 50.0, 53.4, 59.0, 64.8, 70.3, 70.5, 70.7, 71.9, 73.1. ESI/APCI (pos) expected for C$_{12}$H$_{25}$Cl$_2$NO$_5$S: 365.08; LRMS (ESI/APCI) m/z 366 [M+H]$^+$, 388 [M+Na]$^+$.

Example 2

2-(3-(Dichloroamino)-3-methylbutylsulfonyl)ethanol (Compound 38-25)

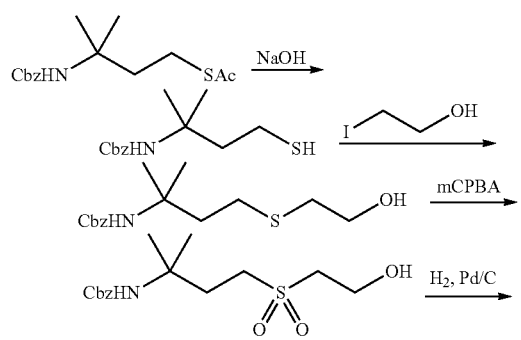

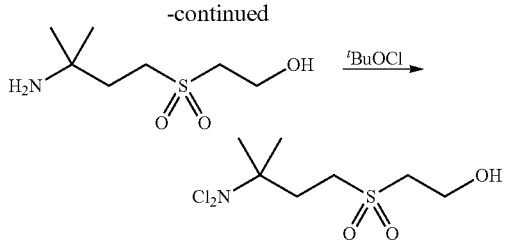

Benzyl 4-mercapto-2-methylbutan-2-ylcarbamate

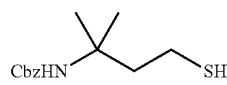

To a solution of S-3-(benzyloxycarbonylamino)-3-methylbutyl ethanethioate (10.60 g, 35.88 mmol, prepared as described in WO 2008/083347) in methanol (100 ml) was added 5.0 M NaOH in H$_2$O (15 ml, 75 mmol). The solution was stirred for 2 hour, concentrated in vacuo, and the residue suspended in ethyl acetate (300 ml), washed with 3×100 ml 5% NaHSO$_4$, 1×100 ml saturated NaCl, dried on MgSO$_4$, and concentrated in vacuo. The material was used without further purification.

Benzyl 4-(2-hydroxyethylthio)-2-methylbutan-2-ylcarbamate

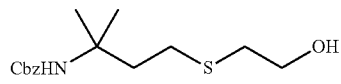 [SMILES: CC(C)(CCSCCO)NC(=O)OCc1ccccc1]

To a solution of benzyl 4-mercapto-2-methylbutan-2-ylcarbamate (3.30 g, 12.2 mmol) in N,N-dimethylformamide (50 ml) was added iodoethanol (1.4 ml, 18.0 mmol) and cesium carbonate (390 mg, 1.20 mmol). The solution was heated to 85° C. for 16 hours, cooled to room temperature, and concentrated in vacuo. The residue was purified by flash chromatography (30% to 100% ethyl acetate in hexanes) to afford the title compound as a clear oil (1.01 g, 3.40 mmol, 26%). $^1$H NMR (400 MHz, CDCl$_3$) δ 1.31 (s, 6H), 2.0-2.1 (m, 2H), 2.47-2.51 (m, 2H), 2.72 (m, 2H), 3.70 (m, 2H), 4.7 (s, 1H), 5.06 (s, 2H), 7.3-7.4 (m, 5H); LRMS (ESI/APCI) m/z 298 [M+H]$^+$, 320 [M+Na]$^+$.

Benzyl 4-(2-hydroxyethylsulfonyl)-2-methylbutan-2-ylcarbamate

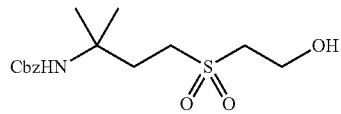 [SMILES: CC(C)(CCS(=O)(=O)CCO)NC(=O)OCc1ccccc1]

A solution of benzyl 4-(2-hydroxyethylthio)-2-methylbutan-2-ylcarbamate (1.01 g, 3.06 mmol) in dichloromethane (10 ml) was cooled to 0° C. and 3-chloroperbenzoic acid (77%, 2.01 g, 8.97 mmol) was added. The solution was stirred for 1.5 hour, concentrated in vacuo, and the residue partitioned between 150 ml ethyl acetate and 50 ml saturated NaHCO₃. The organic phase was washed with 2×50 ml saturated NaHCO₃, 1×100 ml saturated NaCl, dried on MgSO₄ and concentrated in vacuo. The residue was purified by flash chromatography (20% to 100% ethyl acetate in hexanes) to afford the title compound as a clear oil (790 mg, 2.40 mmol, 71%). $^1$H NMR (400 MHz, CDCl₃) δ 1.33 (s, 6H), 2.26-2.30 (m, 2H), 2.4-2.5 (br s, 1H), 3.0-3.1 (m, 2H), 3.17 (m, 2H), 4.04 (m, 2H), 4.74 (s, 1H), 5.06 (s, 2H), 7.34-7.39 (m, 5H); LRMS (ESI/APCI) m/z 330 [M+H]⁺, 352 [M+Na]⁺.

2-(3-Amino-3-methylbutylsulfonyl)ethanol

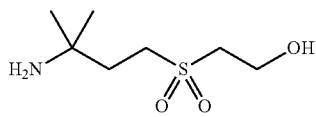

A solution of benzyl 4-(2-hydroxyethylsulfonyl)-2-methylbutan-2-ylcarbamate (790 mg, 2.40 mmol) in methanol (30 ml) was purged with nitrogen and palladium on carbon (10%, 120 mg) was added. The solution was put under a blanket of hydrogen (1.3 atmospheres) and stirred for 1.5 hours at room temperature. The suspension was filtered through 0.45 um PTFE and concentrated in vacuo to afford the title compound which was used without further purification. LRMS (ESI/APCI) m/z 196 [M+H]⁺.

2-(3-(Dichloroamino)-3-methylbutylsulfonyl)ethanol

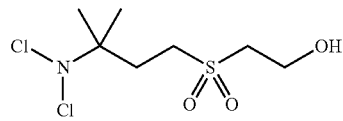

A solution of 2-(3-amino-3-methylbutylsulfonyl)ethanol (x mg, 2.40 mmol) in methanol (10 ml) was cooled to 0° C. and tert-butylhypochlorite (700 μl, 5.9 mmol) was added drop-wise. The solution was stirred for 30 minutes, concentrated in vacuo, and the residue purified by flash chromatography (50% to 100% ethyl acetate in hexanes) to afford the title compound as a white solid (500 mg, 1.89 mmol, 79% over two steps). $^1$H NMR (400 MHz, D₂O) δ 1.42 (s, 6H), 2.18-2.22 (m, 2H), 2.94-2.97 (t, J=5.6 Hz, 1H), 3.15-3.23 (m, 4H), 4.08 (m, 2H). $^{13}$C NMR (100 MHz, D₂O) δ 23.49, 31.57, 49.61, 55.11, 56.27, 72.99. LRMS (ESI/APCI) m/z 264 [M+H]⁺.

Example 3

3-(3-(Dichloroamino)-3-methylbutylsulfonyl)propane-1,2-diol (Compound 38-27)

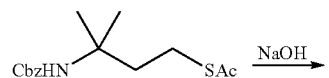

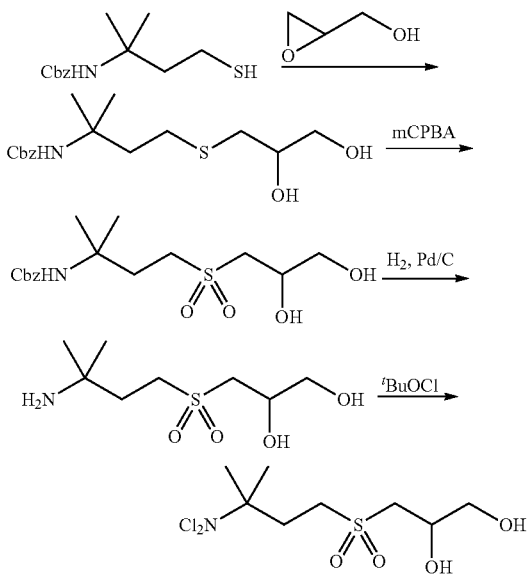

Benzyl 4-mercapto-2-methylbutan-2-ylcarbamate

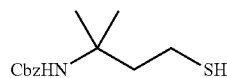 [SMILES: CC(C)(CCS)NC(=O)OCc1ccccc1]

To a solution of S-3-(benzyloxycarbonylamino)-3-methylbutyl ethanethioate (10.60 g, 35.88 mmol, prepared as described in WO 2008/083347) in methanol (100 ml) was added 5.0 M NaOH in H₂O (15 ml, 75 mmol). The solution was stirred for 2 hour, concentrated in vacuo, and the residue suspended in ethyl acetate (300 ml), washed with 3×100 ml 5% NaHSO₄, 1×100 ml saturated NaCl, dried on MgSO₄, and concentrated in vacuo. The reaction product was used without further purification.

Benzyl 4-(2,3-dihydroxypropylthio)-2-methylbutan-2-ylcarbamate

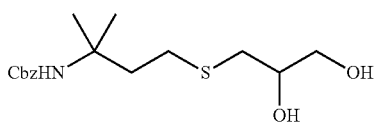 [SMILES: CC(C)(CCSCC(O)CO)NC(=O)OCc1ccccc1]

To a solution of benzyl 4-mercapto-2-methylbutan-2-ylcarbamate (3.04 g, 12.0 mmol) in N,N-dimethylformamide (50 ml) was added oxiran-2-ylmethanol (1.10 ml, 16.6 mmol) and cesium carbonate (520 mg, 1.6 mmol). The solution was heated to 85° C. for 16 hour, cooled to room temperature, and concentrated in vacuo. The residue was purified by flash chromatography (30% to 80% ethyl acetate in hexanes) to afford the title compound as a clear oil (3.52 g, 10.8 mmol, 90%). $^1$H NMR (400 MHz, CDCl₃) δ 1.30 (m, 6H), 2.0-2.1 (m, 2H), 2.24 (m, 1H), 2.49-2.62 (m, 3H), 2.71 (m, 1H), 3.5

(m, 1H), 3.7 (m, 2H), 4.75 (s, 1H), 5.06 (s, 2H), 7.3-7.4 (m, 5H); LRMS (ESI/APCI) m/z 328 [M+H]+, 350 [M+Na]+.

Benzyl 4-(2,3-dihydroxypropylsulfonyl)-2-methylbutan-2-ylcarbamate

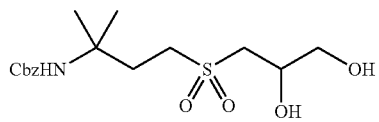 [SMILES: CC(C)(CCS(=O)(=O)CC(O)CO)NC(=O)OCc1ccccc1]

A solution of benzyl 4-(2,3-dihydroxypropylthio)-2-methylbutan-2-ylcarbamate (3.52 g, 9.8 mmol) in dichloromethane (15 ml) was cooled to 0° C. and 77% 3-chloroperbenzoic acid (5.39 g, 24.0 mmol) was added. The solution was stirred for 1 hour, concentrated in vacuo, and the residue partitioned between 200 ml ethyl acetate and 100 ml saturated NaHCO$_3$. The organic phase was washed with 2×100 ml saturated NaHCO$_3$, 1×100 ml saturated NaCl, dried on MgSO$_4$ and concentrated in vacuo. The residue was purified by flash chromatography (20% to 100% ethyl acetate in hexanes) to afford the title compound as a clear oil (2.34 g, 6.51 mmol, 60%). $^1$H NMR (400 MHz, CDCl$_3$) δ 1.30 (m, 6H), 2.2-2.3 (m, 2H), 2.4-2.5 (br s, 1H), 3.0-3.3 (m, 4H), 3.4 (br s, 1H), 3.60 (m, 1H), 3.68 (m, 1H), 4.3 (br s, 1H), 4.80 (s, 1H), 5.06 (s, 2H), 7.34-7.39 (m, 5H); LRMS (ESI/APCI) m/z 360 [M+H]+, 382 [M+Na]+.

3-(3-Amino-3-methylbutylsulfonyl)propane-1,2-diol

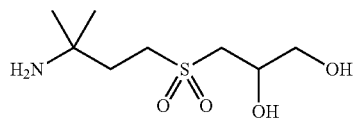

A solution of benzyl 4-(2,3-dihydroxypropylsulfonyl)-2-methylbutan-2-ylcarbamate (2.34 g, 10.4 mmol) in methanol (50 ml) was purged with nitrogen and palladium on carbon (10%, 230 mg) was added. The suspension was put under a blanket of hydrogen (1.3 atmospheres) and stirred for 2 hours. The suspension was filtered through Celite® and concentrated in vacuo to afford the title compound which was used without further purification. LRMS (ESI/APCI) m/z 226 [M+H]+.

3-(3-(Dichloroamino)-3-methylbutylsulfonyl)propane-1,2-diol

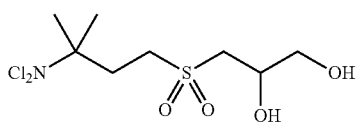

A solution of 3-(3-amino-3-methylbutylsulfonyl)propane-1,2-diol (10.4 mmol) in methanol (20 ml) was cooled to 0° C. and tert-butylhypochlorite (1.8 ml, 15 mmol) was added drop-wise. The solution was stirred for 30 minutes, concentrated in vacuo, and the residue purified by flash chromatography (50% to 100% ethyl acetate in hexanes) to afford the title compound as a clear oil (1.16 g, 3.94 mmol, 61% over two steps). $^1$H NMR (400 MHz, D$_2$O) δ 1.43 (s, 6H), 2.18-2.22 (m, 2H), 3.11-3.32 (m, 4H), 3.5-3.7 (m, 3H), 4.1 (s, 1H), 4.3 (s, 1H). $^{13}$C NMR (100 MHz, D$_2$O) δ 23.49, 31.45, 49.62, 55.66, 65.52, 66.85, 73.04; LRMS (ESI/APCI) m/z 296 [M+H]+.

Example 4

4-(3-(Dichloroamino)-3-methylbutylsulfonyl)butane-1,2,3-triol (Compound 38-29)

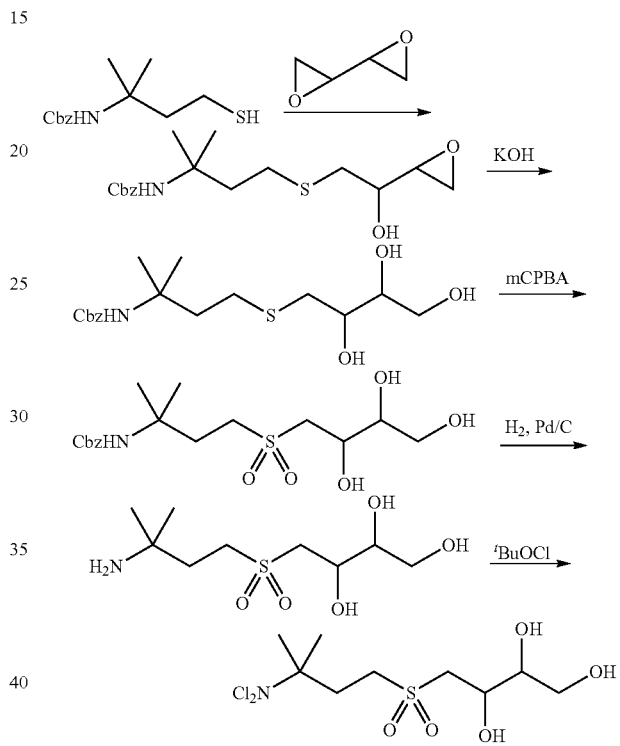

Benzyl 4-(2-hydroxy-2-(oxiran-2-yl)ethylthio)-2-methylbutan-2-yl)carbamate

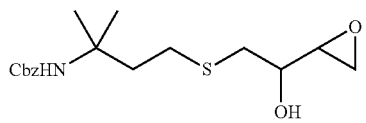 [SMILES: CC(C)(CCSCC(O)C1CO1)NC(=O)OCc1ccccc1]

To a solution of benzyl 4-mercapto-2-methylbutan-2-ylcarbamate (3.50 g, 13.8 mmol, prepared as described in WO 2008/083347) in N,N-dimethylformamide (100 ml) was added butadiene diepoxide (1.5 ml, 19 mmol) and cesium carbonate (4.31 g, 13.2 mmol). The solution was heated to 80° C. for 1 hour, cooled to room temperature, and concentrated in vacuo. The residue was purified by flash chromatography (30% to 60% ethyl acetate in hexanes) to afford the title compound as a clear oil (1.14 g, 3.36 mmol, 24.3%) and a 3:2 mixture of diastereomers. $^1$H NMR (400 MHz, CDCl$_3$) δ 1.29 (m, 6H), 2.0-2.1 (m, 2H), 2.55-2.83 (m, 6H), 2.86 (m, 0.4H), 3.1 (m, 0.6H), 3.8 (m, 0.6H), 3.9 (br s, 0.4H), 4.74 (s, 0.6H), 4.76 (s, 0.4H), 5.06 (s, 2H), 7.3-7.4 (m, 5H). LRMS (ESI/APCI) m/z 340 [M+H]⁺, 362 [M+Na]⁺.

Benzyl 2-methyl-4-(2,3,4-trihydroxybutylthio)butan-2-ylcarbamate

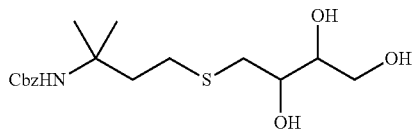 [SMILES: CC(C)(CCSCC(O)C(O)CO)NC(=O)OCc1ccccc1]

To a solution of benzyl 4-(2-hydroxy-2-(oxiran-2-yl)ethylthio)-2-methylbutan-2-ylcarbamate (3.33 g, 9.81 mmol) in dimethylsulfoxide (50 ml) and H$_2$O (10 ml) was added 5.0 M KOH (600 μl, 3.0 mmol). The solution was heated to 90° C. for 5 hour, cooled to room temperature, diluted with 400 ml ethyl acetate, washed with 1×200 ml 5% NaHSO$_4$, 5×200 ml saturated NaCl, dried on MgSO$_4$, and concentrated in vacuo. The residue was purified by preparatory HPLC (H$_2$O/acetonitrile) to give the title compound as a clear oil (159.3 mg, 0.446 mmol, 45%) as a mixture of diastereomers. $^1$H NMR (400 MHz, CDCl$_3$) δ 1.28 (s, 6H), 1.9-2.1 (m, 2H), 2.50 (m, 2H), 2.6-2.7 (m, 2H), 3.6-3.8 (m, 4H), 3.85 (br s, 3H), 4.93 (s, 1H), 5.04 (s, 2H), 7.3-7.4 (m, 5H); LRMS (ESI/APCI) m/z 358 [M+H]⁺, 380 [M+Na]⁺.

Benzyl 2-methyl-4-(2,3,4-trihydroxybutylsulfonyl)butan-2-ylcarbamate

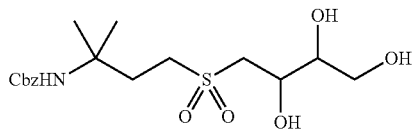 [SMILES: CC(C)(CCS(=O)(=O)CC(O)C(O)CO)NC(=O)OCc1ccccc1]

A solution of benzyl 2-methyl-4-(2,3,4-trihydroxybutylthio)butan-2-ylcarbamate (159.3 mg, 0.4456 mmol) in dichloromethane (5 ml) was cooled to 0° C. and 77% 3-chloroperbenzoic acid (260 mg, 1.16 mmol) was added. The solution was stirred for 2 hours, concentrated in vacuo, and the residue purified by preparatory HPLC (H$_2$O/acetontirile) to afford the title compound as a clear oil (116.4 mg, 0.2989 mmol, 67%); LRMS (ESI/APCI) m/z 390 [M+H]⁺, 412 [M+Na]⁺.

4-(3-Amino-3-methylbutylsulfonyl)butane-1,2,3-triol

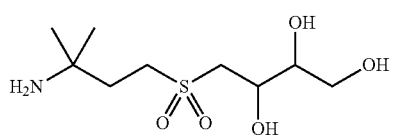 [SMILES: CC(C)(N)CCS(=O)(=O)CC(O)C(O)CO]

A solution of benzyl 2-methyl-4-(2,3,4-trihydroxybutylsulfonyl)butan-2-ylcarbamate (172.1 mg, 0.4418 mmol) in methanol (5 ml) was purged with nitrogen and palladium on carbon (10%, 40 mg) was added. The suspension was put under a blanket of hydrogen (1.3 atmospheres) and stirred for 3.5 hours. The suspension was filtered through a 0.45 um PTFE filter and concentrated in vacuo to afford the title compound which was used without further purification. LRMS (ESI/APCI) m/z 256 [M+H]⁺

4-(3-(Dichloroamino)-3-methylbutylsulfonyl)butane-1,2,3-triol

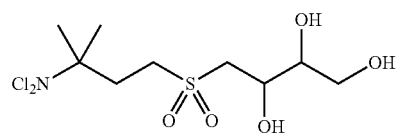

A solution of 4-(3-amino-3-methylbutylsulfonyl)butane-1,2,3-triol (112 mg, 0.4418 mmol) in methanol (5 ml) was cooled to 0° C. and tert-butylhypochlorite (160 μl, 1.34 mmol) was added drop-wise. The solution was stirred for 3 hours, concentrated in vacuo, and the residue purified by preparatory HPLC (H$_2$O/acetonitrile) to afford the title compound as a clear oil (63.0 mg, 0.194 mmol, 44% over two steps). $^1$H NMR (400 MHz, D$_2$O) δ 1.36 (d, J=2.8 Hz, 6H), 2.16 (m, 2H), 3.26-3.32 (m, 3H), 3.45-3.63 (m, 4H), 4.22 (m, 1H). $^{13}$C NMR (100 MHz, D$_2$O) δ 22.65, 22.71, 30.43, 49.41, 55.62, 62.06, 65.92, 73.29, 73.39; LRMS (ESI/APCI) m/z 324 [M+H]⁺, 346 [M+Na]⁺.

Example 5

2-(2-(2-(3-(Dichloroamino)-3-methylbutylsulfonyl)ethoxy)ethoxy)ethanol (Compound 38-85)

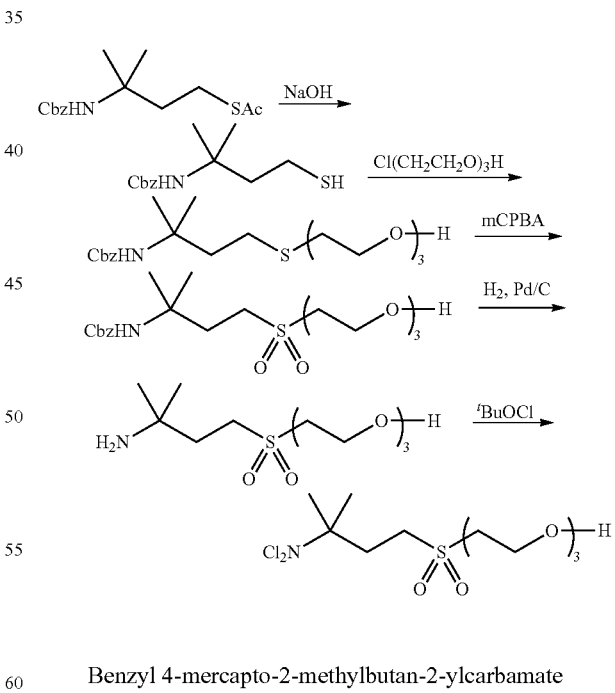

Benzyl 4-mercapto-2-methylbutan-2-ylcarbamate

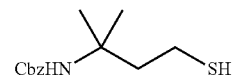 [SMILES: CC(C)(CCS)NC(=O)OCc1ccccc1]

To a solution of S-3-(benzyloxycarbonylamino)-3-methylbutyl ethanethioate (45.0 g, 152 mmol, prepared as described in WO 2008/083347) in methanol (300 ml) was added 5.0 M NaOH in H$_2$O (60.0 ml, 300 mmol). The solution was stirred for 1 hour, concentrated in vacuo, diluted with saturated NaHSO$_4$ (200 ml), filtered through a coarse glass funnel, and extracted with 5×100 ml ethyl acetate. The organic layers were combined, washed with 100 ml saturated NaCl, dried on MgSO$_4$, and concentrated in vacuo. The residue was used without further purification (24.10 g, 95.1 mmol, 63%).

Benzyl 4-(2-(2-(2-hydroxyethoxy)ethoxy)ethylthio)-2-methylbutan-2-ylcarbamate

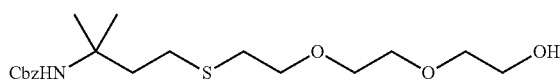 [SMILES: CC(C)(CCSCCOCCOCCO)NC(=O)OCc1ccccc1]

To a solution of benzyl 4-mercapto-2-methylbutan-2-ylcarbamate (6.70 g, 26.4 mmol) in N,N-dimethylformamide (100 ml) was added 2-(2-(2-chloroethoxy)ethoxy)ethanol (4.0 ml, 28 mmol) and cesium carbonate (8.06 g, 24.7 mmol). The suspension was heated to 70° C. for 17 hours, cooled to room temperature, and concentrated in vacuo. The residue was purified by flash chromatography (20% to 100% ethyl acetate in hexanes) to afford the title compound as a clear oil (3.32 g, 8.61 mmol, 33%). $^1$H NMR (CDCl$_3$, 400 MHz) δ 1.31 (s, 6H), 1.95-1.99 (m, 2H), 2.51-2.56 (m, 3H), 2.71 (t, J=5.6 Hz, 2H), 3.55-3.79 (m, 10H), 4.85 (s, 1H), 5.05 (s, 2H), 7.2-7.4 (m, 5H); LRMS (ESI/APCI) m/z 386 [M+H]$^+$, 408 [M+Na]$^+$.

Benzyl 4-(2-(2-(2-hydroxyethoxy)ethoxy)ethylsulfonyl)-2-methylbutan-2-ylcarbamate

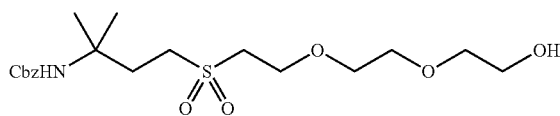 [SMILES: CC(C)(CCS(=O)(=O)CCOCCOCCO)NC(=O)OCc1ccccc1]

A solution of benzyl 4-(2-(2-(2-hydroxyethoxy)ethoxy)ethylthio)-2-methylbutan-2-ylcarbamate (3.32 g, 8.61 mmol) in dichloromethane (50 ml) was cooled to 0° C. and 77% mCPBA (4.67 g, 20.8 mmol) was added portionwise over 15 minutes. The solution was stirred for 45 minutes, concentrated in vacuo, and the residue purified by flash chromatography (50% to 100% ethyl acetate in hexanes) to afford the title compound as a clear oil (1.97 g, 4.72 mmol, 55%). $^1$H NMR (CDCl$_3$, 400 MHz) δ 1.34 (s, 6H), 2.17-2.21 (m, 2H), 2.7 (br s, 1H), 3.15-3.19 (m, 4H), 3.52-3.54 (m, 2H), 3.56-3.62 (m, 4H), 3.69 (m, 2H), 5.05 (s, 2H), 5.12 (s, 1H), 7.3-7.4 (m, 5H); LRMS (ESI/APCI) m/z 418 [M+H]$^+$, 440 [M+Na]$^+$.

2-(2-(2-(3-Amino-3-methylbutylsulfonyl)ethoxy)ethoxy)ethanol

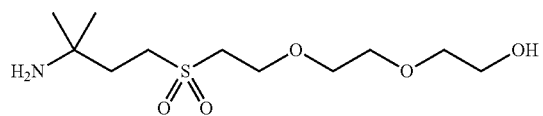 [SMILES: CC(C)(N)CCS(=O)(=O)CCOCCOCCO]

To a solution of benzyl 4-(2-(2-(2-hydroxyethoxy)ethoxy)ethylsulfonyl)-2-methylbutan-2-ylcarbamate (223 mg, 0.534 mmol) in methanol (5 ml) was added palladium on carbon (10%, 35 mg). The suspension was put under a N$_2$ atmosphere and H$_2$ (1.3 atmospheres) introduced. The suspension was stirred for 1 hour, filtered (0.45 um, PTFE), and concentrated in vacuo. The residue was used without any further purification. LRMS (ESI/APCI) m/z 284 [M+H]$^+$.

2-(2-(2-(3-(Dichloroamino)-3-methylbutylsulfonyl)ethoxy)ethoxy)ethanol

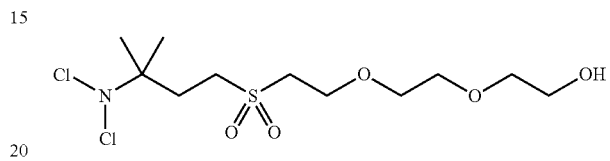

A solution of 2-(2-(2-(3-amino-3-methylbutylsulfonyl)ethoxy)ethoxy)ethanol (x mg, 0.534 mmol) in methanol (3 ml) was cooled to 0° C. and tert-butylhypochlorite (150 µl, 1.26 mmol) was added drop-wise. The solution was stirred for 3 hours and concentrated in vacuo. The residue was purified by flash chromatography (50% to 100% ethyl acetate in hexanes, then 0% to 20% methanol in ethyl acetate) to afford the title compound as a clear oil (154.9 mg, 0.4395 mmol, 82% over two steps). $^1$H NMR (CDCl$_3$, 400 MHz) δ 1.37 (s, 6H), 2.13-2.18 (m, 2H), 2.7-2.9 (br s, 1H), 3.15-3.20 (m, 4H), 3.52-3.56 (m, 2H), 3.62 (s, 4H), 3.67-3.70 (m, 2H), 3.88 (dd, J=6.8, 7.2 Hz, 2H). $^{13}$C NMR (CDCl$_3$, 100 MHz) δ 23.5, 31.5, 49.9, 53.3, 61.6, 64.7, 70.1, 70.5, 72.5, 73.1; LRMS (ESI/APCI) m/z 353 [M+H]$^+$, 375 [M+Na]$^+$.

Example 6

2-(2-(2-(3-(Dichloroamino)-3-methylbutylsulfonyl)ethoxy)ethoxy)ethyl acetate (Compound 38-87)

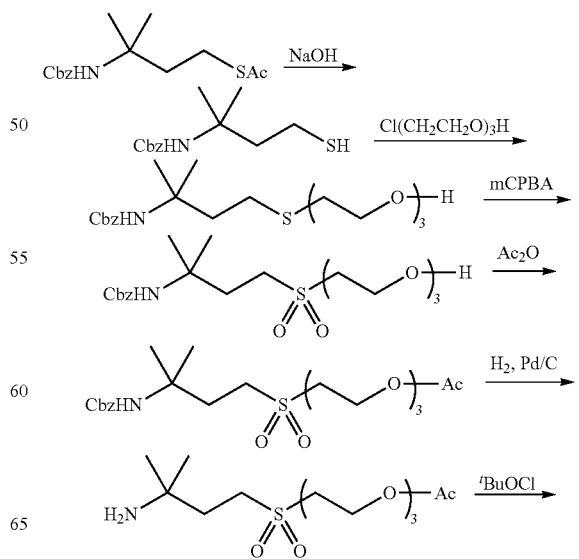

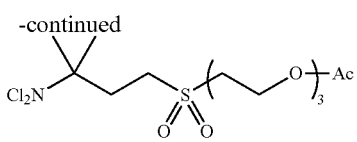

Benzyl 4-mercapto-2-methylbutan-2-ylcarbamate

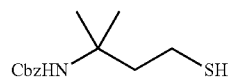

To a solution of S-3-(benzyloxycarbonylamino)-3-methylbutyl ethanethioate (45.0 g, 152 mmol, prepared as described in WO 2008/083347) in methanol (300 ml) was added 5.0 M NaOH in $H_2O$ (60.0 ml, 300 mmol). The solution was stirred for 1 hour, concentrated in vacuo, diluted with saturated $NaHSO_4$ (200 ml), filtered through a coarse glass funnel, and extracted with 5×100 ml ethyl acetate. The organic layers were combined, washed with 100 ml saturated NaCl, dried on $MgSO_4$, and concentrated in vacuo. The residue was used without further purification (24.10 g, 95.1 mmol, 63%).

Benzyl 4-(2-(2-(2-hydroxyethoxy)ethoxy)ethylthio)-2-methylbutan-2-ylcarbamate

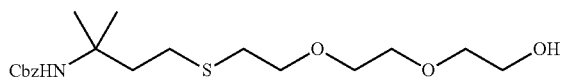 [SMILES: CC(C)(CCSCCOCCOCCO)NC(=O)OCc1ccccc1]

To a solution of benzyl 4-mercapto-2-methylbutan-2-ylcarbamate (6.70 g, 26.4 mmol) in N,N-dimethylformamide (100 ml) was added 2-(2-(2-chloroethoxy)ethoxy)ethanol (4.0 ml, 28 mmol) and cesium carbonate (8.06 g, 24.7 mmol). The suspension was heated to 70° C. for 17 hours, cooled to room temperature, and concentrated in vacuo. The residue was purified by flash chromatography (20% to 100% ethyl acetate in hexanes) to afford the title compound as a clear oil (3.32 g, 8.61 mmol, 33%). $^1$H NMR (CDCl$_3$, 400 MHz) δ 1.31 (s, 6H), 1.95-1.99 (m, 2H), 2.51-2.56 (m, 3H), 2.71 (t, J=5.6 Hz, 2H), 3.55-3.79 (m, 10H), 4.85 (s, 1H), 5.05 (s, 2H), 7.2-7.4 (m, 5H); LRMS (ESI/APCI) m/z 386 [M+H]$^+$, 408 [M+Na]$^+$.

Benzyl 4-(2-(2-(2-hydroxyethoxy)ethoxy)ethylsulfonyl)-2-methylbutan-2-ylcarbamate

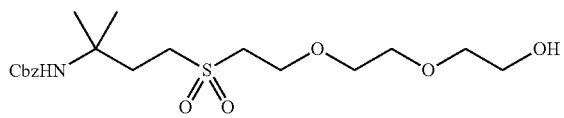 [SMILES: CC(C)(CCS(=O)(=O)CCOCCOCCO)NC(=O)OCc1ccccc1]

A solution of benzyl 4-(2-(2-(2-hydroxyethoxy)ethoxy)ethylthio)-2-methylbutan-2-ylcarbamate (3.32 g, 8.61 mmol) in dichloromethane (50 ml) was cooled to 0° C. and 77% 4-chloroperoxybenzoic acid (4.67 g, 20.8 mmol) was added portionwise over 15 minutes. The solution was stirred for 45 minutes, concentrated in vacuo, and the residue purified by flash chromatography (50% to 100% ethyl acetate in hexanes) to afford the title compound as a clear oil (1.97 g, 4.72 mmol, 55%). $^1$H NMR (CDCl$_3$, 400 MHz) δ 1.34 (s, 6H), 2.17-2.21 (m, 2H), 2.7 (br s, 1H), 3.15-3.19 (m, 4H), 3.52-3.54 (m, 2H), 3.56-3.62 (m, 4H), 3.69 (m, 2H), 5.05 (s, 2H), 5.12 (s, 1H), 7.3-7.4 (m, 5H); LRMS (ESI/APCI) m/z 418 [M+H]$^+$, 440 [M+Na]$^+$.

Benzyl 4-(2-(2-(2-acetoxyethoxy)ethoxy)ethylsulfonyl)-2-methylbutan-2-ylcarbamate

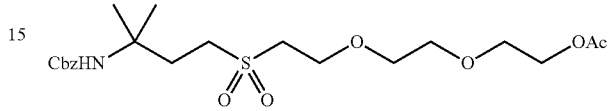

A solution of benzyl 4-(2-(2-(2-hydroxyethoxy)ethoxy)ethylsulfonyl)-2-methylbutan-2-ylcarbamate (451 mg, 1.08 mmol) in dichloromethane (5 ml) was cooled to 0° C. Pyridine (200 μl, 2.48 mmol), then acetic anhydride (150 μl, 1.59 mmol) were added. The solution was stirred for 3 hours, and another portion of pyridine (200 μl, 2.48 mmol) then acetic anhydride (150 μl, 1.59 mmol) were added. The solution was stirred for an additional 20 hours, concentrated in vacuo, and the residue purified by flash chromatography (20% to 100% ethyl acetate in hexanes) to afford the title compound as a clear oil (440.2 mg, 0.959 mmol, 89%). $^1$H NMR (CDCl$_3$, 400 MHz) δ 1.31 (s, 6H), 2.04 (s, 3H), 2.15-2.20 (m, 2H), 3.09-3.16 (m, 4H), 3.54-3.61 (m, 6H), 3.85 (t, J=5.6 Hz, 2H), 4.16 (m, 2H), 5.02 (s, 3H), 7.3-7.4 (m, 5H); LRMS (ESI/APCI) m/z 460 [M+H]$^+$, 482 [M+Na]$^+$.

2-(2-(2-(3-Amino-3-methylbutylsulfonyl)ethoxy)ethoxy)ethyl acetate

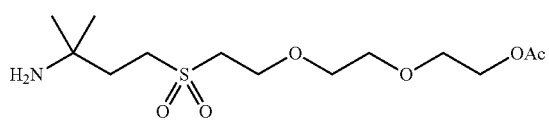 [SMILES: CC(=O)OCCOCCOCCS(=O)(=O)CCC(C)(C)N]

To a solution of benzyl 4-(2-(2-(2-acetoxyethoxy)ethoxy)ethylsulfonyl)-2-methylbutan-2-ylcarbamate (440.2 mg, 0.959 mmol) in methanol (5 ml) was added Pd on carbon (10%, 83 mg). The suspension was put under a $N_2$ atmosphere and $H_2$ (1.3 atm) introduced. The suspension was stirred for 1.5 hours, filtered (0.45 um, PTFE), and concentrated in vacuo. The residue was used without any further purification. LRMS (ESI/APCI) m/z 326 [M+H]$^+$.

2-(2-(2-(3-(Dichloroamino)-3-methylbutylsulfonyl)ethoxy)ethoxy)ethyl acetate

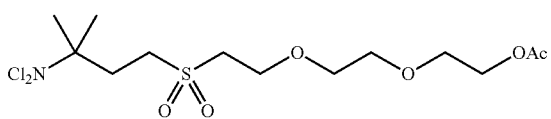

A solution of 2-(2-(2-(3-amino-3-methylbutylsulfonyl)ethoxy)ethoxy)ethyl acetate (0.959 mmol) in methanol (3 ml)

was cooled to 0° C. and tert-butylhypochlorite (400 μl, 3.35 mmol) was added drop-wise. The solution was stirred for 1 hour and concentrated in vacuo. The residue was purified by flash chromatography (50% to 100% ethyl acetate in hexanes) to afford the title compound as a clear oil (338.6 mg, 0.8587 mmol, 90% over two steps). $^1$H NMR (CDCl$_3$, 400 MHz) δ 1.41 (s, 6H), 2.08 (s, 3H), 2.18-2.22 (m, 2H), 3.18-3.22 (m, 4H), 3.66 (s, 4H), 3.67-3.69 (m, 2H), 3.91 (dd, J=4.8, 5.6 Hz, 2H), 4.22 (m, 2H). $^{13}$C NMR (CDCl$_3$, 100 MHz) δ 21.0, 23.5, 31.6, 49.9, 53.4, 63.4, 64.9, 69.2, 70.2, 70.7, 73.0, 171.0; LRMS (ESI/APCI) m/z 416 [M+Na]$^+$.

Example 7

3-(3-(Dichloroamino)-3-methylbutylsulfonyl)propane-1,2-diyl diacetate (Compound 38-51)

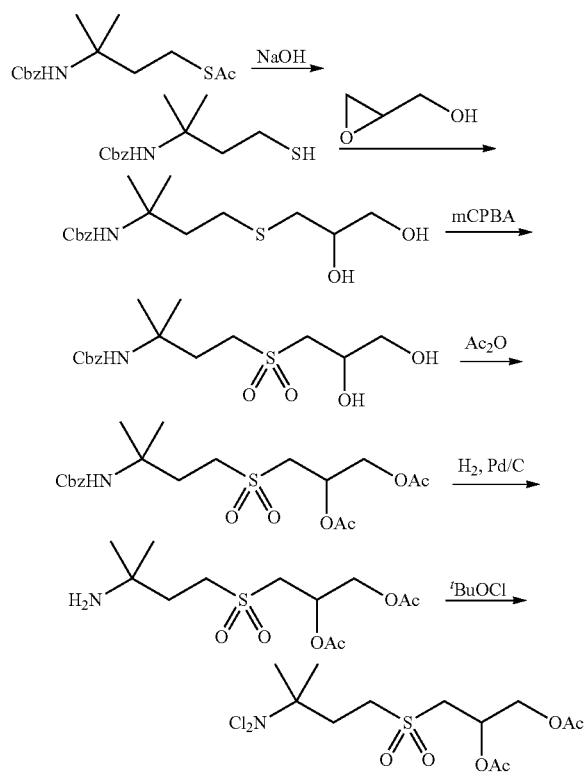

Benzyl 4-mercapto-2-methylbutan-2-ylcarbamate

To a solution of S-3-(benzyloxycarbonylamino)-3-methylbutyl ethanethioate (45.0 g, 152 mmol, prepared as described in WO 2008/083347) in methanol (300 ml) was added 5.0 M NaOH in H$_2$O (60.0 ml, 300. mmol). The solution was stirred for 1 hour, concentrated in vacuo, diluted with saturated NaHSO$_4$ (200 ml), filtered through a coarse glass funnel, and extracted with 5×100 ml ethyl acetate. The organic layers were combined, washed with 100 ml saturated NaCl, dried on MgSO$_4$, and concentrated in vacuo. The residue was used without further purification (24.10 g, 95.1 mmol, 63%).

Benzyl 4-(2,3-dihydroxypropylthio)-2-methylbutan-2-ylcarbamate

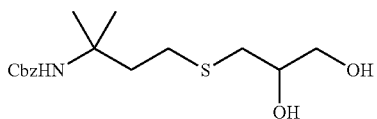 [SMILES: CC(C)(CCSCC(O)CO)NC(=O)OCc1ccccc1]

To a solution of benzyl 4-mercapto-2-methylbutan-2-ylcarbamate (17.4 g, 68.7 mmol) in N,N-dimethylformamide (200 ml) was added glycidol (5.0 ml, 75 mmol) and cesium carbonate (1.55 g, 4.76 mmol). The suspension was heated to 70° C. for 17 hours, then cooled to room temperature and concentrated in vacuo. The residue was purified by flash chromatography (20% to 100% ethyl acetate in hexanes) to afford the title compound as a clear oil (13.48 g, 41.22 mmol, 60%). $^1$H NMR (400 MHz, CDCl$_3$) δ 1.30 (m, 6H), 2.0-2.1 (m, 2H), 2.24 (m, 1H), 2.49-2.62 (m, 3H), 2.71 (m, 1H), 3.5 (m, 1H), 3.7 (m, 2H), 4.75 (s, 1H), 5.06 (s, 2H), 7.3-7.4 (m, 5H); LRMS (ESI/APCI) m/z 328 [M+H]$^+$, 350 [M+Na]$^+$.

Benzyl 4-(2,3-dihydroxypropylsulfonyl)-2-methylbutan-2-ylcarbamate

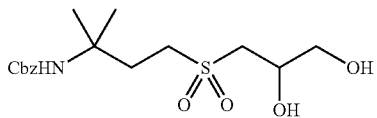 [SMILES: CC(C)(CCS(=O)(=O)CC(O)CO)NC(=O)OCc1ccccc1]

A solution of benzyl 4-(2,3-dihydroxypropylthio)-2-methylbutan-2-ylcarbamate (13.48 g, 41.17 mmol) in dichloromethane (400 ml) was cooled to 0° C. 3-Chloroperbenzoic acid (77%, 32.3 g, 144 mmol) was added in about 0.5 g portions over 15 minutes, and the solution stirred for an additional 45 min. The solution was concentrated in vacuo, and the residue purified by flash chromatography (50% to 100% ethyl acetate in hexanes) to afford the title compound as a clear oil which solidifies upon addition of dichloromethane. $^1$H NMR (400 MHz, CDCl$_3$) δ 1.30 (m, 6H), 2.2-2.3 (m, 2H), 2.4-2.5 (br s, 1H), 3.0-3.3 (m, 4H), 3.4 (br s, 1H), 3.60 (m, 1H), 3.68 (m, 1H), 4.3 (br s, 1H), 4.80 (s, 1H), 5.06 (s, 2H), 7.34-7.39 (m, 5H); LRMS (ESI/APCI) m/z 360 [M+H]$^+$, 382 [M+Na]$^+$.

3-(3-(Benzyloxycarbonylamino)-3-methylbutylsulfonyl)propane-1,2-diyl diacetate

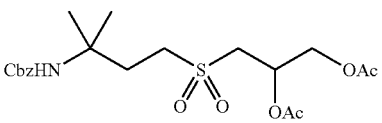 [SMILES: CC(=O)OCC(CS(=O)(=O)CCC(C)(C)NC(=O)OCc1ccccc1)OC(C)=O]

To a solution of benzyl 4-(2,3-dihydroxypropylsulfonyl)-2-methylbutan-2-ylcarbamate (455.6 mg, 1.268 mmol) in dichloromethane (10 ml) was added pyridine (500 μl, 6.2 mmol) and acetic anhydride (600 μl, 6.4 mmol) portionwise over 3 hours. The solution was stirred for 18 hours, concentrated in vacuo, dissolved in ethyl acetate (250 ml), washed with 2×100 ml 5% NaHSO$_4$, 2×100 ml saturated NaHCO$_3$, 1×100 ml saturated NaCl, dried on MgSO$_4$, and concentrated in vacuo. The residue was purified by flash chromatography (50% to 100% ethyl acetate in hexanes) to afford the title compound as a clear oil (530.0 mg, 1.195 mmol, 94%). $^1$H NMR (CDCl$_3$, 400 MHz) δ 1.32 (s, 6H), 2.07 s, 3H), 2.09 (s, 3H), 2.23-2.27 (m, 2H), 3.03-3.08 (m, 2H), 3.21 (dd, J=4.4, 14.8 Hz, 1H), 3.34 (dd, J=8.0, 14.8 Hz, 1H), 4.16 (dd, J=4.8, 12.0 Hz, 1H), 4.36 (dd, J=4.0, 12.0 Hz, 1H), 4.87 (s, 1H), 5.04 (s, 2H), 5.50-5.52 (m, 1H), 7.3-7.4 (m, 5H); LRMS (ESI/APCI) m/z 444 [M+H]$^+$, 466 [M+Na]$^+$.

3-(3-Amino-3-methylbutylsulfonyl)propane-1,2-diyl diacetate

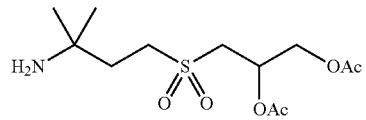 [SMILES: CC(=O)OCC(CS(=O)(=O)CCC(C)(C)N)OC(C)=O]

To a solution of 3-(3-(benzyloxycarbonylamino)-3-methylbutylsulfonyl)propane-1,2-diyl diacetate (401.9 mg, 0.9062 mmol) in methanol (10 ml) was added palladium on carbon (10%, 45 mg). The solution was purged with nitrogen gas, and then the suspension was put under a blanket of hydrogen gas (1.3 atm). The suspension was stirred for 1.5 hours, filtered through a 0.45 um PTFE filter, and concentrated in vacuo. The residue was used without any further purification. LRMS (ESI/APCI) m/z 310 [M+H]$^+$.

3-(3-(Dichloroamino)-3-methylbutylsulfonyl)propane-1,2-diyl diacetate

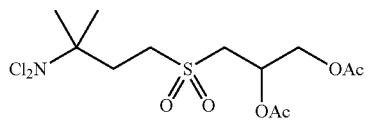

A solution of 3-(3-amino-3-methylbutylsulfonyl)propane-1,2-diyl diacetate (0.9062 mmol) in methanol (10 ml) was cooled to 0° C. and tert-butylhypochlorite (300 μl, 2.51 mmol) was added drop-wise. The solution was stirred for 1 h, concentrated in vacuo, and the residue purified by flash chromatography (50% to 100% ethyl acetate in hexanes) to afford the title compound as a clear oil. $^1$H NMR (CDCl$_3$, 400 MHz) δ 1.42 (s, 6H), 2.08 (s, 3H), 2.11 (s, 3H), 2.17-2.22 (m, 2H), 3.13 (t, J=8.4 Hz, 2H), 3.25 (dd, J=3.6, 15.2 Hz, 1H), 3.38 (dd, J=8.0, 15.2 Hz, 1H), 4.17 (dd, J=4.8, 12.0 Hz, 1H), 4.39 (dd, J=4.0, 12.0 Hz, 1H), 5.48-5.51 (m, 1H). $^{13}$C NMR (CDCl$_3$, 100 MHz) δ 20.7, 20.8, 23.4, 23.5, 31.4, 49.1, 53.4, 63.7, 66.2, 72.9, 169.6, 170.3. ESI/APCI (pos) expected for C$_{12}$H$_{21}$Cl$_2$NO$_6$S: 377.05. Found: 395 (M$^+$+H$_2$O), 400 (MNa$^+$), 441 (MNa$^+$+CH$_3$CN). LRMS (ESI/APCI) m/z 400 [M+Na]$^+$, 441 [M+Na+CH$_3$CN]$^+$.

Example 8

3-(3-(Dichloroamino)-3-methylbutylsulfonyl)-2-hydroxypropyl acetate (Compound 38-49)

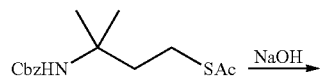

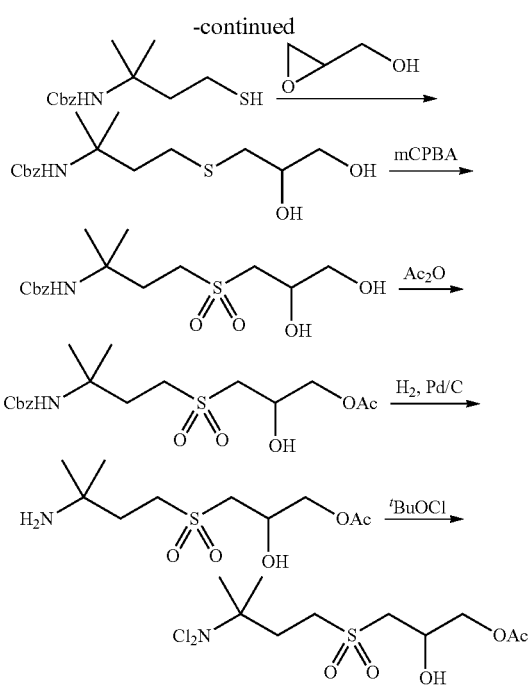

Benzyl 4-mercapto-2-methylbutan-2-ylcarbamate

To a solution of S-3-(benzyloxycarbonylamino)-3-methylbutyl ethanethioate (45.0 g, 152 mmol, prepared as described in WO 2008/083347) in methanol (300 ml) was added 5.0 M NaOH in H$_2$O (60.0 ml, 300 mmol). The solution was stirred for 1 hour, concentrated in vacuo, diluted with saturated NaHSO$_4$ (200 ml), filtered through a coarse glass funnel, and extracted with 5×100 ml ethyl acetate. The organic layers were combined, washed with 100 ml saturated NaCl, dried on MgSO$_4$, and concentrated in vacuo. The residue was used without further purification (24.10 g, 95.1 mmol, 63%).

Benzyl 4-(2,3-dihydroxypropylthio)-2-methylbutan-2-ylcarbamate

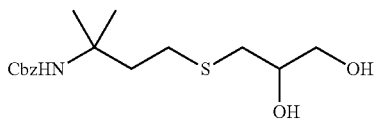 [SMILES: CC(C)(CCSCC(O)CO)NC(=O)OCc1ccccc1]

To a solution of benzyl 4-mercapto-2-methylbutan-2-ylcarbamate (17.4 g, 68.7 mmol) in N,N-dimethylformamide (200 ml) was added glycidol (5.0 ml, 75 mmol) and cesium carbonate (1.55 g, 4.76 mmol). The suspension was heated to 70° C. for 17 hours, then cooled to room temperature and concentrated in vacuo. The residue was purified by flash chromatography (20% to 100% ethyl acetate in hexanes) to afford the title compound as a clear oil (13.48 g, 41.17 mmol, 60%). $^1$H NMR (400 MHz, CDCl$_3$) δ 1.30 (m, 6H), 2.0-2.1 (m, 2H), 2.24 (m, 1H), 2.49-2.62 (m, 3H), 2.71 (m, 1H), 3.5 (m, 1H), 3.7 (m, 2H), 4.75 (s, 1H), 5.06 (s, 2H), 7.3-7.4 (m, 5H); LRMS (ESI/APCI) m/z 328 [M+H]$^+$, 350 [M+Na]$^+$.

Benzyl 4-(2,3-dihydroxypropylsulfonyl)-2-methylbutan-2-ylcarbamate

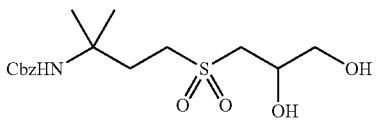 [SMILES: CC(C)(CCS(=O)(=O)CC(O)CO)NC(=O)OCc1ccccc1]

A solution of benzyl 4-(2,3-dihydroxypropylthio)-2-methylbutan-2-ylcarbamate (13.48 g, 41.17 mmol) in dichloromethane (400 ml) was cooled to 0° C. 77% 3-Chloroperbenzoic acid (32.3 g, 144 mmol) was added in about 0.5 g portions over 15 minutes, and the solution stirred for an additional 45 min. The solution was concentrated in vacuo, and the residue purified by flash chromatography (50% to 100% ethyl acetate in hexanes) to afford the title compound as a clear oil which solidifies upon addition of dichloromethane. $^1$H NMR (400 MHz, CDCl$_3$) δ 1.30 (m, 6H), 2.2-2.3 (m, 2H), 2.4-2.5 (br s, 1H), 3.0-3.3 (m, 4H), 3.4 (br s, 1H), 3.60 (m, 1H), 3.68 (m, 1H), 4.3 (br s, 1H), 4.80 (s, 1H), 5.06 (s, 2H), 7.34-7.39 (m, 5H); LRMS (ESI/APCI) m/z 360 [M+H]$^+$, 382 [M+Na]$^+$.

3-(3-(Benzyloxycarbonylamino)-3-methylbutylsulfonyl)-2-hydroxypropyl acetate

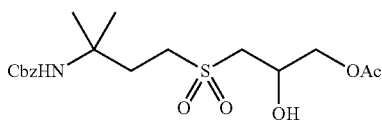 [SMILES: CC(=O)OCC(O)CS(=O)(=O)CCC(C)(C)NC(=O)OCc1ccccc1]

A solution of benzyl 4-(2,3-dihydroxypropylsulfonyl)-2-methylbutan-2-ylcarbamate (1.017 g, 2.829 mmol) in dichloromethane (20 ml) was cooled to 0° C. and pyridine (300 μl, 3.7 mmol) and acetic anhydride (400 μl, 4.2 mmol) portion-wise over 3 hour. The solution was concentrated in vacuo, dissolved in ethyl acetate (250 ml), washed with 2×100 ml 5% NaHSO$_4$, 2×100 ml saturated NaHCO$_3$, 1×100 ml saturated NaCl, dried on MgSO$_4$, and concentrated in vacuo. The residue was purified by flash chromatography (50% to 100% ethyl acetate in hexanes) to afford the diacetate (401.9 mg, 0.9062 mmol, 31%) and the title compound (368.7 mg, 0.9184 mmol, 33%), both as a clear oils which solidified upon standing. $^1$H NMR (CDCl$_3$, 400 MHz) δ 1.29 (s, 3H), 1.32 (s, 3H), 2.09 (s, 3H), 2.09-2.20 (m, 2H), 3.00-3.25 (m, 4H), 3.55 (br s, 1H), 4.09-4.11 (m, 2H), 4.38-4.43 (m, 1H), 4.95 (s, 1H), 5.03 (s, 2H), 7.3-7.4 (m, 5H); LRMS (ESI/APCI) m/z 424 [M+Na]$^+$.

3-(3-Amino-3-methylbutylsulfonyl)-2-hydroxypropyl acetate

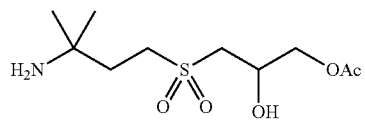 [SMILES: CC(=O)OCC(O)CS(=O)(=O)CCC(C)(C)N]

To a solution of 3-(3-(benzyloxycarbonylamino)-3-methylbutylsulfonyl)-2-hydroxypropyl acetate (368.7 mg, 0.9184 mmol) in methanol (10 ml) was added palladium on carbon (10%, 37 mg). The solution was purged with nitrogen gas, and then put under a blanket of hydrogen gas (1.3 atm). The suspension was stirred for 1.5 hours, filtered through a 0.45 um PTFE filter, and concentrated in vacuo. The residue was used without any further purification. LRMS (ESI/APCI) m/z 268 [M+H]$^+$.

3-(3-(Dichloroamino)-3-methylbutylsulfonyl)-2-hydroxypropyl acetate

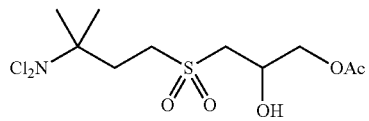

A solution of 3-(3-amino-3-methylbutylsulfonyl)-2-hydroxypropyl acetate (x mg, 0.9184 mmol) in methanol (10 ml) was cooled to 0° C. and tert-butylhypochlorite (300 μl, 2.51 mmol) was added drop-wise. The solution was stirred for 1 hour, concentrated in vacuo, and the residue purified by flash chromatography (50% to 100% ethyl acetate in hexanes) to afford the title compound as a clear oil. $^1$H NMR (CDCl$_3$, 400 MHz) δ 1.41 (s, 6H), 2.10 (s, 3H), 2.17-2.22 (m, 2H), 3.09 (dd, J=2.4, 14.8 Hz, 1H), 3.19-3.28 (m, 3H), 3.54 (d, J=4.0 Hz, 1H), 4.12-4.14 (m, 2H), 4.4-4.5 (m, 1H). $^{13}$C NMR (CDCl$_3$, 100 MHz) δ 20.8, 23.5, 31.5, 49.8, 56.0, 65.0, 66.8, 73.0, 171.0. LRMS (ESI/APCI) m/z 361 [M+Na]$^+$, 402 [M+Na+CH$_3$CN]$^+$.

Example 9

3-(dichloroamino)-N-(2-(2-(2-methoxyethoxy)ethoxy)ethyl)-N,N,3-trimethylbutan-1-aminium 4-methylbenzenesulfonate (Compound 38-45)

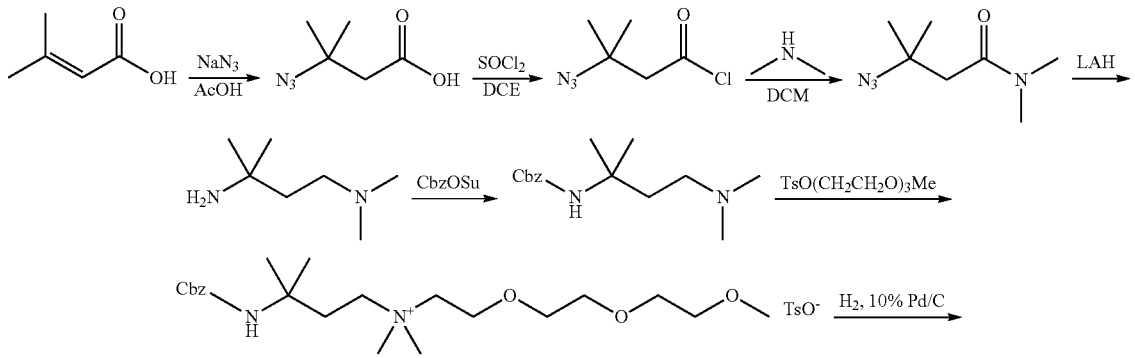

-continued

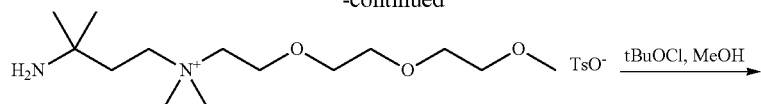
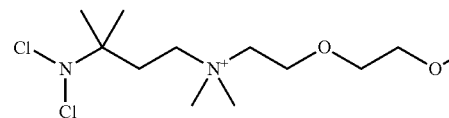

3-Azido-3-methylbutanoic acid

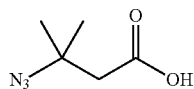

To a stirred solution of 3,3-dimethylacrylic acid (20 g, 0.2 mol) in glacial acetic acid (50 mL) was added a solution of sodium azide (52 g, 0.8 mol) in water (100 mL) in one portion. The clear yellow solution was stirred for 1 hour at room temperature and then heated in an oil bath at 95° C. for 2 days. Water (50 mL) was added to the cooled orange solution. This solution was poured into a separatory funnel and extracted with ether (5×200 mL). The combined organic extracts were dried over anhydrous MgSO$_4$ and concentrated to an orange oil. This oil was used without further purification. $^1$H NMR (CDCl$_3$, 400 MHz): δ 1.44 (s, 6H), 2.55 (s, 2H), 11.80 (bs, 1H).

3-Azido-3-methylbutanoyl chloride

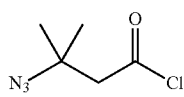

To a stirred solution of 3-azido-3-methylbutanoic acid (10 g, 69.8 mmol) in anhydrous 1,2-dichloroethane (50 mL) was added thionyl chloride (10.0 mL, 140 mmol). The flask was fitted with a condenser and the reaction was heated in a 50° C. oil bath for 2 hours. The reaction was concentrated to a brownish-black suspension. The residue was vacuum distilled through a short path distillation apparatus. The forerun was discarded and the major fraction distilled at 66° C. at 18 mbar as a pale yellow liquid (9.66 g, 59.7 mmol, 85.6%). $^1$H NMR (CDCl$_3$, 400 MHz): δ 1.41 (s, 6H), 2.51 (s, 2H), 2.98 (s, 2H). $^1$H NMR (CDCl$_3$, 400 MHz): δ 1.44 (s, 6H), 3.10 (s, 2H).

3-Azido-N,N-3-trimethylbutanamide

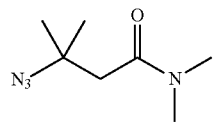

To a stirred ice cold solution of 3-azido-3-methylbutanoyl chloride (9.66 g, 56.8 mmol) in anhydrous dichloromethane (150 mL) was added a solution of 40% aqueous dimethylamine (23.7 mL, 3 equiv, 0.14 mol) in one portion. A white solid formed immediately and the suspension was stirred vigorously until a clear biphasic mixture formed. The speed of stirring was reduced and the reaction was left at 0° C. for 1 hour. Dichloromethane (200 mL) was added to the reaction mixture and the contents poured into a separatory funnel. The organic layer was separated and washed with water (3×50 mL) and brine (50 mL). It was dried over anhydrous MgSO$_4$, filtered, concentrated and dried under high vacuum to give a crude oil (10.16 g, quant). This material was used without further purification. $^1$H NMR (CDCl$_3$, 400 MHz): δ 1.33 (s, 6H), 2.40 (s, 2H), 2.83 (s, 3H), 2.94 (s, 3H).

N$^1$,N$^1$-3-Trimethylbutane-1,3-diamine

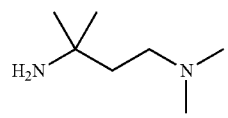

A solution of 3-azido-N,N-3-trimethylbutanamide (10.16 g, 59.7 mmol) in anhydrous tetrahydrofuran (100 mL, 0.2 M) was added dropwise to an ice cold suspension of lithium aluminum hydride (4.50 g, 2.0 equiv, 0.12 mol) in anhydrous tetrahydrofuran (150 mL) over 1 hour. After complete addition, the flask was fitted with a condenser and the reaction heated in a 70° C. oil bath for 4 hours. The reaction mixture was removed from the bath and stirred at room temperature for 17 hours. The reaction mixture was cooled in an ice bath and water (3.5 mL) was added drop-wise over 20 min. Then 15% NaOH solution (3.5 mL) was added dropwise over 10 min. The suspension was stirred for a further 10 minutes and water (7.0 mL) was added in one portion and the mixture stirred for 30 minutes to a give fine white suspension. The suspension was filtered through a pad of Celite® and the white cake was re-suspended into diethyl ether (200 mL) to give a white granular solid. The suspension was filtered and the cake washed with diethyl ether (2×100 mL) and the combined filtrate was carefully concentrated on a rotary evaporator with the bath temperature set to 20° C. to give a pale yellow liquid which was briefly dried under high vacuum to give the crude amine (8.15 g, 62.7 mmol, quant.). The crude amine was not dried completely to minimize loss of product due to its low boiling point and used without further purification.

Benzyl 4-(dimethylamino)-2-methylbutan-2-ylcarbamate

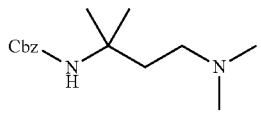 [SMILES: CN(C)CCC(C)(C)NC(=O)OCc1ccccc1]

N-(Benzyloxycarbonyloxy)succinimide (15.6 g, 1 equiv, 62.6 mmol) was added in one portion to a solution of $N^1,N^1$-3-trimethylbutane-1,3-diamine (8.15 g, 62.6 mmol) in tetrahydrofuran (100 mL). The reaction was left to stir at room temperature for 17 hours. The solvent was removed and the residue was taken up in a mixture of ethyl acetate (500 mL) and water (100 mL). The layers were separated and the organic layer washed with saturated sodium bicarbonate (2×100 mL), water (100 mL) and brine (100 mL). The organic layer was dried over anhydrous $MgSO_4$, filtered and concentrated to a pale yellow oil. The crude oil was purified by flash chromatography (1% to 5% methanol in dichloromethane). The desired fractions were collected and concentrated to give a colorless oil (11.49 g, yield: 69.6%) $^1$H NMR ($CDCl_3$, 400 MHz): δ 1.35 (s, 6H), 1.67-1.72 (t, J=6.6, 2H), 2.23 (s, 6H), 2.36-2.40 (t, J=7.2, 2H), 6.46 (s, 1H), 7.27-7.36 (m, 5H); LRMS (ESI/APCI) m/z 265 [M+H]$^+$.

3-(((Benzyloxy)carbonyl)amino)-N-(2-(2-(2-methoxyethoxy)ethoxy)ethyl)-N,N,3-trimethylbutan-1-aminium 4-methylbenzenesulfonate

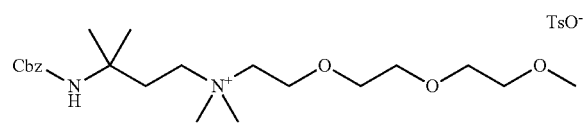 [SMILES: COCCOCCOCC[N+](C)(C)CCC(C)(C)NC(=O)OCc1ccccc1 ; "TsO-"]

A mixture of benzyl 4-(dimethylamino)-2-methylbutan-2-ylcarbamate (0.54 g, 2 mmol) and [2-[2-(2-methoxyethoxy)ethoxy]ethoxy]p-toluenesulfonate (1.3 g, 4 mmol) was stirred overnight at 45° C. The crude reaction mixture was directly purified by reverse phase HPLC eluting from a C18 column with a gradient of 5 to 95% acetonitrile in water (with 0.01% acetic acid) to give a clear oil (0.95 g, 2.3 mmol). $^1$H NMR ($D_2O$, 400 MHz) δ 1.18 (s, 6H), 2.05 (br m, 2H), 2.29 (s, 3H), 2.86 (s, 6H), 3.17-3.21 (m, 2H), 3.26 (s, 3H), 3.30 (br s, 2H), 3.48-3.56 (m, 8H), 3.71 (br s, 2H), 4.91 (br S, 2H), 7.25-7.27 (d, J=8.1 Hz, 2H), 7.30-7.36 (m, 5H), 7.57-7.59 (d, J=8.1 Hz, 2H); LRMS (ESI/APCI) m/z 411 [M]$^+$

3-Amino-N-(2-(2-(2-methoxyethoxy)ethoxy)ethyl)-N,N,3-trimethylbutan-1-aminium 4-methylbenzenesulfonate

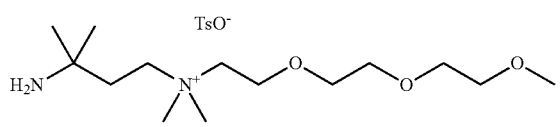 [SMILES: COCCOCCOCC[N+](C)(C)CCC(C)(C)N ; "TsO-"]

Under a nitrogen atmosphere, palladium on carbon (10%, 200 mg) was added to a solution of 3-(((benzyloxy)carbonyl)amino)-N-(2-(2-(2-methoxyethoxy)ethoxy)ethyl)-N,N,3-trimethylbutan-1-aminium 4-methylbenzenesulfonate (0.93 g, 2.2 mmol) in 15 mL of methanol. The flask was degassed and placed under a hydrogen atmosphere, stirring for 18 hours at room temperature. The suspension was filtered through a pad of Celite® washing with methanol, and the filtrate was concentrated under reduced pressure to give a clear oil (700 mg, 2.5 mmol). $^1$H NMR ($D_2O$, 400 MHz) δ 1.08 (s, 6H), 1.79-1.83 (m, 2H), 2.29 (s, 3H), 3.04 (s, 6H), 3.27 (s, 3H), 3.36-3.41 (m, 2H), 3.45-3.51 (m, 4H), 3.56-3.60 (m, 6H), 3.84 (br m, 2H), 7.26-7.28 (d, J=8.0 Hz, 2H), 7.57-7.60 (d, J=8.0 Hz, 2H). LRMS (ESI/APCI) m/z 277 [M]$^+$

3-(Dichloroamino)-N-(2-(2-(2-methoxyethoxy)ethoxy)ethyl)-N,N,3-trimethylbutan-1-aminium 4-methylbenzenesulfonate

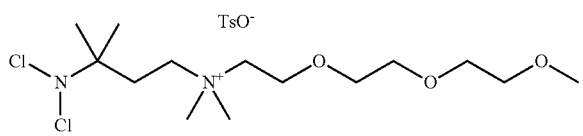 [SMILES: COCCOCCOCC[N+](C)(C)CCC(C)(C)N(Cl)Cl ; "TsO-"]

A solution of 3-amino-N-(2-(2-(2-methoxyethoxy)ethoxy)ethyl)-N,N,3-trimethylbutan-1-aminium 4-methylbenzenesulfonate (716 mg, 2.6 mmol) in methanol (6 ml) was cooled to 0° C. tert-Butylhypochlorite (450 µl, 4 mmol) was added. The resulting solution was stirred for 45 minutes at 0° C., and then concentrated under reduced pressure. The residue was purified by reverse phase HPLC eluting from a C18 column with a gradient of 5 to 95% acetonitrile in water (with 0.01% acetic acid) to give a clear oil (658 mg, 1.9 mmol). $^1$H NMR ($D_2O$, 400 MHz) δ 1.34 (s, 6H), 2.11-2.16 (m, 2H), 2.29 (s, 3H), 3.04 (s, 6H), 3.27 (s, 3H), 3.39-3.43 (m, 2H), 3.44-3.48 (m, 2H), 3.50-3.53 (m, 2H), 3.56-3.60 (m, 6H), 3.83-3.85 (m, 2H), 7.26-7.28 (d, J=8.2 Hz, 2H), 7.57-7.60 (d, J=8.2 Hz, 2H). $^{13}$C NMR ($D_2O$, 100 MHz) δ 142.4, 139.5, 129.4, 125.3, 73.0, 71.0, 69.7, 69.5, 69.4, 69.1, 64.1, 63.0, 60.7, 58.0, 51.3, 31.3, 22.7, 20.5; LRMS (ESI/APCI) m/z 345 [M]$^+$

Example 10

3-(dichloroamino)-N-(2-methoxyethyl)-N,N,3-trimethylbutan-1-aminium chloride (Compound 38-43)

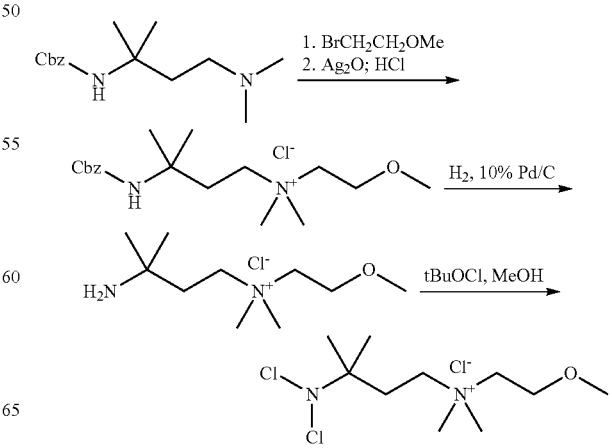

3-(((benzyloxy)carbonyl)amino)-N-(2-methoxy-ethyl)-N,N,3-trimethylbutan-1-aminium chloride

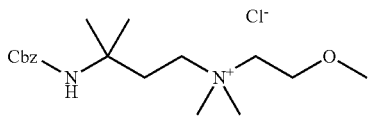 [SMILES: [Cl-] ; COCC[N+](C)(C)CCC(C)(C)NC(=O)OCc1ccccc1]

A mixture of benzyl 4-(dimethylamino)-2-methylbutan-2-ylcarbamate (from example 9, 1 g, 3.8 mmol) and 2-bromo-ethyl methyl ether (1 g, 7.2 mmol) was stirred for 5 hours at 50° C. The crude reaction mixture was concentrated under reduced pressure to a white solid, which was washed with hexanes. The solid was dissolved in 4 mL of water and treated with 437 mg of Ag$_2$O (1.9 mmol). The resultant slurry was stirred for 30 minutes. The solid was removed by filtration through a pad of Celite®, washing with water. The aqueous solution was acidified with 6 N HCl, filtered through a 0.45 micron filter, and concentrated to 1.26 g of a clear viscous oil. $^1$H NMR (D$_2$O, 400 MHz) δ 1.18 (s, 6H), 2.05 (br m, 2H), 2.86 (s, 6H), 3.17-3.21 (m, 2H), 3.25 (s, 3H), 3.30 (br s, 2H), 3.65 (br s, 2H), 4.98 (br s, 2H), 7.30-7.36 (m, 5H); LRMS (ESI/APCI) m/z 323 [M]$^+$

3-amino-N-(2-methoxyethyl)-N,N,3-trimethylbutan-1-aminium chloride

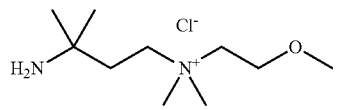

Under a nitrogen atmosphere, palladium on carbon (10%, 280 mg) was added to a solution of 3-(((benzyloxy)carbonyl)amino)-N-(2-methoxyethyl)-N,N,3-trimethylbutan-1-aminium chloride (1.3 g, 3.5 mmol) in 12 mL of methanol. The flask was degassed and placed under a hydrogen atmosphere, stirring for 18 hours at room temperature. The suspension was filtered through a pad of Celite® washing with methanol, and the filtrate was concentrated under reduced pressure to give about 835 mg of a clear oil. $^1$H NMR (D$_2$O, 400 MHz) δ 1.15 (s, 6H), 1.87-1.92 (m, 2H), 3.06 (s, 6H), 3.30 (s, 3H), 3.39-3.43 (m, 2H), 3.49-3.51 (m, 2H), 3.79-3.80 (m, 2H); LRMS (ESI/APCI) m/z 189 [M]$^+$

3-(dichloroamino)-N-(2-methoxyethyl)-N,N,3-trimethylbutan-1-aminium chloride

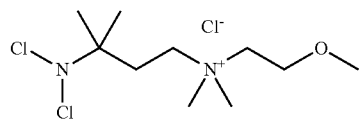

A solution of 3-amino-N-(2-methoxyethyl)-N,N,3-trimethylbutan-1-aminium chloride (830 mg, 3.5 mmol) in methanol (14 ml) was cooled to 0° C. tert-Butylhypochlorite (984 μl, 2.5 mmol) was added. The resulting solution was stirred for 45 minutes at 0° C. and then concentrated under reduced pressure. The residue was purified by reverse phase high pressure liquid chromatography eluting from a C18 column with a gradient of 5 to 95% CH$_3$CN in water (with 0.01% acetic acid) to give 618 mg of a clear oil. $^1$H NMR (D$_2$O, 400 MHz) δ 1.33 (s, 6H), 2.15-2.20 (m, 2H), 3.08 (s, 6H), 3.40 (s, 3H), 3.40-3.44 (m, 2H), 3.49-3.51 (m, 2H), 3.80-3.82 (m, 2H). $^{13}$C NMR (D$_2$O, 100 MHz) δ 73.1, 65.5, 62.9, 62.9, 62.8, 60.8, 60.8, 60.7, 58.2, 51.5, 51.4, 51.4, 31.3, 22.8; LRMS (ESI/APCI) m/z 257 [M]$^+$.

Example 11

136-{[3-(dichloroamino)-3-methylbutane]sulfonyl}-2,5,8,11,14,17,20,23,26,29,32,35,38,41,44,47,50,53,56,59,62,65,68,71,74,77,80,83,86,89,92,95,98,101,104,107,110,113,116,119,122,125,128,131,134-pentatetracontaoxa136ne (Compound 38-131)

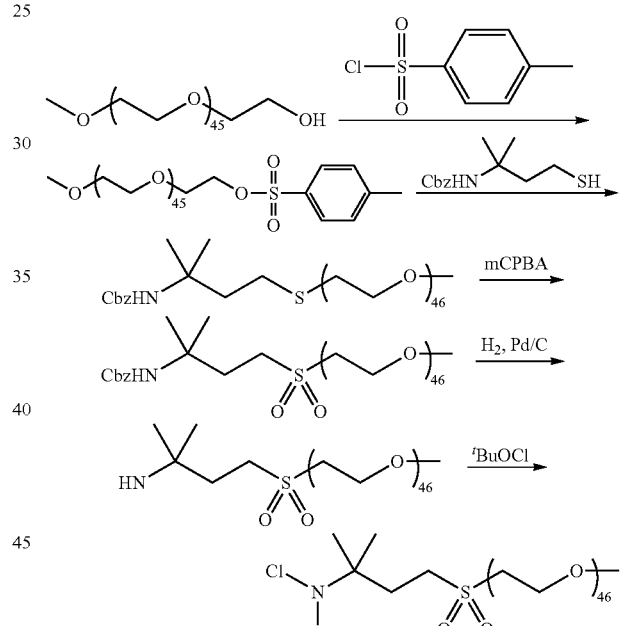

2,5,8,11,14,17,20,23,26,29,32,35,38,41,44,47,50,53,56,59,62,65,68,71,74,77,80,83,86,89,92,95,98,101,104,107,110,113,116,119,122,125,128,131,134-pentatetracontaoxa136n-136-yl 4-methylbenzene-1-sulfonate

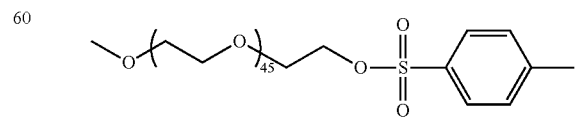

Poly(ethylene glycol)methyl ether (average molecular weight=2000, Aldrich cat#202509, 7.05 g, 3.5 mmol) is dissolved in tetrahydrofuran (5 ml). To the stirring mixture is added an aqueous solution of sodium hydroxide (390 mg, 9.8 mmol) in water (5 ml). The combined mixture is cooled to 0° C., and 4-methylbenzene-1-sulfonyl chloride is added drop-wise over a 2 hour period. The reaction mixture is stirred for an additional 4 hours. The mixture is poured into ice-water (10 ml) and extracted with dichloromethane. The organic layer is washed with saturated sodium chloride solution, and dried over sodium sulfate. The solvent was removed in vacuo to give the title compound.

benzyl N-(140-methyl-2,5,8,11,14,17,20,23,26,29, 32,35,38,41,44,47,50,53,56,59,62,65,68,71,74,77,80, 83,86,89,92,95,98,101,104,107,110,113,116,119, 122,125,128,131,134-pentatetracontaoxa-137-thia141n-140-yl)carbamate

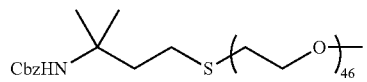

To a solution of benzyl 4-mercapto-2-methylbutan-2-yl-carbamate (from example 1, 683 mg, 1.7 mmol) in N,N-dimethylformamide (10 ml) is added cesium carbonate (757 mg, 2.3 mmol) and 2,5,8,11,14,17,20,23,26,29,32,35,38,41, 44,47,50,53,56,59,62,65,68,71,74,77,80,83,86,89,92,95,98, 101,104,107,110,113,116,119,122,125,128,131,134-pentatetracontaoxa136n-136-yl 4-methylbenzene-1-sulfonate (5.20 g, 2.4 mmol). The solution is heated to 60° C. for 2 hours, then 70° C. for 16 hours, and cooled to room temperature. The mixture is concentrated in vacuo. The residue is dissolved in 50 ml 5% NaHSO₄, extracted with ethyl acetate, dried on MgSO₄, and concentrated in vacuo. The residue is purified by flash chromatography (10% to 60% ethyl acetate in hexanes) to give the title compound.

benzyl N-[2-methyl-4-(2,5,8,11,14,17,20,23,26,29, 32,35,38,41,44,47,50,53,56,59,62,65,68,71,74,77,80, 83,86, 89,92,95,98,101,104,107,110,113,116,119, 122,125,128,131,134-pentatetracontaoxa136ne-136-sulfonyl)butan-2-yl]carbamate

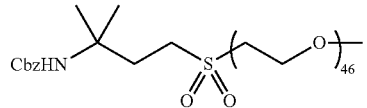

A solution of benzyl N-(140-methyl-2,5,8,11,14,17,20,23, 26,29,32,35,38,41,44,47,50,53,56,59,62,65,68,71,74,77,80, 83,86,89,92,95,98,101,104,107,110,113,116,119,122,125, 128,131,134-pentatetracontaoxa-137-thia141n-140-yl)carbamate (3.00 g, 1.3 mmol) in dichloromethane (10 ml) is cooled to 0° C. 3-Chloroperbenzoic acid (77%, 916 mg, 4.1 mmol) is added portion-wise, and the solution is stirred for 2 hours. The solution is diluted with 500 ml ethyl acetate, washed 3 times with 100 ml saturated NaHCO₃, once with 100 ml saturated NaCl, dried on MgSO₄, and is concentrated in vacuo. The residue is purified by flash chromatography (10% to 80% ethyl acetate in hexanes) to afford the title compound.

136-[(3-amino-3-methylbutane)sulfonyl]-2,5,8,11, 14,17,20,23,26,29,32,35,38,41,44,47,50,53,56,59,62, 65,68,71,74,77,80,83,86,89,92,95,98,101,104,107, 110,113,116,119,122,125,128,131,134-pentatetracontaoxa136ne

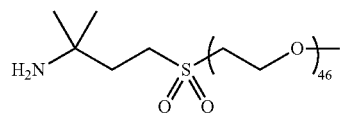

A solution of benzyl N-[2-methyl-4-(2,5,8,11,14,17,20, 23,26,29,32,35,38,41,44,47,50,53,56,59,62,65,68,71,74,77, 80,83,86,89,92,95,98,101,104,107,110,113,116,119,122, 125,128,131,134-pentatetracontaoxa136ne-136-sulfonyl) butan-2-yl]carbamate (2.28 g, 1.0 mmol) is dissolved in methanol (50 ml) is purged with nitrogen. Palladium on carbon (10%, 40 mg) is added, and the suspension is put under a hydrogen (1.3 atmospheres). The suspension is stirred for 18 hours, filtered through a 0.45 um polytetrafluoroethylene filter, and the solution is concentrated in vacuo. The material is used without further purification.

136-{[3-(dichloroamino)-3-methylbutane]sulfonyl}-2,5,8,11,14,17,20,23,26,29,32,35,38,41,44,47,50,53, 56,59,62,65,68,71,74,77,80,83,86,89,92,95,98,101, 104,107,110,113,116,119,122,125,128,131,134-pentatetracontaoxa136ne

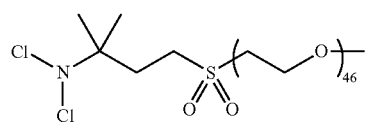

A solution of 136-[(3-amino-3-methylbutane)sulfonyl]-2, 5,8,11,14,17,20,23,26,29,32,35,38,41,44,47,50,53,56,59,62, 65,68,71,74,77,80,83,86, 89,92,95,98,101,104,107,110,113, 116,119,122,125,128,131,134-pentatetracontaoxa136ne (2.00 g, 0.9 mmol) in methanol (20 ml) is cooled to 0° C. tert-Butylhypochlorite (300 μl, 2.5 mmol) is added drop-wise over 10 minutes, and the solution is stirred for 1 hour. The solution is concentrated in vacuo and the residue is purified by preparatory high pressure liquid chromatography (H₂O/acetonitrile) to afford the title compound.

Example 12

3-(dichloroamino)-N-(2-(hexyloxy)ethyl)-N,N,3-trimethylbutan-1-aminium 4-methylbenzenesulfonate (Compound 38-135)

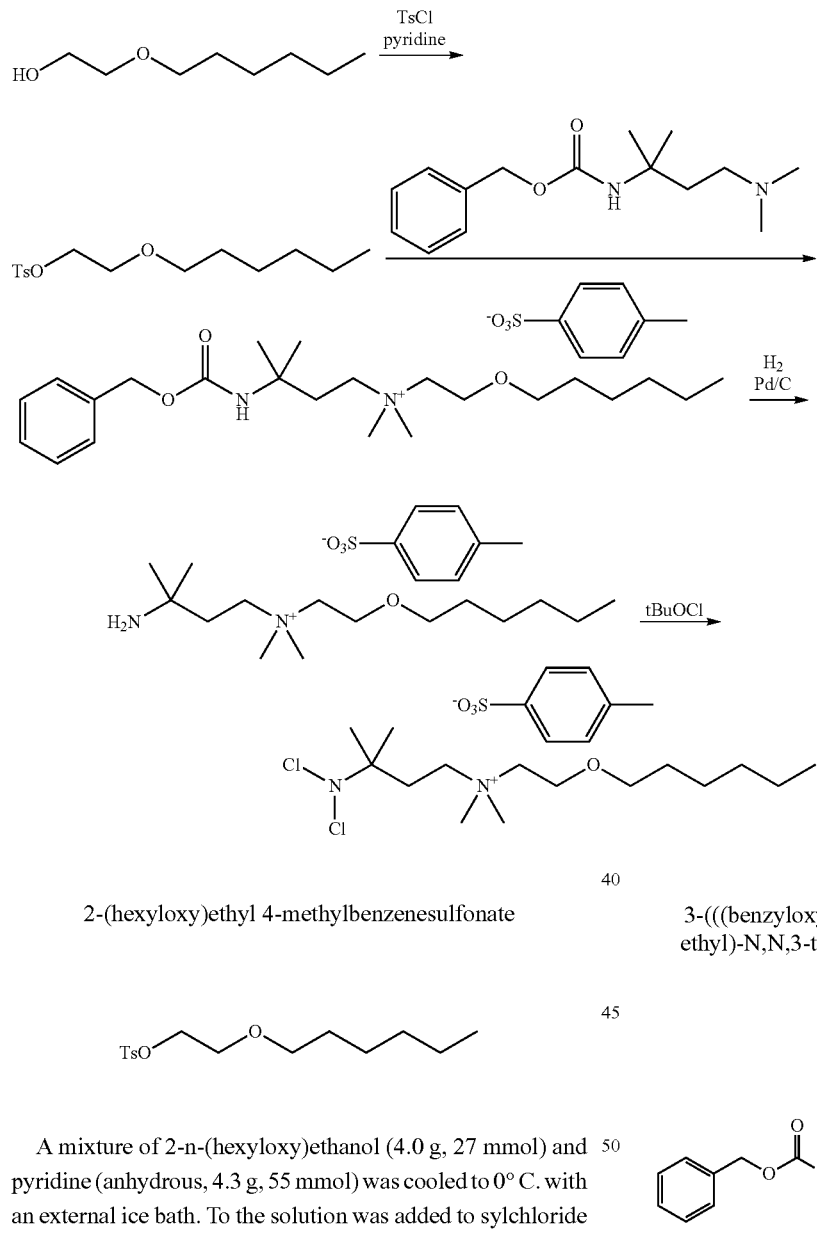

2-(hexyloxy)ethyl 4-methylbenzenesulfonate 3-(((benzyloxy)carbonyl)amino)-N-(2-(hexyloxy)ethyl)-N,N,3-trimethylbutan-1-aminium 4-methylbenzenesulfonate A mixture of 2-n-(hexyloxy)ethanol (4.0 g, 27 mmol) and pyridine (anhydrous, 4.3 g, 55 mmol) was cooled to 0° C. with an external ice bath. To the solution was added tosylchloride (5.2 g, 27 mmol) followed by 5 mL of dichloromethane and the resultant mixture was stirred for 4 hours at 0° C. and 2 hours at room temperature. The mixture was diluted with toluene and washed successively twice with 1 N HCl and once with brine. The organic fraction was dried over sodium sulfate and concentrated under reduced pressure to 8.4 g of clear liquid. $^1$H NMR (400 MHz, $D_2O$) δ 0.88-0.91 (m, 3H), 1.25-1.31 (m, 6H), 1.48-1.52 (m, 2H), 2.46 (s, 3H), 3.37-3.40 (t, J=6.7 Hz, 2H), 3.61-3.63 (m, 2H) 4.16-4.19 (m, 2H), 7.74-7.36 (d, J=8.2 Hz, 2H), 7.81-7.83 (d, J=8.2 Hz, 2H). LRMS (ESI/APCI) m/z 301 [M+H]$^+$.

A mixture of benzyl(4-(dimethylamino)-2-methylbutan-2-yl)carbamate (0.72 g, 2.7 mmol) and 2-(hexyloxy)ethyl 4-methylbenzenesulfonate (1.8 g, 6.0 mmol) was stirred overnight at 75° C. The crude reaction mixture was purified by reverse phase HPLC eluting from a C18 column with a gradient of 5 to 95% $CH_3CN$ in water (with 0.01% acetic acid) to give 0.96 g of white solid (64% yield). $^1$H NMR (400 MHz, $D_2O$) δ 0.75-78 (m, 3H), 1.18 (s, 6H), 1.44-1.27 (m, 2H), 2.06 (br m, 2H), 2.29 (s, 3H), 3.03 (s, 6H), 3.17-3.21 (m, 2H), 3.30 (br m, 2H), 3.36-3.39 (t, J=6.5 Hz, 2H), 3.67 (br s, 2H), 4.97 (br s, 2H), 7.26-7.28 (d, J=8.1 Hz, 2H), 7.30-7.37 (m, 5H), 7.58-7.60 (d, J=8.1 Hz, 2H). LRMS (ESI/APCI) m/z 393 [M]$^+$.

3-amino-N-(2-(hexyloxy)ethyl)-N,N,3-trimethylbutan-1-aminium 4-methylbenzenesulfonate

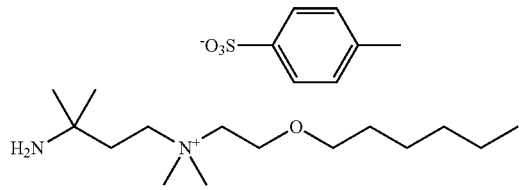

Under a nitrogen atmosphere, 10% palladium on carbon (200 mg) was added to a solution of 3-(((benzyloxy)carbonyl) amino)-N-(2-(hexyloxy)ethyl)-N,N,3-trimethylbutan-1-aminium 4-methylbenzenesulfonate (0.95 g, 1.7 mmol) in 7 mL of methanol. The flask was degassed and placed under a hydrogen atmosphere, stirring for 18 hours at room temperature. The suspension was filtered through a pad of celite, washing with methanol, and the filtrate was concentrated under reduced pressure to give 725 mg of clear viscous oil (quantitative yield). $^1$H NMR (400 MHz, D$_2$O) δ 0.75-78 (t, J=6.4 Hz, 3H), 1.09 (s, 6H), 1.7-1.26 (m, 6H), 1.47-1.51 (m, 2H), 1.80-1.84 (m, 2H), 2.30 (s, 3H), 3.03 (s, 6H), 3.36-3.40 (m, 2H), 3.44-3.48 (m, 4H), 3.81 (br s, 2H), 7.27-7.28 (d, J=8.1 Hz, 2H), 7.58-7.60 (d, J=8.1 Hz, 2H). LRMS (ESI/APCI) m/z 259 [M]$^+$.

3-(dichloroamino)-N-(2-(hexyloxy)ethyl)-N,N,3-trimethylbutan-1-aminium 4-methylbenzenesulfonate

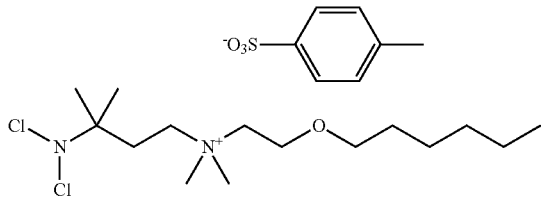

A solution of 3-amino-N-(2-(hexyloxy)ethyl)-N,N,3-trimethylbutan-1-aminium 4-methylbenzenesulfonate (722 mg, 1.7 mmol) in methanol (6 ml) was cooled to 0° C. tert-Butylhypochlorite (472 ul, 4.2 mmol) was added. The resulting solution was stirred for 60 minutes, and then concentrated under reduced pressure. The crude material was purified by preparative high pressure liquid chromatography on a C18 column, eluting the desired product with a gradient of 5-95% acetonitrile in water (with 0.01% acetic acid) to give 655 mg of a white solid (78% yield). $^1$H NMR (400 MHz, D$_2$O) δ 0.85-0.89 (t, J=6.5 Hz, 3H), 1.29-0.37 (m, 6H), 1.43 (s, 6H), 1.56-1.60 (m, 2H), 2.21-2.25 (m, 2H), 2.38 (s, 3H), 3.13 (s, 6H), 3.48-3.56 (m, 6H), 3.87 (br s, 2H), 7.32-7.34 (d, J=8.1 Hz, 2H), 7.66-7.68 (d, J=8.1 Hz, 2H). $^{13}$C NMR (100 MHz, D$_2$O) δ 11.8, 18.9, 20.5, 21.2, 23.8, 27.2, 29.5, 30.0, 49.7, 59.0, 62.0, 62.4, 69.9, 71.4, 123.8, 127.7, 138.6, 140.4. LRMS (ESI/APCI) m/z 327 [M]$^+$.

Example 13

N-(2-butoxyethyl)-3-(dichloroamino)-N,N,3-trimethylbutan-1-aminium chloride (Compound 38-133)

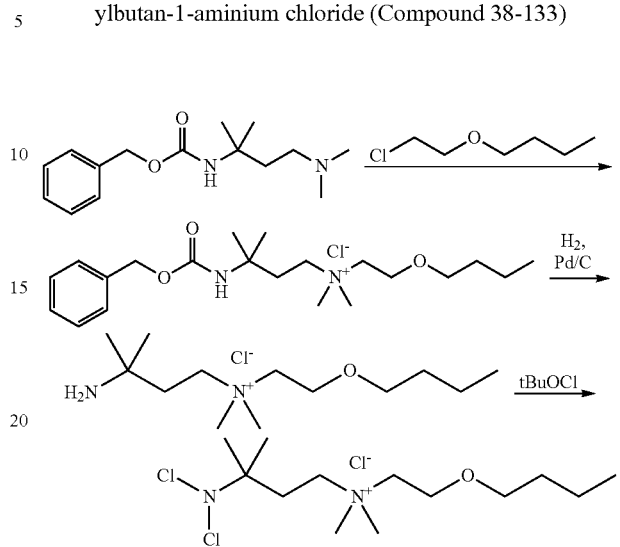

3-(((benzyloxy)carbonyl)amino)-N-(2-butoxyethyl)-N,N,3-trimethylbutan-1-aminium chloride

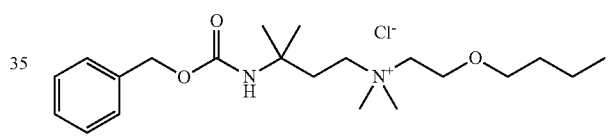

A mixture of benzyl(4-(dimethylamino)-2-methylbutan-2-yl)carbamate (500 mg, 1.9 mmol, preparation described in previous experiment) and 2-(chloroethyl)-n-butyl ether (517 mg, 3.8 mmol) was stirred overnight at 75° C. An additional portion of 2-(chloroethyl)-n-butyl ether (517 mg, 3.8 mmol) was added and the mixture stirred for 24 hours at 80° C. The resultant white precipitate was collected on a glass fritted filter and washed with ether to give 388 mg of a white solid (51%). $^1$H NMR (400 MHz, MeOD) δ 0.86-0.89 (t, J=7.4 Hz, 3H), 1.23 (s, 6H), 1.27-1.33 (sext, J=7.5 Hz, 2H), 1.45-1.50 (m, 2H), 2.05-2.09 (m, 2H), 3.03 (s, 6H), 3.29-3.34 (m, 2H), 3.39-3.34 (t, J=Hz, 2H), 3.48-3.50 (br m, 2H), 3.74 (br s, 2H), 4.99 (s, 2H), 7.17 (s, 1H), 7.31-7.36 (m, 5H). LRMS (ESI/APCI) m/z 365 [M]$^+$.

3-amino-N-(2-butoxyethyl)-N,N,3-trimethylbutan-1-aminium chloride

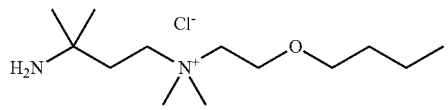 [SMILES: CCCCOCC[N+](C)(C)CCC(C)(C)N ; [Cl-]]

Under a nitrogen atmosphere, 10% pd/C (100 mg) was added to a solution of 3-(((benzyloxy)carbonyl)amino)-N-(2-butoxyethyl)-N,N,3-trimethylbutan-1-aminium chloride (0.38 g, 0.95 mmol) in 4 mL of methanol. The flask was degassed and placed under a hydrogen atmosphere, stirring for 24 hours at room temperature. The suspension was filtered through a pad of celite washing with methanol, and the filtrate was concentrated under reduced pressure to give 252 mg of clear viscous oil (quantitative yield). $^1$H NMR (400 MHz, D$_2$O) δ 0.78-0.82 (t, J=7.4 Hz, 3H), 1.08 (s, 6H), 1.22-1.30 (sext, J=7.4 Hz, 6H), 1.45-1.52 (m, 2H), 1.77-1.81 (m, 2H), 3.04 (s, 6H), 3.36-3.40 (m, 2H), 3.45-3.49 (t, J=6.5 Hz, 2H), 3.82-3.83 (br m, 2H); LRMS (ESI/APCI) m/z 231 [M]$^+$.

N-(2-butoxyethyl)-3-(dichloroamino)-N,N,3-trimethylbutan-1-aminium chloride

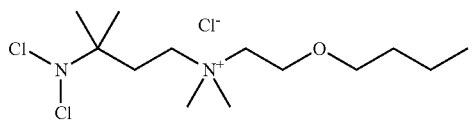 [SMILES: CCCCOCC[N+](C)(C)CCC(C)(C)N(Cl)Cl ; [Cl-]]

A solution of (1,4,7,10-tetraoxacyclododecan-2-yl)methanol (250 mg, 1.21 mmol) in CH$_2$Cl$_2$ (10 ml) was cooled to 0° C. and pyridine (300 ul, 3.7 mmol) and tosyl chloride (260 mg, 1.36 mmol) were added. The solution was warmed to room temperature overnight and concentrated in vacuo. The residue was purified by flash chromatography (50%-100% ethylacetate in hexanes) to afford the titled compound as a clear oil (218.4 mg, 0.6060 mmol, 50%). $^1$H NMR (CDCl$_3$, 400 MHz) δ 2.37 (s, 3H), 3.4-3.9 (m, 16H), 4.0-4.2 (m, 1H), 7.27 (dd, J=0.8, 8.8 Hz, 2H), 7.71 (dd, J=1.6, 6.8 Hz, 2H); LRMS (ESI/APCI) m/z 361 [M]$^+$.

Benzyl 4-((1,4,7,10-tetraoxacyclododecan-2-yl)methylthio)-2-methylbutan-2-ylcarbamate

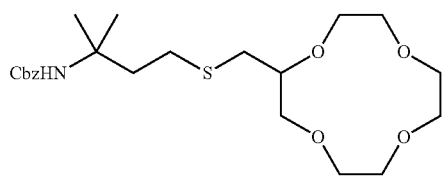 [SMILES: CC(C)(CCSCC1COCCOCCOCCO1)NC(=O)OCc1ccccc1]

To a solution of benzyl 4-mercapto-2-methylbutan-2-ylcarbamate (242 mg, 0.955 mmol) in N,N-dimethylformamide (1 ml) was added (1,4,7,10-tetraoxacyclododecan-2-yl)methyl 4-methylbenzenesulfonate (218.4 mg, 0.6060 mmol) and cesium carbonate (253 mg, 0.776 mmol). The solution was heated to 60° C. for 15 hours, cooled to room temperature, concentrated in vacuo, and the residue purified by flash chromatography (30%-100% ethylacetate in hexanes) to afford the title compound as a clear oil (quantitative); LRMS (ESI/APCI) m/z 442 [M]$^+$.

Benzyl 4-((1,4,7,10-tetraoxacyclododecan-2-yl)methylsulfonyl)-2-methylbutan-2-ylcarbamate

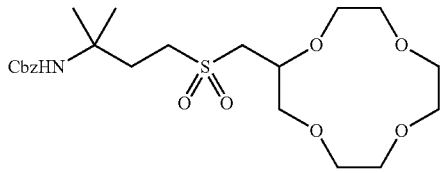 [SMILES: CC(C)(CCS(=O)(=O)CC1COCCOCCOCCO1)NC(=O)OCc1ccccc1]

A solution of benzyl 4-((1,4,7,10-tetraoxacyclododecan-2-yl)methylthio)-2-methylbutan-2-ylcarbamate (0.6060 mmol) in CH$_2$Cl$_2$ (3 ml) was cooled to 0° C. and 77% 4-chloroperoxybenzoic acid (260 mg, 1.16 mmol) was added in small portions. The solution was stirred for 2 hours, warmed to room temperature, concentrated in vacuo, and the residue purified by flash chromatography (30%-100% ethylacetate in hexanes) to afford the title compound as a clear oil (120.8 mg, 0.255 mmol, 42% over two steps). $^1$H NMR (CDCl$_3$, 400 MHz) δ 1.36 (s, 6H), 2.2-2.3 (m, 2H), 3.11-3.13 (m, 2H), 3.41 (dd, J=9.2, 15.2 Hz, 1H), 3.6-4.0 (m, 15H), 4.1-4.2 (m, 1H), 4.8 (s, 1H), 5.06 (s, 2H), 7.3-7.4 (m, 5H); LRMS (ESI/APCI) m/z 496 [M+Na]$^+$.

4-((1,4,7,10-Tetraoxacyclododecan-2-yl)methylsulfonyl)-2-methylbutan-2-amine

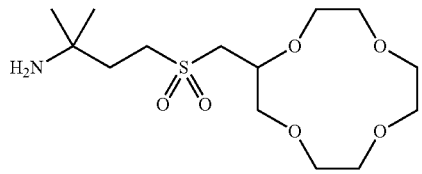 [SMILES: CC(C)(N)CCS(=O)(=O)CC1COCCOCCOCCO1]

A solution of benzyl 4-((1,4,7,10-tetraoxacyclododecan-2-yl)methylsulfonyl)-2-methylbutan-2-ylcarbamate (120.8 mg, 0.255 mmol) in methanol (1 ml) was put under N$_2$, and 10% palladium on carbon (30 mg) was added. The vessel was purged with hydrogen (1.3 atmospheres) and the suspension stirred for 3.5 hours. The suspension was filtered through a polytetrafluoroethylene filter (0.45 um), and the filtrate concentrated in vacuo to give the title compound as a clear oil (quantitative); LRMS (ESI/APCI) m/z 340 [M]$^+$.

4-((1,4,7,10-Tetraoxacyclododecan-2-yl)methylsulfonyl)-N,N-dichloro-2-methylbutan-2-amine

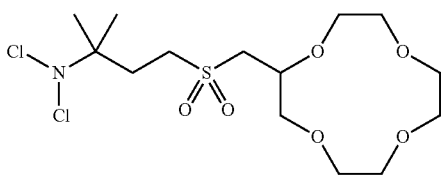 [SMILES: CC(C)(CCS(=O)(=O)CC1COCCOCCOCCO1)N(Cl)Cl]

A solution of 4-((1,4,7,10-tetraoxacyclododecan-2-yl)methylsulfonyl)-2-methylbutan-2-amine (0.255 mmol) in methanol (2 ml) was cooled to 0° C., and tert-butylhypochlorite (80 ul, 0.67 mmol) was added dropwise. The solution was stirred for 15 minutes, concentrated in vacuo, and the residue purified by flash chromatography (50%-100% ethylacetate in hexanes) to afford the title compound as an amorphous solid (77.5 mg, 0.190 mmol, 74% over two steps). $^1$H NMR (CD$_3$OD, 400 MHz) δ 1.43 (5, 3H), 1.45 (5, 3H), 2.20-2.23 (m, 2H), 3.12 (dd, J=2.8, 15.2 Hz, 1H), 3.26 (t, J=8.8 Hz, 2H), 3.4-3.9 (m, 15H), 4.1 (m, 1H). $^{13}$C NMR (CD$_3$OD, 100 MHz) δ 22.2, 22.4, 30.9, 49.4, 54.7, 69.4, 69.9, 70.1, 70.1, 70.5, 70.6, 71.3, 73.0, 74.3; LRMS (ESI/APCI) m/z 408 [M]$^+$.

Example 15

Synthesis of 2-(2-(3-(dichloroamino)-3-methylbutyl-sulfonyl)ethoxy)ethanesulfonic acid (Compound 38-83)

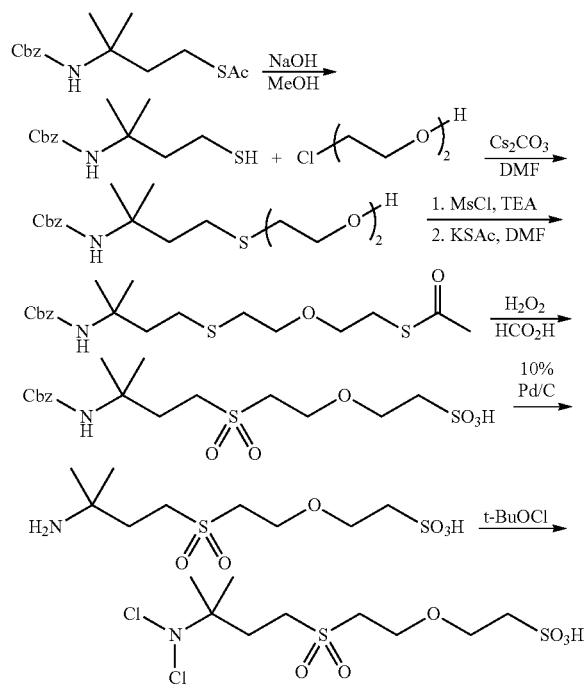

Benzyl 4-mercapto-2-methylbutan-2-ylcarbamate

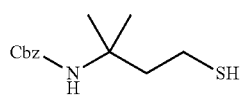

S-3-(Benzyloxycarbonylamino)-3-methylbutyl ethanethioate (3.00 g, 10.2 mmol) was dissolved into methanol (100 mL). Sodium hydroxide solution (5 N, 6.1 mL, 30.6 mmol) was added to the solution in one portion and stirred at room temperature for 1 hour. Thin-layer chromatography (40% ethyl acetate in hexanes) analysis of reaction mixture indicated all the starting material was consumed. The organic solvent was removed and the resulting aqueous solution was made acidic (~pH 5) with 1 N HCl, while cooled in an ice bath. The aqueous suspension was extracted with ethyl acetate (2×100 mL) and the combined organic layer washed with water (50 mL) and brine (50 mL), dried over anhydrous MgSO$_4$, filtered and concentrated to a pale yellow oil (2.83 g, quant). The material was used without further purification. $^1$H NMR (CDCl$_3$, 400 MHz): δ 1.29 (s, 6H), 2.02 (m, 2H), 2.48-2.5 (m, 2H), 2.83 (t, 20 Hz, 2H), 3.60 (t, 20 Hz, 2H), 4.63 (br s, 2H), 5.05 (s, 2H), 7.29-7.37 (m, 5H). LRMS (ESI/APCI) m/z 316 [M+H]$^+$.

Benzyl 4-(2-(2-hydroxyethoxy)ethylthio)-2-methylbutan-2-ylcarbamate

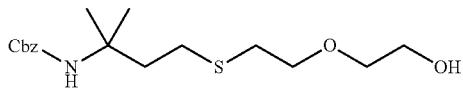 [SMILES: CC(C)(CCSCCOCCO)NC(=O)OCc1ccccc1]

The crude benzyl 4-mercapto-2-methylbutan-2-ylcarbamate (2.83 g, 10.2 mmol) from the previous reaction was dissolved into dimethylformamide (60 mL). Cesium carbonate (6.65 g, 2 equiv, 20.4 mmol) was added in one portion to the solution to give a suspension followed by 2-(2-chloroethoxy)ethanol (1.39 g, 11.2 mmol). The flask was sealed with a septum and vigorously stirred at 50° C. under nitrogen atmosphere for 16 hours. The suspension was concentrated to an oily solid residue. This material was mixed with ethyl acetate (200 mL) and water (50 mL). The layers were separated and the organic layer was washed with brine (2×50 mL). The organic layer was dried over anhydrous MgSO$_4$, filtered and concentrated to a yellow oil. The crude oil was used without purification (2.23 g, 64.3%). LRMS (ESI/APCI) m/z 342 [M+H]$^+$.

S-Benzyl N-[4-({2-[2-(acetylsulfanyl)ethoxy]ethyl}sulfanyl)-2-methylbutan-2-yl]carbamate

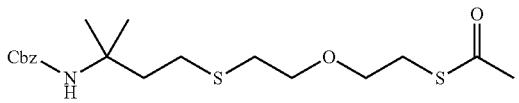 [SMILES: CC(=O)SCCOCCSCCC(C)(C)NC(=O)OCc1ccccc1]

To an ice cooled solution of benzyl 4-(2-(2-hydroxyethoxy)ethylthio)-2-methylbutan-2-ylcarbamate (2.23 g, 6.53 mmol) and triethylamine (1.28 mL, 9.14 mmol) dissolved in anhydrous dichloromethane (50 mL, 0.13 M) was added mesyl chloride (0.66 mL, 8.49 mmol) over 15 minutes. The cooling bath was removed and the reaction was stirred at room temperature for 1 hour. Thin-layer chromatography analysis (40% ethyl acetate/hexanes) indicated the reaction was complete. The reaction mixture was concentrated to a white residue and redissolved into ethyl acetate (150 mL) and water (50 mL) poured into a separatory funnel and washed 1 N HCl (2×50 mL) and brine (2×50 mL). The organic layer was dried over anhydrous MgSO$_4$, filtered and concentrated to give a yellow oil (2.97 g, quantitative). This material was used without further purification.

The crude benzyl N-[4-({2-[2-(methanesulfonyloxy)ethoxy]ethyl}sulfanyl)-2-methylbutan-2-yl]carbamate (6.53 mmol) was dissolved into dimethylformamide (50 mL, 0.13 M). Potassium thioacetate (0.74 g, 6.53 mmol) was added to the flask to give a pale yellow solution. The flask was sealed with a rubber septum and heated at 50° C. for 1 hour. The suspension formed was concentrated to an oily residue. This material was suspended into ethyl acetate (100 mL), filtered and the solid washed with ethyl acetate (2×100 mL) and concentrated to a dark red residue. This residue was purified an ISCO purification system using 40 g of SiO$_2$ with elution using 10% ethyl acetate in hexanes for 5 minutes, then gradient to 100% ethyl acetate for 10 minutes hold at 100% ethyl acetate for 5 minutes. The combined fractions gave a yellow oil. $^1$H NMR (CDCl$_3$, 400 MHz): δ 1.32 (s, 6H), 1.9 (t, 2H), 2.33 (s, 3H), 2.50-2.58 (m, 2H), 2.69 (t, 6.6 Hz, 2H), 3.09 (t, 6.4 Hz, 2H), 3.57 (t, 6.4 Hz, 2H), 3.62 (6.6 Hz, 2H), 4.78 (br s, 1H), 5.05 (s, 2H), 7.30-7.39 (m, 5H). LRMS (ESI/APCI) m/z 400 [M+H]$^+$.

2-{2-[(3-{[(benzyloxy)carbonyl]amino}-3-methylbutane)sulfonyl]ethoxy}ethane-1-sulfonic acid

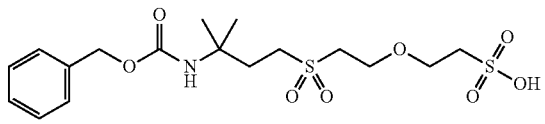 [SMILES: CC(C)(CCS(=O)(=O)CCOCCS(=O)(=O)O)NC(=O)OCc1ccccc1]

A premixed solution of 88% formic acid (4.2 mL) and 30% hydrogen peroxide (4.2 mL) was added in one portion to a solution of S-benzyl N-[4-({2-[2-(acetylsulfanyl)ethoxy]ethyl}sulfanyl)-2-methylbutan-2-yl]carbamate (1.67 g, 4.2 mmol) in 88% formic acid (12 mL) to give an exothermic reaction. The reaction was cooled in a room temperature water bath and stirred at room temperature for 17 hours. The solvent was removed to give a clear oil which was dissolved into water (10 mL). Palladium on carbon (10%, 200 mg) was added to the solution which immediately started to evolved gas. The reaction was heated to 50° C. for 3 hours, then cooled and filtered through a bed of Celite® and washed with water (2×20 mL). The filtrate was concentrated to a white solid, 1.80 g (quantitative). $^1$H NMR (CDCl$_3$, 400 MHz): δ 1.31 (s, 6H), 2.10-2.18 (t, 2H), 3.17-3.25 (m, 6H), 3.82-3.85 (m, 4H), 5.13 (s, 2H), 7.28-7.38 (m, 5H). LRMS (ESI/APCI) m/z 436 [M−H]$^-$.

2-(2-(3-amino-3-methylbutylsulfonyl)ethoxy)ethanesulfonic acid

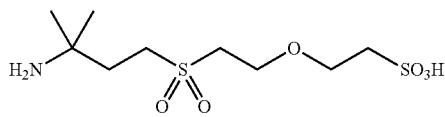 [SMILES: CC(C)(N)CCS(=O)(=O)CCOCCS(=O)(=O)O]

2-{2-[(3-{[(Benzyloxy)carbonyl]amino}-3-methylbutane)sulfonyl]ethoxy}ethane-1-sulfonic acid (1.50 g, 3.4 mmol) was dissolved into methanol (70 mL) and water (30 mL). The flask was flushed with nitrogen for 5 minutes and 10% palladium on carbon (150 mg) was added to the solution in one portion. The reaction mixture was degassed under vacuum and flushed with hydrogen (3×). The reaction was then stirred under atmospheric pressure with a balloon filled with hydrogen for 17 hours. The suspension was filtered through a pad of Celite® wetted with methanol and the solid was rinsed with methanol (50 mL) and water (50 mL). The filtrate was concentrated to give a white solid (1.60 g, 88.5%). This material was used without further purification. $^1$H NMR (D$_2$O, 400 MHz): δ 1.32 (s, 6H), 2.06-2.10 (m, 2H), 3.12 (t, 5.2 Hz, 2H), 3.37-3.40 (m, 2H), 3.82 (t, 5.90 Hz, 2H), 3.88 (t, 5.2 Hz, 2H). $^{13}$C NMR (D$_2$O, 100 MHz) δ 24.3, 30.8, 49.2, 50.6, 52.7, 53.5, 64.0, 66.0. LRMS (ESI/APCI) m/z 302 [M−H]$^-$.

2-(2-(3-(Dichloroamino)-3-methylbutylsulfonyl)ethoxy)ethanesulfonic acid

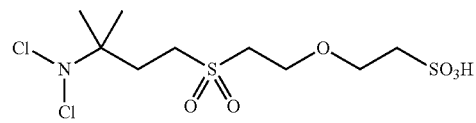 [SMILES: CC(C)(CCS(=O)(=O)CCOCCS(=O)(=O)O)N(Cl)Cl]

A solution of 2-(2-(3-amino-3-methylbutylsulfonyl)ethoxy)ethanesulfonic acid (0.80 g, 2.6 mmol) in a mixture of methanol (70 mL) and water (50 mL) was cooled in an ice bath for 15 min. t-BuOCl (0.93 mL, 7.9 mmol) was added in one portion via syringe to the colorless solution to give a deep yellow solution. The reaction mixture was stirred for 30 minutes at 0° C., then concentrated under reduced pressure to yield a white solid. This solid was dissolved into water and purified via reverse phase chromatography on a Shimadzu Prep-LC utilizing water/acetonitrile and 0.05% acetic acid as modifier. Fractions were collected monitoring ultra violet absorbance at 254 nm. Fractions were pooled and concentrated via rotovap with the water bath set at 25° C. to give a white solid, (0.78 g, 80.0%). $^1$H NMR (D$_2$O, 400 MHz): δ 1.31 (s, 6H), 2.09-2.14 (m, 2H), 3.10 (t, 6.5 Hz, 2H), 3.23-3.27 (m, 2H), 3.41 (t, 10.8 Hz, 2H), 3.79 (t, 6.5 Hz, 2H), 3.86 (t, 10.8 Hz, 2H). $^{13}$C NMR (D$_2$O, 100 MHz) δ 22.6, 30.2, 49.4, 50.4, 52.2, 63.7, 65.9, 73.3. LRMS (ESI/APCI) m/z 370, 372 [M−H]$^-$.

Example 16

Synthesis of N,N-dichloro-4-(2-(2-(2-tert-butoxyethoxy)ethoxy)ethylsulfonyl)-2-methylbutan-2-amine (Compound 38-91)

Benzyl 4-(2-(2-(2-tert-butoxyethoxy)ethoxy)ethylsulfonyl)-2-methylbutan-2-ylcarbamate

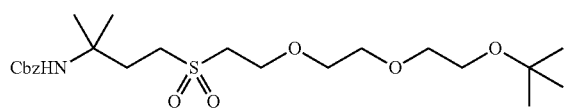 [SMILES: CC(C)(CCS(=O)(=O)CCOCCOCCOC(C)(C)C)NC(=O)OCc1ccccc1]

To a solution of benzyl 4-(2-(2-(2-hydroxyethoxy)ethoxy)ethylsulfonyl)-2-methylbutan-2-ylcarbamate (132.3 mg, 0.317 mmol) in tert-butanol (500 ul) was added conc. sulfuric acid (100 ul). The solution was stirred at RT for 6 d, concentrated in vacuo, and the residue purified by flash chromatography (30%→80% EtOAc in hexanes) to afford the title compound as a clear oil (79.5 mg, 0.168 mmol, 53%). $^1$H NMR (CDCl$_3$, 400 MHz) δ 1.18 (s, 9H), 1.27 (s, 6H), 2.17-2.20 (m, 2H), 3.12-3.18 (m, 4H), 3.46-3.49 (m, 2H), 3.53-3.56 (m, 2H), 3.60 (s, 4H), 3.89 (t, J=6.8 Hz, 2H), 5.01-5.04 (m, 3H), 7.3-7.4 (m, 5H). LRMS (ESI/APCI): 496 [M+Na]$^+$.

4-(2-(2-(2-tert-Butoxyethoxy)ethoxy)ethylsulfonyl)-2-methylbutan-2-amine

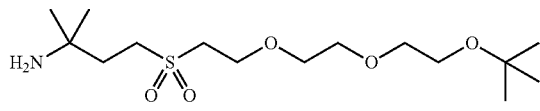 [SMILES: CC(C)(N)CCS(=O)(=O)CCOCCOCCOC(C)(C)C]

A solution of benzyl 4-(2-(2-(2-tert-butoxyethoxy)ethylsulfonyl)-2-methylbutan-2-ylcarbamate (79.5 mg, 0.168 mmol) in MeOH (2 ml) was put under a N$_2$ atmosphere and 10% Pd/C (30 mg) was added. A H$_2$ atmosphere (1.3 atm) was added, and the slurry stirred for 2 h. The suspension was filtered (0.45 um PTFE) and the solution concentrated in vacuo. The residue was used without further purification. LRMS (ESI/APCI): 340 [M+H]$^+$.

N,N-Dichloro-4-(2-(2-(2-tert-butoxyethoxy)ethoxy)ethylsulfonyl)-2-methylbutan-2-amine

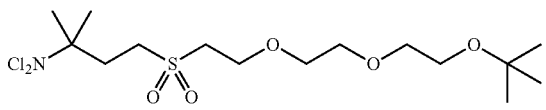

To a solution of 4-(2-(2-(2-tert-butoxyethoxy)ethylsulfonyl)-2-methylbutan-2-amine (0.168 mmol) in MeOH (2 ml) was added tert-butylhypochlorite (50 ul, 0.42 mmol). The solution was stirred for 30 min, concentrated in vacuo, and the residue purified by flash chromatography (30%→80% EtOAc in hexanes) to afford the titled compound as a clear oil (36 mg, 0.088 mmol, 53%). $^1$H NMR (CDCl$_3$, 400 MHz) δ 1.21 (s, 9H), 1.43 (s, 6H), 2.21-2.25 (m, 2H), 3.20-3.23 (m, 4H), 3.53-3.54 (m, 2H), 3.59-3.62 (m, 2H), 3.67 (s, 4H), 3.92-3.94 (m, 2H). $^{13}$C NMR (CDCl$_3$, 100 MHz) δ 23.5, 27.5, 31.6, 50.0, 53.5, 61.2, 64.9, 70.3, 70.8, 71.3, 73.1. LRMS (ESI/APCI): 430 [M+Na]$^+$.

Example 17

Synthesis of N,N-dichloro-4-(2-(2-(2-ethoxyethoxy)ethoxy)ethylsulfonyl)-2-methylbutan-2-amine (Compound 38-89)

Benzyl 4-(2-(2-(2-ethoxyethoxy)ethoxy)ethylsulfonyl)-2-methylbutan-2-ylcarbamate

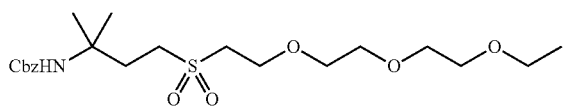 [SMILES: CCOCCOCCOCCS(=O)(=O)CCC(C)(C)NC(=O)OCc1ccccc1]

A solution of 60% sodium hydride (50 mg, 1.3 mmol) in DMF (4 ml) was cooled to 0° C. under N$_2$ and benzyl 4-(2-(2-(2-hydroxyethoxy)ethoxy)ethylsulfonyl)-2-methylbutan-2-ylcarbamate (419.6 mg, 1.005 mmol) in DMF (1 ml) was added dropwise. Ethyl iodide (100 ul, 1.25 mmol) was added dropwise. The solution was stirred for 3 h, diluted with EtOAc (300 ml), washed with 2×100 ml sat. NaCl, dried on MgSO$_4$, and concentrated in vacuo. The resulting residue was purified by flash chromatography (30% to 80% EtOAc in hexanes) to afford the title compound as a clear oil (119.8 mg, 0.2691 mmol, 27%). $^1$H NMR (CDCl$_3$, 400 MHz) δ 1.18 (t, J=4.4 Hz, 3H), 1.32 (s, 6H), 2.17-2.21 (m, 2H), 3.12-3.17 (m, 2H), 3.48-3.58 (m, 10H), 3.87 (dd, J=5.6, 5.6 Hz, 2H), 5.03-5.06 (m, 3H), 7.3-7.4 (m, 5H). LRMS (ESI/APCI): 446 [M+H]$^+$, 468 [M+Na]$^+$.

4-(2-(2-(2-Ethoxyethoxy)ethoxy)ethylsulfonyl)-2-methylbutan-2-amine

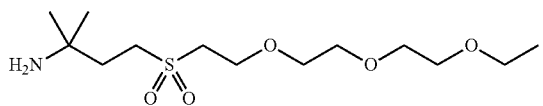 [SMILES: CCOCCOCCOCCS(=O)(=O)CCC(C)(C)N]

A solution of benzyl 4-(2-(2-(2-ethoxyethoxy)ethylsulfonyl)-2-methylbutan-2-ylcarbamate (119.8 mg, 0.2691 mmol) in MeOH (3 ml) was put under N$_2$ and 10% Pd/C (12.6 mg) was added. The vessel was pressurized with H$_2$ (1.3 atm) and the suspension stirred vigorously for 1.5 h. The suspension was filtered through a PTFE (0.45 um) filter and concentrated in vacuo, and the residue used without any further purification. LRMS (ESI/APCI): 312 [M+H]$^+$.

N,N-Dichloro-4-(2-(2-(2-ethoxyethoxy)ethoxy)ethylsulfonyl)-2-methylbutan-2-amine (Compound 38-89)

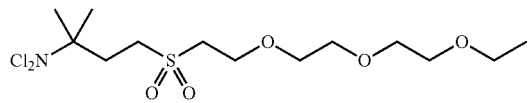

To a solution of 4-(2-(2-(2-ethoxyethoxy)ethoxy)ethylsulfonyl)-2-methylbutan-2-amine (0.2691 mmol) in MeOH (2 ml) was added tert-butylhypochlorite (100 ul, 0.838 mmol). The solution was stirred for 15 min, concentrated in vacuo, and the resulting residue purified by flash chromatography (40% to 100% EtOAc in hexanes) to afford the title compound as a clear oil (99.5 mg, 0.262 mmol, 97% over two steps). $^1$H NMR (CDCl$_3$, 400 MHz) δ 1.21 (t, J=7.2 Hz, 3H), 1.41 (s, 6H), 2.19-2.23 (m, 2H), 3.19-3.22 (m, 4H), 3.53 (q, J=7.2 Hz, 2H), 3.57-3.66 (m, 8H), 3.92 (t, J=6.8 Hz, 2H). $^{13}$C NMR (CDCl$_3$, 100 MHz) δ 15.2, 23.5, 31.6, 50.0, 53.5, 64.8, 66.7, 69.8, 70.3, 70.7, 70.7, 73.1. LRMS (ESI/APCI): 402 [M+Na]$^+$.

Example 18

Synthesis of 3-(3-Amino-3-methylbutylsulfonyl)butane-1,2,4-triol (Compound 38-145)

Benzyl 4-(2-hydroxybut-3-enylthio)-2-methylbutan-2-ylcarbamate and benzyl 4-(1-hydroxybut-3-en-2-ylthio)-2-methylbutan-2-ylcarbamate To a solution of benzyl 4-mercapto-2-methylbutan-2-ylcarbamate (248 mmol) in N,N-dimethylformamide (248 ml)

was added cesium carbonate (4.09 g, 12.6 mmol) and butadiene monoepoxide (15 g, 214 mmol). The suspension was stirred for 16 hours, concentrated in vacuo, diluted with 2 L EtOAc, and washed with twice with 400 ml 5% NaHSO$_4$, 400 ml saturated NaCl, dried on MgSO$_4$, and concentrated in vacuo. The residue was purified by flash chromatography (20% to 40% ethylacetate in hexanes) to give the allylic alcohol (43.2 g, 133 mmol, 54%) and homoallylic alcohol (22.0 g, 68.1 mmol, 27%) as yellow oils.

Benzyl 4-(2-hydroxybut-3-enylthio)-2-methylbutan-2-ylcarbamate

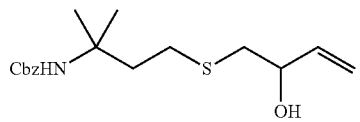 [SMILES: C=CC(O)CSCCC(C)(C)NC(=O)OCc1ccccc1]

$^1$H NMR (CDCl$_3$, 400 MHz) δ 1.31 (s, 3H), 1.31 (s, 3H), 1.9-2.1 (m, 2H), 2.50 (br s, 1H), 2.53 (dd, J=8.0, 9.2 Hz, 1H), 2.58 (dd, J=8.4, 14.0 Hz, 1H), 2.77 (dd, J=4.0, 13.6 Hz, 1H), 4.18-4.22 (m, 1H), 4.8 (br s, 1H), 5.06 (s, 2H), 5.18 (td, J=1.2, 10.4 Hz, 1H), 5.35 (td, J=1.2, 19.2 Hz, 1H), 5.88 (ddd, J=5.6, 10.4, 19.2 Hz, 1H), 7.3-7.4 (m, 5H). LRMS (ESI/APCI): 324 [M+H]$^+$, 346 [M+Na]$^+$.

Benzyl 4-(1-hydroxybut-3-en-2-ylthio)-2-methylbutan-2-ylcarbamate

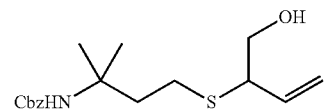 [SMILES: C=CC(CO)SCCC(C)(C)NC(=O)OCc1ccccc1]

$^1$H NMR (CDCl$_3$, 400 MHz) δ 1.31 (s, 6H), 1.9-2.1 (m, 2H), 2.47 (t, J=8.4 Hz, 2H), 3.39 (q, J=8.0 Hz, 1H), 3.67 (ddd, J=6.8, 11.2, 25.6 Hz, 2H), 4.70 (s, 1H), 5.07 (s, 2H), 5.17 (s, 1H), 5.20 (d, J=4.0 Hz, 1H), 5.72 (ddd, J=8.4, 10.0, 18.4 Hz, 1H), 7.3-7.4 (m, 5H). LRMS (ESI/APCI): 324 [M+H]$^+$, 346 [M+Na]$^+$.

Benzyl 2-methyl-4-(1,3,4-trihydroxybutan-2-ylsulfonyl)butan-2-ylcarbamate

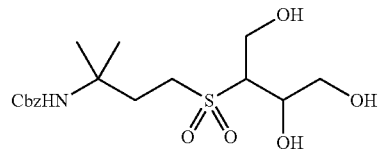 [SMILES: CC(C)(CCS(=O)(=O)C(CO)C(O)CO)NC(=O)OCc1ccccc1]

To a solution of benzyl 4-(1-hydroxybut-3-en-2-ylthio)-2-methylbutan-2-ylcarbamate (22.01 g, 68.05 mmol) in acetone (200 ml) was added N-methylmorpholine oxide (24.32 g, 207.6 mmol) and osmium tetroxide (0.8 g, 3 mmol). The reaction was strongly exothermic and the solution was brought to a vigorous boil over 30 minutes, then cooled to room temperature overnight. The solution was concentrated in vacuo, suspended in 400 ml ethylacetate, washed with twice 100 ml 1.0 M Na$_2$SO$_3$, 100 ml sat. NaCl, dried on MgSO$_4$, and concentrated in vacuo. The residue was purified by flash chromatography (1% to 20% methanol in CH$_2$Cl$_2$) to give the title compound (6.69 g, 17.2 mmol, 25%) as a yellow oil (1:1 mix of diastereomers). $^1$H NMR (CDCl$_3$, 400 MHz) δ 1.33 (m, 6H), 2.3-2.4 (m, 2.5H), 2.54 (s, 1H), 2.7-2.9 (br s, 2H), 3.10-3.15 (br s, 0.7H), 3.15-3.33 (m, 2.5H), 3.4 (br s, 0.6H), 3.65 (br s, 0.6H), 3.7-4.0 (m, 3H), 4.0 (m, 0.6H, 4.2 (m, 0.3H), 4.3 (m, 0.6H, 4.4 (m, 0.3H), 4.8 (br s, 1H), 5.06 (s, 2H), 7.3-7.4 (m, 5H). LRMS (ESI/APCI): 390 [M+H]$^+$, 412 [M+Na]$^+$.

3-(3-Amino-3-methylbutylsulfonyl)butane-1,2,4-triol

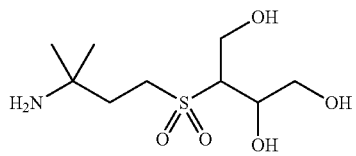 [SMILES: CC(C)(N)CCS(=O)(=O)C(CO)C(O)CO]

To a solution of benzyl 2-methyl-4-(1,3,4-trihydroxybutan-2-ylsulfonyl)butan-2-ylcarbamate (6.69 g, 17.2 mmol) in MeOH (100 ml) was added 10% palladium on carbon (490 mg). The suspension was put under an atmosphere of H$_2$ (1.3 atmospheres) and stirred for 12 hours, filtered through Celite, and concentrated in vacuo. The residue was used without further purification. LRMS (ESI/APCI): 256 [M+H]$^+$.

3-(3-(Dichloroamino)-3-methylbutylsulfonyl)butane-1,2,4-triol

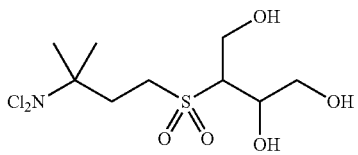

A solution of 3-(3-amino-3-methylbutylsulfonyl)butane-1,2,4-triol (17.2 mmol) was cooled to 0° C. and tert-butylhypochlorite (3.0 ml, 25 mmol) was added dropwise over 5 minutes. The solution was stirred for 1 hour, concentrated in vacuo, and the residue purified by flash chromatography (5% to 10% methanol in CH$_2$Cl$_2$) to give the title compound as a 2:1 mix of diastereomers as a white powder after lyophilization (3.34 g, 10.3 mmol, 60% over two steps). $^1$H NMR (CDCl$_3$, 400 MHz) δ 1.46 (s, 6H), 2.23-2.27 (m, 2H), 2.8-3.2 (br s, 2H), 3.32-3.36 (m, 3H), 3.8 (br s, 1H), 3.82-3.86 (m, 1.35H), 3.94 (dd, J=3.6, 12.0 Hz, 0.65H), 4.10 (dd, J=5.2, 18.0 Hz, 0.65H), 4.20-4.27 (m, 1.35H), 4.34-4.39 (m, 0.65H), 4.51-4.54 (m, 0.35H). $^{13}$C NMR (CDCl$_3$, 100 MHz) δ 23.5, 30.8, 31.0, 48.9, 50.8, 57.1, 57.6, 64.0, 64.4, 66.0, 66.4, 73.2, 73.2. LRMS (ESI/APCI): 346 [M+Na]$^+$.

Example 19

Synthesis of (2S,3S,4S,5R,6S)-2-(((3-(dichloro-amino)-3-methylbutyl)sulfonyl)methyl)-6-methoxytetrahydro-2H-pyran-3,4,5-triol (Compound 38-141)

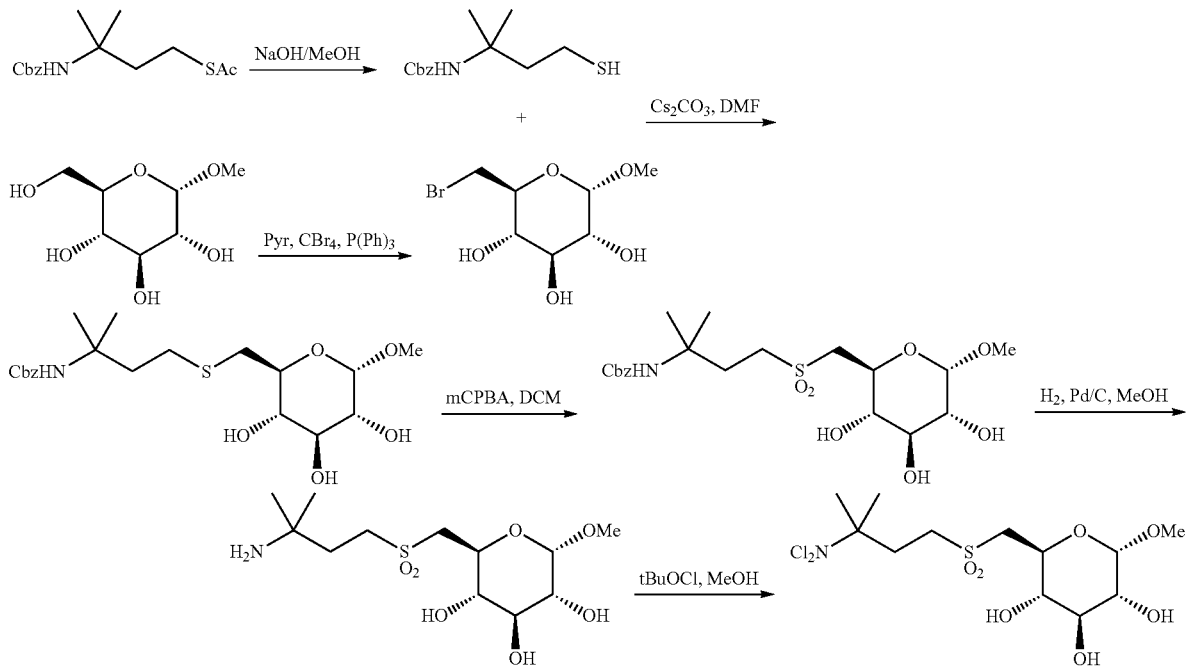

Methyl 6-bromo-α-D-glucopyranoside

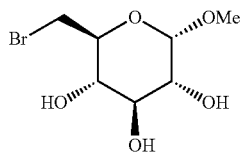 [SMILES: CO[C@H]1O[C@H](CBr)[C@@H](O)[C@H](O)[C@H]1O]

To a 0° C. solution of methyl α-D-glucopyranoside (3.9 g, 20 mmol) in 125 mL of anhydrous pyridine was added triphenylphosphine (10.5 g, 40 mmol) followed by carbon tetrabromide (9.9 g, 30 mmol). The reaction was stirred at 0° C. for 10 minutes then warmed to 65° C. for 4 hours. The reaction was quenched with 20 mL of methanol and concentrated to a crude residue, a portion of which was purified by column chromatography eluting from silica gel with a gradient of 0 to 15% methanol in dichloromethane to give 1.1 g of an off-white solid (64%). $^1$H NMR (400 MHz, d$_6$-DMSO) δ 3.00-3.06 (m, 1H), 3.16-3.23 (m, 1H), 3.30 (s, 3H), 3.30-3.41 (m, H), 3.47-3.57 (m, 2H), 3.73-3.76 (dd, J=1.6, 10.3 Hz, 1H), 4.56-4.57 (d, J=3.6 Hz, 1H), 4.82-4.83 (d, J=6.4 Hz, 1H), 4.90-4.91 (d, J=5.0 Hz, 1H), 5.21-5.23 (d, J=5.9 Hz, 1H). $^{13}$C NMR (100 MHz, d$_6$-DMSO) δ 35.2, 55.0, 71.0, 71.9, 72.3, 73.0, 99.9.

Benzyl(2-methyl-4-(((((2S,3S,4S,5R,6S)-3,4,5-trihydroxy-6-methoxytetrahydro-2H-pyran-2-yl)methyl)thio)butan-2-yl)carbamate

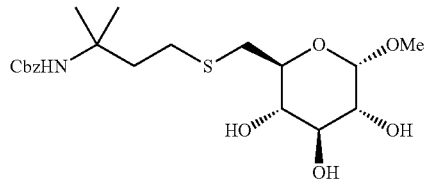 [SMILES: CO[C@H]1O[C@H](CSCCC(C)(C)NC(=O)OCc2ccccc2)[C@@H](O)[C@H](O)[C@H]1O]

Under a nitrogen atmosphere, cesium carbonate (2.1 g, 6.5 mmol) was added to a stirring solution of benzyl 4-mercapto-2-methylbutan-2-ylcarbamate (1.4 g, 5.4 mmol) and methyl 6-bromo-α-D-glycopyranoside (1.1 g, 4.3 mmol) in 10 mL of anhydrous N,N-dimethylformamide. The reaction mixture was stirred for 18 hours, concentrated under vacuum to a residue, and partitioned between ethyl acetate and water. The organic fraction was washed with water and brine, dried over sodium sulfate, and concentrated to a crude residue, which was purified by column chromatography, eluting from silica gel with a gradient of 0-10% methanol in dichloromethane to give 0.97 g of desired product (54% yield). $^1$H NMR (400 MHz, CD$_3$OD) δ 1.28 (br s, 6H), 1.96-2.0 (m, 2H), 2.57-2.64 (m, 3H), 2.93-2.98 (dd, J=2.0, 14.0 Hz, 1H), 3.19-3.23 (dd, J=8.9, 9.6 Hz, 1H), 3.39-3.42 (m, 1H), 3.42 (s, 3H), 3.57-3.67 (m, 2H), 4.63-4.64 (d, J=3.7 Hz, 1H), 5.03 (s, 2H), 7.28-7.35 (m, 5H). $^{13}$C NMR (100 MHz, MeOD) δ 27.1, 27.7, 33.5, 40.2, 52.8, 55.2, 66.2, 71.7, 72.1, 72.9, 74.3, 99.2, 128.1, 128.1, 128.6, 136.5, 154. LRMS (ESI/APCI) m/z 452 [M+Na]$^+$.

Benzyl(2-methyl-4-(((((2S,3S,4S,5R,6S)-3,4,5-trihydroxy-6-methoxytetrahydro-2H-pyran-2-yl)methyl)sulfonyl)butan-2-yl)carbamate

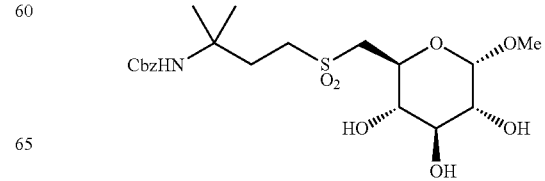

To a 0° C. mixture of benzyl(2-methyl-4-((((2S,3S,4S,5R,6S)-3,4,5-trihydroxy-6-methoxytetrahydro-2H-pyran-2-1l)methyl)thio)butan-2-yl)carbamate (950 mg, 2.2 mmol) and sodium bicarbonate (500 mg) in 10 mL of dichloromethane was added 4-chloroperoxybenzoic acid (77%, 1.35 g, 6.0 mmol). The reaction mixture was stirred for 2 hours and then concentrated under reduced pressure to a crude residue. The residue was partitioned between ethyl acetate and aqueous sodium bicarbonate solutions. The organic fraction was successively washed with sodium bicarbonate and brine solutions, dried over sodium sulfate, and concentrated to a white solid, which was purified by column chromatography, eluting from silica gel with a gradient of 0-20% methanol in dichloromethane to give 0.70 g of desired product (70% yield). $^1$H NMR (400 MHz, CD$_3$OD) δ 1.30 (s, 3H), 1.31 (s, 3H), 2.17-2.27 (m, 2H), 3.14-3.24 (m, 3H), 3.36-3.39 (m, 1H), 3.42 (s, 3H), 3.44-3.46 (m, 2H), 3.63-3.68 (t, J=9.2 Hz, 1H), 4.04-4.10 (m, 1H), 4.68-4.66 (d, J=3.7 Hz, 1H), 5.00-5.08 (m, 2H), 7.28-7.35 (m, 5H).). $^{13}$C NMR (100 MHz, MeOD) δ 26.2, 31.0, 50.9, 51.4, 53.9, 55.1, 65.6, 67.4, 71.8, 72.7, 73.4, 127.5, 127.7, 128.2, 136.9, 155.6. LRMS (ESI/APCI) m/z 484 [M+Na]$^+$.

(2S,3S,4S,5R,6S)-2-(((3-amino-3-methylbutyl)sulfonyl)methyl)-6-methoxytetrahydro-2H-pyran-3,4,5-triol

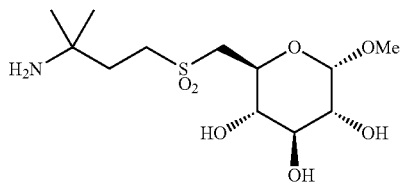 [SMILES: CO[C@H]1O[C@H](CS(=O)(=O)CCC(C)(C)N)[C@@H](O)[C@H](O)[C@H]1O]

Under a nitrogen atmosphere, 175 mg of 10% Pd on carbon was added to a solution of benzyl(2-methyl-4-((((2S,3S,4S,5R,6S)-3,4,5-trihydroxy-6-methoxytetrahydro-2H-pyran-2-yl)methyl)sulfonyl)butan-2-yl)carbamate (700 mg, 1.5 mmol) in 5 mL of methanol. The resultant mixture was degassed and placed under a hydrogen atmosphere, stirring for 3 hours. The suspension was filtered through a pad of celite, washing with methanol, and the filtrate was concentrated under reduced pressure to give ca 496 mg of white foam (quantitative yield). $^1$H NMR (400 MHz, CD$_3$OD) δ 1.19 (s, 6H), 1.90-1.95 (m, 2H), 3.13-3.18 (dd, J=8.9, 9.9 Hz, 1H), 3.21-3.30 (m, 2H), 3.4-3.43 (m, 3H), 3.48 (s, 3H), 3.61-3.66 (t, J=9.2 Hz, 1H), 4.04-4.10 (m, 1H), 4.69-4.70 (d, J=3.7 Hz, 1H). $^{13}$C NMR (100 MHz, MeOD) δ 27.6, 27.7, 34.8, 48.8, 50.8, 53.9, 54.9, 67.3, 71.9, 72.8, 73.3, 100.1. LRMS (ESI/APCI) m/z 328 [M+H]$^+$.

(2S,3S,4S,5R,6S)-2-(((3-(dichloroamino)-3-methylbutyl)sulfonyl)methyl)-6-methoxytetrahydro-2H-pyran-3,4,5-triol

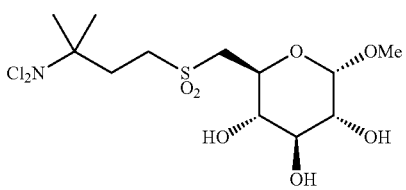

A solution of (2S,3S,4S,5R,6S)-2-(((3-amino-3-methylbutyl)sulfonyl)methyl)-6-methoxytetrahydro-2H-pyran-3,4,5-triol (460 mg, 1.4 mmol) in methanol (4 ml) was cooled to 0° C. tert-Butylhypochlorite (393 ul, 3.5 mmol) was added. The resulting solution was stirred for 30 minutes, and then concentrated under reduced pressure. The crude material was purified by column chromatography, eluting from silica gel with a gradient of 0 to 12% methanol in dichloromethane to give 430 mg of a white solid (78% yield). $^1$H NMR (400 MHz, D$_2$O) δ 1.33 (s, 3H), 1.35 (s, 3H), 2.14-2.18 (m, 2H), 3.21-3.26 (m, 1H), 3.30-3.35 (m, 2H), 3.38 (s, 3H), 3.46-3.60 (m, 4H), 3.99-4.05 (t of d, J=3.6, 9.3 Hz, 1H) 4.74-4.75 (d, J=3.6 Hz, 1H). $^{13}$C NMR (100 MHz, D$_2$O) δ 22.5, 22.6, 30.5, 49.8, 53.4, 55.7, 66.5, 70.9, 71.9, 72.6, 73.2, 99.5. LRMS (ESI/APCI) m/z 418 [M+Na]$^+$.

Example 20

Synthesis of N,N-dichloro-2-methyl-4-(2-(2-(2-(2-methoxyethoxy)ethoxy)ethoxy)ethylsulfonyl)butan-2-amine (38-147)

Benzyl 17-methyl-2,5,8,11-tetraoxa-14-thiaoctadecan-17-ylcarbamate

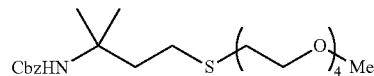

To a solution of benzyl 4-mercapto-2-methylbutan-2-ylcarbamate (20 mmol) in N,N-dimethylformamide (20 ml) was added cesium carbonate (6.49 g, 19.9 mmol) and 13-bromo-2,5,8,11-tetraoxatridecane (5.00 g, 18.4 mmol). The solution was stirred for 16 hours, concentrated in vacuo, and the residue dissolved in 500 ml ethylacetate, washed with 3 times with 100 ml 5% NaHSO$_4$, 1×200 ml sat. NaCl, dried on MgSO$_4$, and concentrated in vacuo. The residue was purified by flash chromatography (10% to 60% ethylacetate in hexanes) to give the titled compound as a clear oil (7.47 g, 18.1 mmol, 98%). $^1$H NMR (400 MHz, CDCl$_3$) δ 1.31 (s, 6H), 1.95-1.99 (m, 2H), 2.51-2.55 (m, 2H), 2.69-2.73 (m, 2H), 3.38 (s, 3H), 3.54-3.58 (m, 2H, 3.6-3.7 (m, 14H), 4.77 (br s, 1H), 5.06 (s, 2H), 7.3-7.4 (m, 5H). LRMS (ESI/APCI): 466 [M+Na]$^+$.

Benzyl 2-methyl-4-(2-(2-(2-(2-methoxyethoxy)ethoxy)ethoxy)ethylsulfonyl)butan-2-ylcarbamate

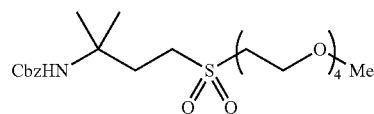

A solution of benzyl 17-methyl-2,5,8,11-tetraoxa-14-thiaoctadecan-17-ylcarbamate (7.47 g, 18.1 mmol) in CH$_2$Cl$_2$ (300 ml) was cooled to 0° C. 77% 3-Chloroperbenzoic acid (10.47 g, 46.72 mmol) was added portionwise, and the solution stirred for 2 hours. The solution was diluted with 800 ml ethylacetate, washed with 3 times with 200 ml saturates NaHCO$_3$, once with 200 ml sat. NaCl, dried on MgSO$_4$, and concentrated in vacuo. The residue was purified by flash chromatography (30% to 100% ethylacetate in hexanes) to afford the titled compound as a clear oil (6.07 g, 12.8 mmol, 71%). $^1$H NMR (400 MHz, CDCl$_3$) δ1.35 (s, 6H), 2.20-2.24

(m, 2H), 3.15-3.22 (m, 4H), 3.38 (s, 3H), 3.53-3.55 (m, 2H), 3.60-3.63 (m, 12H), 3.89-3.92 (m, 2H), 5.00 (br s, 1H), 5.06 (s, 2H), 7.3-7.4 (m, 5H). LRMS (ESI/APCI): 498 [M+Na]+, 476 [M+H]+.

2-Methyl-4-(2-(2-(2-(2-methoxyethoxy)ethoxy)ethoxy)ethylsulfonyl)butan-2-amine

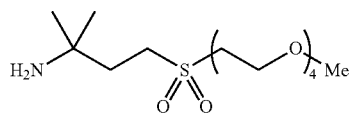

A solution of benzyl 2-methyl-4-(2-(2-(2-(2-methoxyethoxy)ethoxy)ethoxy)ethylsulfonyl)butan-2-ylcarbamate (6.07 g, 12.8 mmol) was dissolved in methanol (150 ml) was purged with N$_2$. 10% palladium on carbon (890 mg) was added, and the suspension was put under a H$_2$ (1.3 atmospheres) atmosphere. The suspension was stirred for 5 hours, filtered through Celite, and the solution concentrated in vacuo. The material was used without further purification. LRMS (ESI/APCI): 342 [M+H]+.

N,N-Dichloro-2-methyl-4-(2-(2-(2-(2-methoxyethoxy)ethoxy)ethoxy)ethylsulfonyl)butan-2-amine

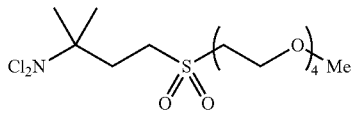

A solution of 2-methyl-4-(2-(2-(2-(2-methoxyethoxy)ethoxy)ethoxy)ethylsulfonyl)butan-2-amine (12.8 mmol) in methanol (150 ml) was cooled to 0° C. tert-Butylhypochlorite (3.5 ml, 29 mmol) was added dropwise over 10 minutes, and the solution stirred for 1 hour. The solution was concentrated in vacuo and the residue purified by flash chromatography (30% to 80% ethylacetate in hexanes) to afford the titled compound as a clear oil (4.20 g, 10.2 mmol, 80% over two steps). $^1$H NMR (400 MHz, CDCl$_3$) δ 1.43 (s, 6H), 2.18-2.22 (m, 2H), 3.17-3.22 (m, 2H), 3.37 (s, 3H), 3.53-3.55 (m, 2H), 3.62-3.64 (m, 10H), 3.91 (t, J=5.6 Hz, 2H). $^{13}$C NMR (100 MHz, CDCl$_3$) δ 23.5, 31.6, 50.0, 53.4, 59.0, 64.8, 70.3, 70.5, 70.6, 70.6, 70.7, 71.9, 73.1. LRMS (ESI/APCI): 432 [M+Na]+.

Example 21

3-(dichloroamino)-3-methylbutan-1-ol (38-171)

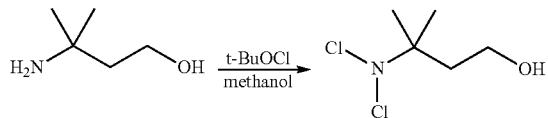

3-Amino-3-methylbutan-1-ol (420 mg, 4.1 mmol, prepared as described in Low, Eddy; Nair, Satheesh; Shiau, Timothy; Belisle, Barbara; Debabov, Dmitri; Celeri, Chris; Zuck, Meghan; Najafi, Ron; Georgopapadakou, Nafsika; Jain, Rakesh *Bioorganic and Medicinal Chemistry Letters*, 2009, 19, 196-198) was dissolved in methanol (50 ml) and cooled to 0° C. tert-Butylhypochlorite (1.33 g, 12.3 mmol) was added to the mixture, and the combined reaction mixture was stirred at 0° C. for 30 minutes. The reaction was concentrated in vacuo to give 632 mg (90%) of 3-(dichloroamino)-3-methylbutan-1-ol as an oil. $^1$H NMR (CDCl$_3$, 400 MHz) δ 3.78 (t, J=6.8 Hz, 2H), 2.01 (t, J=6.8 Hz, 2H), 1.67 (s, 1H), 1.42 (s, 6H). $^{13}$C NMR (CDCl$_3$, 100 MHz) δ 74.2, 59.0, 41.6, 23.0.

Example 22

1-Chloro-3-(2-(2-(2-methoxyethoxy)ethoxy)ethyl)-2,2,5,5-tetramethylimidazolidin-4-one (Compound 39-04)

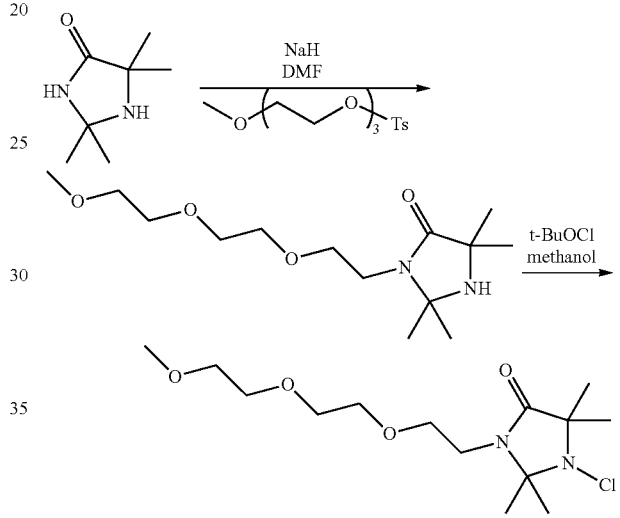

3-(2-(2-(2-Methoxyethoxy)ethoxy)ethyl)-2,2,5,5-tetramethylimidazolidin-4-one

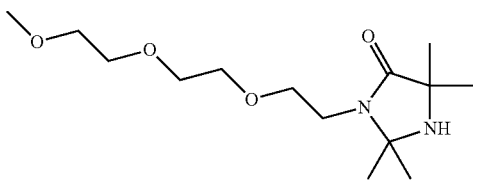

2,2,5,5-Tetramethylimidazolidin-4-one (20.00 g, 140.6 mmol), prepared as described in U.S. Pat. No. 5,126,057 (Worely et al., Jun. 30, 1992), was dissolved in N,N-dimethylformamide (300 ml). To the stirring room temperature solution was added sodium hydride (60%, 5.06 g, 126.5 mmol), in 8 portions over 30 minutes. After an additional one hour of stirring at room temperature, [2-[2-(2-methoxyethoxy)ethoxy]ethoxy]p-toluenesulfonate (40.15 g, 126.1 mmol) was slowly added to the basic solution over a 20 minute period. The reaction mixture was stirred for an additional 18 hours at room temperature. The reaction mixture was concentrated under high vacuum. The solid material was dissolved in dichloromethane and the solution was filtered to remove any solid material. The organic layer was concentrated in vacuo, and crude material was purified by silica gel column chromatography (0 to 10% methanol in dichloromethane) to give 15.51 g (38%) of the title compound. $^1$H NMR (D$_2$O, 400 MHz) δ 3.70-3.46 (m, 12H), 3.64-3.59 (m, 2H), 3.46 (t, J=6.2 Hz, 2H), 3.26 (s, 3H), 1.31 (s, 6H), $^{13}$C NMR (D$_2$O, 100 MHz) δ 179.48, 76.22, 70.99, 69.59, 69.56, 69.39, 67.71, 58.90, 58.00, 39.70, 27.28, 25.67; LRMS (ESI/APCI) m/z 289 [M+H]$^+$.

1-Chloro-3-(2-(2-(2-methoxyethoxy)ethoxy)ethyl)-2,2,5,5-tetramethylimidazolidin-4-one

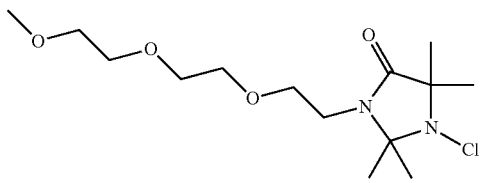

To a 0° C. solution of 3-(2-(2-(2-methoxyethoxy)ethyl)-2,2,5,5-tetramethylimidazolidin-4-one (15.03 g, 52.1 mmol) in methanol (150 ml) was added tert-butylhypochlorite (8.50 g of 0.91 g/mL, 78.3 mmol), over a 10 minute period. The mixture was stirred for 1 hour at 0° C. The reaction mixture was checked for completion by high pressure liquid chromatography. The reaction mixture was concentrated in vacuo, and crude material was purified by silica gel flash chromatography (0 to 10% methanol in dichloromethane) to give 15.43 g (92%) of the title compound. $^1$H NMR (D$_2$O, 400 MHz) δ 3.74-3.65 (m, 8H), 3.62-3.60 (m, 2H), 3.55 (t, J=6 Hz, 2H), 3.37 (s, 3H), 1.53 (s, 6H), 1.36 (s, 6H). $^{13}$C NMR (D$_2$O, 100 MHz) δ 175.00, 83.68, 70.98, 69.59 (2 peaks), 69.39, 67.65, 66.02, 57.99, 40.16, 24.07, 22.52. LRMS (ESI/APCI) m/z 323 [M+H]$^+$.

Example 23

3,3'-(2,2'-(2,2'-Oxybis(ethane-2,1-diyl)bis(oxy))bis(ethane-2,1-diyl))bis(1-chloro-2,2,5,5-tetramethylimidazolidin-4-one) (Compound 39-32)

3,3'-(2,2'-(2,2'-Oxybis(ethane-2,1-diyl)bis(oxy))bis(ethane-2,1-diyl))bis(2,2,5,5-tetramethylimidazolidin-4-one)

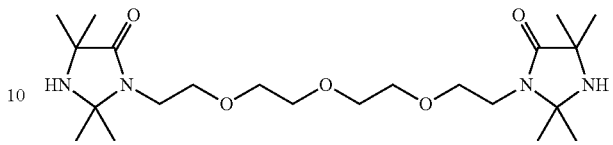

2,2,5,5-Tetramethylimidazolidin-4-one (3.95 g, 27.8 mmol), prepared as described in U.S. Pat. No. 5,126,057 (Worely et al., Jun. 30, 1992), was dissolved in N,N-dimethylformamide (300 ml). The stirring solution was cooled to 0° C., and sodium hydride (60%, 1.07 g, 26.8 mmol) was added in 3 portions over a 15 minute period. The reaction mixture was stirred for an additional hour at 0° C., and tetraethylene glycol di(p-toluenesulfonate) (4.5 ml of 1.24 g/mL, 11.1 mmol) was added. The reaction mixture was slowly warmed to room temperature and allowed to stir for 18 hours. The mixture was concentrated in vacuo, and crude material was purified by preparative-high pressure liquid chromatography to give 800 mg (7%) of the title compound. $^1$H NMR (D$_2$O, 400 MHz) δ 3.73-3.65 (m, 12H), 3.47 (t, J=6.2 Hz, 4H), 1.47 (s, 12H), 1.33 (s, 12H); LRMS (ESI/APCI) m/z 443 [M+H]$^+$.

3,3'-(2,2'-(2,2'-oxybis(ethane-2,1-diyl)bis(oxy))bis(ethane-2,1-diyl))bis(1-chloro-2,2,5,5-tetramethylimidazolidin-4-one)

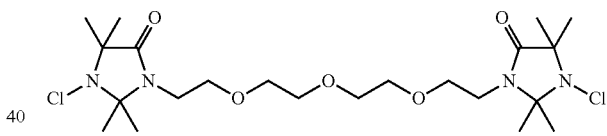

To a 0° C. solution of 3,3'-(2,2'-(2,2'-oxybis(ethane-2,1-diyl)bis(oxy))bis(ethane-2,1-diyl))bis(2,2,5,5-tetrameth-

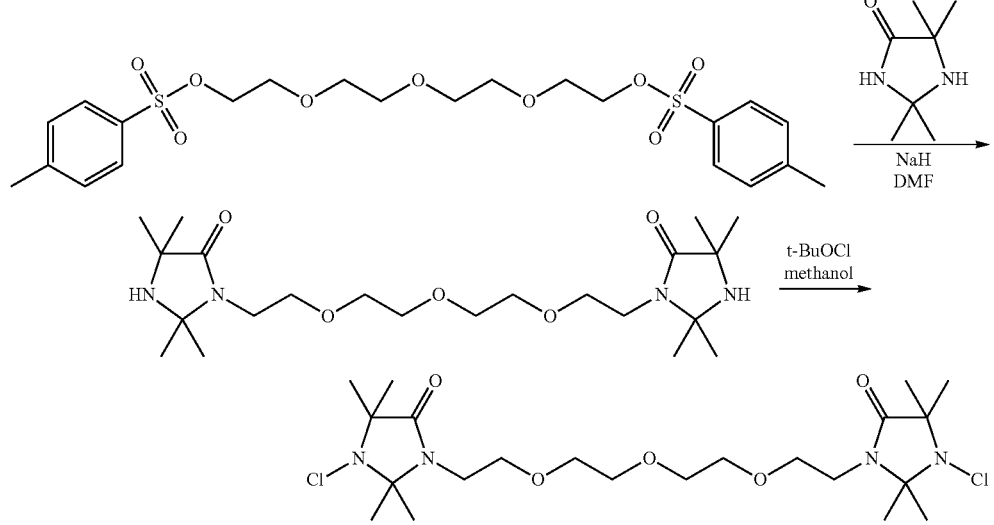

ylimidazolidin-4-one) (300 mg, 0.7 mmol) in methanol (80 ml) was added tert-butylhypochlorite (220 mg, 2.0 mmol). The mixture was stirred for 1 hour at 0° C. The reaction mixture was checked for completion by high pressure liquid chromatography. The reaction mixture was concentrated in vacuo, and crude material was purified by preparative-high pressure liquid chromatography to give 186 mg (51%) of the title compound. $^1$H NMR ($D_2O$, 400 MHz) δ 3.75-3.65 (m, 12H), 3.56 (t, J=6.2 Hz, 4H), 1.54 (s, 12H), 1.37 (s, 12H); $^{13}$C NMR ($D_2O$, 100 MHz) δ 175.00, 83.67, 69.66, 69.63, 67.65, 66.02, 40.18, 24.10, 22.54; LRMS (ESI/APCI) m/z 511 [M+H]$^+$.

Example 24

1-chloro-3-(2-(2-(2-methoxyethoxy)ethoxy)ethyl)-5,5-dimethylimidazolidine-2,4-dione (Compound 39-78)

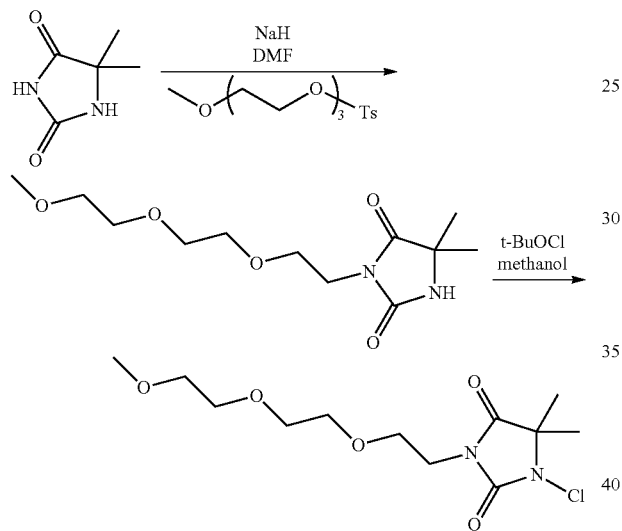

3-(2-(2-(2-methoxyethoxy)ethoxy)ethyl)-5,5-dimethylimidazolidine-2,4-dione

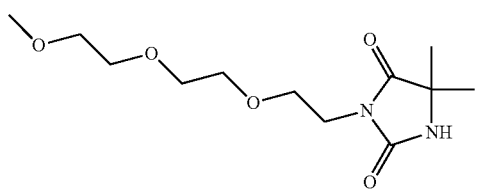

5,5-Dimethylhydantoin (1.32 g, 10.3 mmol) was dissolved in N,N-dimethylformamide (100 ml). To the stirring room temperature solution was added sodium hydride (60%, 412 mg, 10.2 mmol). After an additional one hour of stirring at room temperature, [2-[2-(2-methoxyethoxy)ethoxy]ethoxy] p-toluenesulfonate (3.28 g, 10.3 mmol) was slowly added to the basic solution over a 20 minute period. The reaction mixture was stirred for an additional 18 hours at room temperature. The reaction mixture was concentrated under high vacuum. The solid material was dissolved in dichloromethane and the solution was filtered to remove any solid material. The organic layer was concentrated in vacuo, and crude material was purified by preparative-high pressure liquid chromatography to give 900 mg (31%) of the title compound. $^1$H NMR ($D_2O$, 400 MHz) δ 3.56-3.51 (m, 12H), 3.37 (s, 3H), 1.42 (s, 6H); LRMS (ESI/APCI) m/z 275 [M+H]$^+$.

1-chloro-3-(2-(2-(2-methoxyethoxy)ethoxy)ethyl)-5,5-dimethylimidazolidine-2,4-dione

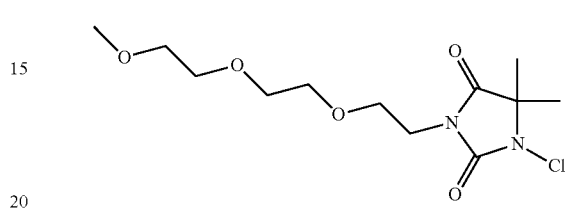

To a 0° C. solution of 3-(2-(2-(2-methoxyethoxy)ethoxy)ethyl)-5,5-dimethylimidazolidine-2,4-dione (900 mg, 3.3 mmol) in methanol (80 ml) was added tert-butylhypochlorite (220 mg, 2.0 mmol). The mixture was stirred for 1 hour at 0° C. The reaction mixture was checked for completion by high pressure liquid chromatography. The reaction mixture was concentrated in vacuo, and crude material was purified by preparative-high pressure liquid chromatography to give 30 mg (3%) of the title compound. $^1$H NMR ($D_2O$, 400 MHz) δ 3.79 (t, J=4.8 Hz, 2H), 3.73 (t, J=4.8 Hz, 2H), 3.69-3.58 (m, 8H), 3.37 (s, 3H), 1.49 (s, 6H); LRMS (ESI/APCI) m/z 309 [M+H]$^+$.

Example 25

3-Chloro-4-methyl-4-((2,3,4-trihydroxybutylsulfonyl)methyl)oxazolidin-2-one (Compound 39-66)

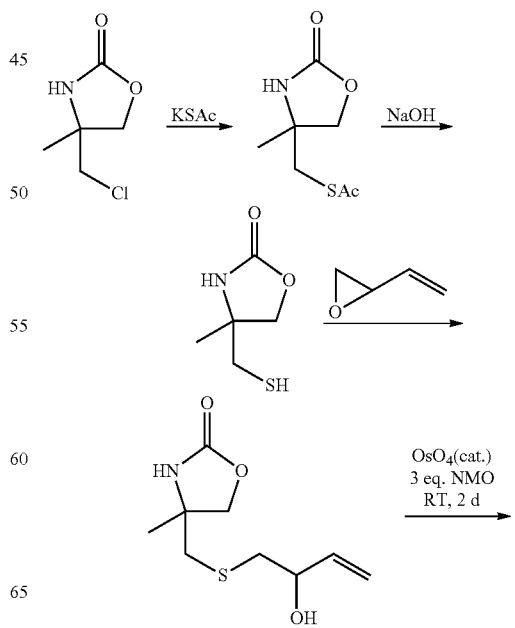

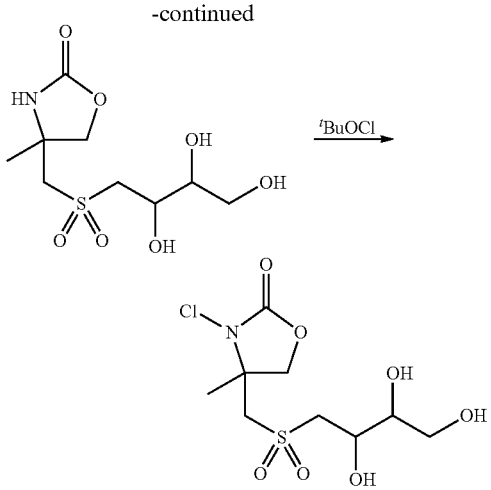

S-(4-Methyl-2-oxooxazolidin-4-yl)methyl ethanethioate

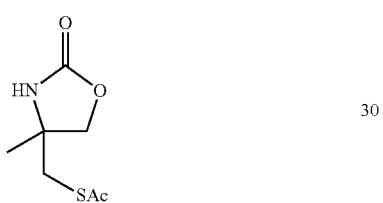

To a solution of 4-(chloromethyl)-4-methyloxazolidin-2-one (10.22 g, 68.32 mmol) in N,N-dimethylformamide (100 ml) was added potassium thioacetate (9.07 g, 79.6 mmol). The suspension was heated to 90° C. for 18 hour, cooled to room temperature, and concentrated in vacuo. The residue was suspended in 400 ml ethyl acetate, washed three times with 100 ml saturated NaHCO$_3$, 100 ml saturated NaCl, dried on MgSO$_4$, and concentrated in vacuo. Flash chromatography (30% to 100% ethyl acetate in hexanes) afforded the title compound as a yellow oil (6.07 g, 31.2 mmol, 46%). $^1$H NMR (CDCl$_3$, 400 MHz) δ 1.45 (s, 3H), 2.42 (s, 3H), 3.07 (d, J=14.0 Hz, 1H), 3.21 (d, J=14.0 Hz, 1H), 4.08 (d, J=8.8 Hz, 1H), 4.15 (d, J=8.8 Hz, 1H), 5.59 (br s, 1H); LRMS (ESI/APCI) m/z 190 [M+H]$^+$.

4-(Mercaptomethyl)-4-methyloxazolidin-2-one

To a solution of S-(4-methyl-2-oxooxazolidin-4-yl)methyl ethanethioate (6.07 g, 31.2 mmol) in methanol (30 ml) was added 5.0 M NaOH in H$_2$O (10 ml, 50 mmol). The solution was stirred for 2.5 hour, concentrated in vacuo, suspended in ethyl acetate (400 ml), washed three times with 100 ml 5% NaHSO$_4$, 100 ml saturated NaCl, dried on MgSO$_4$, and concentrated in vacuo. The material was used without any further purification. LRMS (ESI/APCI) m/z 148 [M+H]$^+$.

4-((2-Hydroxybut-3-enylthio)methyl)-4-methyloxazolidin-2-one

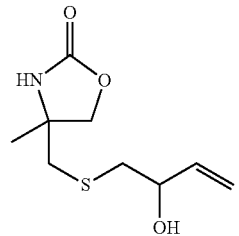

To a solution of 4-(mercaptomethyl)-4-methyloxazolidin-2-one (1.79 g, 12.2 mmol) in N,N-dimethylformamide (20 ml) was added cesium carbonate (520 mg, 1.60 mmol) and 2-vinyloxirane (2.34 g, 33.4 mmol). The solution was heated to 60° C. for 14 hours, cooled to room temperature, concentrated in vacuo, and purified by flash chromatography (30% to 100% ethyl acetate in hexanes) to afford the title compound as a clear oil (quantitative). LRMS (ESI/APCI) m/z 218 [M+H]$^+$.

4-Methyl-4-((2,3,4-trihydroxybutylsulfonyl)methyl)oxazolidin-2-one

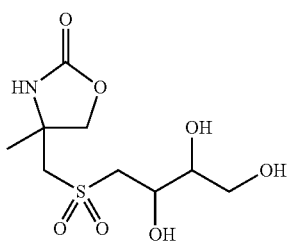 [SMILES: CC1(CS(=O)(=O)CC(O)C(O)CO)COC(=O)N1]

To a solution of 4-((2-hydroxybut-3-enylthio)methyl)-4-methyloxazolidin-2-one (12.2 mmol) in acetone (20 ml) was added 4-Methylmorpholine N-oxide (4.32 g, 36.9 mmol). 2.5 wt % OSO$_4$ in tert-butanol (4.65 ml, 0.46 mmol) was added portion-wise over 3 hours, the solution was stirred for 24 hours, diluted with 600 ml dichloromethane, and extracted three times with 100 ml 2% Na$_2$S$_2$O$_3$ in H$_2$O. The aqueous layer was concentrated in vacuo, and the residue purified by RP-HPLC (H$_2$O/acetonitrile) and then flash chromatography (5% to 20% methanol in dichloromethane) to afford the titled compound as a clear oil (990 mg, 3.49 mmol, 29%). LRMS (ESI/APCI) m/z 284 [M+H]$^+$.

3-Chloro-4-methyl-4-((2,3,4-trihydroxybutylsulfonyl)methyl)oxazolidin-2-one

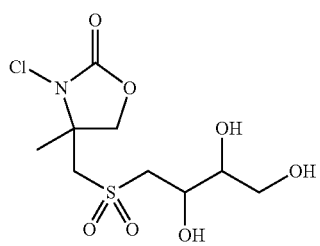 [SMILES: CC1(CS(=O)(=O)CC(O)C(O)CO)COC(=O)N1Cl]

A solution of 4-methyl-4-((2,3,4-trihydroxybutylsulfonyl)methyl)oxazolidin-2-one (990 mg, 3.49 mmol) in methanol (5 ml) was cooled to 0° C. and tert-butylhypochlorite (400 ul, 3.35 mmol) was added drop-wise. The solution was stirred for 2 hours, concentrated in vacuo, and the residue purified by flash chromatography (5% to 20% methanol in dichloromethane) to afford the title compound as a mixture of diastereomers (364.5 mg, 1.147 mmol, 33%). $^1$H NMR (D$_2$O, 400 MHz) δ 1.50 (s, 3H), 3.3-4.3 (m, 7H), 4.4-4.5 (m, 1H), 4.9-5.0 (m, 1H); LRMS (ESI/APCI) m/z 318 [M+H]$^+$.

Example 26

4-chloro-1-(2-hydroxyethyl)-3,3-dimethylpiperazine-2,5-dione (Compound 39-74)

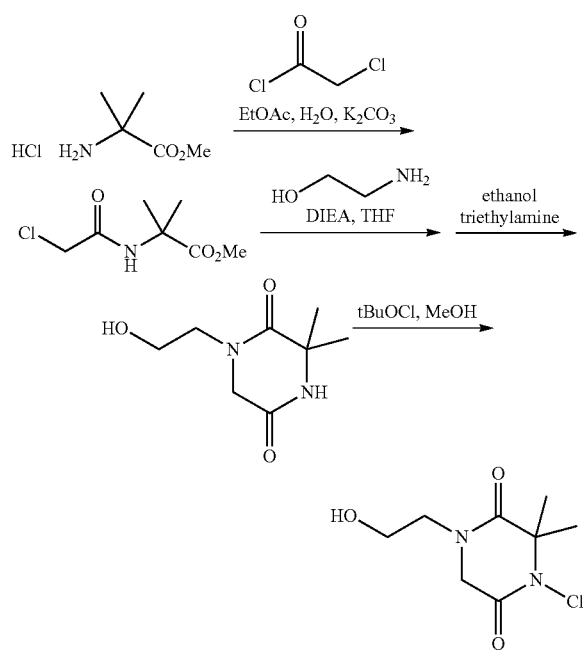

methyl 2-(2-chloroacetamido)-2-methylpropanoate

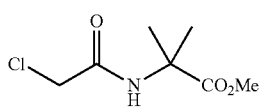

To a rapidly stirring biphasic solution of aminoisobutyric acid methyl ester hydrochloride (5.1 g, 33 mmol) in ethyl acetate (40 mL) and water (27 mL) was added potassium carbonate (13.7 g, 99.6 mmol) followed by chloroacetyl chloride (3.4 mL, 43 mmol). The reaction was cooled with an ice bath to prevent warming above ambient temperature, and stirred at room temperature for four hours. The mixture was diluted with ethyl acetate and the organic layer was successively washed with 10% citric acid and sat. NaCl, dried over sodium sulfate and concentrated in vacuo to give the desired product as a white solid (5.78 g, 29.9 mmol, 91%). $^1$H NMR (CDCl$_3$, 400 MHz) δ 1.61 (s, 6H), 3.78 (s, 3H), 4.01 (s, 2H); LRMS (ESI/APCI) m/z 194 [M+H]$^+$.

1-(2-hydroxyethyl)-3,3-dimethylpiperazine-2,5-dione

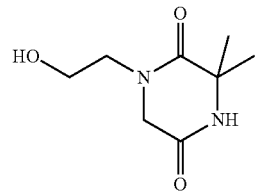

A solution of methyl 2-(2-chloroacetamido)-2-methylpropanoate (2.5 g, 13 mmol), ethanolamine (1.3 g, 21.3 mmol), and N,N-diisopropylethylamine (4.0 mL, 23 mmol) in 250 mL of anhydrous tetrahydrofuran was heated at reflux temperature for 24 hours. The mixture was concentrated to a residue in vacuo and dissolved in ethanol (approximately 300 mL). The mixture was heated in a sealed tube at 155° C. for 24 hours then concentrated to a crude residue and purified by column chromatography (5 to 12% methanol in dichloromethane) to give the title compound as a white solid (1.03 g, 5.5 mmol, 42%). $^1$H NMR (DMSO-d$_6$, 400 MHz) δ 1.30 (s, 6H), 3.32-3.35 (t, J=5.7, 2H), 3.48-3.53 (q, J=5.7, 2H) 4.02 (s, 2H), 4.75-4.77 (t, J=5.4 Hz, 1H). LRMS (ESI/APCI) m/z 187 [M+H]$^+$.

4-chloro-1-(2-hydroxyethyl)-3,3-dimethylpiperazine-2,5-dione

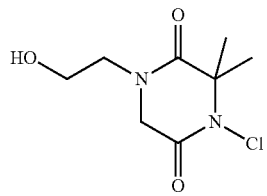

A solution of 1-(2-hydroxyethyl)-3,3-dimethylpiperazine-2,5-dione (300 mg, 1.61 mmol) in methanol (3 ml) was cooled to 0° C. tert-Butylhypochlorite (272 ul, 2.4 mmol) was added. The resulting solution was stirred for 35 minutes, and then concentrated under reduced pressure. The crude material was purified by column chromatography, eluting the desired product from silica gel with a gradient of 1 to 10% methanol in dichloromethane to give the title compound as a white solid (284 mg, 1.28 mmol, 80%). $^1$H NMR (D$_2$O, 400 MHz) δ 1.67 (s, 6H), 2.26-2.28 (t, J=5.0 Hz, 1H), 3.59-3.62 (t, J=5.0 Hz, 2H), 3.86-3.90 (q, J=5.0 Hz, 2H), 4.32 (s, 2H); LRMS (ESI/APCI) m/z 221 [M+H]$^+$.

Example 27

1-chloro-3-(2-((2-(2-(2-methoxyethoxy)ethoxy)ethyl)sulfonyl)ethyl)-5,5-dimethylimidazolidine-2,4-dione (Compound 39-79)

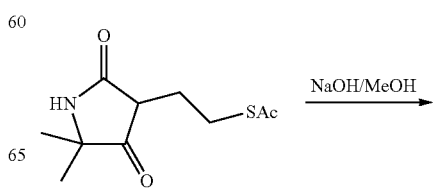

5,5-dimethyl-3-(2,5,8-trioxa-11-thiatridecan-13-yl)imidazolidine-2,4-dione

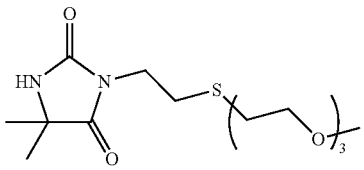

To a mixture of 3-(2-mercaptoethyl)-5,5-dimethylimidazolidine-2,4-dione (2 g, 10.6 mmol) and cesium carbonate (2.07 g, 6.4 mmol) in 25 mL of N,N-dimethylformamide was added [2-[2-(2-methoxyethoxy)ethoxy)ethoxy]ethoxy]p-toluenesulfonate (3.7 g, 11.8 mmol). The resultant mixture was stirred overnight at room temperature, then concentrated in vacuo to give a crude residue, which was purified by column chromatography, (50-100% ethyl acetate in hexanes) to give the desired product (2.24 g, 6.7 mmol, 63%). $^1$H NMR (CDCl$_3$, 400 MHz) δ 1.46 (s, 6H), 2.74-2.78 (t, J=6.8 Hz, 2H), 2.83-2.86 (t, J=6.6 Hz, 2H), 3.39 (s, 3H), 3.54-3.57 (m, 2H), 3.64-3.69 (m, 8H), 3.71-3.73 (t, J=6.8 Hz, 2H), 5.96 (br s, 1H); LRMS (ESI/APCI) m/z 334 [M+H]$^+$.

3-(2-((2-(2-(2-methoxyethoxy)ethoxy)ethyl)sulfonyl)ethyl)-5,5-dimethylimidazolidine-2,4-dione

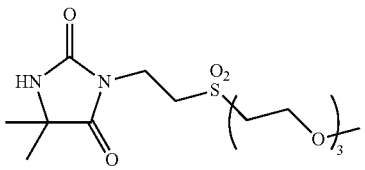

To a solution of 5,5-dimethyl-3-(2,5,8-trioxa-11-thiatridecan-13-yl)imidazolidine-2,4-dione (2.2 g, 6.5 mmol) in 5 mL of formic acid was added a 13 mL of a 1:1 mixture of 30% aqueous hydrogen peroxide and formic acid. The reaction was stirred overnight at room temperature. The solution was concentrated in vacuo to give 2.7 g of a clear liquid, which was purified by column chromatography (5-12% methanol in dichloromethane) to give a clear viscous oil (1.9 g, 5.2 mmol, 80%). $^1$H NMR (CDCl$_3$, 400 MHz) δ 1.44 (s, 6H), 3.36-3.37 (t, J=5.2 Hz, 2H), 3.39 (s, 3H), 3.50-3.54 (m, 4H), 3.59-3.64 (m, 6H), 3.87-3.89 (t, J=5.0 Hz, 2H), 4.0-4.03 (m, 2H), 6.25 (s, 1H). LRMS (ESI/APCI) m/z 367 [M+H]$^+$.

1-chloro-3-(2-((2-(2-(2-methoxyethoxy)ethoxy)ethyl)sulfonyl)ethyl)-5,5-dimethylimidazolidine-2,4-dione

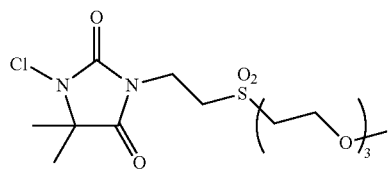

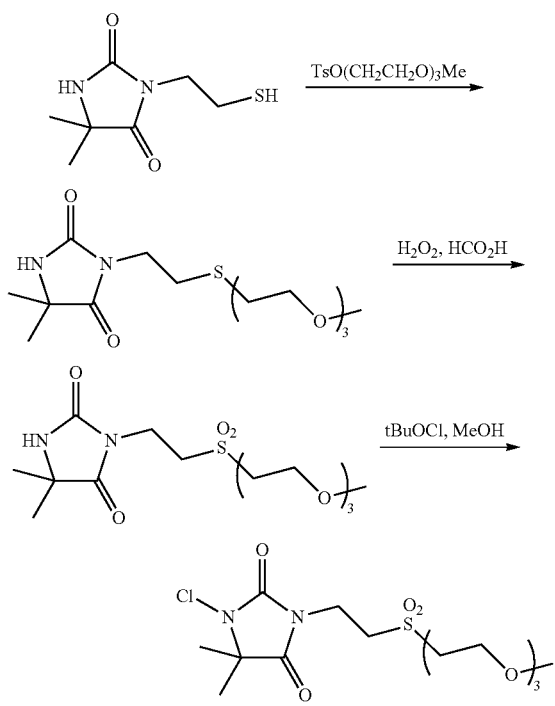

3-(2-mercaptoethyl)-5,5-dimethylimidazolidine-2,4-dione

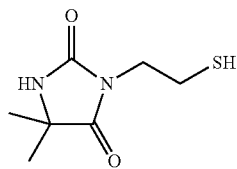

To a cold (0° C.) solution of S-(2-(4,4-dimethyl-2,5-dioxoimidazolidin-1-yl)ethyl) ethanethioate (17 g, 74 mmol) prepared as described in International Patent Publication Number WO 2010/054009 A1 (Jain et al., Apr. 11, 2009), in 150 mL of methanol and 100 mL of water was added 22.5 mL of 5 N NaOH. The external ice bath was removed and the mixture was allowed to warm to room temperature, and stirred for 18 hours. Concentrated hydrochloric acid (8 mL) and 10 mL of water were added and the resultant solution was concentrated to about half of its original volume. White solid product precipitated out of solution and was collected on a glass fritted filter. The remaining aqueous solution was extracted with ethyl acetate, and the organic layer was then successively washed with water and sat. NaCl solutions. The organic fraction was dried overسodium sulfate and concentrated to a white solid, which was combined with the precipitated material to give the desired product (13.2 g, 70.2 mmol, 95%). $^1$H NMR (CDCl$_3$, 400 MHz) δ 1.37-1.41 (t, J=8.5 Hz, 1H), 1.48 (s, 6H), 2.81-2.86 (m, 2H), 3.69-3.73 (t, J=7.0 Hz, 1H), 5.53 (br s, 1H); LRMS (ESI/APCI) m/z 189 [M+H]$^+$.

A solution of 3-(2-((2-(2-(2-methoxyethoxy)ethoxy)ethyl)sulfonyl)ethyl)-5,5-dimethylimidazolidine-2,4-dione (1.9 g, 5.2 mmol) in methanol (10 ml) was cooled to 0° C. tert-Butylhypochlorite (613 ul, 5.45 mmol) was added. The resulting solution was stirred for 3 hours at 0° C., and then concentrated under reduced pressure. The crude material was purified by column chromatography, eluting from silica gel with a gradient of 5-12% methanol in dichloromethane to give 1.1 g of a clear oil. $^1$H NMR (D$_2$O, 400 MHz) δ 1.39 (s, 6H), 3.28 (s, 3H), 3.43-3.47 (t, J=5.4 Hz, 2H), 3.51-3.61 (m, 10H) 3.85-3.88 (t, 5.2 Hz, 2H), 4.02-4.05 (m, 2H). LRMS (ESI/APCI) m/z 401 [M+H]$^+$.

Example 28

3-chloro-1-(2-((2-(2-(2-hydroxyethoxy)ethoxy)ethyl)sulfonyl)ethyl)-4,4-dimethylimidazolidin-2-one
(Compound 39-80)

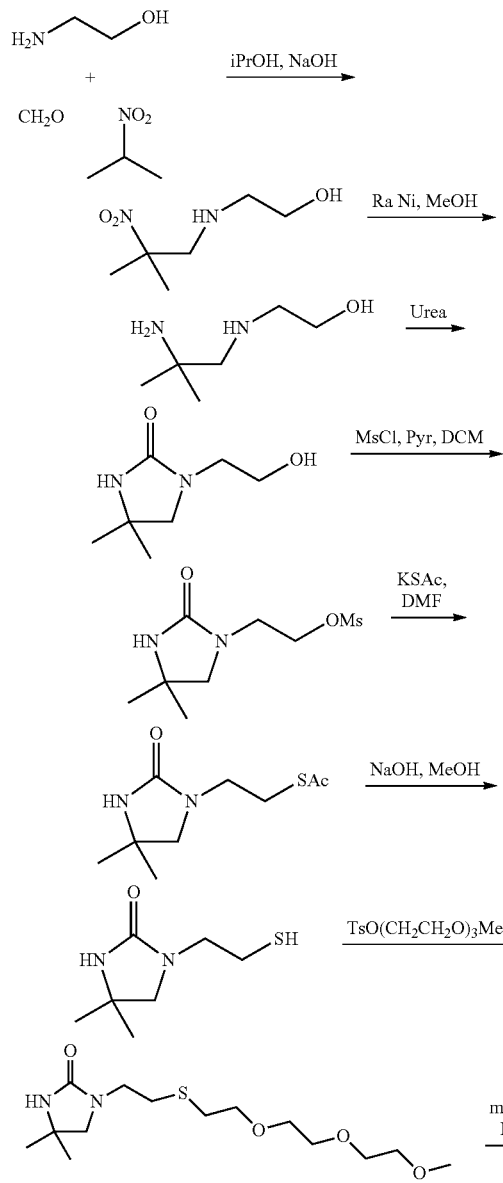

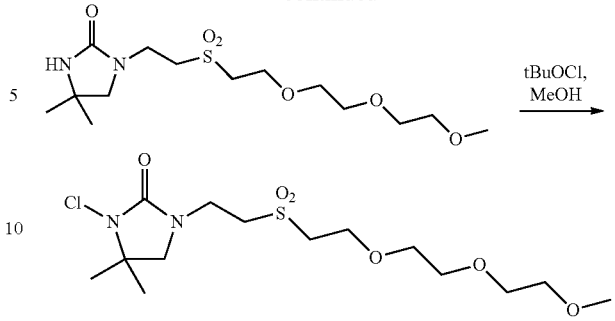

2-((2-methyl-2-nitropropyl)amino)ethanol

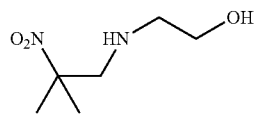

To a stirring solution of ethanolamine (7.5 mL, 124 mmol), nitropropane (11.1 mL, 124 mmol), water (2.4 mL) in isopropanol (21 mL) was added 5 N NaOH (148 uL, 0.74 mmol) followed by the slow addition of 37% aq formaldehyde (9.2 mL). The resulting mixture was stirred for 19 hours at room temperature, then diluted with 130 mL of 1 N HCl. The mixture was successively washed with ether and ethyl acetate, then the pH was adjusted to about 10 with 50% NaOH. The basic solution was extracted twice with dichloromethane. The combined organic fractions were concentrated under reduced pressure to give 17.4 g of a pale yellow liquid. $^1$H NMR (CDCl$_3$, 400 MHz) δ 1.60 (s, 6H), 2.79-2.82 (t, J=5.1 Hz, 2H), 3.04 (s, 2H), 3.60-3.62 (t, J=5.1 Hz, 2H). LRMS (ESI/APCI) m/z 163 [M+H]$^+$.

2-((2-amino-2-methylpropyl)amino)ethanol

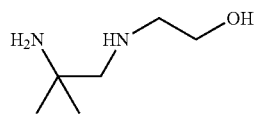

To a solution of 2-((2-methyl-2-nitropropyl)amino)ethanol (9.7 g, 60 mmol) in Methanol (65 ml) was added a slurry of 50% Raney Nickel® in H$_2$O (3 ml). The vessel was pressurized with H$_2$ (450 psi) and the suspension stirred for 48 h. The mixture was filtered through Celite® and concentrated in vacuo to give 7.4 g of a crude liquid, which was used directly in the next step without purification. LRMS (ESI/APCI) m/z 133 [M+H]$^+$.

1-(2-hydroxyethyl)-4,4-dimethylimidazolidin-2-one

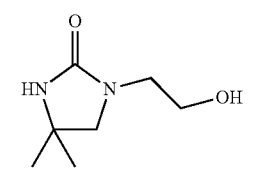

A mixture of urea (5.4 g, 91 mmol) and 2-((2-amino-2-methylpropyl)amino)ethanol (12 g, 91 mmol) was heated in a 200° C. sand bath for approximately 45 min until ammonia evolution had ceased. The crude mixture was purified by column chromatography, eluting from silica gel with a gradient of 0-10% methanol in dichloromethane to give 6.0 g of a white solid. $^1$H NMR (CDCl$_3$, 400 MHz) δ 1.33 (s, 6H), 3.21 (s, 2H), 3.27-3.30 (t, J=5.2, 2H), 3.69-3.71 (q, J=5.2 Hz, 2H), 4.01-4.04 (t, J=5.4, 1H), 5.31 (br s, 1H); LRMS (ESI/APCI) m/z 159 [M+H]$^+$.

2-(4,4-dimethyl-2-oxoimidazolidin-1-yl)ethyl methanesulfonate

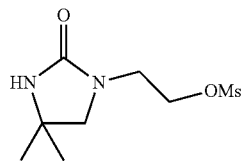

To a solution of 1-(2-hydroxyethyl)-4,4-dimethylimidazolidin-2-one (5.9 g, 37 mmol) and pyridine (3.6 mL, 44.4 mmol) in 150 mL of anhydrous dichloromethane was added methanesulfonyl chloride (3.3 mL, 43 mmol). The reaction was stirred at room temperature for 20 hours, then diluted with 100 mL of dichlormethane and washed twice with 40 mL of 1 N HCl and once with brine. The organic fraction was dried over sodium sulfate and concentrated in vacuo to 3.54 g of the desired product as white solid. $^1$H NMR (CDCl$_3$, 400 MHz) δ 1.33 (s, 6H), 3.06 (s, 3H), 3.23 (s, 2H), 3.54-3.57 (t, J=5.2, 2H), 4.36-4.39 (t, J=5.2 Hz, 2H); LRMS (ESI/APCI) m/z 237 [M+H]$^+$.

S-(2-(4,4-dimethyl-2-oxoimidazolidin-1-yl)ethyl) ethanethioate

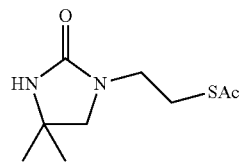

To a solution of 2-(4,4-dimethyl-2-oxoimidazolidin-1-yl) ethyl methanesulfonate (3.5 g, 15 mmol) in 40 mL anhydrous N,N-dimethylformamide was added potassium thioacetate (3.4 g, 30 mmol). The reaction was stirred for 18 hours. The mixture was concentrated to a residue under reduced pressure, which was extracted with 1:1 ethyl acetate: dichloromethane. The organic extract was concentrated under reduced pressure to give a crude red oil which was purified by column chromatography, eluting from silica gel with a gradient of 0 to 10% methanol in dichloromethane to give 2.6 g of a off-white solid. $^1$H NMR (CDCl$_3$, 400 MHz) δ 1.30 (s, 6H), 2.36 (s, 3H), 3.04-3.07 (t, J=6.9 Hz, 2H), 3.24 (s, 2H), 3.35-3.38 (t, J=6.9 Hz, 2H), 4.47 (br s, 1H); LRMS (ESI/APCI) m/z 217 [M+H]$^+$.

1-(2-mercaptoethyl)-4,4-dimethylimidazolidin-2-one

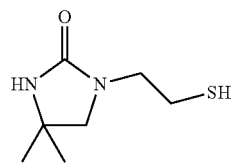

To a cold (0° C.) solution of S-(2-(4,4-dimethyl-2-oxoimidazolidin-1-yl)ethyl) ethanethioate (1.5 g, 6.9 mmol) in 14 mL of methanol and 7.2 mL of water was added 2.1 mL of 5 N NaOH. The external ice bath was removed and the mixture was allowed to warm to room temperature and stirred for 18 hours. Concentrated HCl (11 mL) was added and the resultant solution was concentrated to about ½ its original volume and extracted with ethyl acetate. The organic layer was washed with a brine solution, dried over sodium sulfate, and concentrated to give 1.2 g of a tan liquid. $^1$H NMR (CDCl$_3$, 400 MHz) δ 1.32 (s, 6H), 1.39-1.43 (t, J=8.1 Hz, 1H) 2.66-2.27 (q, J=6.8 Hz, 2H), 3.24 (s, 2H), 3.36-3.340 (t, J=7.2 Hz, 2H), 4.94 (br s, 1H); LRMS (ESI/APCI) m/z 175 [M+H]$^+$.

4,4-dimethyl-1-(2,5,8-trioxa-11-thiatridecan-13-yl) imidazolidin-2-one

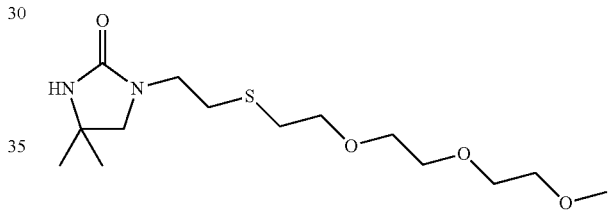

To a solution of 1-(2-mercaptoethyl)-4,4-dimethylimidazolidin-2-one (1.2 g, 6.9 mmol) and [2-[2-(2-methoxyethoxy)ethoxy]ethoxy]ethoxy]p-toluenesulfonate (2.4 g, 7.6 mmol) in anhydrous N,N-dimethylformamide (14 mL) was added cesium carbonate (1.3 g, 4.1 mmol) and the reaction was stirred for 20 hours at room temperature. The crude reaction mixture was concentrated under reduced pressure to give a semisolid residue, which was then extracted with ethyl acetate. The ethyl acetate was filtered to remove insoluble material and concentrated to a red oil, which was purified by column chromatography, eluting from silica gel with a gradient of 2 to 12% methanol in dichloromethane to give 1.4 g of a pale-tan colored liquid. $^1$H NMR (CDCl$_3$, 400 MHz) δ 1.31 (s, 6H), 2.71-2.77 (m, 4H), 3.24 (s, 2H), 3.38-3.42 (m, 5H), 3.54-3.57 (m, 2H), 3.64-3.68 (m, 8H), 4.37 (br s, 1H); LRMS (ESI/APCI) m/z 321 [M+H]$^+$.

1-(2-((2-(2-(2-hydroxyethoxy)ethoxy)ethyl)sulfonyl) ethyl)-4,4-dimethylimidazolidin-2-one

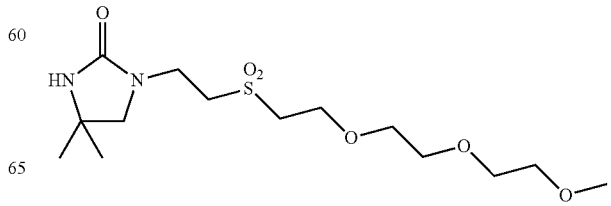

To a cold (0° C.) solution of 4,4-dimethyl-1-(2,5,8-trioxa-11-thiatridecan-13-yl)imidazolidin-2-one (700 mg, 2.1 mmol) in dichloromethane (7 mL) was added 4-chloroperoxybenzoic acid (77%, 1.1 g, 4.8 mmol). The reaction was stirred for 1 hour at 0° C., then diluted with dichloromethane and washed twice with 1 N NaOH and once with brine. The organic fraction was dried over sodium sulfate, concentrated to a clear oil, and purified by column chromatography, eluting from silica gel with a gradient of 1 to 10% methanol in dichloromethane to give 0.68 g of a clear oil. $^1$H NMR (CDCl$_3$, 400 MHz) δ 1.32 (s, 6H), 3.29-3.31 (m, 4H), 3.38-3.40 (m, 5H), 3.54-3.57 (m, 2H), 3.62-3.68 (m, 6H), 3.70-3.73 (t, J=6.2 Hz, 2H), 3.92-3.94 (t, J=5.3 Hz, 2H), 4.36 (br s, 1H); LRMS (ESI/APCI) m/z 353 [M+H]$^+$.

3-chloro-1-(2-((2-(2-(2-hydroxyethoxy)ethoxy)ethyl)sulfonyl)ethyl)-4,4-dimethylimidazolidin-2-one

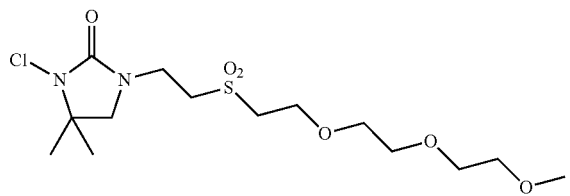 [SMILES: COCCOCCOCCS(=O)(=O)CCN1CC(C)(C)N(Cl)C1=O]

A solution of 1-(2-((2-(2-(2-hydroxyethoxy)ethoxy)ethyl)sulfonyl)ethyl)-4,4-dimethylimidazolidin-2-one (0.67 g, 1.9 mmol) in methanol (4 ml) was cooled to 0° C. tert-Butylhypochlorite (267 ul, 2.37 mmol) was added. The resulting solution was stirred for 30 min. at 0° C., and then concentrated under reduced pressure. The crude material was purified by column chromatography, eluting from silica gel with a gradient of 0-10% methanol in dichloromethane to give 255 mg of a clear oil. $^1$H NMR (D$_2$O, 400 MHz) δ 1.24 (s, 6H), 3.28 (s, 3H), 3.35 (s, 2H), 3.43-3.49 (m, 4H), 3.51-3.3.54 (m, 2H), 3.58-3.61 (m, 6H), 3.71-3.74 (t, J=6.3 Hz, 2H), 3.87-3.89 (t, J=5.3 Hz, 2H). $^{13}$C NMR (D$_2$O, 100 MHz) δ 161.1, 71.0, 69.7, 69.5, 69.4, 63.7, 62.5, 58.0, 55.1, 53.1, 50.9, 37.6, 22.3; LRMS (ESI/APCI) m/z 387 [M+H]$^+$.

Example 29

4-chloro-1-(2-hydroxyethyl)-3,3,5,5-tetramethylpiperazin-2-one (Compound 39-81)

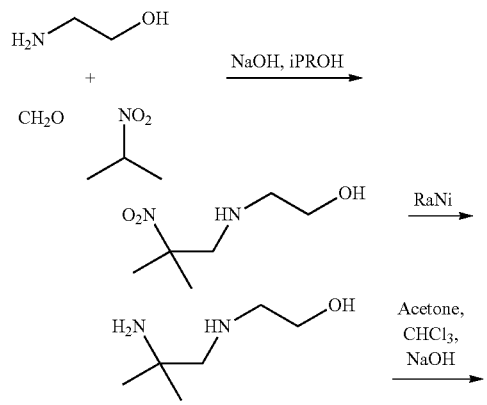

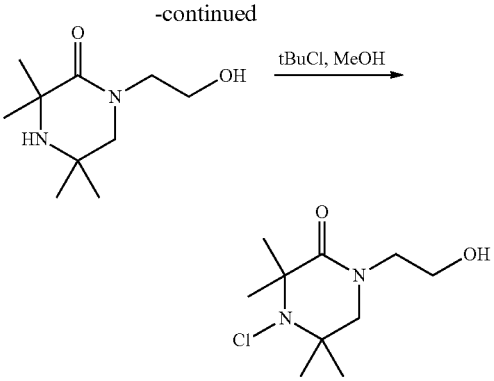

2-((2-methyl-2-nitropropyl)amino)ethanol

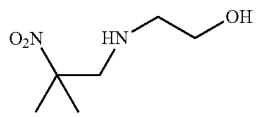

To a stirring solution of ethanolamine (7.5 mL, 124 mmol), nitropropane (11.1 mL, 124 mmol), water (2.4 mL) in isopropanol (21 mL) was added 5 N NaOH (148 uL, 0.74 mmol) followed by the slow addition of 37% aq formaldehyde (9.2 mL). The resulting mixture was stirred for 19 hours at room temperature, then diluted with 130 mL of 1 N HCl. The mixture was successively washed with ether and ethyl acetate, then the pH was adjusted to about 10 with 50% NaOH. The basic solution was extracted twice with dichloromethane. The combined organic fractions were concentrated under reduced pressure to give 17.4 g of a pale yellow liquid. $^1$H NMR (CDCl$_3$, 400 MHz) δ 1.60 (s, 6H), 2.79-2.82 (t, J=5.1 Hz, 2H), 3.04 (s, 2H), 3.60-3.62 (t, J=5.1 Hz, 2H). LRMS (ESI/APCI) m/z 163 [M+H]$^+$.

2-((2-amino-2-methylpropyl)amino)ethanol

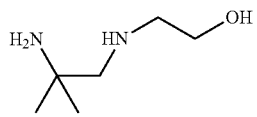

To a solution of 2-((2-methyl-2-nitropropyl)amino)ethanol (20.4 g, 126 mmol) in methanol (120 ml) was added a slurry of 50% Raney Nickel® in H$_2$O (6 ml). The vessel was pressurized with H$_2$ (450 psi) and the suspension stirred for 19 h. The mixture was filtered through Celite and concentrated in vacuo to give 20 g of a crude liquid, which was distilled under vacuum (<1 mbar, 100-125° C.) to give 13 g of a clear liquid, which was found to be partially purified and was used directly in the next step without purification. LRMS (ESI/APCI) m/z 133 [M+H]$^+$.

1-(2-hydroxyethyl)-3,3,5,5-tetramethylpiperazin-2-one

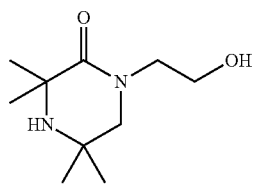

To a solution of 2-((2-amino-2-methylpropyl)amino)ethanol (12 g, 91 mmol) in 90 mL of acetone was added chloroform (10.9 mL, 136 mmol) and the solution was cooled to 0° C. with an external ice bath. A solution of NaOH (50% by weight, 43.6 g, 545 mmol) was added slowly to the cold solution over several minutes and the resultant solution was stirred at 0° C. for 2 hours then allowed to warm to room temperature and stirred for an additional 18 hr. The crude reaction mixture was filtered to remove solids, washing with acetone, and the solution was concentrated to 20 g of a clear oil. A portion of the crude material was purified by a bulb-to-bulb distillation under reduced pressure to give 1.45 g of a clear oil, which was used directly in the next step without further purification. LRMS (ESI/APCI) m/z 201 [M+H]+.

4-chloro-1-(2-hydroxyethyl)-3,3,5,5-tetramethylpiperazin-2-one

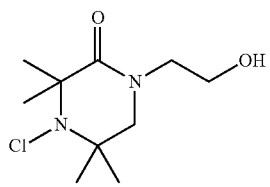

A solution of 1-(2-hydroxyethyl)-3,3,5,5-tetramethylpiperazin-2-one (125 mg, 0.63 mmol) in methanol (1 ml) was cooled to 0° C. tert-Butylhypochlorite (106 ul, 0.94 mmol) was added. The resulting solution was stirred for 60 minutes, and then concentrated under reduced pressure. The crude material was purified by column chromatography eluting from silica gel with a gradient of 0-8% methanol in dichloromethane to give 111 mg of a white solid. $^1$H NMR (D$_2$O, 400 MHz) δ 1.21 (s, 3H), 1.43 (s, 3H), 3.36 (s, 2H), 3.43-3.345 (t, J=5.6 Hz, 2H), 3.64-3.66 (t, J=5.6 Hz, 2H). $^{13}$C NMR (D$_2$O, 100 MHz) δ 172.9, 68.1, 60.0, 58.4, 57.4, 49.6, 25.5, 22.7. LRMS (ESI/APCI) m/z 235 [M+H]+.

Example 30

2-(3-chloro-4,4-dimethyl-2-oxoimidazolidin-1-yl)-N-(2-(2-(2-methoxyethoxy)ethoxy)ethyl)-N,N-dimethylethanaminium 4-methylbenzenesulfonate (Compound 39-85)

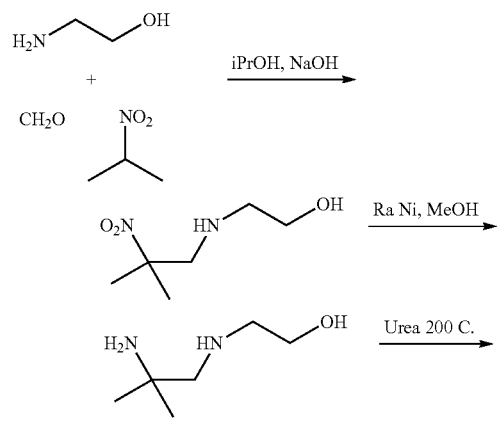

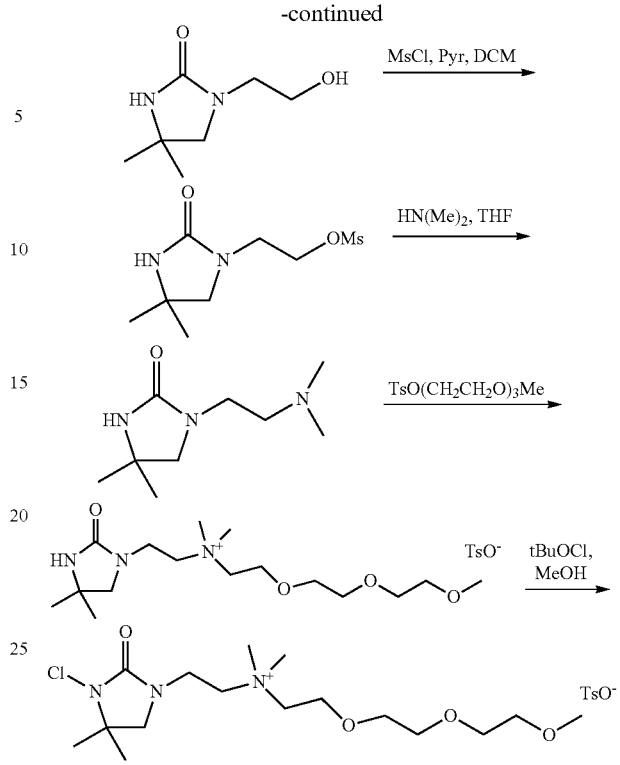

2-((2-methyl-2-nitropropyl)amino)ethanol

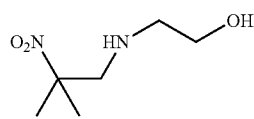

To a stirring solution of ethanolamine (7.5 mL, 124 mmol), nitropropane (11.1 mL, 124 mmol), water (2.4 mL) in isopropanol (21 mL) was added 5 N NaOH (148 uL, 0.74 mmol) followed by the slow addition of 37% aq formaldehyde (9.2 mL). The resulting mixture was stirred for 19 hours at room temperature, then diluted with 130 mL of 1 N HCl. The mixture was successively washed with ether and ethyl acetate, then the pH was adjusted to about 10 with 50% NaOH. The basic solution was extracted twice with dichloromethane. The combined organic fractions were concentrated under reduced pressure to give 17.4 g of a pale yellow liquid. $^1$H NMR (CDCl$_3$, 400 MHz) δ 1.60 (s, 6H), 2.79-2.82 (t, J=5.1 Hz, 2H), 3.04 (s, 2H), 3.60-3.62 (t, J=5.1 Hz, 2H). LRMS (ESI/APCI) m/z 163 [M+H]+.

2-((2-amino-2-methyl)propyl)amino)ethanol

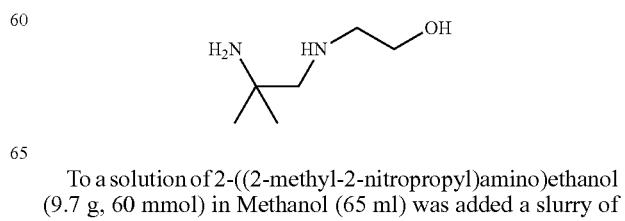

To a solution of 2-((2-methyl-2-nitropropyl)amino)ethanol (9.7 g, 60 mmol) in Methanol (65 ml) was added a slurry of 50% Raney Nickel® in H₂O (3 ml). The vessel was pressurized with H$_2$ (450 psi) and the suspension stirred for 48 hours. The mixture was filtered through Celite® and concentrated in vacuo to give 7.4 g of a crude liquid, which was used directly in the next step without purification. LRMS (ESI/APCI) m/z 133 [M+H]$^+$.

1-(2-hydroxyethyl)-4,4-dimethylimidazolidin-2-one

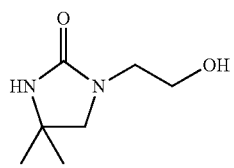

A mixture of urea (5.4 g, 91 mmol) and 2-((2-amino-2-methylpropyl)amino)ethanol (12 g, 91 mmol) was heated in a 200° C. sand bath for approximately 45 min until ammonia evolution had ceased. The crude mixture was purified by column chromatography, eluting from silica gel with a gradient of 0-10% methanol in dichloromethane to give 6.0 g of a white solid. $^1$H NMR (CDCl$_3$, 400 MHz) δ 1.33 (s, 6H), 3.21 (s, 2H), 3.27-3.30 (t, J=5.2, 2H), 3.69-3.71 (q, J=5.2 Hz, 2H), 4.01-4.04 (t, J=5.4, 1H), 5.31 (br s, 1H); LRMS (ESI/APCI) m/z 159 [M+H]$^+$.

2-(4,4-dimethyl-2-oxoimidazolidin-1-yl)ethyl methanesulfonate

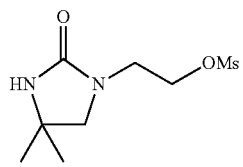

To a solution of 1-(2-hydroxyethyl)-4,4-dimethylimidazolidin-2-one (5.9 g, 37 mmol) and pyridine (3.6 mL, 44.4 mmol) in 150 mL of anhydrous dichloromethane was added methanesulfonyl chloride (3.3 mL, 43 mmol). The reaction was stirred at room temperature for 20 hours, then diluted with 100 mL of dichloromethane and washed twice with 40 mL of 1 N HCl and once with brine. The organic fraction was dried over sodium sulfate and concentrated in vacuo to 3.54 g of the desired product as white solid. $^1$H NMR (CDCl$_3$, 400 MHz) δ 1.33 (s, 6H), 3.06 (s, 3H), 3.23 (s, 2H), 3.54-3.57 (t, J=5.2, 2H), 4.36-4.39 (t, J=5.2 Hz, 2H); LRMS (ESI/APCI) m/z 237 [M+H]$^+$.

1-(2-(dimethylamino)ethyl)-4,4-dimethylimidazolidin-2-one

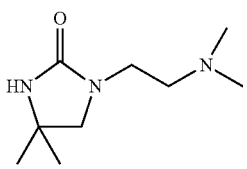

In a sealed tube, a solution of 2-(4,4-dimethyl-2-oxoimidazolidin-1-yl)ethyl methanesulfonate (500 mg, 2.1 mmol) and dimethyl amine (4.6 mmol) in tetrahydrofuran (2.3 mL) was heated at 60° C. for 5 hours. Additional dimethylamine (1 mL of a 2M tetrahydrofuran solution) was added and the reaction was heated for 3 additional hours. The solution was concentrated to a crude residue under reduced pressure, then dissolved in 5 mL of 1 N HCl. The aqueous solution was washed with dichloromethane, then made basic (pH>8) with sodium carbonate and extracted with dichloromethane twice. The aqueous solution was further adjusted to pH>10 with NaOH, and extracted with twice with dichloromethane. The combined organic fractions were dried over sodium sulfate and concentrated under reduced pressure to give 316 mg of an off-white solid. $^1$H NMR (CDCl$_3$, 400 MHz) δ 1.30 (s, 6H), 2.27 (s, 6H), 2.41-2.45 (t, 6.8 Hz, 2H) 3.24 (s, 2H), 3.29-3.33 (t, J=6.8 Hz, 2H), 3.51-3.61 (m, 14H), 3.88 (br m, 2H), 7.27-7.29 (d, J=8.1 Hz, 2H), 7.58-7.60 (d, J=8.2 Hz, 2H); LRMS (ESI/APCI) m/z 186 [M+H]$^+$.

2-(4,4-dimethyl-2-oxoimidazolidin-1-yl)-N-(2-(2-(2-methoxyethoxy)ethoxy)ethyl)-N,N-dimethylethanaminium 4-methylbenzenesulfonate

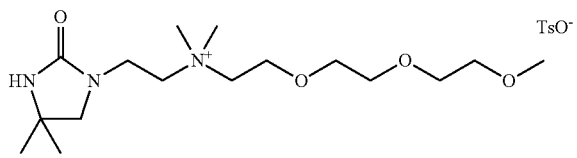

In a sealed tube, 1-(2-(dimethylamino)ethyl)-4,4-dimethylimidazolidin-2-one (92 mg, 0.5 mmol) and [2-[2-(2-methoxyethoxy)ethoxy]ethoxy]ethyl]p-toluenesulfonate (318 mg, 1.0 mmol) were heated at 60° C. for 4.5 hours. The crude reaction mixture was purified by reverse phase HPLC eluting from a C18 column with a gradient of 5 to 95% CH$_3$CN in water (with 0.01% acetic acid) to give 165 mg of a clear oil. $^1$H NMR (D$_2$O, 400 MHz) δ 1.19 (s, 6H), 2.30 (s, 3H), 3.11 (s, 6H) 3.27 (s, 3H), 3.27 (s, 2H), 3.51-3.61 (m, 14H), 3.88 (br m, 2H), 7.27-7.29 (d, J=8.1 Hz, 2H), 7.58-7.60 (d, J=8.2 Hz, 2H); LRMS (ESI/APCI) m/z 332 [M]$^+$.

2-(3-chloro-4,4-dimethyl-2-oxoimidazolidin-1-yl)-N-(2-(2-(2-methoxyethoxy)ethoxy)ethyl)-N,N-dimethylethanaminium 4-methylbenzenesulfonate

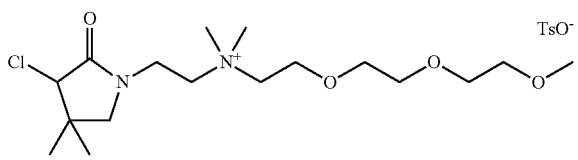 [SMILES: COCCOCCOCC[N+](C)(C)CCN1CC(C)(C)C(Cl)C1=O ; "TsO-"]

A solution of 2-(4,4-dimethyl-2-oxoimidazolidin-1-yl)-N-(2-(2-(2-methoxyethoxy)ethoxy)ethyl)-N,N-dimethylethanaminium 4-methylbenzenesulfonate (162 mg, 0.32 mmol) in methanol (1 ml) was cooled to 0° C. tert-Butylhypochlorite (45 ul, 0.4 mmol) was added. The resulting solution was stirred for 2 hours at 0° C. and then concentrated under reduced pressure. The residue was purified by reverse phase HPLC eluting from a C18 column with a gradient of 5 to 95% CH$_3$CN in water (with 0.01% acetic acid) to give 75 mg of a clear oil. $^1$H NMR (D$_2$O, 400 MHz) δ 1.21 (s, 6H), 2.29 (s, 3H), 3.09 (s, 6H) 3.26 (s, 3H), 3.31 (s, 2H), 3.48-3.36 (m, 14H), 3.84 (br m, 2H), 7.25-7.27 (d, J=8.1 Hz, 2H), 7.58-7.60 (d, J=8.2 Hz, 2H). $^{13}$C NMR (D$_2$O, 100 MHz) δ 161.2, 142.4, 139.6, 129.4, 125.3, 70.9, 69.7, 69.4, 69.4, 63.9, 63.6, 62.4, 61.1, 58.0, 55.5, 51.8, 38.9, 22.3, 20.5; LRMS (ESI/APCI) m/z 366 [M]$^+$.

Example 31

1-chloro-2,2,5,5-tetramethyl-3-(2,5,8,11,14,17,20,23,26,29,32,35,38,41,44,47,50,53,56,59,62,65,68,71,74,77,80,83,86,89,92,95,98,101,104,107,110,113,116-nonatriacontaoxaoctadecahectan-118-yl)imidazolidin-4-one (Compound 39-94)

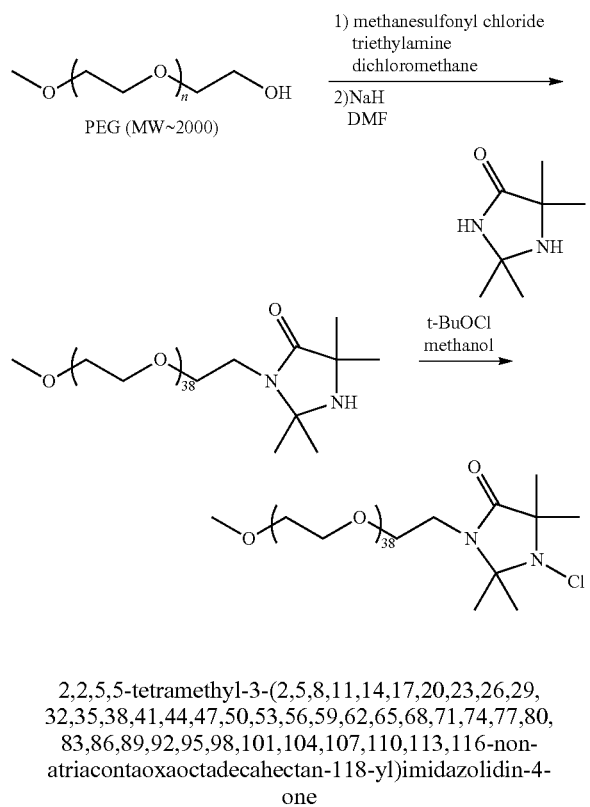

2,2,5,5-tetramethyl-3-(2,5,8,11,14,17,20,23,26,29,32,35,38,41,44,47,50,53,56,59,62,65,68,71,74,77,80,83,86,89,92,95,98,101,104,107,110,113,116-nonatriacontaoxaoctadecahectan-118-yl)imidazolidin-4-one Poly(ethylene glycol)methyl ether (average molecular weight=2000, Aldrich cat#202509, 5.25 g, 2.6 mmol) was dissolved in dichloromethane (150 ml). To the stirring mixture is added triethylamine (1.0 ml, 7.2 mmol), and the combined mixture was cooled to 0° C. methanesulfonyl chloride (0.5 ml, 6.5 mmol) was added dropwise to the stirring solution over a 30 minute period. The combined mixture was stirred at 0° C. for an additional 30 minutes. The reaction mixture was washed with water, and the organic layer was dried over sodium sulfate. The organic layer was concentrated in vacuo, and the PEG-mesylate product was used without further purification.

2,2,5,5-Tetramethylimidazolidin-4-one (2.20 g, 15.8 mmol), prepared as described in U.S. Pat. No. 5,126,057 (Worely et al., Jun. 30, 1992), was dissolved in N,N-dimethylformamide (60 ml). To the stirring room temperature solution was added sodium hydride (60%, 112 mg, 2.8 mmol), in 4 portions over 10 minutes. After an additional one hour of stirring at room temperature, the PEG-mesylate was added to the reaction mixture. After the reaction mixture was stirred for 18 hours at room temperature, the mixture was concentrated in vacuo, and crude material is purified by silica gel column chromatography (0 to 10% methanol in dichloromethane) to give 1.42 g (8%) the title compound.

1-chloro-2,2,5,5-tetramethyl-3-(2,5,8,11,14,17,20,23,26,29,32,35,38,41,44,47,50,53,56,59,62,65,68,71,74,77,80,83,86,89,92,95,98,101,104,107,110,113,116-nonatriacontaoxaoctadecahectan-118-yl)imidazolidin-4-one

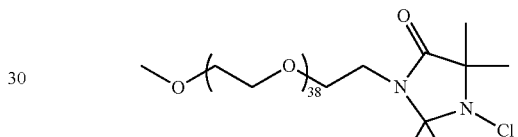

To a 0° C. solution of 2,2,5,5-tetramethyl-3-(2,5,8,11,14,17,20,23,26,29,32,35,38,41,44,47,50,53,56,59,62,65,68,71,74,77,80,83,86,89,92,95 (1.42 g, 0.7 mmol) in methanol (150 ml) was added tert-butylhypochlorite (209 mg, 1.9 mmol). The mixture was stirred for 1 hour at 0° C. The reaction mixture was concentrated in vacuo, and crude material is purified by silica gel flash chromatography (0 to 10% methanol in dichloromethane) to give 775 mg (54%) of the title compound. $^1$H NMR (400 MHz, D$_2$O) δ 3.72 (s, 152H), 3.65 (m, 2H), 3.58 (t, J=7.5 Hz, 2H), 3.40 (s, 3H), 1.55 (s, 6H), 1.38 (s, 6H). $^{13}$C NMR (100 MHz, D$_2$O) δ 174.9, 83.6, 71.0, 69.5 (large peak) 67.7, 66.0, 58.1, 40.2, 24.2, 22.7.

Example 32

1-chloro-3-(2-methoxyethyl)-2,2,5,5-tetramethylimidazolidin-4-one (Compound 39-01)

3-(2-Methoxyethyl)-2,2,5,5-tetramethylimidazolidin-4-one

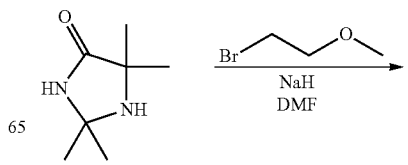

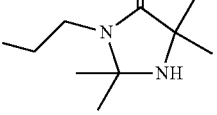

A suspension of 2,2,5,5-tetramethylimidazolidin-4-one (0.71 g, 5.0 mmol), prepared as described in U.S. Pat. No. 5,126,057 (Worely et al., Jun. 30, 1992), and sodium hydride (200 mg, 60% disp, 5.0 mmol, 1.0 equiv) in dry N,N-dimethylformamide (10 mL) was stirred at room temperature under nitrogen for 15 min. Neat 2-bromoethyl methyl ether (0.52 mL, 5.5 mmol, 1.1 equiv.) was added, and the mixture was stirred at room temperature overnight. After 19.5 h, the mixture was concentrated. The residue was absorbed on silica (2 g) and was purified by silica gel flash chromatography (0-6% methanol in dichloromethane) afforded the imidazolidinone as a pale yellow oil (0.71 g, 71%). $^1$H NMR (400 MHz, CDCl$_3$) δ 3.56 (t, J=6.4 Hz, 2H), 3.37 (t, J=6.4 Hz, 2H), 3.36 (s, 3H), 1.82 (s, 1H), 1.40 (s, 6H), 1.33 (s, 6H); LRMS (ESI/APCI) m/z 201 [M+H]$^+$.

1-Chloro-3-(2-methoxyethyl)-2,2,5,5-tetramethylimidazolidin-4-one

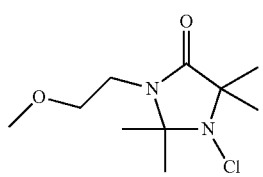

A solution of 3-(2-methoxyethyl)-2,2,5,5-tetramethylimidazolidin-4-one (0.70 g, 3.5 mmol) in methanol (10 mL) was cooled in ice water for 10 minutes, before neat tert-butyl hypochlorite (0.59 mL, 5.25 mmol, 1.5 equiv.) was added in one portion. High pressure liquid chromatography-mass spectroscopy analysis after 5 minutes showed all starting amine had been consumed. After 20 minutes, the mixture was concentrated in vacuo to an oil. The oil absorbed was on silica (2.5 g) and was purified by silica gel flash chromatography (0-4% methanol in dichloromethane) afforded the N-chloro-imidazolidin-4-one as a colorless oil (0.78 g, 95%). $^1$H NMR (400 MHz, CDCl$_3$) δ 3.55 (t, J=5.8 Hz, 2H), 3.44 (t, J=6.4 Hz, 2H), 3.36 (s, 3H), 1.46 (s, 6H), 1.36 (s, 6H); $^{13}$C NMR (100 MHz, CDCl$_3$) δ 172.8, 82.0, 70.1, 65.3, 58.8, 40.5, 25.1, 23.5; LRMS (ESI/APCI) m/z 235 [M+H]$^+$.

Example 33

Preparation of 1-chloro-3-(3-(2-(2-methoxyethoxy)ethoxy)propyl)-2,2,5,5-tetramethylimidazolidin-4-one (Compound 39-114)

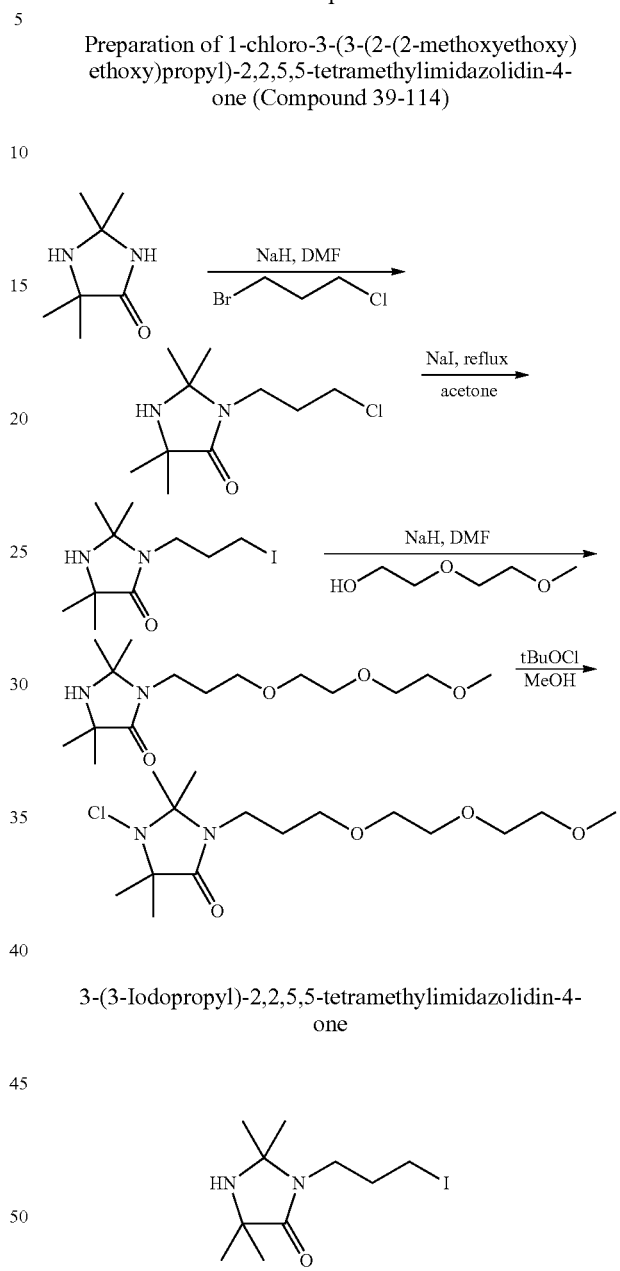

3-(3-Iodopropyl)-2,2,5,5-tetramethylimidazolidin-4-one

A suspension of 2,2,5,5-tetramethylimidazolidin-4-one (2.13 g, 15.0 mmol), prepared as described in U.S. Pat. No. 5,126,057 (Worley et al., Jun. 30, 1992), and sodium hydride (0.63 g, 60% disp, 15.8 mmol, 1.05 equiv) in dry N,N-dimethylformamide (20 mL) was stirred at room temperature under nitrogen for 15 min. The mixture was cooled to 0° C. before neat 3-chloro-1-bromopropane (1.93 mL, 19.5 mmol, 1.3 equiv.) was added, and the mixture was then stirred at room temperature. After 21.5 h, the mixture was concentrated to afford the crude alkyl chloride as a pasty white semi-solid (assumed 15.0 mmol), which was carried forward to the next step without further purification.

The residue (assumed 15 mmol of alkyl chloride) was suspended in acetone (30 mL), sodium iodide (4.50 g, 30 mmol, 2.0 equiv.) was added, and the mixture heated at reflux for 6 hours. The cooled mixture was diluted with ether (50 mL, to precipitate salts), filtered and concentrated to a brown semi-solid, which was suspended in dichloromethane (100 mL), filtered and concentrated. The residue was absorbed on silica (12 g). Chromatography on silica (0-5% methanol in dichloromethane) afforded the title compound as a very pale yellow oil (2.29 g, 49%). $^1$H NMR (400 MHz, CDCl$_3$) δ 3.26 (t, J=7.5 Hz, 2H), 3.21 (t, J=6.8 Hz, 2H), 2.17 (t, J=6.8, 7.5 Hz, 2H), 2.03 (br s, 1H), 1.43 (s, 6H), 1.33 (s, 6H); LRMS (ESI/APCI) m/z 311 [M+H]$^+$.

3-(3-(2-(2-Methoxyethoxy)ethoxy)propyl)-2,2,5,5-tetramethylimidazolidin-4-one

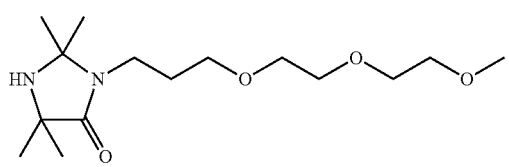

Neat diethylene glycol monomethyl ether (1.30 mL, 11.0 mmol, 1.5 equiv.) was added dropwise to a suspension of sodium hydride (400 mg, 60% disp., 10 mmol, 1.35 equiv.) in N,N-dimethylformamide (10 mL) over 5 minutes. The mixture was stirred at room temperature for 15 minutes, before a solution of 3-(3-iodopropyl)-2,2,5,5-tetramethylimidazolidin-4-one (2.29 g, 7.38 mmol) in N,N-dimethylformamide (10 mL) was added via cannula over 15 minutes. The mixture was then stirred overnight at room temperature. After 23 hours, the mixture was concentrated to a yellow oil which was absorbed on silica (5 g). Chromatography on silica (0-6% methanol in dichloromethane) afforded the title compound (190 mg, 8.5%) as a pale yellow oil. $^1$H NMR (400 MHz, CDCl$_3$) δ 3.68-3.64 (m, 4H), 3.63-3.59 (m, 2H), 3.57-3.54 (m, 2H), 3.53 (t, J=6.1 Hz, 2H), 3.39 (s, 3H), 3.29-3.24 (m, 2H), 1.96-1.89 (m, 2H), 1.82 (br s, 1H), 1.41 (s, 6H), 1.32 (s, 6H); LRMS (ESI/APCI) m/z 303 [M+H]$^+$.

1-Chloro-3-(3-(2-(2-methoxyethoxy)ethoxy)propyl)-2,2,5,5-tetramethylimidazolidin-4-one

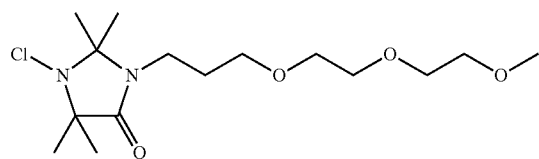 [SMILES: COCCOCCOCCCN1C(=O)C(C)(C)N(Cl)C1(C)C]

A solution of 3-(3-(2-(2-methoxyethoxy)ethoxy)propyl)-2,2,5,5-tetramethylimidazolidin-4-one (182 g, 0.60 mmol) in methanol (10 mL) was cooled in ice water for 10 minutes, before neat tert-butyl hypochlorite (0.10 mL, 0.9 mmol, 1.5 equiv.) was added in one portion. High pressure liquid chromatography-mass spectroscopy analysis after 5 minutes showed all starting amine had been consumed. After 20 min, the mixture was concentrated in vacuo to an oil, which was absorbed on silica (1 g). Chromatography on silica (0-4% methanol in dichloromethane) afforded the title compound as a colorless oil (193 mg, 95%). $^1$H NMR (400 MHz, CDCl$_3$) δ 3.66-3.62 (m, 4H), 361-3.58 (m, 2H), 3.56-3.53 (m, 2H), 3.51 (t, J=6.0 Hz, 2H), 3.38 (s, 3H), 3.35-3.30 (m, 2H), 1.96-1.88 (m, 2H), 1.45 (s, 6H), 1.33 (s, 6H); $^{13}$C NMR (100 MHz, CDCl$_3$) δ 172.6, 82.1, 71.9, 70.59, 70.54, 70.13, 68.6, 65.3, 59.0, 38.2, 29.1, 25.1, 23.5; LRMS (ESI/APCI) m/z 337 [M+H]$^+$.

Example 34

Preparation of 3-chloro-5-(hydroxymethyl)-4,4-dimethyloxazolidin-2-one (Compound 39-122)

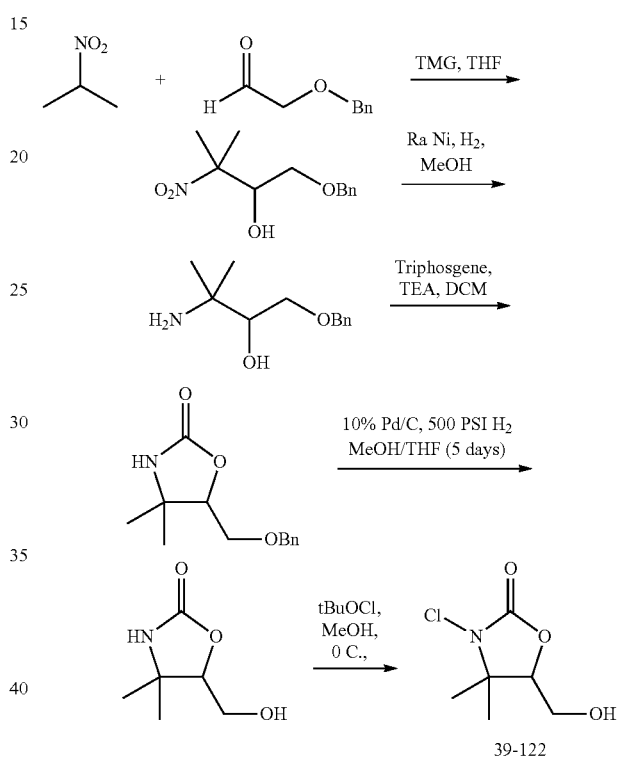

1-(benzyloxy)-3-methyl-3-nitrobutan-2-ol

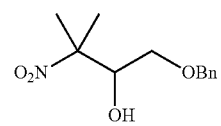

1,1,3,3-Tetramethylguanidine (620 μL, 5 mmol) was added slowly to a cold, 0° C., stirring solution of benzyloxy acetaldehyde (4.6 g, 31 mmol) and 2-nitropropane (30 mL, 333 mmol) in 100 mL of anhydrous THF. The reaction was stirred at 0° C. for ten minutes then allowed to warm to room temperature and stirred for 18 hours. The reaction was concentrated under reduced pressure and the product purified by column chromatography (5 to 50% ethyl acetate in hexanes) to give the title compound as a clear liquid (6.4 g, 27 mmol, 84%). $^1$H NMR (CDCl$_3$, 400 MHz) δ 1.58 (s, 3H), 1.63 (s, 2H), 2.87-2.89 (d, J=5.0 Hz, 1H), 3.48-3.53 (dd, 6.8, 9.8 Hz, 1H), 3.60-3.63 (dd, J=4.5, 9.8 Hz, 1H) 4.29-4.33 (m, 1H), 4.57 (s, 2H), 7.32-7.39 (m, 5H). LRMS (ESI/APCI) m/z 238 [M−H⁺].

3-amino-1-(benzyloxy)-3-methylbutan-2-ol

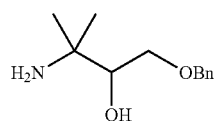

To a solution of 1-(benzyloxy)-3-methyl-3-nitrobutan-2-ol (5.2 g, 21.7 mmol) in MeOH (40 ml) was added a slurry of Raney Nickel in H₂O (50%, 1 ml). The vessel was pressurized with H₂ (450 psi) and the suspension stirred for 24 h. The mixture was filtered through Celite and concentrated in vacuo to give the title compound as a clear liquid (4.0 g, 19 mmol, 89%). ¹H NMR (CDCl₃, 400 MHz) δ 1.09 (s, 3H), 1.14 (s, 2H), 1.90 (br s, 2H) 3.50-3.54 (m, 2H), 3.61-3.67 (m, 1H), 4.57 (s, 2H), 7.28-7.39 (m, 5H). LRMS (ESI/APCI) m/z 210 [M+H]⁺.

5-((benzyloxy)methyl)-4,4-dimethyloxazolidin-2-one

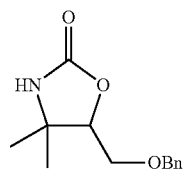 [SMILES: CC1(C)NC(=O)OC1COCc1ccccc1]

To a cold, 0° C., solution of 3-amino-1-(benzyloxy)-3-methylbutan-2-ol (2 g, 9.6 mmol) and triethylamine (3.3 mL, 24 mmol) in 95 mL of anhydrous dichloromethane was added triphosgene (3.1 g, 10.5 mmol). The reaction was stirred at 0° C. for 3.5 hr and at RT for 1.5 hr. A solution of saturated sodium bicarbonate (95 mL) was added and the mixture was stirred for 15 min, then the organic layer was isolated and washed successively with 0.25N HCl, sat. NaHCO₃, and brine. The organic layer was dried over sodium sulfate, concentrated to a residue and purified by column chromatography (30 to 75% ethyl acetate in hexanes) to give the title compound (1.8 g, 7.4 mmol, 78%). ¹H NMR (CDCl₃, 400 MHz) δ 1.27 (s, 3H), 1.40 (s, 2H), 1.90 3.67-3.76 (m, 2H), 4.37-4.41 (t, J=6.4 Hz, 1H), 4.56-4.64 (dd, J=9.6, 12 Hz, 2H), 5.27 (s, H), 7.28-7.40 (m, 5H). LRMS (ESI/APCI) m/z 236 [M+H]⁺.

5-(hydroxymethyl)-4,4-dimethyloxazolidin-2-one

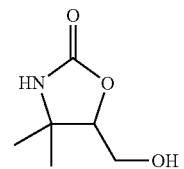

To a solution of 5-((benzyloxy)methyl)-4,4-dimethyloxazolidin-2-one (2.6 g, 11 mmol) in EtOH (40 ml) was added 500 mg of 10% Pd/C (wet, Degussa type E101). The vessel was pressurized with H₂ (450 psi) and the suspension stirred for 24 h. An additional 500 mg of 10% Pd/C was added and the reaction was stirred under 450 PSI H₂ for 5 days. The mixture was filtered through celite, concentrated in vacuo, and purified by column chromatography (1 to 10% methanol in dichloromethane) to give a clear liquid which solidified to a white solid upon standing (1.8 g, 12 mmol, 100%). ¹H NMR (CDCl₃, 400 MHz) δ 1.30 (s, 3H), 1.41 (s, 3H), 2.45 (br s, 1H), 3.76-3.81 (m, 1H), 3.87-3.92 (m, 1H), 4.30-4.32 (dd, J=4.4, 7.2 Hz, 1H) 5.59 (br s, H). LRMS (ESI/APCI) m/z 146 [M+H]⁺.

3-chloro-5-(hydroxymethyl)-4,4-dimethyloxazolidin-2-one

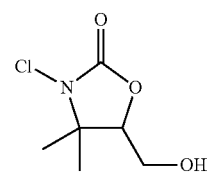

To a 0° C. solution of 5-(hydroxymethyl)-4,4-dimethyloxazolidin-2-one (250 mg, 1.72 mmol) in 2 mL of methanol was added tertbutyl hypochlorite (290 uL, 2.58 mmol). The reaction was stirred at 0° C. for 1 hour, then concentrated to a crude residue under reduced pressure. The crude product was purified by column chromatography (20 to 80% ethyl acetate in hexanes) to give the title compound as a clear liquid (248 mg, 1.38 mmol, 80%). ¹H NMR (CDCl₃, 400 MHz) δ 1.29 (s, 3H), 1.42 (s, 3H), 2.28-2.31 (dd, J=4.8, 7.7 1H), 3.85-3.88 (m, 1H), 3.91-3.98 (m, 1H), 4.37-4.40 (dd, J=4.7 6.9 Hz, 1H). LRMS (ESI/APCI) m/z 180 [M+H]⁺.

Example 35

3-chloro-6-(2-hydroxyethyl)-4,4-dimethyl-1,3-oxazinan-2-one (Compound 39-123)

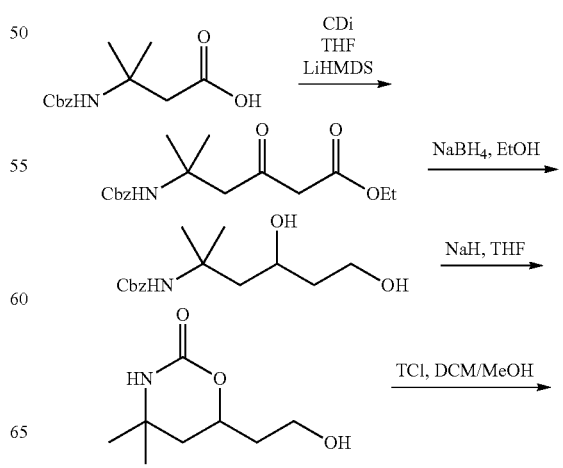

-continued

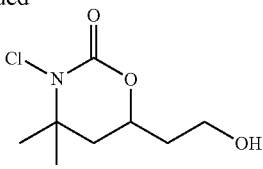

ethyl 5-(benzyloxycarbonylamino)-5-methyl-3-oxohexanoate

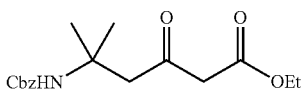

In a flask, 3-(Benzyloxycarbonylamino)-3-methylbutanoic acid (14.77 g, 58.8 mmol, prepared as described in Low, Eddy; Nair, Satheesh; Shiau, Timothy; Belisle, Barbara; Debabov, Dmitri; Celeri, Chris; Zuck, Meghan; Najafi, Ron; Georgopapadakou, Nafsika; Jain, Rakesh *Bioorganic and Medicinal Chemistry Letters*, 2009, 19, 196-198) was dissolved in tetrahydrofuran (200 ml). N,N-dicarbonyldiimidazole (9.54 g, 58.8 mmol) was added to the mixture, and the combined reaction mixture was stirred for about 1 hour at room temperature. In a second flask, lithium bis(trimethylsilyl)amide (1.0 M in tetrahydronfuran, 117 ml, 117 mmol) was cooled to −78° C., and ethylacetate was slowly added. The second flask was stirred for 20 minutes and then added to the first flask, which was also cooled to −78° C. The combined mixture was stirred at −78° C., for 2 hours. The reaction mixture was quenched with saturated, aqueous NaHCO₃ solution, and the mixture was extracted with ethylacetate. The ethylacetate layer was concentrated, and purified by column chromatography (0 to 20% ethylacetate in hexanes) to give 10.08 g (53%) of the title compound.

Benzyl 4,6-dihydroxy-2-methylhexan-2-ylcarbamate

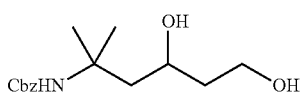 [SMILES: CC(C)(CC(O)CCO)NC(=O)OCc1ccccc1]

Ethyl 5-(benzyloxycarbonylamino)-5-methyl-3-oxohexanoate (3.49, 10.9 mmol) was dissolved in ethanol (100 ml). Sodium borohydride (1.64 g, 43.4 mmol) was added to the mixture, and the reaction mixture was stirred for 3 hours at room temperature. The reaction was quenched with 1 N HCl, and the mixture was stirred for 1 hour. The mixture was extracted with ethylacetate, and the combined organic layers were dried over sodium sulfate, filtered, and purified by column chromatography (0 to 4% methanol on dichloromethane) to give 2.14 g (70%) of the title compound.

6-(2-hydroxyethyl)-4,4-dimethyl-1,3-oxazinan-2-one

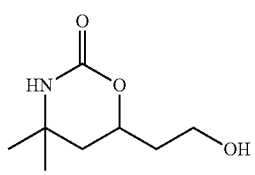

To a cold (0° C.) solution of benzyl(4,6-dihydroxy-2-methylhexan-2-yl)carbamate (460 mg, 1.6 mmol) in 30 mL of anhydrous THF was added sodium hydride (60% dispersion in oil, 128 mg, 3.2 mmol). The reaction was stirred at 0° C. for 15 min then allowed to warm to room temperature and stirred for an additional 4 hours. Acetic acid (ca 3.5 mmol) was added and the mixture was concentrated under reduced pressure. The crude residue was purified by column chromatography (5 to 12% methanol in dichloromethane) to give a white solid (219 mg, 1.26 mmol, 77%). ¹H NMR (d₆-DMSO, 400 MHz) δ 1.17 (s, 6H), 1.41-1.48 (dd, J=12.3, 13.4 Hz, 1H), 1.64-1.71 (m, 2H), 1.79-1.83 (dt, J=1.8, 13.7 Hz, 1H), 3.49-3.55 (m, 2H), 4.37-4.41 m, 1H), 4.54-4.57 (t, J=5.0 Hz, 1H), 7.2 (br s, 1H). LRMS (ESI/APCI) m/z 174 [M+H]⁺.

3-chloro-6-(2-hydroxyethyl)-4,4-dimethyl-1,3-oxazinan-2-one

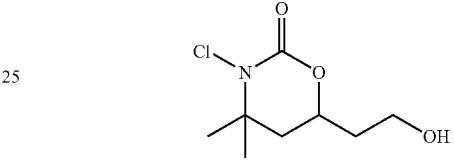

To a solution of 6-(2-hydroxyethyl)-4,4-dimethyl-1,3-oxazinan-2-one (278 mg, 1.6 mmol) in 4 mL dichloromethane and 250 uL methanol was added trichloroisocyanuric acid (370 mg, 1.6 mmol). The reaction mixture was stirred at room temperature for 4 hours and then directly purified by column chromatography (0 to 10% methanol in dichloromethane) to give a white solid (291 mg, 1.40 mmol, 87%). ¹H NMR (D₂O, 400 MHz) δ 1.35 (s, 6H), 1.78-1.83 (m, 2H), 1.97-2.03 (dd, J=11.9, 14.2 Hz, 1H), 2.13-2.17 (dd, J=2.1, 14.2 Hz, 1H), 3.64-3.68 (m, 2H), 4.55-4.60 (m, 2H). ¹³C NMR (D₂O, 100 MHz) δ 24.3, 27.9, 35.8, 41.5, 63.0, 72.5, 155.15. LRMS (ESI/APCI) m/z 208 [M+H]⁺.

Example 36

1-chloro-3-(2-(2-methoxyethoxy)ethyl)-2,2,5,5-tetramethylimidazolidin-4-one (Compound 39-100)

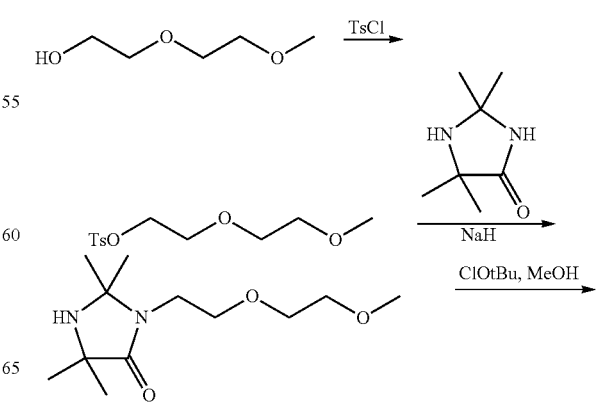

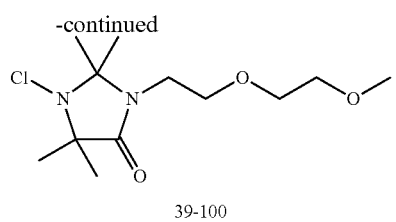

39-100

2-(2-methoxyethoxy)ethyl
4-methylbenzenesulfonate

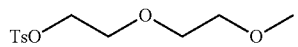 [SMILES: COCCOCCOS(=O)(=O)c1ccc(C)cc1]

2-(2-methoxyethoxy)ethyl 4-methylbenzenesulfonate was synthesized using the procedure described in Heathcote R; et al, *Dalton Trans.*, 2007, 1309-1315 at Experimental, subsection C, which portion is incorporated herein by reference in its entirety.

3-(2-(2-methoxyethoxy)ethyl)-2,2,5,5-tetramethylimidazolidin-4-one

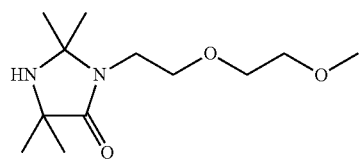

To a solution of 2,2,5,5-tetramethylimidazolidin-4-one (1 g, 7.0 mmol) in 14 mL of anhydrous DMF was added sodium hydride (60% dispersion in oil, 282 mg, 7.0 mmol), and the resultant mixture was stirred for 1 hour at room temperature. 2-(2-methoxyethoxy)ethyl 4-methylbenzenesulfonate (1.9 g, 7 mmol) was added dropwise and the solution was stirred at room temperature for 18 hr. The reaction mixture was concentrated under vacuum to a crude residue. The crude solid was suspended in dichloromethane and filtered to remove solids. The solution was purified by column chromatography (0 to 12% methanol in dichloromethane) to give a clear liquid (724 mg, 2.96 mmol, 43%). $^1$H NMR (400 MHz, D$_2$O) δ 1.22 (s, 6H), 1.35 (s, 6H), 3.27 (s, 3H), 3.34-3.37 (t, J=6.3 Hz, 3H), 3.49-3.52 (m, 2H), 3.58-3.61 (m, 4H). $^{13}$C NMR (100 MHz, D$_2$O) δ 25.7, 27.3, 39.6, 57.9, 58.9, 67.7, 69.4, 71.0, 76.2, 179.5. LRMS (ESI/APCI) m/z 245 [M+H]$^+$.

1-chloro-3-(2-(2-methoxyethoxy)ethyl)-2,2,5,5-tetramethylimidazolidin-4-one

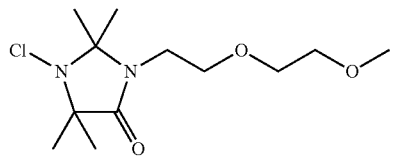 [SMILES: COCCOCCN1C(=O)C(C)(C)N(Cl)C1(C)C]

A solution of 3-(2-(2-methoxyethoxy)ethyl)-2,2,5,5-tetramethyl-imidazolidin-4-one (715 mg, 2.9 mmol) in methanol (7 ml) was cooled to 0° C. tert-Butylhypochlorite (393 ul, 3.5 mmol) was added. The resulting solution was stirred for 30 minutes, and then concentrated under reduced pressure. The crude material was purified by column chromatography (0 to 12% methanol in dichloromethane) to give the title compound as a clear liquid (666 mg, 2.39 mmol, 82%). $^1$H NMR (400 MHz, D$_2$O) δ 1.26 (s, 6H), 1.43 (s, 6H), 3.27 (s, 3H), 3.44-3.46 (m, 2H), 3.49-3.51 (m, 2H), 3.57-3.63 (m, 4H). $^{13}$C NMR (100 MHz, D$_2$O) δ 22.5, 24.0, 40.1, 57.9, 66.0, 67.6, 69.4, 71.0, 83.7, 175.0. LRMS (ESI/APCI) m/z 279 [M+H]$^+$.

Example 37

1-chloro-2,2,5,5-tetramethyl-3-(2,5,8,11-tetraoxatridecan-13-yl)imidazolidin-4-one (Compound 39-12)

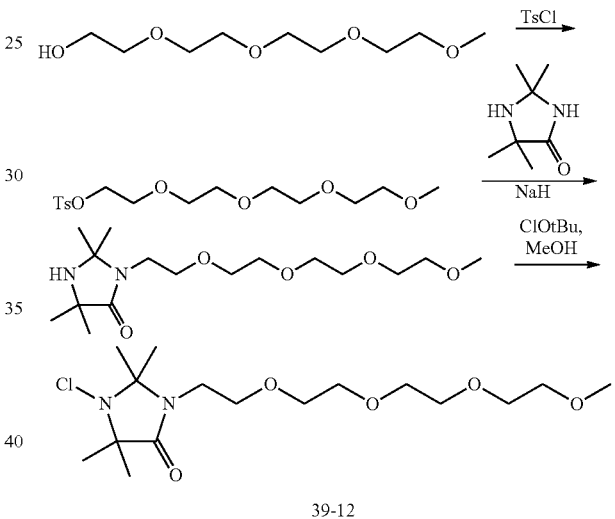

39-12

2,5,8,11-tetraoxatridecan-13-yl
4-methylbenzenesulfonate

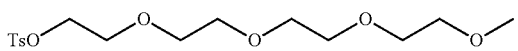 [SMILES: COCCOCCOCCOCCOS(=O)(=O)c1ccc(C)cc1]

To a solution of tetraethyleneglycol monomethyl ester (tech. grade, Aldrich, 10 g, 48 mmol) in 27 ml of tetrahydrofuran was added a solution of aqueous sodium hydroxide (5 M, 27 ml, 134 mmol). The solution was cooled to 0° C. and a solution of tosyl chloride (16.5 g, 86.4 mmol) in 27 mL THF was added dropwise to the cold stirring solution. The reaction mixture was stirred at 0° C. for 5 h, then diluted with 50 mL of water and extracted twice with dichloromethane. The organic fractions were washed twice with water and once with brine, then dried over magnesium sulfate and concentrated under reduced pressure to give a clear liquid (17.1 g, 47.1 mmol, 99%) the crude product was used directly without purification. LRMS (ESI/APCI) m/z 363 [M+H]$^+$.

2,2,5,5-tetramethyl-3-(2,5,8,11-tetraoxatridecan-13-yl)imidazolidin-4-one

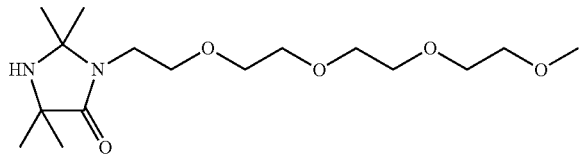

To a solution of 2,2,5,5-tetramethylimidazolidin-4-one (1 g, 7.0 mmol) in 12 mL of anhydrous N,N-dimethylformamide was added sodium hydride (60% dispersion in oil, 282 mg, 7.0 mmol), and the resultant mixture was stirred for 1 hour at room temperature. 2,5,8,11-tetraoxatridecan-13-yl 4-methyl-benzenesulfonate (2.5 g, 7 mmol) was added dropwise and the solution was stirred at room temperature for 18 hours. The reaction mixture was concentrated under vacuum to a crude residue. The crude solid was suspended in dichloromethane and filtered to remove solids, then purified by column chromatography (0 to 12% methanol in dichloromethane) to give a clear liquid (0.99 g, 3.0 mmol, 43%). $^1$H NMR (400 MHz, D$_2$O) δ 1.33 (s, 6H), 1.41 (s, 6H), 3.6-3.39 (m, 5H), 3.54-3.56 (m, 2H), 3.62-3.66 (m, 10H). LRMS (ESI/APCI) m/z 333 [M+H]$^+$.

1-chloro-2,2,5,5-tetramethyl-3-(2,5,8,11-tetraoxatridecan-13-yl)imidazolidin-4-one

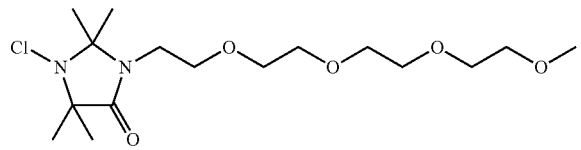 [SMILES: COCCOCCOCCOCCN1C(=O)C(C)(C)N(Cl)C1(C)C]

A solution of 3-(2-(2-methoxyethoxy)ethyl)-2,2,5,5-tetramethyl-imidazolidin-4-one (980 mg, 2.95 mmol) in methanol (7 ml) was cooled to 0° C. tert-Butylhypochlorite (395 ul, 3.5 mmol) was added. The resulting solution was stirred for 30 min, and then concentrated under reduced pressure. The crude material was purified by column chromatography (0 to 10% methanol in dichloromethane) to give a clear liquid (978 mg 2.67 mmol, 91% yield). $^1$H NMR (400 MHz, CDCl$_3$) δ 1.34 (s, 6H), 1.46 (s, 6H), 3.38 (s, 3H), 3.44-3.46 (m, 2H), 3.54-3.57 (m, 2H), 3.62-3.67 (m, 4H). $^{13}$C NMR (100 MHz, CDCl$_3$) δ 23.5, 25.2, 40.6, 59.0, 65.2, 68.5, 70.4, 70.4, 70.5, 70.6, 70.6, 71.9, 82.0, 172.7. LRMS (ESI/APCI) m/z 367 [M+H]$^+$.

Example 38

3-chloro-4-(hydroxymethyl)-1,4-dimethylimidazolidin-2-one (Compound 39-124)

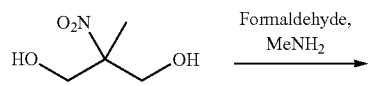

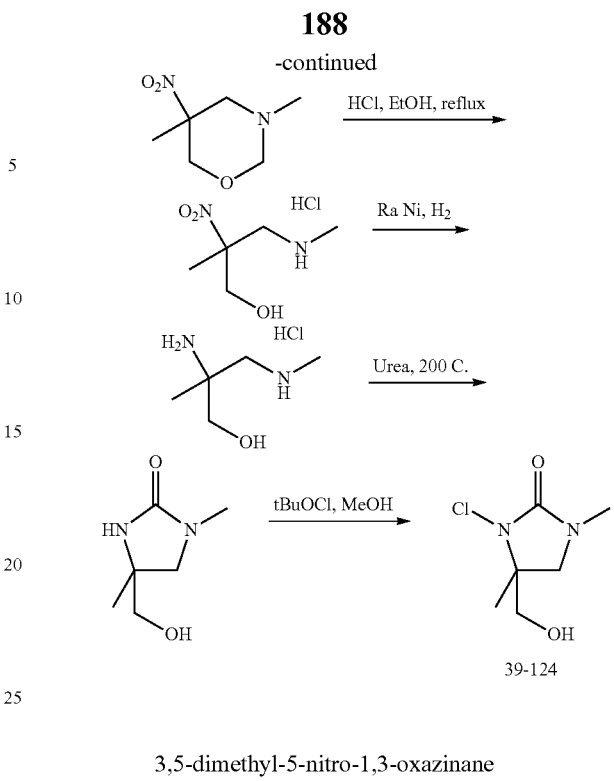

3,5-dimethyl-5-nitro-1,3-oxazinane

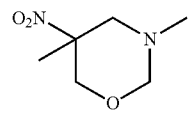

To a solution of 2-nitro-2-methyl-1,3-propanediol (20.4 g, 151 mmol) in 40% aqueous methylamine (11.7 g, 151 mmol), was added an aqueous solution of formaldehyde (37% formaldehyde, 12.2 g, 151 mmol). The reaction was stirred at room temperature for one week, then extracted with ether three times. The organic fractions were dried over sodium sulfate and concentrated under reduced pressure to give a crude oil which was purified by column chromatography (50 to 100% ethyl acetate in hexanes) to give the desired product (15.4 g, 96.1 mmol, 63%). $^1$H NMR (400 MHz, CDCl$_3$) δ 1.45 (s, 3H), 2.32 (s, 3H), 2.63-2.66 (d, J=13.2 Hz, 1H), 3.51-3.54 (d, J=12.6 Hz, 1H), 3.67-3.71 (dt, J=1.9, 13.2 Hz, 1H), 3.86-3.89 (d, J=8.5 Hz, 1H), 4.29-4.32 (dd, J=1.2, 8.6 Hz, 1H), 4.61-4.66 (dd, J=2.4, 12.6 Hz, 1H). $^{13}$C NMR (100 MHz, CDCl$_3$) δ 22.0, 39.9, 59.8, 71.2, 83.1, 86.1. LRMS (ESI/APCI) m/z 161 [M+H]$^+$.

2-methyl-3-(methylamino)-2-nitropropan-1-ol hydrochloride

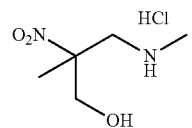

A solution of 3,5-dimethyl-5-nitro-1,3-oxazinane (11.5 g, 71.8 mmol) in 280 ml ethanol and 50 ml water, was equipped with a Dean-Stark trap and heated at reflux temperature. To the refluxing reaction was slowly added a solution of 280 ml ethanol and 50 ml water. The rate of addition of the solution was matched to the rate of distillation and removal of equal volume of solvent over the course of about 2 hours. After 4 hours at reflux temperature, the remaining solvent was distilled off and the crude residue was lyophilized from water to give a white solid (14.1 g, 100%), which was used directly in the next step without further purification. $^1$H NMR (400 MHz, D$_2$O) δ 1.53 (s, 3H), 2.74 (s, 3H), 3.62-3.66 (d, J=14.6 Hz, 1H), 3.68-3.72 (d, J=14.6 Hz, 1H), 3.84-3.87 (d, J=12.5 Hz, 1H), 4.10-4.13 (d, J=12.5 Hz, 1H). $^{13}$C NMR (100 MHz, D$_2$O) δ 18.9, 34.4, 52.8, 66.2, 88.9. LRMS (ESI/APCI) m/z 149 [M+H]$^+$.

2-amino-2-methyl-3-(methylamino)propan-1-ol hydrochloride

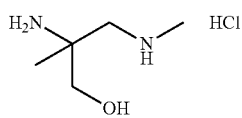

To a solution of 2-methyl-3-(methylamino)-2-nitropropan-1-ol hydrochloride (5.4 g) in methanol (32 ml) was added a slurry of Raney Nickel in H$_2$O (1.5 ml). The vessel was pressurized with H$_2$ (450 psi) and the suspension stirred for 48 h. The mixture was filtered through Celite and concentrated in vacuo to give a crude liquid (7.4 g, >100%), which was used directly in the next step without purification. $^1$H NMR (400 MHz, CDCl$_3$) δ 1.01 (s, 3H), 2.26 (s, 3H), 2.99 (s, 2H), 3.41-3.44 (d, J=11.6, 1H), 3.48-3.51 (d, J=11.6 Hz, 1H). LRMS (ESI/APCI) m/z 145 [M+H]$^+$.

4-(hydroxymethyl)-1,4-dimethylimidazolidin-2-one

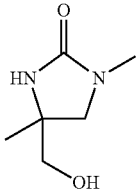

In a round bottom flask, a mixture of 2-amino-2-methyl-3-(methylamino)propan-1-ol hydrochloride (3.3 g, 21 mmol) and urea (1.26 g, 21 mmol) were heated in a 200° C. sand bath for 1 hour until ammonia gas ceased to evolve. The resultant mixture was suspended in dichloromethane and filtered to remove insoluble material. The organic solution was concentrated to a black solid and purified by purified by column chromatography (1 to 12% methanol in dichloromethane) to give the desired product as a tan oil (1.3 g, 9.0 mmol, 45% yield). $^1$H NMR (400 MHz, CDCl$_3$) δ 1.26 (s, 3H), 2.76 (s, 3H), 3.07-3.9 (d, J=8.8 Hz, 1H), 3.36-3.36 (d, J=8.8 Hz, 1H), 3.43-3.44 (d, J=2.1 Hz, 2H), 3.46 (s, 1H). $^{13}$C NMR (100 MHz, CDCl$_3$/MeOD) δ 23.5, 30.1, 50.0, 55.7, 67.7, 161.9. LRMS (ESI/APCI) m/z 145 [M+H]$^+$.

3-chloro-4-(hydroxymethyl)-1,4-dimethylimidazolidin-2-one

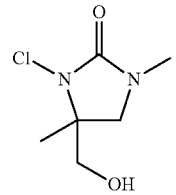

A solution of 4-(hydroxymethyl)-1,4-dimethylimidazolidin-2-one (250 mg, 1.72 mmol) in methanol (2.5 ml) was cooled to 0° C. tert-Butylhypochlorite (236 ul, 2.1 mmol) was added. The resulting solution was stirred for 30 minutes, then concentrated under reduced pressure to a crude residue. The crude material was purified by column chromatography (1 to 12% methanol in dichloromethane) to give the desired product as a white solid (168 mg, 0.941 mmol, 54%). $^1$H NMR (400 MHz, D$_2$O) δ 1.16 (s, 3H), 2.74 (s, 3H), 3.25-3.27 (d, J=9.2 Hz, 1H), 3.38-3.41 (d, J=12.6 Hz, 1H), 3.47-3.49 (d, J=9.2 Hz, 2H), 3.64-3.67 (d, J=12.6 Hz, 1H). $^{13}$C NMR (100 MHz, D$_2$O) δ 18.1, 30.8, 53.2, 62.8, 64.5, 161.6. LRMS (ESI/APCI) m/z 179 [M+H]$^+$.

Example 39

1-chloro-3-(2-hydroxyethyl)imidazolidin-2-one (Compound 39-120)

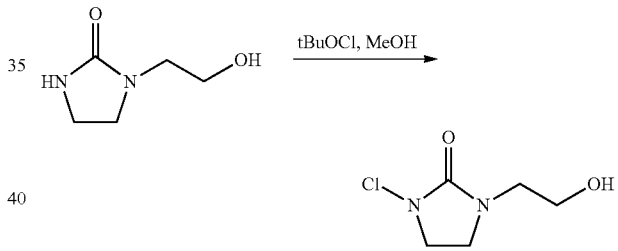

A solution of 1-(2-hydroxyethyl)imidazolidin-2-one (418 mg, 3.2 mmol) in MeOH (6 ml) was cooled to 0° C. tert-Butylhypochlorite (450 ul, 4 mmol) was added. The resulting solution was stirred for 90 min and then concentrated under reduced pressure. The crude material was purified by column chromatography (0 to 12% methanol in dichloromethane) to give a white solid (317 mg, 1.93 mmol, 60%). $^1$H NMR (400 MHz, D$_2$O) δ 3.28-3.31 (t, J=5.3 Hz, 2H), 3.47-3.51 (m, 2H), 3.56-3.59 (m, 2H), 3.62-3.64 (t, J=5.3 Hz, 2H). $^{13}$C NMR (100 MHz, D$_2$O) δ 43.31, 46.6, 51.9, 58.3, 163.9. LRMS (ESI/APCI) m/z 165 [M+H]$^+$.

Example 40

1-chloro-2,2,5,5-tetramethyl-3-(2,5,8,11,14,17,20,23,26,29,32,35,38,41-tetradecaoxatritetracontan-43-yl)imidazolidin-4-one (Compound 39-132)

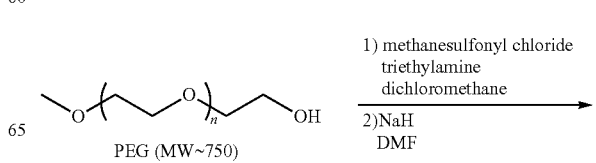

191

-continued

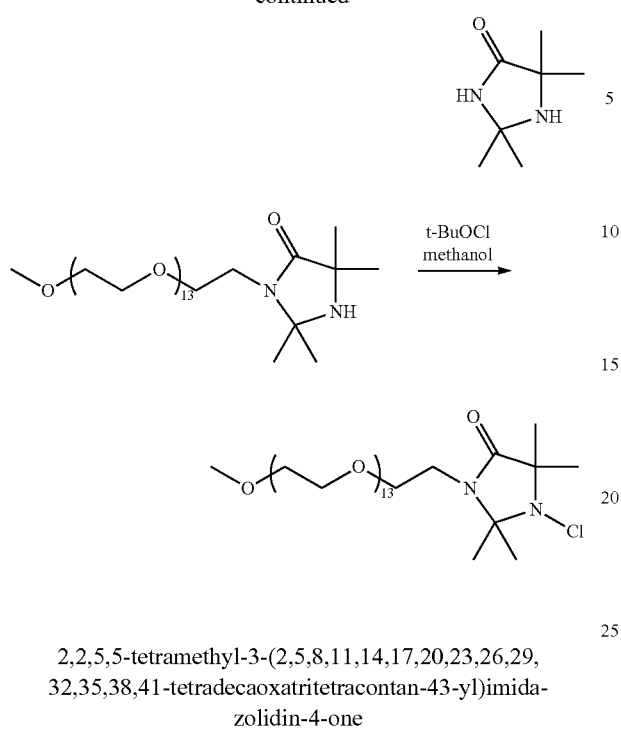

2,2,5,5-tetramethyl-3-(2,5,8,11,14,17,20,23,26,29,32,35,38,41-tetradecaoxatritetracontan-43-yl)imidazolidin-4-one Poly(ethylene glycol)methyl ether (average molecular weight=750, Aldrich cat#202509, 5.77 g, 7.7 mmol) was dissolved in dichloromethane (150 ml). To the stirring mixture is added triethylamine (3.3 ml, 23.7 mmol), and the combined mixture was cooled to 0° C. Methanesulfonyl chloride (1.8 ml, 23.3 mmol) was added dropwise to the stirring solution over a 30 minute period. The combined mixture was stirred at 0° C. for an additional 30 minutes. The reaction mixture was washed with water, and the organic layer was dried over sodium sulfate. The organic layer was concentrated in vacuo, and the PEG-mesylate product was used without further purification.

2,2,5,5-Tetramethylimidazolidin-4-one (2.20 g, 15.5 mmol), prepared as described in U.S. Pat. No. 5,126,057 (Worely et al., Jun. 30, 1992), was dissolved in N,N-dimethylformamide (60 ml). To the stirring room temperature solution was added sodium hydride (60%, 550 mg, 13.8 mmol), in 4 portions over 10 minutes. After an additional one hour of stirring at room temperature, the PEG-mesylate was added to the reaction mixture. After the reaction mixture was stirred for 18 hours at room temperature, the mixture was concentrated in vacuo, and crude material is purified by silica gel column chromatography (0 to 10% methanol in dichloromethane) to give 1.13 g (16%) the title compound.

192

1-chloro-2,2,5,5-tetramethyl-3-(2,5,8,11,14,17,20,23,26,29,32,35,38,41-tetradecaoxatritetracontan-43-yl)imidazolidin-4-one

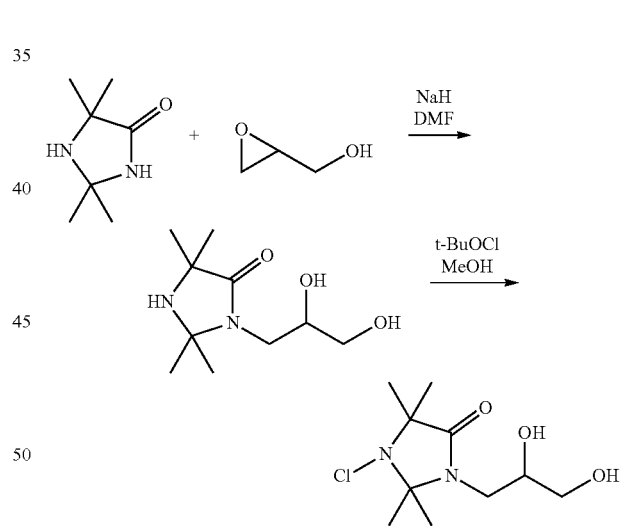

To a 0° C. solution of 2,2,5,5-tetramethyl-3-(2,5,8,11,14,17,20,23,26,29,32,35,38,41-tetradecaoxatritetracontan-43-yl)imidazolidin-4-one (1.13 g, 1.2 mmol) in methanol (150 ml) was added tert-butylhypochlorite (393 mg, 3.6 mmol). The mixture was stirred for 1 hour at 0° C. The reaction mixture was concentrated in vacuo, and crude material is purified by silica gel flash chromatography (0 to 10% methanol in dichloromethane) to give 764 mg (66%) of the title compound. $^1$H NMR (400 MHz, D$_2$O) δ 3.70 (s, 54H), 3.64 (m, 2H), 3.56 (t, J=7.5 Hz, 2H), 3.39 (s, 3H), 1.54 (s, 6H), 1.37 (s, 6H). $^{13}$C NMR (100 MHz, D$_2$O) δ 175.0, 83.6, 71.0, 69.4 (large peak), 67.7, 66.0, 58.0, 40.2, 24.1, 22.6.

Example 41

1-chloro-3-(2,3-dihydroxypropyl)-2,2,5,5-tetramethylimidazolidin-4-one (Compound 39-27)

3-(2,3-dihydroxypropyl)-2,2,5,5-tetramethylimidazolidin-4-one

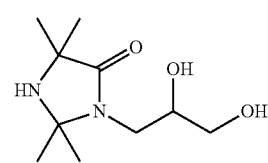

2,2,5,5-Tetramethylimidazolidin-4-one (3.54 g, 24.9 mmol), prepared as described in U.S. Pat. No. 5,126,057 (Worely et al., Jun. 30, 1992), was dissolved in N,N-dimethylformamide (150 ml). To the stirring room temperature solution was added sodium hydride (60%, 913 mg, 22.8 mmol), in 4 portions over 10 minutes. After an additional one hour of stirring at room temperature, the glycidol (1.4 ml, 21.1 mmol) was added to the reaction mixture. After the reaction mixture was stirred for 18 hours at room temperature, the mixture was concentrated in vacuo, and crude material is purified by silica gel column chromatography (0 to 20% methanol in dichloromethane) to give 250 mg (5%) the title compound.

1-chloro-3-(2,3-dihydroxypropyl)-2,2,5,5-tetramethylimidazolidin-4-one

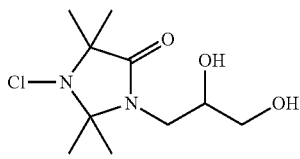 [SMILES: CC1(C)C(=O)N(CC(O)CO)C(C)(C)N1Cl]

To a 0° C. solution of 3-(2,3-dihydroxypropyl)-2,2,5,5-tetramethylimidazolidin-4-one (250 mg, 1.2 mmol) in methanol (150 ml) was added tert-butylhypochlorite (150 mg, 1.4 mmol). The mixture was stirred for 1 hour at 0° C. The reaction mixture was concentrated in vacuo, and crude material is purified by silica gel flash chromatography (0 to 10% methanol in dichloromethane) to give 256 mg (88%) of the title compound. $^{1}$H NMR (400 MHz, D$_{2}$O) δ 4.06-3.98 (m, 1H), 3.62 (dd, J=12.0, 4.0 Hz, 1H), 3.56-3.44 (m, 2H), 3.36 (dd, J=14.8, 8.4 Hz, 1H), 1.54 (s, 6H), 1.38-1.37 (m, 6H). $^{13}$C NMR (100 MHz, D$_{2}$O) δ 175.5, 83.9, 69.4, 66.0, 63.4, 43.6, 24.2, 23.9, 22.72, 22.4. LRMS (ESI/APCI) m/z 251 [M+H]$^{+}$.

Example 42

1-chloro-3-(4-hydroxybutyl)-2,2,5,5-tetramethylimidazolidin-4-one (Compound 39-125)

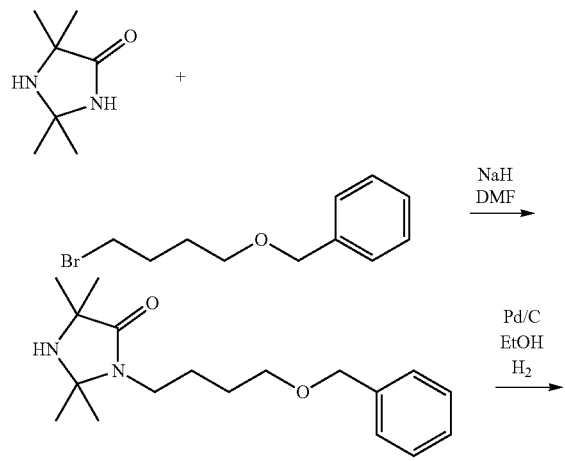

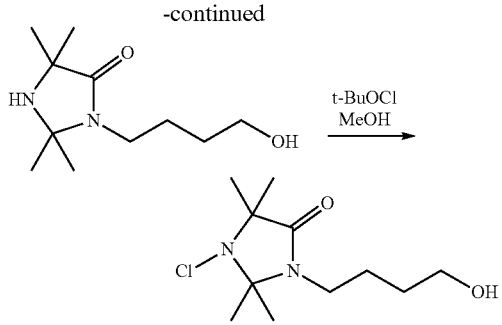

3-(4-(benzyloxy)butyl)-2,2,5,5-tetramethylimidazolidin-4-one

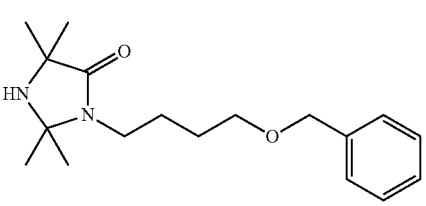 [SMILES: CC1(C)NC(C)(C)N(CCCCOCc2ccccc2)C1=O]

2,2,5,5-Tetramethylimidazolidin-4-one (3.54 g, 24.9 mmol), prepared as described in U.S. Pat. No. 5,126,057 (Worely et al., Jun. 30, 1992), was dissolved in N,N-dimethylformamide (150 ml). To the stirring room temperature solution was added sodium hydride (60%, 913 mg, 22.8 mmol), in 4 portions over 10 minutes. After an additional one hour of stirring at room temperature, the benzyl 5-bromobutyl ether (90%, 5.05 g, 20.8 mmol) was added to the reaction mixture. After the reaction mixture was stirred for 18 hours at room temperature, the mixture was concentrated in vacuo, and crude material is purified by silica gel column chromatography (0 to 20% methanol in dichloromethane) to give 3.40 g (45%) the title compound. $^{1}$H NMR (400 MHz, D$_{2}$O) δ 7.46-7.24 (m, 5H), 4.50 (s, 2H), 3.51 (t, J=6.0 Hz, 2H), 3.20-3.15 (m, 2H), 1.74-1.62 (m, 4H), 1.47 (s, 6H), 1.36 (s, 6H).

3-(4-hydroxybutyl)-2,2,5,5-tetramethylimidazolidin-4-one

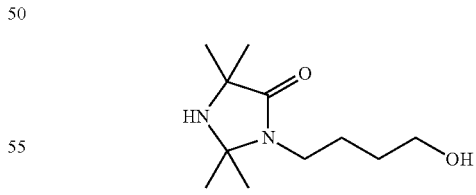

3-(4-(benzyloxy)butyl)-2,2,5,5-tetramethylimidazolidin-4-one (3.40 g, 11.2 mmol), was dissolved in ethanol (100 ml), and palladium (10% on carbon, 410 mg, 0.4 mmol) was added to the solution. The flask was purged several times with nitrogen, and then several times with hydrogen. The reaction was stirred at room temperature for 18 hours under hydrogen. The mixture was filtered and purified by silica gel column chromatography (0 to 20% methanol in dichloromethane) to give 628 mg (26%) the title compound. $^{1}$H NMR (400 MHz, D$_{2}$O)

δ 3.72 (t, 6.0 Hz, 2H), 3.49 (s, 1H), 3.28-3.20 (m, 2H), 1.76-1.66 (m, 4H), 1.64-1.56 (m, 2H), 1.40 (s, 6H), 1.32 (s, 6H).

1-chloro-3-(4-hydroxybutyl)-2,2,5,5-tetramethylimidazolidin-4-one

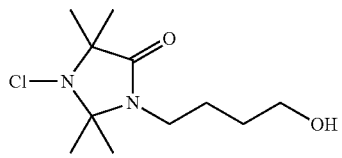 [SMILES: CC1(C)C(=O)N(CCCCO)C(C)(C)N1Cl]

To a 0° C. solution of 3-(4-hydroxybutyl)-2,2,5,5-tetramethylimidazolidin-4-one, (622 mg, 2.9 mmol) in methanol (80 ml) was added tert-butylhypochlorite (473 mg, 4.4 mmol). The mixture was stirred for 1 hour at 0° C. The reaction mixture was concentrated in vacuo, and crude material is purified by silica gel flash chromatography (0 to 15% methanol in dichloromethane) to give 213 mg (30%) of the title compound. $^1$H NMR (400 MHz, D$_2$O) δ 3.74-3.66 (m, 2H), 3.34-3.30 (m, 2H), 2.08 (s, 1H), 1.78-1.71 (m, 2H), 1.65-1.57 (m, 2H), 1.47 (s, 6H), 1.36 (s, 6H). $^{13}$C NMR (100 MHz, D$_2$O) δ 173.0, 82.3, 65.5, 62.5, 40.5, 29.8, 26.1, 25.5, 23.8. LRMS (ESI/APCI) m/z 249 [M+H]$^+$.

While the foregoing description describes specific embodiments, those with ordinary skill in the art will appreciate that various modifications and alternatives can be developed. Accordingly, the particular embodiments described above are meant to be illustrative only, and not to limit the scope of the invention, which is to be given the full breadth of the appended claims, and any and all equivalents thereof.

What is claimed is:

1. A compound of Formula I

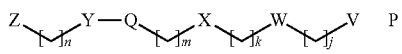

I or a pharmaceutically acceptable salt thereof,
wherein
Z is

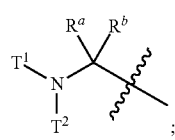

;

T$^1$ is —Cl or —Br;
T$^2$ is —Cl or —Br;
R$^a$ and R$^b$ are each independently H or alkyl, wherein each alkyl may be optionally substituted by alkoxy, halo or hydroxy;
Y is —S(=O)$_2$—, —S(=O)$_2$CH$_2$—, —S(=O)$_2$NR$^5$— or —N$^+$(R$^1$)(R$^2$)—;
W is —S(=O)$_2$—, —S(=O)$_2$CH$_2$—, —S(=O)$_2$NR$^5$—, —N$^+$(R$^1$)(R$^2$)— or absent;
Q is —CH$_2$— or absent;
X is —(CHR$^4$—O)$_h$—, —(CH$_2$—CHR$^4$—O)$_h$—, —(CHOR$^3$)$_h$—, —(CH(CH$_2$OR$^3$))$_h$—, —(CH$_2$—CR$^4$(OR$^3$))$_h$—, or a combination thereof;
h is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50;
V is H, acyl, alkyl, Z, or —SO$_3$H;
n is 1, 2 or 3;
m, k and j are each independently 0, 1, 2 or 3;
R$^1$ and R$^2$ are each independently selected from the group consisting of alkyl, aryl, heteroalkyl, and heteroaryl, each of which may be optionally substituted by alkoxy, halo and hydroxy; or R$^1$ and R$^2$ together with the nitrogen atom to which they are attached form a heterocycloalkyl group, each of which may be optionally substituted by alkoxy, halo and hydroxy;
each R$^3$ is independently H, alkyl, acyl, aryl, heteroalkyl, heteroaryl, or heterocycloalkyl, each of which may be optionally substituted by alkoxy, halo and hydroxy;
each R$^4$ is independently H or alkyl;
R$^5$ is H or alkyl;
and P is a counterion or absent, wherein the counterion is selected from the group consisting of sodium, potassium, tetramethylammonium, tetrabutylphosphonium, acetate, phosphate, sulfonate and citrate.

2. The compound of claim 1, wherein Z is

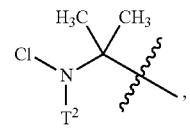

, and T$^2$ is Cl.

3. The compound of claim 2, wherein
Y is —S(=O)$_2$—;
Q is absent;
k is 0;
W is absent; and
V is H, acyl or alkyl.

4. The compound of claim 3, wherein X is —(CH$_2$—CHR$^4$—O)$_h$—, wherein R$^4$ is H.

5. The compound of claim 3, wherein X is —(CHOR$^3$)$_h$—, wherein R$^3$ is H.

6. A pharmaceutical composition comprising a compound of claim 1 and a pharmaceutically acceptable carrier or excipient.

7. A compound selected from the group consisting of:
4-(2-(2-(2-methoxy)ethoxy)ethoxy)ethylsulfonyl)-N,N-dichloro-2-methylbutan-2-amine,
4-(3-(dichloroamino)-3-methylbutylsulfonyl)butane-1,2,3-triol,
3-(3-(dichloroamino)-3-methylbutylsulfonyl)propane-1,2-diol,
2-(3-(dichloroamino)-3-methylbutylsulfonyl)ethanol,
2-(2-(2-(3-(dichloroamino)-3-methylbutylsulfonyl)ethoxy)ethoxy)ethanol,
2-(2-(2-(3-(dichloroamino)-3-methylbutylsulfonyl)ethoxy)ethoxy)ethyl acetate,
3-(dichloroamino)-N-(2-(2-(2-methoxyethoxy)ethoxy)ethyl)-N,N,3-trimethylbutan-1-aminium 4-methylbenzenesulfonate,
3-(3-(dichloroamino)-3-methylbutylsulfonyl)propane-1,2-diyl diacetate, 3-(3-(dichloroamino)-3-methylbutylsulfonyl)-2-hydroxypropyl acetate,
3-(dichloroamino)-N-(2-methoxyethyl)-N,N,3-trimethylbutan-1-aminium chloride,
3-(dichloroamino)-N-(3-hydroxypropyl)-N,N,3-trimethylbutan-1-aminium chloride,
N-(2-butoxyethyl)-3-(dichloroamino)-N,N,3-trimethylbutan-1-aminium chloride,
4-((1,4,7,10-tetraoxacyclododecan-2-yl)methylsulfonyl)-N,N-dichloro-2-methylbutan-2-amine,
3-(dichloroamino)-N-(2-(hexyloxy)ethyl)-N,N,3-trimethylbutan-1-aminium 4-methylbenzenesulfonate,
3-(dichloroamino)-N-(3-methoxypropyl)-N,N,3-trimethylbutan-1-aminium chloride,
3-(3-(dichloroamino)-3-methylbutylsulfonyl)butane-1,2,4-triol,
N,N-Dichloro-4-(2-(2-(2-tert-butoxyethoxy)ethylsulfonyl)-2-methylbutan-2-amine,
N,N-dichloro-4-(2-(2-(2-(2 methoxyethoxy)ethoxy)ethoxy)ethylsulfonyl)-2-methylbutan-2-amine,
3-(dichloroamino)-N-(3-hydroxypropyl)-N,3-dimethylbutane-1-sulfonamide,
(2S,3S,4S,5R,6S)-2-((3-(dichloroamino)-3-methylbutylsulfonyl)methyl)-6-methoxytetrahydro-2H-pyran-3,4,5-triol,
N,N-dichloro-4-(2-(2-(2-ethoxyethoxy)ethoxy)ethylsulfonyl)-2-methylbutan-2-amine,
N,N-dichloro-4-(2-methoxyethylsulfonyl)-2-methylbutan-2-amine,
N,N-dichloro-4-(2-(2-methoxyethoxy)ethylsulfonyl)-2-methylbutan-2-amine,
3-(dichloroamino)-N-(2-hydroxyethyl)-N,3-dimethylbutane-1-sulfonamide,
8-((3-(dichloroamino)-3-methylbutyl)sulfonyl)octan-1-ol,
2-((2-(dichloroamino)-2-methylpropyl)sulfonyl)ethanol,
3-((3-(dichloroamino)-3-methylbutyl)sulfonyl)propan-1-ol,
N,N-dichloro-2-methyl-4-(tetrahydrofuran-3-ylsulfonyl)butan-2-amine, and
4-(3-(dichloroamino)-3-methylbutylsulfonyl)butane-1,2-diol.

* * * * *